United States Patent
Coenye et al.

(10) Patent No.: US 10,023,602 B2
(45) Date of Patent: Jul. 17, 2018

(54) HAMAMELITANNIN ANALOGUES AND USES THEREOF

(71) Applicant: Universiteit Gent, Ghent (BE)

(72) Inventors: Tom Coenye, Mariakerke (BE); Gilles Brackman, Laarne (BE); Martijn Risseeuw, Ghent (BE); Arno Vermote, Nieuwpoort (BE); Serge Van Calenbergh, De Pinte (BE)

(73) Assignee: UNIVERSITEIT GENT, Ghent (BE)

( * ) Notice: Subject to any disclaimer, the term of this patent is extended or adjusted under 35 U.S.C. 154(b) by 43 days.

(21) Appl. No.: 15/324,000

(22) PCT Filed: Jul. 6, 2015

(86) PCT No.: PCT/EP2015/065394
§ 371 (c)(1),
(2) Date: Jan. 5, 2017

(87) PCT Pub. No.: WO2016/005340
PCT Pub. Date: Jan. 14, 2016

(65) Prior Publication Data
US 2017/0158727 A1  Jun. 8, 2017

(30) Foreign Application Priority Data
Jul. 8, 2014  (EP) .................................... 14176218

(51) Int. Cl.
| | | |
|---|---|---|
| *C07H 13/04* | (2006.01) | |
| *C07D 493/04* | (2006.01) | |
| *C07D 405/12* | (2006.01) | |
| *C07D 307/20* | (2006.01) | |
| *A61K 31/7012* | (2006.01) | |
| *A61K 31/357* | (2006.01) | |
| *A61K 31/501* | (2006.01) | |
| *A61K 31/443* | (2006.01) | |
| *A61K 31/506* | (2006.01) | |
| *A61K 31/497* | (2006.01) | |
| *A61K 45/06* | (2006.01) | |
| *A61K 31/404* | (2006.01) | |

(52) U.S. Cl.
CPC .......... *C07H 13/04* (2013.01); *A61K 31/357* (2013.01); *A61K 31/404* (2013.01); *A61K 31/443* (2013.01); *A61K 31/497* (2013.01); *A61K 31/501* (2013.01); *A61K 31/506* (2013.01); *A61K 31/7012* (2013.01); *A61K 45/06* (2013.01); *C07D 307/20* (2013.01); *C07D 405/12* (2013.01); *C07D 493/04* (2013.01)

(58) Field of Classification Search
CPC .... C07H 13/04; C07D 493/04; C07D 405/12; C07D 307/20; A61K 31/7012; A61K 31/357; A61K 31/501; A61K 31/443; A61K 31/506; A61K 31/497; A61K 45/06
See application file for complete search history.

(56) References Cited

U.S. PATENT DOCUMENTS

| | | |
|---|---|---|
| 4,997,834 A | 3/1991 | Muro et al. |
| 6,369,086 B1 | 4/2002 | Davis et al. |
| 6,369,087 B1 | 4/2002 | Whittle et al. |
| 6,372,733 B1 | 4/2002 | Caldwell et al. |
| 6,372,778 B1 | 4/2002 | Tung et al. |

FOREIGN PATENT DOCUMENTS

| | | |
|---|---|---|
| EP | 0370498 A2 | 5/1990 |
| JP | 06-234784 A | 8/1994 |
| WO | WO9509615 A1 | 4/1995 |
| WO | WO2007147098 A2 | 12/2007 |

OTHER PUBLICATIONS

Greenhill et al., J. Chem. Soc. Perkin I, 1972, p. 1667-1669. (Year: 1972).*
Batra et al., "A Concise, Efficient and Production-Scale Synthesis of a Protected L-Lyxonolactone Derivative: An Important Aldonolactone Core"; Organic Process Research & Development 2006, vol. 10, No. 3, pp. 484-486.
Boren et al., "Ruthenium-Catalyzed Azide-Alkyne Cycloaddition: Scope and Mechanism", J. Am. Chem. Soc. 2008, 130, pp. 8923-8930.
Bouisset et al., "Synthesis of 2'-C-methyl-branched isonucleosides", Elsevier, Tetrahedron 64, 2008, pp. 6657-6661.
Brackman et al., "Quorum Sensing Inhibitors Increase the Susceptibility of Bacterial Biofilms to Antibiotics In Vitro and In Vivo", American Society for Microbiology, Antimicrobial Agents and Chemotherapy, Jun. 2011, vol. 55, No. 6, pp. 2655-2661.
Demon et al., "The intramammary efficacy of first generation cephalosporins against *Staphyloccus aureus* mastitis in mice", Elsevier, Veterinary Microbiology, 160, 2012, pp. 141-150.
Garcia-Moreno et al., "Nitrogen versus sulfur acylation in sugar thioureas: regioselectivity and conformational consequences", Tetrahedron: Asymmetry 11, 2000, pp. 1331-1341.

(Continued)

*Primary Examiner* — Jonathan S Lau
(74) *Attorney, Agent, or Firm* — Dinsmore & Shohl LLP

(57) ABSTRACT

The present invention relates to hamamelitannin analogues, pharmaceutical compositions comprising the same, and combinations thereof with anti-microbial agents such as antibiotics or disinfectants. It in particular relates to the use of the compounds, compositions and combinations according to this invention in human or veterinary medicine, more in particular for use in the prevention and/or treatment of bacterial infections, such as *Staphylococcus aureus* infections, in humans or animals.

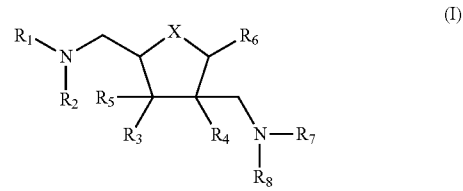

18 Claims, 4 Drawing Sheets

(56) References Cited

OTHER PUBLICATIONS

Simone et al., "Carbon-branched -tetrahydrofuran sugar amino acids (SAAs) as dipeptide isostere scaffolds", Tetrahedron: Asymmetry, 19, 2008, pp. 2887-2894.
Vermote et al., "Hamamelitannin Analogues that Modulate Quorum Sensing as Potentiators of Antibiotics against *Staphylococcus aureus*", Angewandte Chem. Int. Ed., 2016-Wiley-VCH Verlag BmbH & Co. KGaA, Weinheim, Germany, 55, pp. 6551-6555.
Taki et al., "Fluorescence Imaging of Intracelluar Cadmium Using a Dual-Excitation Ratiometric Chemosensor", J. Am. Chem. Soc. 2008, 130, pp. 12564-12565.
International Search Report and Written Opinion, completed Aug. 4, 2015, pertaining to PCT/EP2015065394 filed Jul. 6, 2015.
Extended European Search Report, dated Oct. 22, 2014, pertaining to EP14176218.7-1452.

\* cited by examiner

HAMAMELITANNIN ANALOGUES AND USES THEREOF

FIELD OF THE INVENTION

The present invention relates to hamamelitannin analogues, pharmaceutical compositions comprising the same, and combinations thereof with antimicrobial agents such as antibiotics or disinfectants. It in particular relates to the use of the compounds, compositions and combinations according to this invention in human or veterinary medicine, more in particular for use in the prevention and/or treatment of bacterial infections, such as *Staphylococcus aureus* infections, in humans or animals.

BACKGROUND TO THE INVENTION

For a long time, microorganisms such as bacteria, yeasts or fungi were considered non-complex organisms that could easily be eradicated with antimicrobials. However, today we are confronted with an alarming growth of disease-causing microbes that can no longer efficiently be controlled by available antibiotics or antifungals. This phenomenon is generally referred to as "antimicrobial resistance" or AMR. Clinicians in many different disciplines are experiencing difficulties to treat patients due to ineffective antimicrobials.

The impact of AMR is also evidenced by the problem of infections acquired during a stay at a healthcare related institution (hospitals, elderly care) also known as "nosocomial infections". To combat the spread of AMR, there is an increasing pressure towards a more rational use of antibiotics. As a result, almost every Western country has launched campaigns to make people aware that misuse of antimicrobials makes them ineffective. In fact, the problem of AMR has grown to such a dramatic level that the World Health Organization moved it to the top-3 of global health risks.

Hence, there is a continuous need for new antimicrobial compositions, or agents that increase sensitivity of microorganisms towards existing antimicrobials in order to combat the spread of AMR. A particular way of sensitizing microorganisms for certain antimicrobials is by interfering with their quorum sensing system.

Microorganisms such as bacteria use quorum sensing to coordinate certain behaviors such as biofilm formation, virulence, and antibiotic resistance, based on the local density of the bacterial population. Quorum sensing (QS) can occur within a single bacterial species as well as between diverse species, and can regulate different processes, in essence, serving as a simple indicator of population density or the diffusion rate of the cell's immediate environment. Several non-peptide small molecules, peptides and proteins have been shown to affect quorum sensing in bacteria and are suitable in the prevention and/or treatment of bacterial infections. For example hamamelitannin (HAM) or 2',5-di-O-galloyl-D-hamamelose, a natural compound found in the bark and leaves of *Hamamelis virginana* (witch hazel), was found to act as a quorum sensing inhibitor (QSI) (WO2007147098). HAM interferes with a quorum sensing system in bacteria. It was found that when combining HAM with an antibiotic, a potentiating or synergistic effect is observed, in particular HAM increases the susceptibility of bacterial biofilms to antibiotics in vitro as well as in vivo (Brackman et al., 2011).

It is important to emphasize that HAM may not be considered as a classical antibiotic drug, since it does not exert bactericidal nor bacteriostatic effects. HAM probably interferes with mechanisms that are responsible for the exceptional resistance in biofilms and thus can cause a potentiating or synergistic effect in combination with antibiotics.

The natural HAM product is metabolically unstable and only moderately active, and therefore less preferable in the treatment of microbial infections. Nevertheless, interesting results obtained with this molecule provide a conspicuous lead for further optimization, and present an opportunity for the development of a novel class of pharmaceutical compounds, capable of combating microbial infections. It was therefore an object of the present invention to provide novel non-carbohydrate, drug-like HAM analogues with an improved metabolic and chemical stability and increased activity. Furthermore, we have developed an efficient synthetic route to produce these novel compounds from easily available starting materials.

SUMMARY OF THE INVENTION

The invention includes a method of preventing or reducing the growth or proliferation of microorganisms or biofilm-embedded microorganisms, e.g. on a surface of a medical device or in or on subject's body.

In a first aspect, the present invention provides a compound of Formula I or a stereoisomer, tautomer, racemic, salt, hydrate, or solvate thereof, and optionally a metabolite, pre- or prodrug thereof,

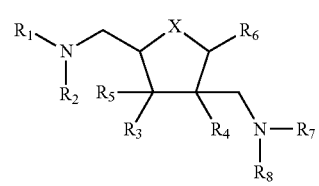

Wherein
X is selected from N—$R_9$, O and S—$R_9$;
$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;
$R_2$ is selected from —H and —$C_{1-6}$alkyl, or $R_1$ taken together with $R_2$ forms $Het_3$;
$R_3$ is absent or selected from —H, —OH, and -halo;
$R_4$ is selected from —H, —OH, and -halo;
or $R_3$ taken together with $R_4$ forms a dioxolane moiety, which is optionally substituted with from 1 to 3 substituents selected from —OH, —$C_{1-6}$alkyl, and -halo;
$R_5$ is selected from —H, —OH, =O, and -halo;
$R_6$ is selected from —H, —OH, -halo, —$C_{1-6}$alkyl, —O—$C_{1-6}$alkyl, —S—$C_{1-6}$alkyl, and —CN;
$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;
$R_8$ is selected from —H and —$C_{1-6}$alkyl;
or $R_7$ taken together with $R_8$ forms $Het_4$;
$R_9$ is
  selected from —H, —$C_{1-6}$alkyl, —(C=O)—$C_{1-6}$alkyl, —(C=O)—$Ar_3$ and —$Ar_3$ when X is N;
  absent when X is O; or
  absent or selected from =O, and —$O_2$ when X is S;
$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—C$_{1-6}$alkyl, —S—C$_{1-6}$alkyl, —CN, —NR$_{16}$R$_{17}$, —C$_{3-6}$cycloalkyl, -Het$_1$ and —Ar$_1$;

R$_{10}$, R$_{11}$ and R$_{12}$ are each independently selected from —C$_{1-6}$alkyl, —C$_{3-6}$cycloalkyl, —Ar$_2$, Het$_2$, —NH-Het$_2$ and —NH—Ar$_2$; wherein each of said —C$_{1-6}$alkyl is optionally substituted with from 1 to 3 substituents selected from =O, —OH, -halo, —O—C$_{1-6}$alkyl, —S—C$_{1-6}$alkyl, —CN, —NR$_{18}$R$_{19}$, —C$_{3-6}$cycloalkyl, -Het$_2$ and —Ar$_2$;

R$_{16}$, R$_{17}$, R$_{18}$, R$_{19}$, R$_{20}$, R$_{21}$, R$_{22}$ and R$_{23}$ are each independently selected from —H, and —C$_{1-6}$alkyl;

Ar$_1$, Ar$_2$, Ar$_3$, Ar$_4$ and Ar$_5$ are each independently a 5-10 membered aromatic mono- or bicycle; wherein each of said Ar$_1$, Ar$_2$, Ar$_3$, Ar$_4$ and Ar$_5$ is optionally and independently substituted with from 1 to 3 substituents selected from =O, —OH, -halo, —C$_{1-6}$alkyl, —O—C$_{1-6}$alkyl, —CF$_3$, —NR$_{20}$R$_{21}$, and -phenyl; wherein said phenyl is optionally substituted with from 1 to 3 substituents selected from =O, —OH, -halo, —C$_{1-6}$alkyl, —O—C$_{1-6}$alkyl, —O—C$_{1-6}$alkyl, —CN, —CF$_3$, or —NR$_{20}$R$_{21}$;

Het$_1$, Het$_2$, Het$_3$ and Het$_4$ are each independently a 5-10 membered mono- or bicyclic heteroaryl comprising from 1 to 3 heteroatoms selected from N, O and S; wherein each of said Het$_1$, Het$_2$, Het$_3$ and Het$_4$ is optionally and independently substituted with from 1 to 3 substituents selected from =O, —OH, -halo, —C$_{1-6}$alkyl, —O—C$_{1-6}$alkyl, —CN, —CF$_3$, —NR$_{22}$R$_{23}$, and -phenyl; wherein said phenyl is optionally substituted with from 1 to 3 substituents selected from =O, —OH, -halo, —C$_{1-6}$alkyl, —O—C$_{1-6}$alkyl, —CN, —CF$_3$, or —NR$_{22}$R$_{23}$.

In a particular embodiment, the present invention provides a compound according to formula I,
Wherein
X is selected from N—R$_9$, O and S—R$_9$;
R$_1$ is selected from —C$_{1-6}$alkyl, —Ar$_4$, —(C=O)—R$_{13}$, —(C=S)—R$_{14}$, and —SO$_2$—R$_{15}$; wherein said —C$_{1-6}$alkyl may be further substituted with —R$_{24}$;
R$_2$ is selected from —H and —C$_{1-6}$alkyl, or R$_1$ taken together with R$_2$ forms Het$_3$;
R$_3$ taken together with R$_4$ forms a dioxolane moiety, which is optionally substituted with from 1 to 3 substituents selected from —OH, —C$_{1-6}$alkyl, and -halo;
R$_5$ is selected from —H, —OH, =O, and -halo;
R$_6$ is selected from —H, —OH, -halo, —C$_{1-6}$alkyl, —O—C$_{1-6}$alkyl, —S—C$_{1-6}$alkyl, and —CN;
R$_7$ is selected from —C$_{1-6}$alkyl, —Ar$_5$, —(C=O)—R$_{10}$, —(C=S)—R$_{11}$, and —SO$_2$—R$_{12}$; wherein said —C$_{1-6}$alkyl may be further substituted with —R$_{25}$;
R$_8$ is selected from —H and —C$_{1-6}$alkyl;
or R$_7$ taken together with R$_8$ forms Het$_4$;
R$_9$ is
selected from —H, —C$_{1-6}$alkyl, —(C=O)—C$_{1-6}$alkyl, —(C=O)—Ar$_3$ and —Ar$_3$ when X is N;
absent when X is O; or
absent or selected from =O, and —O$_2$ when X is S;
R$_{13}$, R$_{14}$, R$_{15}$, R$_{24}$, and R$_{25}$ are each independently selected from —C$_{1-6}$alkyl, —C$_{3-6}$cycloalkyl, —Ar$_1$, Het$_1$, —NH—C$_{1-6}$alkyl, —NH-Het$_1$ and —NH—Ar$_1$; wherein each of said —C$_{1-6}$alkyl is optionally and independently substituted with from 1 to 3 substituents selected from =O, —OH, -halo, —O—C$_{1-6}$alkyl, —S—C$_{1-6}$alkyl, —CN, —NR$_{16}$R$_{17}$, —C$_{3-6}$cycloalkyl, -Het$_1$ and —Ar$_1$;
R$_{10}$, R$_{11}$ and R$_{12}$ are each independently selected from —C$_{1-6}$alkyl, —C$_{3-6}$cycloalkyl, —Ar$_2$, Het$_2$, —NH-Het$_2$ and —NH—Ar$_2$; wherein each of said —C$_{1-6}$alkyl is optionally substituted with from 1 to 3 substituents selected from =O, —OH, -halo, —O—C$_{1-6}$alkyl, —S—C$_{1-6}$alkyl, —CN, —NR$_{18}$R$_{19}$, —C$_{3-6}$cycloalkyl, -Het$_2$ and —Ar$_2$;
R$_{16}$, R$_{17}$, R$_{18}$, R$_{19}$, R$_{20}$, R$_{21}$, R$_{22}$ and R$_{23}$ are each independently selected from —H, and —C$_{1-6}$alkyl;
Ar$_1$, Ar$_2$, Ar$_3$, Ar$_4$ and Ar$_5$ are each independently a 5-10 membered aromatic mono- or bicycle; wherein each of said Ar$_1$, Ar$_2$, Ar$_3$, Ar$_4$ and Ar$_5$ is optionally and independently substituted with from 1 to 3 substituents selected from =O, —OH, -halo, —C$_{1-6}$alkyl, —O—C$_{1-6}$alkyl, —CF$_3$, —NR$_{20}$R$_{21}$, and -phenyl; wherein said phenyl is optionally substituted with from 1 to 3 substituents selected from =O, —OH, -halo, —C$_{1-6}$alkyl, —O—C$_{1-6}$alkyl, —CN, —CF$_3$, or —NR$_{20}$R$_{21}$;
Het$_1$, Het$_2$, Het$_3$ and Het$_4$ are each independently a 5-10 membered mono- or bicyclic heteroaryl comprising from 1 to 3 heteroatoms selected from N, O and S; wherein each of said Het$_1$, Het$_2$, Het$_3$ and Het$_4$ is optionally and independently substituted with from 1 to 3 substituents selected from =O, —OH, -halo, —C$_{1-6}$alkyl, —O—C$_{1-6}$alkyl, —CN, —CF$_3$, —NR$_{22}$R$_{23}$, and -phenyl; wherein said phenyl is optionally substituted with from 1 to 3 substituents selected from =O, —OH, -halo, —C$_{1-6}$alkyl, —O—C$_{1-6}$alkyl, —CN, —CF$_3$, or —NR$_{22}$R$_{23}$.

In yet a further particular embodiment, the present invention provides a compound according to formula I,
Wherein
X is selected from N—R$_9$, O and S—R$_9$;
R$_1$ is selected from —C$_{1-6}$alkyl, —Ar$_4$, —(C=O)—R$_{13}$, —(C=S)—R$_{14}$, and —SO$_2$—R$_{15}$; wherein said —C$_{1-6}$alkyl may be further substituted with —R$_{24}$;
R$_2$ is selected from —H and —C$_{1-6}$alkyl, or R$_1$ taken together with R$_2$ forms Het$_3$;
R$_3$ is —OH;
R$_4$ is —OH;
R$_5$ is selected from —H, —OH, =O, and -halo;
R$_6$ is selected from —H, —OH, -halo, —C$_{1-6}$alkyl, —O—C$_{1-6}$alkyl, —S—C$_{1-6}$alkyl, and —CN;
R$_7$ is selected from —C$_{1-6}$alkyl, —Ar$_5$, —(C=O)—R$_{10}$, —(C=S)—R$_{11}$, and —SO$_2$—R$_{12}$; wherein said —C$_{1-6}$alkyl may be further substituted with —R$_{25}$;
R$_8$ is selected from —H and —C$_{1-6}$alkyl;
or R$_7$ taken together with R$_8$ forms Het$_4$;
R$_9$ is
selected from —H, —C$_{1-6}$alkyl, —(C=O)—C$_{1-6}$alkyl, —(C=O)—Ar$_3$ and —Ar$_3$ when X is N;
absent when X is O; or
absent or selected from =O, and —O$_2$ when X is S;
R$_{13}$, R$_{14}$, R$_{15}$, R$_{24}$, and R$_{25}$ are each independently selected from —C$_{1-6}$alkyl, —C$_{3-6}$cycloalkyl, —Ar$_1$, Het$_1$, —NH—C$_{1-6}$alkyl, —NH-Het$_1$ and —NH—Ar$_1$; wherein each of said —C$_{1-6}$alkyl is optionally and independently substituted with from 1 to 3 substituents selected from =O, —OH, -halo, —O—C$_{1-6}$alkyl, —S—C$_{1-6}$alkyl, —CN, —NR$_{16}$R$_{17}$, —C$_{3-6}$cycloalkyl, -Het$_1$ and —Ar$_1$;
R$_{10}$, R$_{11}$ and R$_{12}$ are each independently selected from —C$_{1-6}$alkyl, —C$_{3-6}$cycloalkyl, —Ar$_2$, Het$_2$, —NH-Het$_2$ and —NH—Ar$_2$; wherein each of said —C$_{1-6}$alkyl is optionally substituted with from 1 to 3 substituents selected from =O, —OH, -halo, —O—C$_{1-6}$alkyl, —S—C$_{1-6}$alkyl, —CN, —NR$_{18}$R$_{13}$, —C$_{3-6}$cycloalkyl, -Het$_2$ and —Ar$_2$;
R$_{16}$, R$_{17}$, R$_{18}$, R$_{19}$, R$_{20}$, R$_{21}$, R$_{22}$ and R$_{23}$ are each independently selected from —H, and —C$_{1-6}$alkyl;
Ar$_1$, Ar$_2$, Ar$_3$, Ar$_4$ and Ar$_5$ are each independently a 5-10 membered aromatic mono- or bicycle; wherein each of said Ar$_1$, Ar$_2$, Ar$_3$, Ar$_4$ and Ar$_5$ is optionally and independently substituted with from 1 to 3 substituents selected from =O, —OH, -halo, —C$_{1-6}$alkyl, —O—C$_{1-6}$alkyl, —CN, —CF$_3$, —NR$_{20}$R$_{21}$, and -phenyl; wherein said phenyl is optionally substituted with from 1 to 3 substituents selected from =O, —OH, -halo, —C$_{1-6}$alkyl, —O—C$_{1-6}$alkyl, —CN, —CF$_3$, or —NR$_{20}$R$_{21}$;

Het$_1$, Het$_2$, Het$_3$ and Het$_4$ are each independently a 5-10 membered mono- or bicyclic heteroaryl comprising from 1 to 3 heteroatoms selected from N, O and S; wherein each of said Het$_1$, Het$_2$, Het$_3$ and Het$_4$ is optionally and independently substituted with from 1 to 3 substituents selected from =O, —OH, -halo, —C$_{1-6}$alkyl, —O—C$_{1-6}$alkyl, —CN, —CF$_3$, —NR$_{22}$R$_{23}$, and -phenyl; wherein said phenyl is optionally substituted with from 1 to 3 substituents selected from =O, —OH, -halo, —C$_{1-6}$alkyl, —O—C$_{1-6}$alkyl, —CN, —CF$_3$, or —NR$_{22}$R$_{23}$.

In a further embodiment, the present invention provides a compound according to formula I,
Wherein
X is selected from N—R$_9$, O and S—R$_9$;
R$_1$ is selected from —C$_{1-6}$alkyl, —Ar$_4$, —(C=O)—R$_{13}$, —(C=S)—R$_{14}$, and —SO$_2$—R$_{15}$; wherein said —C$_{1-6}$alkyl may be further substituted with —R$_{24}$;
R$_2$ is selected from —H and —C$_{1-6}$alkyl, or R$_1$ taken together with R$_2$ forms Het$_3$;
R$_3$ is absent or selected from —H, —OH, and -halo;
R$_4$ is selected from —H, —OH, and -halo;
or R$_3$ taken together with R$_4$ forms a dioxolane moiety, which is optionally substituted with from 1 to 3 substituents selected from —OH, —C$_{1-6}$alkyl, and -halo;
R$_5$ is selected from —H, —OH, =O, and -halo;
R$_6$ is —H;
R$_7$ is selected from —C$_{1-6}$alkyl, —Ar$_5$, —(C=O)—R$_{10}$, —(C=S)—R$_{11}$, and —SO$_2$—R$_{12}$; wherein said —C$_{1-6}$alkyl may be further substituted with —R$_{25}$;
R$_8$ is selected from —H and —C$_{1-6}$alkyl or R$_7$ taken together with R$_8$ forms Het$_4$;
R$_9$ is
  selected from —H, —C$_{1-6}$alkyl, —(C=O)—C$_{1-6}$alkyl, —(C=O)—Ar$_3$ and —Ar$_3$ when X is N;
  absent when X is O; or
  absent or selected from =O, and —O$_2$ when X is S;
R$_{13}$, R$_{14}$, R$_{15}$, R$_{24}$, and R$_{25}$ are each independently selected from —C$_{1-6}$alkyl, —C$_{3-6}$cycloalkyl, —Ar$_1$, Het$_1$, —NH—C$_{1-6}$alkyl, —NH-Het$_1$ and —NH—Ar$_1$; wherein each of said —C$_{1-6}$alkyl is optionally and independently substituted with from 1 to 3 substituents selected from =O, —OH, -halo, —O—C$_{1-6}$alkyl, —S—C$_{1-6}$alkyl, —CN, —NR$_{16}$R$_{17}$, —C$_{3-6}$cycloalkyl, -Het$_1$ and —Ar$_1$;
R$_{10}$, R$_{11}$ and R$_{12}$ are each independently selected from —C$_{1-6}$alkyl, —C$_{3-6}$cycloalkyl, —Ar$_2$, Het$_2$, —NH-Het$_2$ and —NH—Ar$_2$; wherein each of said —C$_{1-6}$alkyl is optionally substituted with from 1 to 3 substituents selected from =O, —OH, -halo, —O—C$_{1-6}$alkyl, —S—C$_{1-6}$alkyl, —CN, —NR$_{18}$R$_{19}$, —C$_{3-6}$cycloalkyl, -Het$_2$ and —Ar$_2$;
R$_{16}$, R$_{17}$, R$_{18}$, R$_{19}$, R$_{20}$, R$_{21}$, R$_{22}$ and R$_{23}$ are each independently selected from —H, and —C$_{1-6}$alkyl;
Ar$_1$, Ar$_2$, Ar$_3$, Ar$_4$ and Ar$_5$ are each independently a 5-10 membered aromatic mono- or bicycle; wherein each of said Ar$_1$, Ar$_2$, Ar$_3$, Ar$_4$ and Ar$_5$ is optionally and independently substituted with from 1 to 3 substituents selected from =O, —OH, -halo, —C$_{1-6}$alkyl, —O—C$_{1-6}$alkyl, —CN, —CF$_3$, —NR$_{20}$R$_{21}$, and -phenyl; wherein said phenyl is optionally substituted with from 1 to 3 substituents selected from =O, —OH, -halo, —C$_{1-6}$alkyl, —O—C$_{1-6}$alkyl, —CN, —CF$_3$, or —NR$_{20}$R$_{21}$;

Het$_1$, Het$_2$, Het$_3$ and Het$_4$ are each independently a 5-10 membered mono- or bicyclic heteroaryl comprising from 1 to 3 heteroatoms selected from N, O and S; wherein each of said Het$_1$, Het$_2$, Het$_3$ and Het$_4$ is optionally and independently substituted with from 1 to 3 substituents selected from =O, —OH, -halo, —C$_{1-6}$alkyl, —O—C$_{1-6}$alkyl, —CN, —CF$_3$, —NR$_{22}$R$_{23}$, and -phenyl; wherein said phenyl is optionally substituted with from 1 to 3 substituents selected from =O, —OH, -halo, —C$_{1-6}$alkyl, —O—C$_{1-6}$alkyl, —CN, —CF$_3$, or —NR$_{22}$R$_{23}$.

In another particular embodiment, the present invention provides a compound of formula I,
Wherein
X is O;
R$_1$ is selected from —C$_{1-6}$alkyl, —Ar$_4$, —(C=O)—R$_{13}$, —(C=S)—R$_{14}$, and —SO$_2$—R$_{15}$; wherein said —C$_{1-6}$alkyl may be further substituted with —R$_{24}$;
R$_2$ is selected from —H and —C$_{1-6}$alkyl, or R$_1$ taken together with R$_2$ forms Het$_3$;
R$_3$ is
  absent or selected from —H, —OH, and -halo;
  or R$_3$ taken together with R$_4$ forms a dioxolane moiety, which is optionally substituted with from 1 to 3 substituents selected from —OH, —C$_{1-6}$alkyl, and -halo;
R$_4$ is selected from —H, —OH, and -halo;
R$_5$ is selected from —H, —OH, =O, and -halo;
R$_6$ is selected from —H, —OH, -halo, —C$_{1-6}$alkyl, —O—C$_{1-6}$alkyl, —S—C$_{1-6}$alkyl, and —CN;
R$_7$ is selected from —C$_{1-6}$alkyl, —Ar$_5$, —(C=O)—R$_{10}$, —(C=S)—R$_{11}$, and —SO$_2$—R$_{12}$; wherein said —C$_{1-6}$alkyl may be further substituted with —R$_{25}$;
R$_8$ is selected from —H and —C$_{1-6}$alkyl or R$_7$ taken together with R$_8$ forms Het$_4$;
R$_9$ is absent;
R$_{13}$, R$_{14}$, R$_{15}$, R$_{24}$, and R$_{25}$ are each independently selected from —C$_{1-6}$alkyl, —C$_{3-6}$cycloalkyl, —Ar$_1$, Het$_1$, —NH—C$_{1-6}$alkyl, —NH-Het$_1$ and —NH—Ar$_1$; wherein each of said —C$_{1-6}$alkyl is optionally and independently substituted with from 1 to 3 substituents selected from =O, —OH, -halo, —O—C$_{1-6}$alkyl, —S—C$_{1-6}$alkyl, —CN, —NR$_{16}$R$_{17}$, —C$_{3-6}$cycloalkyl, -Het$_1$ and —Ar$_1$;
R$_{10}$, R$_{11}$ and R$_{12}$ are each independently selected from —C$_{1-6}$alkyl, —C$_{3-6}$cycloalkyl, —Ar$_2$, Het$_2$, —NH-Het$_2$ and —NH—Ar$_2$; wherein each of said —C$_{1-6}$alkyl is optionally substituted with from 1 to 3 substituents selected from =O, —OH, -halo, —O—C$_{1-6}$alkyl, —S—C$_{1-6}$alkyl, —CN, —NR$_{18}$R$_{19}$, —C$_{3-6}$cycloalkyl, -Het$_2$ and —Ar$_2$;
R$_{16}$, R$_{17}$, R$_{18}$, R$_{19}$, R$_{20}$, R$_{21}$, R$_{22}$ and R$_{23}$ are each independently selected from —H, and —C$_{1-6}$alkyl;
Ar$_1$, Ar$_2$, Ar$_3$, Ar$_4$ and Ar$_5$ are each independently a 5-10 membered aromatic mono- or bicycle; wherein each of said Ar$_1$, Ar$_2$, Ar$_3$, Ar$_4$ and Ar$_5$ is optionally and independently substituted with from 1 to 3 substituents selected from =O, —OH, -halo, —C$_{1-6}$alkyl, —O—C$_{1-6}$alkyl, —CF$_3$, —NR$_{20}$R$_{21}$, and -phenyl; wherein said phenyl is optionally substituted with from 1 to 3 substituents selected from =O, —OH, -halo, —C$_{1-6}$alkyl, —O—C$_{1-6}$alkyl, —CF$_3$, or —NR$_{20}$R$_{21}$;

Het$_1$, Het$_2$, Het$_3$ and Het$_4$ are each independently a 5-10 membered mono- or bicyclic heteroaryl comprising from 1 to 3 heteroatoms selected from N, O and S; wherein each of said Het$_1$, Het$_2$, Het$_3$ and Het$_4$ is optionally and independently substituted with from 1 to 3 substituents selected from =O, —OH, -halo, —$C_{1-6}$alkyl, —O—$C_{1-6}$alkyl, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —$CF_3$, or —$NR_{22}R_{23}$.

In another particular embodiment, the present invention provides a compound of formula I,
Wherein
X is O;
$R_1$ is selected from —$C_{1-6}$alkyl, —(C=O)—$R_{13}$, —(C=S)—$R_{14}$, and —$SO_2$—$R_{15}$; wherein said —$C_{1-6}$alkyl may be further substituted with —$R_{24}$;
$R_2$ is —H; or $R_1$ taken together with $R_2$ forms $Het_3$;
$R_3$ is
  selected from —H, and —OH;
  or $R_3$ taken together with $R_4$ forms a dioxolane moiety, which is optionally substituted with from 1 to 3 —$C_{1-6}$alkyl substituents;
$R_4$ is —OH;
$R_5$ is —H;
$R_6$ is selected from —H, and —OH;
$R_7$ is selected from —$C_{1-6}$alkyl, and —(C=O)—$R_{10}$; wherein said —$C_{1-6}$alkyl may be further substituted with —$R_{25}$;
$R_8$ is —H; or $R_7$ taken together with $R_8$ forms $Het_4$;
$R_9$ is absent;
$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, and —NH—$Ar_1$; wherein each of said —$C_{1-6}$alkyl is optionally and independently substituted with from 1 to 3 substituents selected from -halo and —$Ar_1$; in particular with 1 to 3 $Ar_1$ substituents;
$R_{10}$, is independently selected from —$C_{1-6}$alkyl, —$Ar_2$, and $Het_2$; wherein each of said —$C_{1-6}$alkyl is optionally substituted with from 1 to 3 substituents selected -halo and —$Ar_2$; in particular with 1 to 3 $Ar_2$ substituents;
$R_{20}$, and $R_{21}$, are each independently selected from —H, and —$C_{1-6}$alkyl;
$Ar_1$, and $Ar_2$, are each independently a 5-10 membered aromatic mono- or bicycle; wherein each of said $Ar_1$, and $Ar_2$, is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl;
$Het_1$, $Het_2$, $Het_3$ and $Het_4$ are each independently a 5-10 membered mono- or bicyclic heteroaryl comprising from 1 to 3 heteroatoms selected from N, O and S, in particular N; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, and phenyl.

In another particular embodiment, the present invention provides a compound of formula I,
Wherein
X is O;
$R_1$ is selected from —$C_{1-6}$alkyl, —(C=O)—$R_{13}$, and —$SO_2$—$R_{15}$; wherein said —$C_{1-6}$alkyl may be further substituted with —$R_{24}$;
$R_2$ is —H; or $R_1$ taken together with $R_2$ forms $Het_3$;
$R_3$ and $R_4$ are —OH; or $R_3$ taken together with $R_4$ forms a dioxolane moiety, which is optionally substituted with from 1 to 3 —$C_{1-6}$alkyl substituents;
$R_5$ is —H;
$R_6$ is selected from —H, and —OH;
$R_7$ is selected from —$C_{1-6}$alkyl, and —(C=O)—$R_{10}$; wherein said —$C_{1-6}$alkyl may be further substituted with —$R_{25}$;
$R_8$ is —H; or $R_7$ taken together with $R_8$ forms $Het_4$;
$R_9$ is absent;
$R_{13}$, $R_{15}$, $R_{24}$, and $R_{25}$ are each independently selected from —$C_{1-6}$alkyl, —$C_{3-6}$cycloalkyl, —$Ar_1$, $Het_1$, and —NH—$Ar_1$; wherein each of said —$C_{1-6}$alkyl is optionally and independently substituted with from 1 to 3 substituents selected from -halo and —$Ar_1$; in particular with 1 to 3 $Ar_1$ substituents;
$R_{10}$, is independently selected from —$Ar_2$, and $Het_2$;
$R_{20}$, and $R_{21}$, are each independently selected from —H, and —$C_{1-6}$alkyl; in particular —$C_{1-6}$alkyl;
$Ar_1$, and $Ar_2$, are each independently a 5-10 membered aromatic mono- or bicycle; wherein each of said $Ar_1$, and $Ar_2$, is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl;
$Het_1$, $Het_2$, and $Het_3$ are each independently a 5-10 membered mono- or bicyclic heteroaryl comprising from 1 to 3 heteroatoms selected from N, O and S, in particular N; wherein each of said $Het_1$, $Het_2$, and $Het_3$ is optionally and independently substituted with from 1 to 3 substituents selected from =O, —OH, -halo, and -phenyl.

In a specific embodiment, the invention encompasses a compound as defined herein, such as any and all compounds represented by formulas I or II or in Table 1, or stereoisomer, tautomer, racemic, salt, metabolite, pre- or prodrug, hydrate, or solvate thereof, and more specific a stereoisomer, tautomer, racemic, salt, hydrate, or solvate thereof.

In a specific aspect, the present invention provides a compound as defined herein, with its 'X' and 'R' definitions as defined above, wherein the compound has the stereoisomeric configuration as represented in formula II:

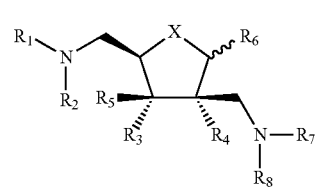

The present invention also provides a pharmaceutical composition comprising a compound according to the present invention and a pharmaceutically acceptable excipient, diluent and/or carrier.

In a further aspect, the present invention provides a combination of a compound according to the present invention with an antimicrobial agent, in particular an antibiotic or disinfectant.

In a specific aspect, the present invention provides a compound, composition or combination according to the present invention, for use as a medicament, more in particular, for use in the prevention and/or treatment of bacterial infections in humans or animals. In a particular embodiment, said bacterial infection is a *Staphylococcus aureus* infection.

In a further aspect, the present invention provides a method for the prevention and/or treatment of bacterial infections; said method comprising administering to a subject in need thereof a therapeutic effective amount of a compound, a composition or a combination as according to the present invention.

BRIEF DESCRIPTION OF THE DRAWINGS

With specific reference to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings makes it apparent to those skilled in the art how the several forms of the invention may be embodied in practice.

DETAILED DESCRIPTION OF THE INVENTION

Figure 1:
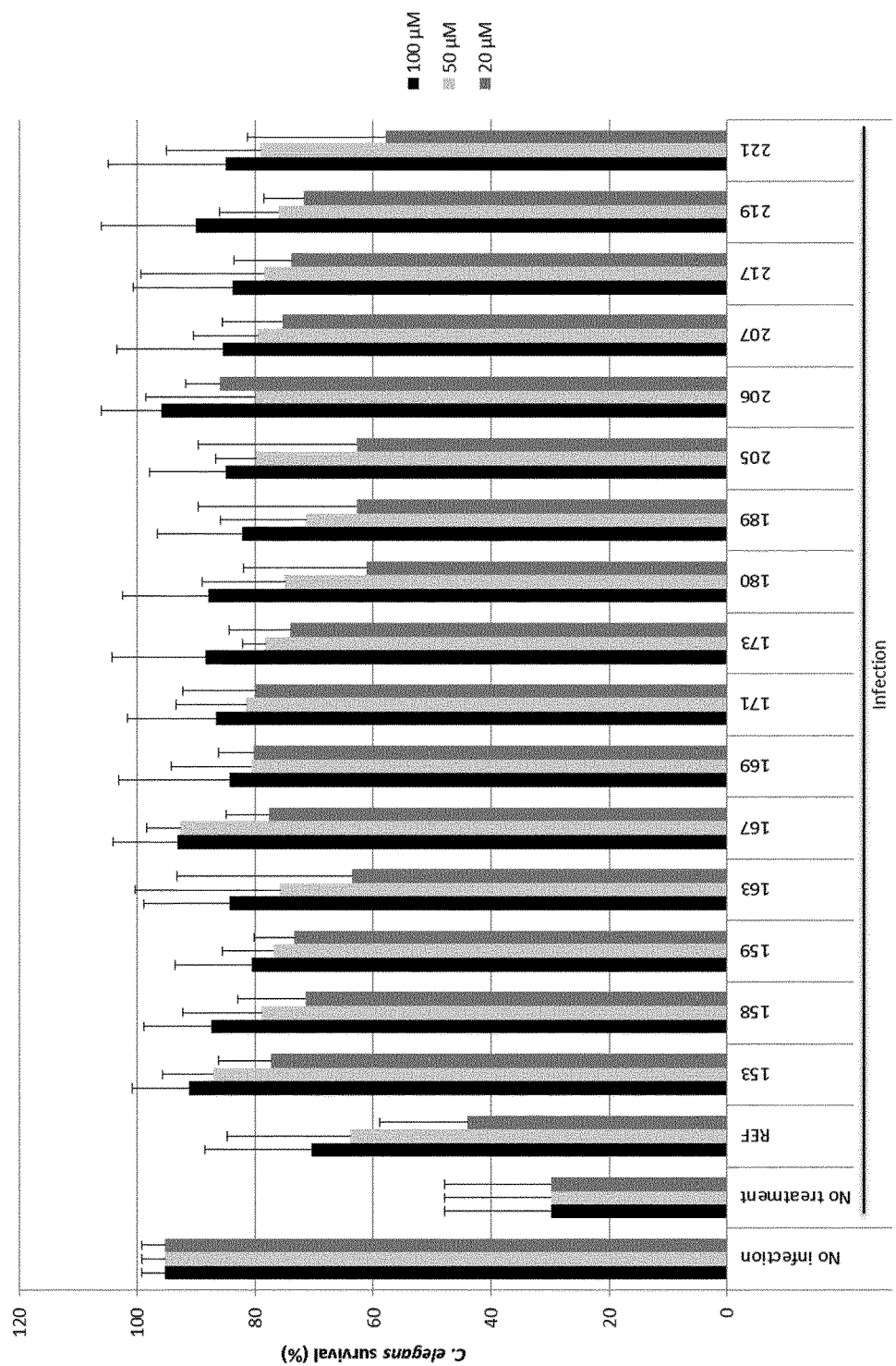
FIG. 1: Survival of infected *C. elegans* nematodes receiving no treatment or a treatment with one of the compounds (100 μM, 50 μM or 20 μM). Survival was scored 48 h p.i.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides compounds of Formula I,

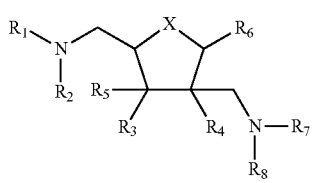

I

Wherein
X is selected from N—$R_9$, O and S;
$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;
$R_2$ is selected from —H and —$C_{1-6}$alkyl, or $R_1$ taken together with $R_2$ forms $Het_3$;
$R_3$ is absent or selected from —H, —OH, and -halo;
$R_4$ is selected from —H, —OH, and -halo;
or $R_3$ taken together with $R_4$ forms a dioxolane moiety, which is optionally substituted with from 1 to 3 substituents selected from —OH, —$C_{1-6}$alkyl, and -halo;
$R_5$ is selected from —H, —OH, =O, and -halo;
$R_6$ is selected from —H, —OH, -halo, —$C_{1-6}$alkyl, —O—$C_{1-6}$alkyl, —S—$C_{1-6}$alkyl, and —CN;
$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;
$R_8$ is selected from —H and —$C_{1-6}$alkyl;
or $R_7$ taken together with $R_8$ forms $Het_4$;
$R_9$ is
  selected from —H, —$C_{1-6}$alkyl, —(C=O)—$C_{1-6}$alkyl, —(C=O)—$Ar_3$ and —$Ar_3$ when X is N;
  absent when X is O; or
  selected from =O, and —$O_2$ when X is S;
$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;
$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{19}$, —$C_{3-6}$cycloalkyl, -$Het_2$ and —$Ar_2$;
$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;
$Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{20}R_{21}$;
$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{22}R_{23}$.

In a particular embodiment, the invention relates to a stereoisomer, tautomer, racemic, metabolite, pro- or predrug, salt, hydrate, or solvate of the compounds provided herein, and especially any and each of the compounds represented by Formula I or II and provided in Table 1. More specific, the invention also encompasses a stereoisomer, tautomer, racemic, salt, hydrate, or solvate of said compounds.

When describing the compounds of the invention, the terms used are to be construed in accordance with the following definitions, unless a context dictates otherwise.

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include halo, hydroxyl, carbonyl, nitro, amino, oxime, imino, azido, hydrazino, cyano, aryl, heteroaryl, cycloalkyl, acyl, alkylamino, alkoxy, thiol, alkylthio, carboxylic acid, acylamino, alkyl esters, carbamate, thioamido, urea, sulfonamido and the like.

The term "cycloalkyl" by itself or as part of another substituent is a cyclic alkyl group, that is to say, a monovalent, saturated, or unsaturated hydrocarbyl group having 1, 2, or 3 cyclic structures. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl and cyclodecyl with cyclopropyl being particularly preferred. An "optionally substituted cycloalkyl" refers to a cycloalkyl having optionally one or more substituents (for example 1 to 3 substituents, for example 1, 2, 3 or 4 substituents), selected from those defined above for substituted alkyl. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a $C_3$ alkylene group may be for example *—$CH_2CH_2CH_2$—*, *—$CH(—CH_2CH_3)$—*, or *—$CH_2CH(—CH_3)$—*. Likewise a $C_3$ cycloalkylene group may be

The terms "heterocyclyl" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclic refers to a heterocyclic having optionally one or more substituents (for example 1 to 4 substituents, or for example 1, 2, 3 or 4), selected from those defined above for substituted aryl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —$SO_2$—$NH_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —$SO_2R^a$, alkylthio, carboxyl, and the like, wherein $R^a$ is alkyl or cycloalkyl.

Where a carbon atom in an aryl group is replaced with a heteroatom, the resultant ring is referred to herein as a heteroaryl ring. The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1 (6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl. Within the context of the instant application the heteroaryls are in particular selected from furanyl, pyrazolyl, imidazolyl, triazolyl, pyridinyl, pyrimidinyl, pyrazinyl, pyridazinyl, indolyl, and isoindolyl.

An "optionally substituted heteroaryl" refers to a heteroaryl having optionally one or more substituents (for example 1 to 4 substituents, for example 1, 2, 3 or 4), selected from those defined above for substituted aryl, such as for example 1,3-dioxoindolyl.

The term "oxo" as used herein refers to the group =O.

The term "alkoxy" or "alkyloxy" as used herein refers to a radical having the Formula —$OR^b$ wherein $R^b$ is alkyl. Preferably, alkoxy is $C_1$-$C_{10}$ alkoxy, $C_1$-$C_6$ alkoxy, or $C_1$-$C_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy; trichloromethoxy, 2-bromoethoxy, pentafluoroethyl, 3,3,3-trichloropropoxy, 4,4,4-trichlorobutoxy.

The term "aryloxy" as used herein denotes a group —O-aryl, wherein aryl is as defined above.

The term "arylcarbonyl" or "aroyl" as used herein denotes a group —C(O)-aryl, wherein aryl is as defined above.

The term "carboxy" or "carboxyl" or "hydroxycarbonyl" by itself or as part of another substituent refers to the group —$CO_2H$. Thus, a carboxyalkyl is an alkyl group as defined above having at least one substituent that is —$CO_2H$.

The term "alkoxycarbonyl" by itself or as part of another substituent refers to a carboxy group linked to an alkyl radical i.e. to form —C(=O)$OR^e$, wherein $R^e$ is as defined above for alkyl.

The term "alkylcarbonyloxy" by itself or as part of another substituent refers to a —O—C(=O)$R^e$ wherein $R^e$ is as defined above for alkyl.

The term "alkylcarbonylamino" by itself or as part of another substituent refers to an group of Formula —NH(C=O)R or —NR'(C=O)R, wherein R and R' are each independently alkyl or substituted alkyl.

The term "thiocarbonyl" by itself or as part of another substituent refers to the group —C(=S)—.

The term "alkoxy" by itself or as part of another substituent refers to a group consisting of an oxygen atom attached to one optionally substituted straight or branched alkyl group, cycloalkyl group, aralkyl, or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy, and the like.

The term "halo" or "halogen" as a group or part of a group is generic for fluoro, chloro, bromo, or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "haloaryl" alone or in combination, refers to an aryl radical having the meaning as defined above wherein one or more hydrogens are replaced with a halogen as defined above. The term "haloalkoxy" alone or in combination refers to a halo-O-alkyl group wherein the alkyl group is substituted by 1, 2, or 3 halogen atoms. For example, "haloalkoxy" includes —$OCF_3$, —$OCHF_2$, —$OCH_2F$, —O—$CF_2$—$CF_3$, —O—$CH_2$—$CF_3$, —O—$CH_2$—$CHF_2$, and —O—$CH_2$—$CH_2F$.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

Where groups may be optionally substituted, such groups may be substituted once or more, and preferably once, twice or thrice. Substituents may be selected from, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I or II, and any subgroup thereof. This term also refers to the compounds as depicted in Table 1, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a further embodiment, the present invention provides compounds of formula I or a stereoisomer, tautomer, racemic, metabolite, pro- or predrug, salt, hydrate, or solvate thereof,
Wherein
X is selected from N—$R_9$, O and S;
$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;
$R_2$ is selected from —H and —$C_{1-6}$alkyl, or $R_1$ taken together with $R_2$ forms $Het_3$;
$R_3$ taken together with $R_4$ forms a dioxolane moiety, which is optionally substituted with from 1 to 3 substituents selected from —OH, —$C_{1-6}$alkyl, and -halo;
$R_5$ is selected from —H, —OH, =O, and -halo;
$R_6$ is selected from —H, —OH, -halo, —$C_{1-6}$alkyl, —O—$C_{1-6}$alkyl, —S—$C_{1-6}$alkyl, and —CN;
$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;
$R_8$ is selected from —H and —$C_{1-6}$alkyl;
or $R_7$ taken together with $R_8$ forms $Het_4$;
$R_9$ is
selected from —H, —$C_{1-6}$alkyl, —(C=O)—$C_{1-6}$alkyl, —(C=O)—$Ar_3$ and —$Ar_3$ when X is N;
absent when X is O; or
selected from =O, and —$O_2$ when X is S;
$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;
$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{19}$, —$C_{3-6}$cycloalkyl, -$Het_2$ and —$Ar_2$;
$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;
$Ar_1$, $Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{20}R_{21}$;
$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{22}R_{23}$.

In a further embodiment, the present invention provides compounds of formula I,
Wherein
X is O;
$R_1$ is selected from —$C_{1-6}$alkyl, —(C=O)—$R_{13}$, —(C=S)—$R_{14}$, and —$SO_2$—$R_{15}$; wherein said —$C_{1-6}$alkyl may be further substituted with —$R_{24}$;
$R_2$ is —H; or $R_1$ taken together with $R_2$ forms $Het_3$;
$R_3$ taken together with $R_4$ forms a dioxolane moiety, which is optionally substituted with from 1 to 3 —$C_{1-6}$alkyl substituents;
$R_5$ represents —H;
$R_6$ is selected from —H, —OH, and —O—$C_{1-6}$alkyl;
$R_7$ is selected from —$C_{1-6}$alkyl, and —(C=O)—$R_{10}$; wherein said —$C_{1-6}$alkyl may be further substituted with —$R_{25}$;
$R_8$ represents —H; or $R_7$ taken together with $R_8$ forms $Het_4$;
$R_9$ is absent;
$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, and —NH—$Ar_1$; wherein each of said —$C_{1-6}$alkyl is optionally and independently substituted with from 1 to 3 substituents selected from -halo, and —$Ar_1$;

$R_{10}$, is independently selected from —$C_{1-6}$alkyl, —$Ar_2$, and $Het_2$; wherein each of said —$C_{1-6}$alkyl is optionally substituted with from 1 to 3 —$Ar_2$ substituents;

$R_{20}$, and $R_{21}$, are each independently selected from —H, and —$C_{1-6}$alkyl;

$Ar_1$, and $Ar_2$, each independently a 5-10 membered aromatic mono- or bicycle; wherein each of said $Ar_1$, and $Ar_2$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, and -phenyl.

In yet a further particular embodiment, the present invention provides a compound according to formula I, Wherein X is selected from N—$R_9$, O and S;

$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;

$R_2$ is selected from —H and —$C_{1-6}$alkyl, or $R_1$ taken together with $R_2$ forms $Het_3$;

$R_3$ is —OH;

$R_4$ is —OH;

$R_5$ is selected from —H, —OH, =O, and -halo;

$R_6$ is selected from —H, —OH, -halo, —$C_{1-6}$alkyl, —O—$C_{1-6}$alkyl, —S—$C_{1-6}$alkyl, and —CN;

$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;

$R_8$ is selected from —H and —$C_{1-6}$alkyl;

or $R_7$ taken together with $R_8$ forms $Het_4$;

$R_9$ is
selected from —H, —$C_{1-6}$alkyl, —(C=O)—$C_{1-6}$alkyl, —(C=O)—$Ar_3$ and —$Ar_3$ when X is N;
absent when X is O; or
selected from =O, and —$O_2$ when X is S;

$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;

$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{19}$, —$C_{3-6}$cycloalkyl, -$Het_2$ and —$Ar_2$;

$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;

$Ar_1$, $Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{20}R_{21}$;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{22}R_{23}$.

In a further embodiment, the present invention provides compounds of formula I,

Wherein

X is O;

$R_1$ is selected from —$C_{1-6}$alkyl, —(C=O)—$R_{13}$, —(C=S)—$R_{14}$, and —$SO_2$—$R_{15}$; wherein said —$C_{1-6}$alkyl may be further substituted with —$R_{24}$;

$R_2$ is —H; or $R_1$ taken together with $R_2$ forms $Het_3$;

$R_3$ and $R_4$ are —OH;

$R_5$ represents —H;

$R_6$ is selected from —H, —OH, and —O—$C_{1-6}$alkyl;

$R_7$ is selected from —$C_{1-6}$alkyl, and —(C=O)—$R_{10}$; wherein said —$C_{1-6}$alkyl may be further substituted with —$R_{25}$; in particular $R_7$ represents —(C=O)—$R_{10}$;

$R_8$ represents —H; or $R_7$ taken together with $R_8$ forms $Het_4$;

$R_9$ is absent;

$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, and —NH—$Ar_1$; wherein each of said —$C_{1-6}$alkyl is optionally and independently substituted with from 1 to 3 substituents selected from -halo, and —$Ar_1$;

$R_{10}$, is independently selected from —$C_{1-6}$alkyl, —$Ar_2$, and $Het_2$; wherein each of said —$C_{1-6}$alkyl is optionally substituted with from 1 to 3 —$Ar_2$ substituents;

$R_{20}$, and $R_{21}$, are each independently selected from —H, and —$C_{1-6}$alkyl;

$Ar_1$, and $Ar_2$, each independently a 5-10 membered aromatic mono- or bicycle; wherein each of said $Ar_1$, and $Ar_2$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, and -phenyl.

In a further embodiment, the present invention provides a compound according to formula I, Wherein X is selected from N—$R_9$, O and S;

$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;

$R_2$ is selected from —H and —$C_{1-6}$alkyl, or $R_1$ taken together with $R_2$ forms $Het_3$;

$R_3$ is absent or selected from —H, —OH, and -halo;

$R_4$ is selected from —H, —OH, and -halo;

or $R_3$ taken together with $R_4$ forms a dioxolane moiety, which is optionally substituted with from 1 to 3 substituents selected from —OH, —$C_{1-6}$alkyl, and -halo;

$R_5$ is selected from —H, —OH, =O, and -halo;

$R_6$ is —H;

$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;

$R_8$ is selected from —H and —$C_{1-6}$alkyl or $R_7$ taken together with $R_8$ forms $Het_4$;

$R_9$ is
selected from —H, —$C_{1-6}$alkyl, —(C=O)—$C_{1-6}$alkyl, —(C=O)—$Ar_3$ and —$Ar_3$ when X is N;
absent when X is O; or
selected from =O, and —$O_2$ when X is S;

$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;

$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{19}$, —$C_{3-6}$cycloalkyl, -$Het_2$ and —$Ar_2$;

$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;

$Ar_1$, $Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{20}R_{21}$;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{22}R_{23}$.

In a further embodiment, the present invention provides compounds of formula I,
Wherein
X is O;
$R_1$ is selected from —$C_{1-6}$alkyl, —(C=O)—$R_{13}$, —(C=S)—$R_{14}$, and —$SO_2$—$R_{15}$; wherein said —$C_{1-6}$alkyl may be further substituted with —$R_{24}$; in particular $R_1$ is selected from —$C_{1-6}$alkyl, —(C=O)—$R_{13}$, and —$SO_2$—$R_{15}$; wherein said —$C_{1-6}$alkyl may be further substituted with —$R_{24}$;
$R_2$ is —H; or $R_1$ taken together with $R_2$ forms $Het_3$;
$R_3$ and $R_4$ are —OH; or
$R_5$ represents —H;
$R_6$ is —H;
$R_7$ is selected from —$C_{1-6}$alkyl, and —(C=O)—$R_{10}$; wherein said —$C_{1-6}$alkyl may be further substituted with —$R_{25}$; in particular $R_7$ represents —(C=O)—$R_{10}$;
$R_8$ represents —H; or $R_7$ taken together with $R_8$ forms $Het_4$;
$R_9$ is absent;

$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, and —NH—$Ar_1$; wherein each of said —$C_{1-6}$alkyl is optionally and independently substituted with from 1 to 3 substituents selected from -halo, and —$Ar_1$;

$R_{10}$, is independently selected from —$C_{1-6}$alkyl, —$Ar_2$, and $Het_2$; wherein each of said —$C_{1-6}$alkyl is optionally substituted with from 1 to 3 —$Ar_2$ substituents;

$R_{20}$, and $R_{21}$, are each independently selected from —H, and —$C_{1-6}$alkyl;

$Ar_1$, and $Ar_2$, each independently a 5-10 membered aromatic mono- or bicycle; wherein each of said $Ar_1$, and $Ar_2$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, and -phenyl.

In a further embodiment, the present invention provides compounds of formula I,
Wherein
X is O;
$R_1$ is selected from —$C_{1-6}$alkyl, —(C=O)—$R_{13}$, —(C=S)—$R_{14}$, and —$SO_2$—$R_{15}$; wherein said —$C_{1-6}$alkyl may be further substituted with —$R_{24}$;
$R_2$ is —H; or $R_1$ taken together with $R_2$ forms $Het_3$;
$R_3$ and $R_4$ are —OH; or $R_3$ taken together with $R_4$ forms a dioxolane moiety, which is optionally substituted with from 1 to 3 —$C_{1-6}$alkyl substituents; in particular $R_3$ and $R_4$ are —OH;
$R_5$ represents —H;
$R_6$ is selected from —H, —OH, and —O—$C_{1-6}$alkyl; in particular $R_6$ represents —H;
$R_7$ is selected from —$C_{1-6}$alkyl, and —(C=O)—$R_{10}$; wherein said —$C_{1-6}$alkyl may be further substituted with —$R_{25}$; in particular $R_7$ represents —(C=O)—$R_{10}$;
$R_8$ represents —H;
$R_9$ is absent;

$R_{13}$, $R_{15}$, $R_{24}$, and $R_{25}$ are each independently selected from —$C_{1-6}$alkyl, —$C_{3-6}$cycloalkyl, —$Ar_1$, $Het_1$, and —NH—$Ar_1$; wherein said —$C_{1-6}$alkyl is optionally substituted with halo or —$Ar_1$;

$R_{10}$, is independently selected from —$C_{1-6}$alkyl, —$Ar_2$, and $Het_2$; wherein said —$C_{1-6}$alkyl is optionally substituted —$Ar_2$; in particular $R_{10}$, is independently selected from —$Ar_2$, and $Het_2$ $R_{20}$, and $R_{21}$, are each independently selected from —H, and —$C_{1-6}$alkyl; in particular $R_{20}$, and $R_{21}$ are each independently —$C_{1-6}$alkyl;

$Ar_1$, and $Ar_2$, each independently a 5-10 membered aromatic mono- or bicycle; wherein each of said $Ar_1$, and $Ar_2$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl;

$Het_1$, $Het_2$, and $Het_3$ are each independently a 5-10 membered mono- or bicyclic heteroaryl comprising from 1 to 3 heteroatoms selected from N, O and S; wherein each of said $Het_1$, $Het_2$, and $Het_3$ is optionally and independently substituted with from 1 to 3 substituents selected from =O, —OH, -halo and -phenyl.

In a further embodiment, the present invention provides compounds of formula I,
Wherein
X is O;
$R_1$ is selected from —$C_{1-6}$alkyl, —(C=O)—$R_{13}$, and —$SO_2$—$R_{15}$; wherein said —$C_{1-6}$alkyl may be further substituted with —$R_{24}$;
$R_2$ is —H; or $R_1$ taken together with $R_2$ forms $Het_3$;
$R_3$ and $R_4$ are —OH; or $R_3$ taken together with $R_4$ forms a dioxolane moiety, which is optionally substituted with from 1 to 3 —$C_{1-6}$alkyl substituents; in particular $R_3$ and $R_4$ are —OH;
$R_5$ represents —H;
$R_6$ is selected from —H, —OH, and —O—$C_{1-6}$alkyl; in particular $R_6$ represents —H;
$R_7$ is selected from —$C_{1-6}$alkyl, and —(C=O)—$R_{10}$; wherein said —$C_{1-6}$alkyl may be further substituted with —$R_{25}$; in particular $R_7$ represents —(C=O)—$R_{10}$;
$R_8$ represents —H;
$R_9$ is absent;
$R_{13}$ is selected from —$C_{1-6}$alkyl, —$C_{3-6}$cycloalkyl, —$Ar_1$, $Het_1$, and —NH—$Ar_1$; wherein said —$C_{1-6}$alkyl is optionally substituted with halo or —$Ar_1$;
$R_{15}$ is selected from —$C_{1-6}$alkyl, and —$Ar_1$; wherein said —$C_{1-6}$alkyl is optionally substituted with -halo (in particular —F) or $Ar_1$;
$R_{24}$ represents —$Ar_1$; in particular phenyl;
$R_{25}$ represents —$Ar_1$; in particular phenyl;
$R_{10}$, is independently selected from —$C_{1-6}$alkyl, —$Ar_2$, and $Het_2$; wherein said —$C_{1-6}$alkyl is optionally substituted —$Ar_2$; in particular $R_{10}$, is independently selected from —$Ar_2$, and $Het_2$
$R_{20}$, and $R_{21}$, are each independently selected from —H, and —$C_{1-6}$alkyl; in particular $R_{20}$, and $R_{21}$ are each independently —$C_{1-6}$alkyl; more in particular $R_{20}$, and $R_{21}$ are methyl;
$Ar_1$, and $Ar_2$, each independently a 5-10 membered aromatic mono- or bicycle (in particular phenyl or napthyl); wherein each of said $Ar_1$, and $Ar_2$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl; in particular $Ar_1$, and $Ar_2$, represent phenyl, wherein each of said phenyl is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl;
$Het_1$, $Het_2$, and $Het_3$ are each independently selected from pyridinyl, 1,3-dioxoindolyl, indolyl, pyrimidyl, pyridazinyl, pyrazinyl, pyrazolyl, imidazolyl, furanyl, '1,2,3-triazolyl', and 1H,3H-isoindolyl; wherein each of said $Het_1$, $Het_2$, and $Het_3$ is optionally and independently substituted with from 1 to 3 substituents selected from =O, —OH, halo and -phenyl.

In particular—$Het_1$, is independently selected from pyridinyl, 1,3-dioxoindolyl, indolyl, pyrimidyl, pyridazinyl, pyrazinyl, pyrazolyl, and imidazolyl; wherein said $Het_1$ is optionally and independently substituted with from 1 to 3 substituents selected from =O, —OH, halo and -phenyl;
$Het_2$ is independently selected from 1,3-dioxoindolyl, pyridazinyl, furanyl, and pyrimidyl; wherein said $Het_2$, is optionally and independently substituted with from 1 to 3 substituents selected from =O, —OH, halo and -phenyl.
$Het_3$, is independently selected from '1,2,3-triazolyl', 1,3-dioxoindolyl, and 1H,3H-isoindolyl; wherein said $Het_3$ is optionally and independently substituted with from 1 to 3 substituents selected from =O, —OH, halo and -phenyl.

In another particular embodiment, the present invention provides a compound of formula I,
Wherein
X is O;
$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;
$R_2$ is selected from —H and —$C_{1-6}$alkyl, or $R_1$ taken together with $R_2$ forms $Het_3$;
$R_3$ is
absent or selected from —H, —OH, and -halo;
or $R_3$ taken together with $R_4$ forms a dioxolane moiety, which is optionally substituted with from 1 to 3 substituents selected from —OH, —$C_{1-6}$alkyl, and -halo;
$R_4$ is selected from —H, —OH, and -halo;
$R_5$ is selected from —H, —OH, =O, and -halo;
$R_6$ is selected from —H, —OH, -halo, —$C_{1-6}$alkyl, —O—$C_{1-6}$alkyl, —S—$C_{1-6}$alkyl, and —CN;
$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;
$R_8$ is selected from —H and —$C_{1-6}$alkyl or $R_7$ taken together with $R_8$ forms $Het_4$;
$R_9$ is absent;
$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;
$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{13}$, —$C_{3-6}$cycloalkyl, -$Het_2$ and —$Ar_2$;
$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;
$Ar_1$, $Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —$CF_3$, or —$NR_{20}R_{21}$;
$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —$CF_3$, or —$NR_{22}R_{23}$.

In a specific aspect, the present invention provides a compound as defined herein, with its 'X' and 'R' definitions as defined above, wherein the compound has the stereoisomeric configuration as represented in formula II:

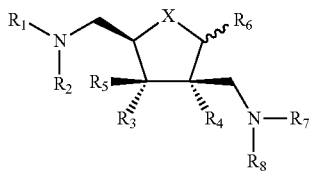

In a further aspect, the $R_1$ and $R_7$ substituents of the compounds of the present invention are each independently selected to comprise an optionally substituted polar heteroaryl moiety; in particular selected from the group consisting of pyridyl, pyridazyl, pyrimidyl, pyrazyl and 1,3-dioxoindolyl (a.k.a. phthalimide). In this embodiment $R_1$ is preferably selected from —$C_{1-6}$alkyl substituted with —$R_{24}$, —(C=O)—$R_{13}$, and —$SO_2$—$R_{15}$; wherein said $R_{24}$, $R_{13}$ and $R_{15}$ are defined as in any one of the different $Het_1$ comprising embodiments herein described and wherein said $Het_1$ is selected from the group consisting of pyridyl, pyridazyl, pyrimidyl, pyrazyl and 1,3-dioxoindolyl (a.k.a. phthalimide). In this embodiment $R_7$ is preferably selected from —$C_{1-6}$alkyl substituted with —$R_{25}$, and —(C=O)—$R_{10}$; wherein said $R_{25}$ and $R_{10}$ are defined as in any one of the different $Het_2$ comprising embodiments herein described and wherein said $Het_2$ is selected from the group consisting of pyridyl, pyridazyl, pyrimidyl, pyrazyl and 1,3-dioxoindolyl (a.k.a. phthalimide). It has been found that such polar heteroaryl analogs have interesting activities due to their specific interactions with the target.

In another aspect, the $R_1$ and $R_7$ substituents of the compounds of the present invention are each independently selected to comprise an optionally substituted phenyl moiety. It has been found that such biphenyl analogs have an increased antibiofilm activity. In this embodiment $R_1$ is preferably selected from —$C_{1-6}$alkyl substituted with —$R_{24}$, —(C=O)—$R_{13}$, and —$SO_2$—$R_{15}$; wherein said $R_{24}$, $R_{13}$ and $R_{15}$ are defined as in any one of the different $Ar_1$ comprising embodiments herein described and wherein said $Ar_1$ is phenyl optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl. In this embodiment $R_7$ is preferably selected from —$C_{1-6}$alkyl substituted with —$R_{25}$, and (C=O)—$R_{10}$; wherein said $R_{25}$ and $R_{10}$ are defined as in any one of the different $Ar_2$ comprising embodiments herein described and wherein said $Ar_2$ is phenyl optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl.

In another aspect the $R_1$ and $R_7$ substituents of the compounds of the present invention are each independently selected to comprise a substituted phenyl moiety or a substituted (in particular a polar) heteroaryl moiety, wherein said phenyl moiety or heteroaryl moiety are substituted with a substituent selected from =O, —OH, -halo, —$C_{1-6}$alkyl, —O—$C_{1-6}$alkyl, —CN, —$CF_3$, —$NR_{20}R_{21}$, and -phenyl, characterized in that said substituent is present at the ortho position in respect to the attachment point of said phenyl moiety or said heteroaryl moiety with the rest of the molecule. In a more particular embodiment the $R_1$ substituent of the compounds of the present invention is selected to comprise a substituted phenyl moiety or a substituted (in particular a polar) heteroaryl moiety, wherein said phenyl moiety or heteroaryl moiety are substituted with a substituent selected from =O, —OH, -halo, —$C_{1-6}$alkyl, —O— $C_{1-6}$alkyl, —CN, —$CF_3$, —$NR_{20}R_{21}$, and -phenyl, characterized in that said substituent is present at the ortho position in respect to the attachment point of said phenyl moiety or said heteroaryl moiety with the rest of the molecule. It has been found that such orthosubstitution results in an increased activity.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

Medical Use

It is an aim of the present invention to provide compounds that interfere with quorum sensing (QS) in bacteria and/or inhibit or prevent biofilm formation.

The present invention thus further provides a pharmaceutical composition comprising a compound according to the present invention and a pharmaceutically acceptable excipient, diluent and/or carrier.

In a further aspect, the present invention provides a combination, as part of a composition or in use, of a compound according to the present invention with an antimicrobial agent, in particular an antibiotic or disinfectant. Hence, one or more compounds as described herein and one or more antimicrobial agents can be part of a single composition or can be used in a separate or sequential application.

In a specific aspect, the present invention provides a compound, composition or combination according to the present invention, for use as a medicament, more in particular, for use in the prevention, reduction and/or treatment of bacterial infections in humans or animals. In a particular embodiment, said bacterial infection is a *Staphylococcus aureus* infection.

The compounds of the present invention can be used as an alternative to replace antibiotics for combating (bacterial) infections or can be used as an adjunct therapy in combination with e.g. antibiotics so that lower doses of the conventional antibiotics are required.

In a particular embodiment, the present invention provides a method of preventing, reducing the risk of and/or treating a bacterial infection, more in particular a disorder associated with biofilm formation in a subject; said method comprising administering to a subject in need thereof a therapeutic effective amount of a compound, a composition or a combination according to the present invention. The term "biofilm" as used herein refers to biological films that develop and persist at interfaces in aqueous environments, on medical implants, or as foci of chronic infections. Biofilms may also form on biological surfaces such as teeth, or any other natural or artificial surfaces that may be exposed to or are in contact with non-sterile aqueous environments that may include nutrients suitable for the colonization and proliferation of the microorganisms. These biological films are composed of microorganisms embedded in organic gelatinous matrices composed of one or more matrix polymers that are secreted by the resident microorganisms. Biofilms can develop into macroscopic structures several millimeters or centimeters in thickness and can cover large surface areas. Biofilms are also capable of trapping nutrients and particulates that can contribute to their enhanced development and stability. Biofilms can also prevent penetration of antimicrobial agents, which may lead to persistent infections. Disorders associated with biofilm formation include but are not limited to, dental caries, periodontitis, otitis media, muscular skeletal infections, necrotizing fasciitis, biliary tract infection, osteomyelitis, bacterial prostatitis, endocarditis, native valve endocarditis, cystic fibrosis pneumonia, meloidosis, or skin lesions associated with bullous impetigo, atopic dermatitis and pemphigus foliaceus or implanted device-related infections. In some embodiments, the disorder is a nosocomial infection, including but not limited to, pneumonia, sepsis (including SIRS (Systemic Inflammatory Response Syndrome), severe sepsis and MODS (multiorgan dysfunction syndrome)), or an infection associated with sutures, exit sites, arteriovenous sites, scleral buckles, contact lenses, urinary catheter cystitis, peritoneal dialysis (CAPD) peritonitis, IUDs, endotracheal tubes, Hickman catheters, central venous catheters, mechanical heart valves, vascular grafts, biliary stent blockage, and orthopedic devices. The compounds of the present invention are of particular interest to prevent, limit the risk of and/or treat post-operative wound infections, skin ulcers, diabetic foot ulcers, pressure ulcers such as decubitus ulcers or bedsores, burn wound infections, catheter associated infections, and infections resulting from animal bites. In a further embodiment, the compounds as described herein are effective in preventing and/or treating mastitis, i.e. inflammation of the breast tissue. *S. aureus* is the most common etiological organism responsible, but *S. epidermidis* and streptococci are occasionally isolated as well. Mastitis in dairy cattle is the persistent, inflammatory reaction of the udder tissue.

The present invention further provides a method for the prevention, reducing the risk of and/or treatment of microbial infections, in particular bacterial infections, more in particular infections with bacteria of the genus *Staphylococcus* such as *Staphylococcus aureus* infections. The method further comprises contacting a surface with the composition in an amount sufficient to prevent or reduce the growth or proliferation of microorganisms or biofilm-embedded microorganisms on said surface.

In the invention, particular preference is given to compounds of Formula I or II, or any subgroup thereof, that in the inhibition assay as described in the examples, inhibit with an $IC_{50}$ value of less than 100 μM, preferably less than 50 μM, and more preferably less than 10 μM.

Said inhibition may be effected in vitro and/or in vivo, and when effected in vivo, is preferably effected in a selective manner, as defined above. In some embodiments, the bacterium is contacted with the compound as provided herein ex vivo. In such an embodiment, for example, the contacting comprises administering the compound to a surface in an amount effective to inhibit biofilm formation on said surface, including but not limited to a medical device.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethylbromides and others. Other pharmaceutically acceptable salts include the sulfate salt ethanolate and sulfate salts.

Generally, for pharmaceutical use, the compounds of the invention may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions, and sterile packaged powders (which are usually reconstituted prior to use) which may be administered as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. Furthermore, the compounds may also be formulated in or may be applied on a medical device, such as skin patches, implantable devices, catheters, tampons, wound dressings and bandages. In a particular embodiment, one or more compounds as described hereinbefore is used to inhibit biofilm formation on a medical device by contacting the device with said compound in an amount effective to inhibit biofilm formation. Percutaneous devices (such as catheters) and implanted medical devices (including, but not limited to, pacemakers, vascular grafts, stents, and heart valves) commonly serve as foci for bacterial infection. The tendency of some microorganisms to adhere to and colonize the surface of the device promotes such infections, which increase the morbidity and mortality associated with use of the devices.

For example, one or more compounds of the present invention can be used or applied on substrates used to manufacture medical devices associated with non-invasive and invasive medical procedures. Such substrates include, without limitation, tubular, sheet, rod and articles of proper shape for use in a number of medical devices such as vascular grafts, aortic grafts, arterial, venous, or vascular tubing, vascular stents, dialysis membranes, tubing or connectors, blood oxygenator tubing or membranes, surgical instruments, ultrafiltration membranes, intra-aortic balloons, stents, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind. In particular, one or more compounds of the present invention can be used or applied on drug-eluting medical implants. These are active implants that induce healing effects in addition to their regular task of support. This effect is achieved by controlled release of the active agent, including the compounds of the present invention, into the surrounding tissue. Examples are drug-eluting vascular stents, drug-eluting wound dressings and protein-eluting scaffolds for tissue regeneration. As such, the present invention encompasses a medical device as mentioned herein comprising one or more compounds of the present invention. The compounds can be incorporated in or applied on the surface of the medical device.

In a particular embodiment, the composition or formulation of the present invention can optionally contain other pharmaceutically active substances, especially antimicrobial agents such as antibiotics or disinfectants (which may or may not lead to a synergistic effect with the compounds of the invention) and/or other substances that are commonly used in pharmaceutical formulations, such as lubricating agents, wetting agents, emulsifying and suspending agents, dispersing agents, disintegrants, bulking agents, fillers, preserving agents, sweetening agents, flavoring agents, flow regulators, release agents, etc.

In some embodiments, the method and use as described herein further comprises the step of administering a standard of care antimicrobial agent to the subject. "Standard of care" as used herein refers to a treatment that is generally accepted by clinicians for a certain type of patient diagnosed with a type of illness. Exemplary standard of care antimicrobial agents include, but are not limited to, (i) β-lactam antibiotics like penicillins either alone (including but not limited to penicillin G, penicillin V, flucloxacillin, oxacillin, ampicillin, methicillin, amoxicillin, temocillin, and piperacillin), or combined with a β-lactamase inhibitors (including but not limited to amoxicillin+clavulanic acid, and piperacillin+tazobactam), carbapenems (including but not limited to biapenem, meropenem and imipenem), monobactams (including but not limited to aztreonam) and cephalosporins (including but not limited to cefadroxil, cefalexine, cefazoline, cefuroxime, cefotaxim, ceftazidim, ceftriaxone, cefepim and ceftarolin), (ii) macrolides (including but not limited to erythromycin, azithromycin, clarithromycin, roxithromycin, and spiramycin), (iii) tetracyclines and glycycicyclines (including but not limited to doxycycline, lymecycline, minocycline, and tigecycline), (iv) lincosamides (including but not limited to clindamycin and lincomycin), (v) (fluoro-)quinolones (including but not limited to ciprofloxacin, levofloxacin, nemonoxacin, garenoxacin, moxifloxacin, norfloxacin, ofloxacin, parfloxacin, gemifloxacin, zabofloxacin and cinafloxacin), (vi) trimethoprim+sulfamethoxazole, (vii) aminoglycosides (including but not limited to streptomycin, amikacin, gentamicin, paromomycin, kanamycin, spectinomycin and tobramycin), (viii) glycopeptides (including but not limited to oritavancin, LY-333328, dalbavancin, teicoplanin and vancomycin), (ix) polymyxins (including but not limited to polymyxin B and colistin), (x) anti-tuberculosis drugs (including but not limited to isoniazide, rifampicin, pyrazinamide, ethambutol and bedaquilin and p-aminosalicylic acid), (xi) oxazolidinones (including but not limited to tedizolid, AZD-2563 and linezolid), (xii) lipopeptides (including but not limited to daptomycin and ramoplanin), (xiii) streptogramins (including but not limited to quinupristin/dalfopristin, pristinamycin, virginiamycin and NXL-103), (xiv) ketolides (including but not limited to telithromycin and solithromycin), (xv) various other antibiotics, including but not limited to cycloserine, fosfomycin, nitrofurantoin, nifurtoinol, thiamphenicol, chloramphenicol, metronidazole, bacitracin and mupirocin, and (xvi) locally applied disinfectants including but not limited to chlorhexidine, PVP-$I_2$ (Povidone-iodine), colloidal silver, Manuka honey, ozonated olive oil, silver nitrate, silver sulfadiazine, ethanol, isopropanol, hydrogen peroxide, chloroxylenol, and cetrimide, benzalkoniumchloride and other quaternary ammonium compounds.

Combination therapy comprising a compound of the present invention and an antimicrobial agent, e.g. an antibiotic or disinfectant, described herein for the treatment of a bacterial infection is specifically contemplated. For example, in one embodiment, the invention provides a method of treating a bacterial infection or a disorder associated with bacterial QS and/or biofilm formation in a subject comprising administering to the subject a therapeutically-effective amount of a combination therapy comprising (a) a compound of formula I or II or any subgroup thereof, and (b) an antimicrobial agent.

Such combination therapy would be provided in a combined amount effective to prevent or inhibit QS and/or biofilm formation of the bacteria and/or prevent or treat the bacterial infection and/or treat the disorder associated with biofilm formation. This process involves administering to a subject in need thereof the compound and a (standard of care) therapeutic agent at the same time, which may be achieved by administering a single composition or pharmacological formulation that includes both the compound of the invention and a therapeutic agent, or by administering two distinct compositions or formulations, at the same time, wherein one composition includes the compound of the invention and the other includes a (standard of care) therapeutic agent. In another embodiment, the combination therapy involves administering to a subject in need thereof the compound of the invention and a (standard of care) therapeutic agent at different times, which may be achieved by administering two distinct compositions or formulations, at different time intervals, wherein one composition includes the compound of the invention and the other includes a (standard of care) therapeutic agent.

The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ $\alpha$-, $\beta$- or $\gamma$-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

Particular reference is made to the compositions, formulations (and carriers, excipients, diluents, etc. for use therein), routes of administration etc., which are known per se for analogous pyridinocarboxamides, such as those described in U.S. Pat. No. 4,997,834 and EP-A-0 370 498.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof. The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. At least one compound of the invention will generally be administered in an "effective amount", by which is meant any amount of a compound of the Formula I or II or any subgroup thereof that, upon suitable administration, is sufficient to achieve the desired therapeutic or prophylactic effect in the individual to which it is administered. More specific, it refers to an amount of the compound at least sufficient to achieve a desired modulation of the activity or physiological property of a microbial population as exemplified in the present examples. The effective amount is determined, at least in part, upon the compound used, the microbial species present, the structure, system, or host, and the desired level of regulation. Modulating the activity or physiological property of the microbial population includes, but is not limited to, slowing, attenuating, inhibiting, or enhancing the colonization of a surface or proliferation of bacteria, inhibiting the formation of a biofilm, and the like. Modulation includes slowing the formation of bacteria or new bacteria if some bacteria are already present, inhibiting the formation of a biofilm. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug. In preferred embodiments, the compounds and compositions of the invention are used locally, for instance topical or in both absorbed and non-adsorbed applications.

In a particular embodiment, compositions comprising a compound of the present invention, either alone or in combination as described herein, can be used as a topical agent. The topical agent is a solution, that is, in one aspect, a liquid formulation comprising the compound and a carrier. Other suitable forms include semi-solid or solid forms comprising a carrier indigenous to topical application and having a dynamic viscosity preferably greater than that of water, provided that the carrier does not deleteriously react with the compound in the composition. Suitable formulations include, but are not limited to, lip balms, suspensions, emulsions, creams, ointments, powders, liniments, salves and the like. If desired, these compositions may be sterilized or mixed with auxiliary agents, including but not limited to, preservatives, stabilizers, wetting agents, buffers or salts for influencing osmotic pressure and the like well known in the art. Preferred vehicles for semi-solid or solid forms topical preparations include ointment bases, conventional ophthalmic vehicles; creams; and gels. These topical preparations optionally contain emollients, perfumes, and/or pigments to enhance their acceptability for various usages, provided that the additives do not deleteriously react with the compound in the composition.

Also suitable for topical application are sprayable aerosol preparations wherein the compound, preferably in combination with a solid or liquid inert carrier material, is packaged in a squeeze bottle or in admixture with a pressurized volatile, normally gaseous propellant, e.g., a Freon (chlorofluorocarbon) or environmentally acceptable volatile propellant. Such compositions are used in one aspect, for application to the skin or to mucous membranes. The aerosol or spray preparations optionally contain solvents, buffers, surfactants, perfumes, and/or antioxidants in addition to the compound.

The compositions of the present invention are further of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

As used herein, the term "subject" includes humans, mammals (e.g., cats, dogs, horses, chicken, pigs, hogs, cows, fish, crabs, shrimps, cattle, and other), and other living species that are in need of treatment. In particular, the term "host" includes humans.

In related variations of the preceding embodiments, a composition comprising a compound of the present invention packaged alone, e.g., in a kit or package or unit dose, or is optionally arranged to permit co-administration with one or more other (therapeutic) agents as described herein, but the compound and the agent are not in admixture. In an alternative variation, the compound and the agent are in admixture. In some embodiments, the two components to the kit/unit dose are packaged with instructions for administering the two agents to a human subject for treatment of one of the above-indicated disorders and diseases. The kit may comprise a composition described herein in combination with a vehicle in a cream or gel base, as a pump-spray, as an aerosol, on an impregnated bandage, or in a dropper.

This invention will be better understood by reference to the experimental details that follow, but those skilled in the art will readily appreciate that these are only illustrative of the invention as described more fully in the claims that follow thereafter. Particular embodiments and examples are not in any way intended to limit the scope of the invention as claimed. Additionally, throughout this application, various publications are cited. The disclosure of these publications is hereby incorporated by reference into this application to describe more fully the state of the art to which this invention pertains.

EXAMPLES

Compound Synthesis—Reaction Schemes

The compounds of the invention may be prepared by methods well known to those skilled in the art, and as described in the synthetic and experimental procedures shown below.

Hamamelitannin (HAM) has been identified as an antimicrobial potentiator, capable of increasing the susceptibility of S. aureus to existing antibiotics. To gain insight into the structure-activity relationship of HAM, as well as to discover analogues with enhanced potency, better drug-like properties and metabolic stability, we set out to synthesize structural analogues of hamamelitannin as to:
  explore the importance of the aromatic hydroxyl groups.
  replace the metabolically unstable ester groups in HAM with isosteric linker moieties.
  replace the central sugar moiety by a polysubstituted tetrahydrofuran ring.

With reference to the specific compounds of the present invention, the following reaction schemes and procedures may be used.

Scheme 1 describes the synthesis of a series of amide analogues of HAM (15-21). The desired compounds are synthesized from isopropylidene-D-ribonolactone. A key step is the aldol condensation of 2 with formaldehyde to afford the 2-C-hydroxymethyl derivative 3 (Simone et al., 2008). Bisazide scaffold 7, readily available from the branched azidolactole 3 via selective protection and deprotection of functional groups, functions as a precursor to generate a series of amide derivatives of HAM.

The central D-hamamelose scaffold is a monosaccharide with anomeric hydroxyl function. To assess the importance of the anomeric hydroxyl group, we synthesized analogues with a cyclic ether (tetrahydrofuran) scaffold. The synthetic strategy to remove the anomeric OH (with the formation of a cyclic ether) is shown in Scheme 2 (Bouisset et al., 2008; Taki et al., 2008). A key step is the tosylate-promoted cyclisation of ribitol 22. The rigidity of the dioxolane ring system ensures that only the cis-bicylic compound 23 is formed. Tetrahydrofuran derivative 24 acts as a versatile orthogonally protected intermediate and gives access to different analogues with different amide groups, as exemplified in Scheme 2 and Scheme 6. Strong acid conditions allow removal of the acetonide to produce the final compounds (Scheme 8).

In addition to the amide derivatives described earlier, analogues with alternative linkers may be synthesized (Boren et al., 2008; Garcia-Moreno et al., 2000). Intermediate 26 serves to construct analogues with alternative linkers, as exemplified in Scheme 3: regioisomers 105 and 106 are synthesized via a copper- or ruthenium-catalyzed 1,3-dipolar cycloaddition reaction, respectively. Intermediate 33, readily available from 26 via Staudinger reduction, may give rise to sulfonamides 94-103). The 2-bromobenzenesulfonamide 103 serves as an intermediate that is used in the synthesis of biphenyl analogue 104 via a Suzuki cross-coupling (Scheme 4). The library is further extended with urea and thiourea derivatives 107 and 108 along with the amide derivatives 109 and 110. Benzylamine 112 is obtained via reductive amination of 33 with benzaldehyde. To obtain the final compounds, the 1,3-dioxolane is cleaved by treatment with aqueous trifluoroacetic acid (Scheme 8). Radical bromination of methyl 2-methylbenzoate and subsequent treatment with amine 33 afforded cyclic amide derivative 114 (Scheme 5).

Monoalkylation of the amide group in 2'-position was achieved via alkylation of intermediate 26 (Scheme 2). Intermediate 117 was subjected to a diazo transfer with freshly prepared $TfN_3$. Resulting azide 148 allowed monoalkylation on the 5-position of the molecule (Scheme 7).

Compound 264 differs from HAM in that the ester linkers are replaced by the metabolically more stable amides and the central sugar moiety is replaced by the cyclic ether structure that gives a more rigid pharmacophore. Scheme 9 shows how this derivative with two identical galloyl groups is synthesized.

In order to investigate the stereochemical requirements at C-4, compound 270 was synthesized. The synthesis starts from 2,3-O-isopropylidene-D-ribonolactone (Scheme 10). After mesylation, this lactone was subjected to alkaline treatment with aqueous KOH. Finally, trituration in acetone gave rise to epimer 265 (Batra et al., 2006). C-4 inversion occurs via an intermediate epoxide that is opened intramolecularly in a 5-exo-tet process.

Compound 265 was converted to the 2-C-branched-chain derivative 267 according to the method of Simone. Borohydride reduction, tosylate-promoted cyclisation and subsequent substitution with sodium azide gave intermediate 269. Reduction of this bis-azide scaffold with trimethylphosphine, coupling with benzoic acid and removal of the acetonide protecting group gave the desired 4-epimer.

Scheme 1

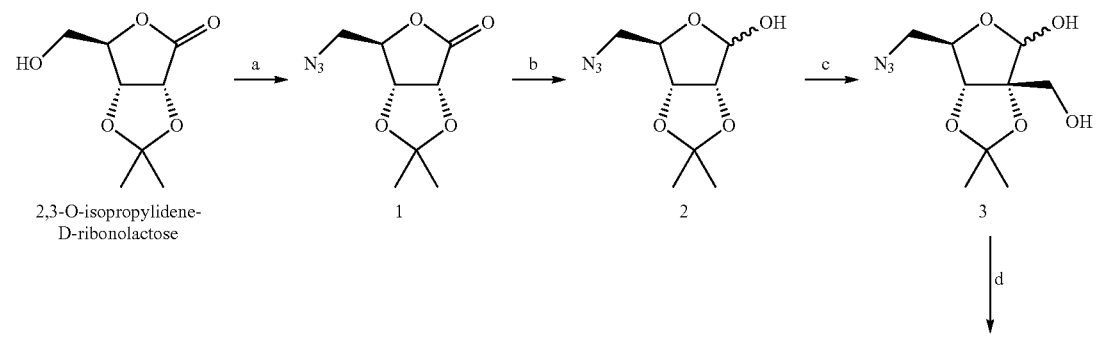

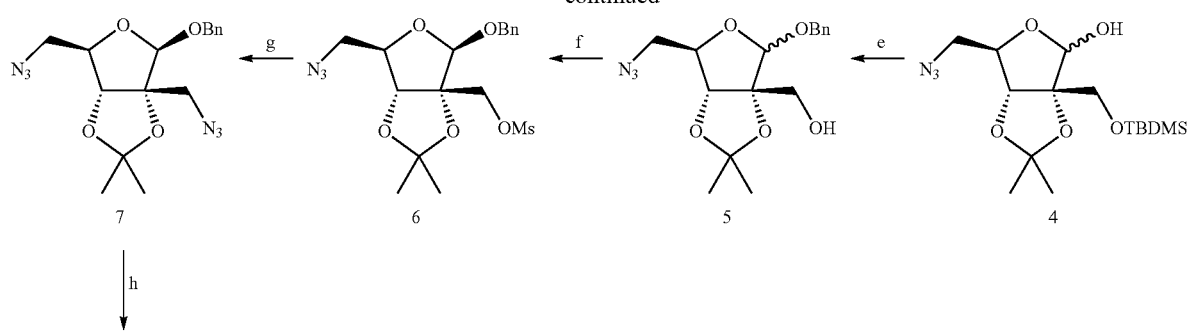
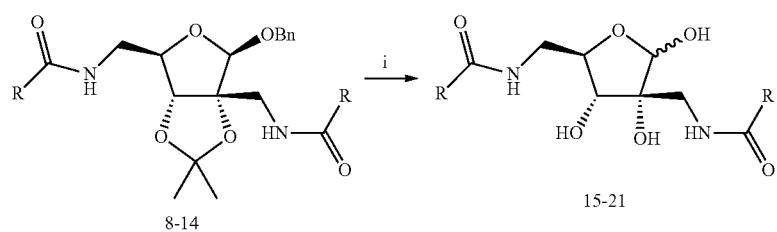
(a) [i] MsCl, Et₃N, CH₂Cl₂, rt, 3 h; [ii] NaN₃, DMF, 60° C., overnight, 94%; (b) DiBAlH, CH₂Cl₂, −78° C., 4 h, 98%; (c) aq. CH₂O, K₂CO₃, MeOH, 50° C., 24 h, 84%; (d) TBDMSCl, Imidazole, DMF, 0° C., 16 h, 63%; (e) [i] BnBr, NaH, DMF, 0° C., overnight, [ii] TBAF, THF, rt, 4 h, 42%; (f) MsCl, Et₃N, CH₂Cl₂, rt, 2 h, 95%; (g) NaN₃, DMF, 90° C., 48 h, 70%; (h) [i] PMe₃, THF, H₂O, [ii] RCOOH, EDC·HCl, DMAP, HOBt, DMF, rt, overnight; (i) [i] H₂, Pd/C, HOAc, 5 h, [ii] 35% TFA, H₂O, rt, 3 h.
Scheme 2
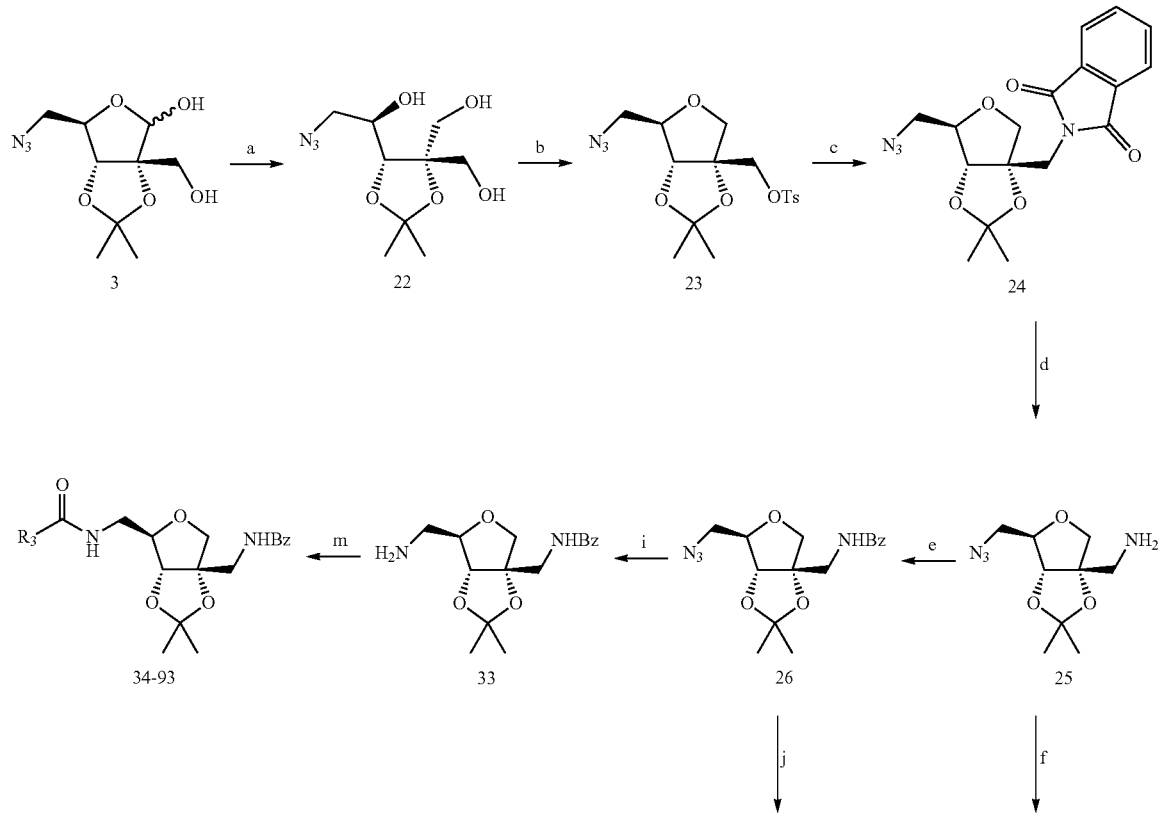

-continued

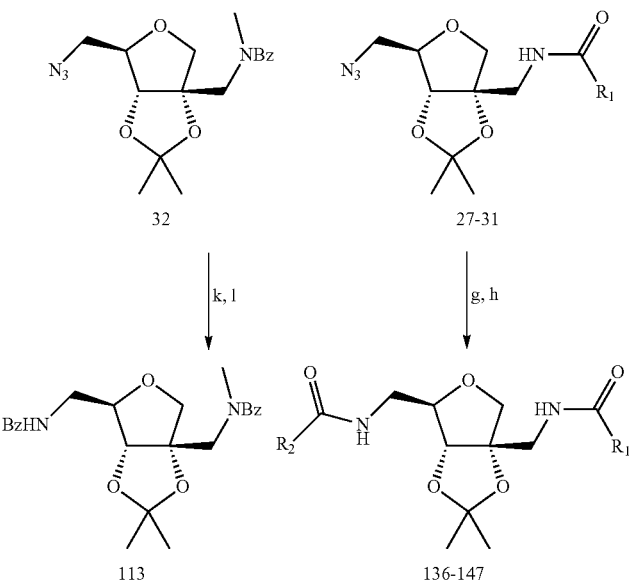

(a) NaBH₄, MeOH, 0° C., overnight, 93%; (b) [i] TsCl, pyridine, rt, 3 h, [ii] 60° C., overnight, 72%; (c) potassium phthalimide, NaI, DMF, 90° C., overnight, 86%; (d) N₂H₄·H₂O, EtOH, reflux, 4 h, 93%; (e) BzCl, TEA, CH₂Cl₂, 0° C., 3 h, 93%; (f) R₁COOH, EDC·HCl, DIPEA, HOBt, DMF, rt, overnight; (g) [i] PMe₃, THF, 3 h [ii] H₂O, 1 h; (h) R₂COOH, EDC·HCl, DIPEA, HOBt, DMF, rt, overnight; (i) [i] PMe₃, THF, 3 h [ii] H₂O, 1 h; (j) [i] NaH, THF, 1 h, [ii] MeI, 68%; (k) PMe₃, THF, 3 h [ii] H₂O, 1 h; (l) Benzoic acid, EDC·HCl, DIPEA, HOBt, DMF, rt, overnight; (m) R₃COOH, EDC·HCl, DIPEA, HOBt, DMF, rt, overnight;.

Scheme 3

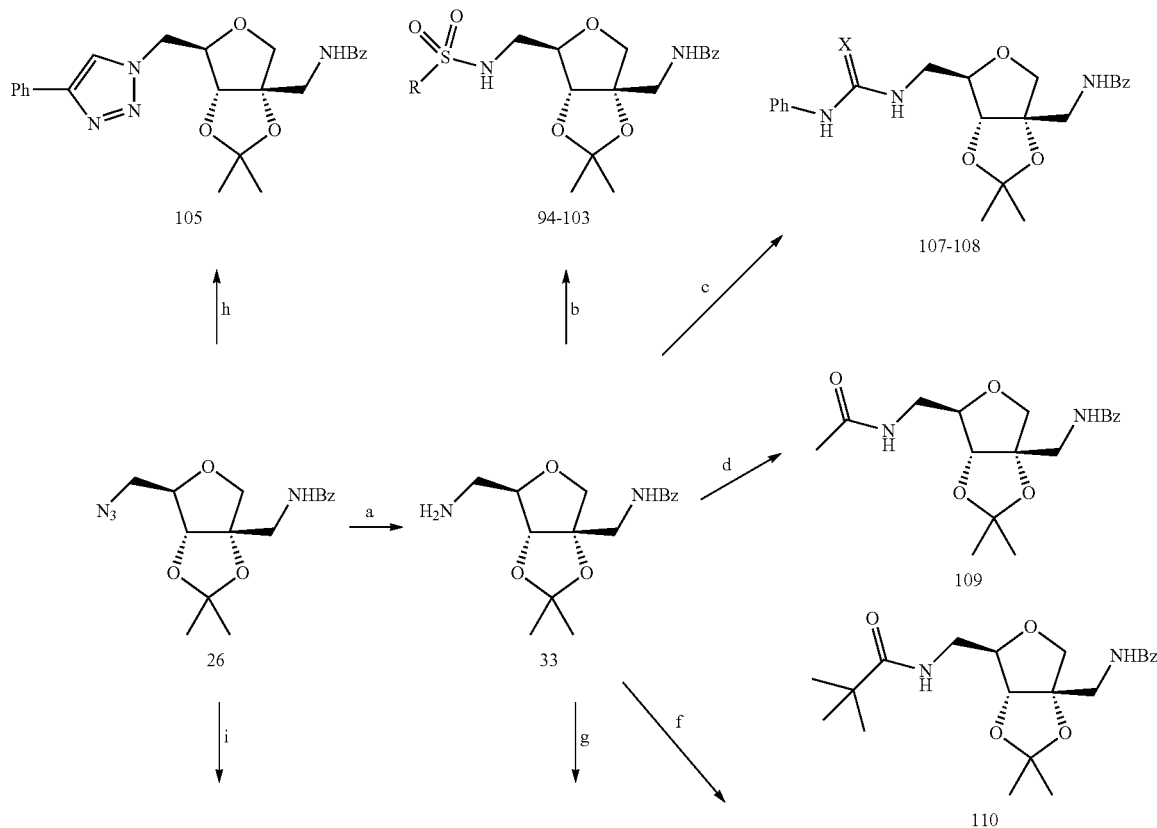

39

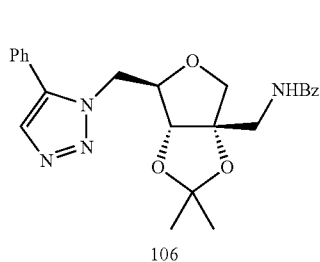
106

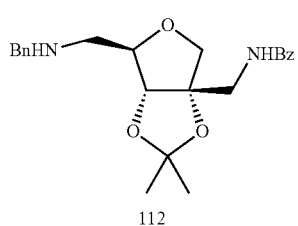
112

-continued

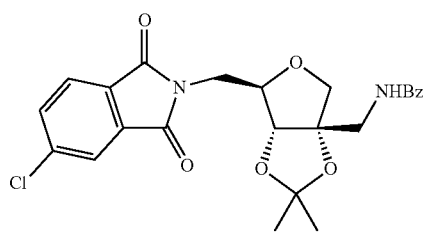
111

(a) [i] PMe₃, THF, 3 h, [ii] H₂O, 1 h; (b) RSO₂Cl, Et₃N, CH₂Cl₂, 0° C., 3 h; (c) PhNCX (X = O, S), pyridine, rt, 3 h, ( X = O, 76%; X = S, 65%); (d) (CH₃CO)₂O, DIPEA, 0° C., overnight, 96%; (e) (CH₃)₃CCOCl, Et₃N, 0° C., overnight, 74%; (f) 4-Cl-phthalic anhydride, CHCl₃, reflux, overnight, 22%; (g) [i] benzaldehyde, mol. sieves, MeOH, [ii] NaBH₄, 47%; (h) PhC≡CH, CuI, TBTA, DMF/H₂O/TEA, 75° C., 4 h, 84%; (i) PhC≡Ch, CpRuCl(PPh₃)₂, dioxane, 60° C., 24 h, 83%.

Scheme 4

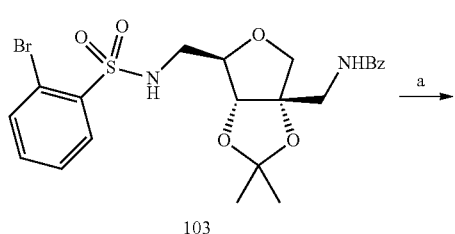
103

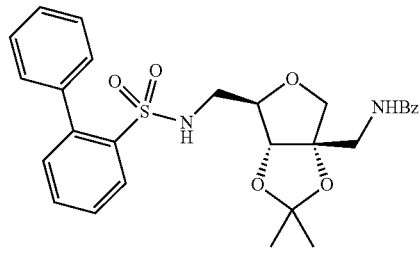
104

(a) PhB(OH)₂, K₂CO₃, Pd(PPh₃)₄, DMF/H₂O, 110° C., overnight, 46%.

Scheme 5

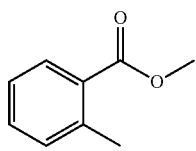

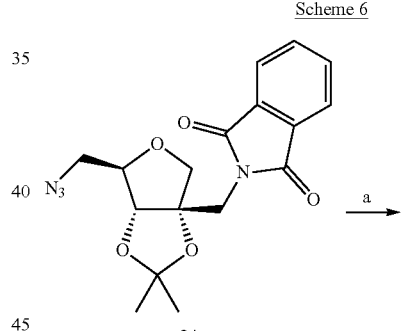
33

271
b

-continued

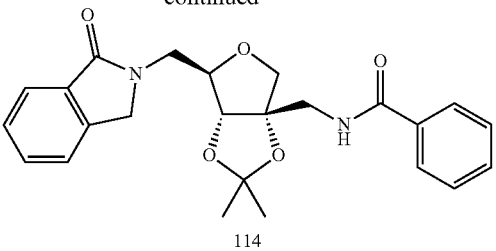
114

(a) NBS, AIBN, CCl₄, reflux, 68%; (b) TEA, MeOH, reflux, 59%.

Scheme 6

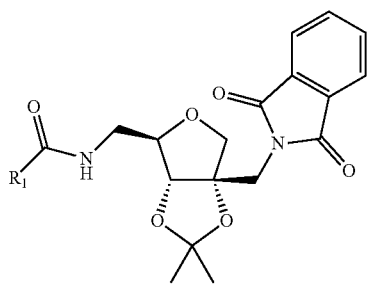
24 a

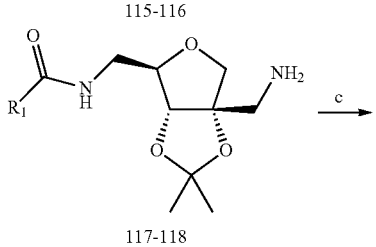
115-116 b 117-118 c

40

41

-continued

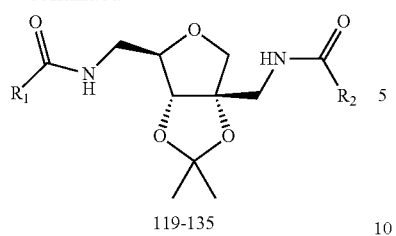

119-135

(a) R₁C(O)Cl, PMe₃, rt, overnight; (b) N₂H₄·H₂O, EtOH, reflux, 5 h; (c) R₂COOH, EDC·HCl, DIPEA, HOBt, DMF, rt, overnight.

Scheme 7

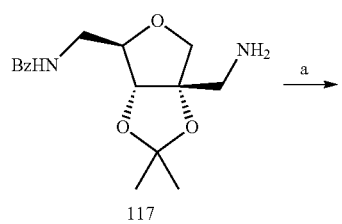

117

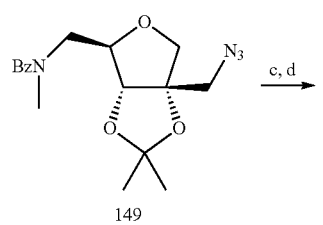

148

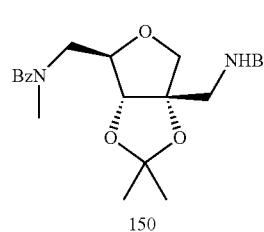

149

150

(a) TfN₃, MeOH, Et₃N, CuSO₄, 90%; [i] NaH, THF, 1 h, [ii] MeI, 88%; (c) [i] PMe₃, THF, 3 h, [ii] H₂O, 1 h; (d) Benzoic acid, EDC·HCl, DIPEA, HOBt, DMF, rt, overnight, 93% over two steps.

42

Scheme 8

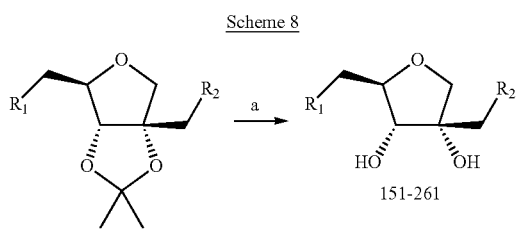

151-261

(a) 35% TFA, H₂O, rt, overnight

Scheme 9

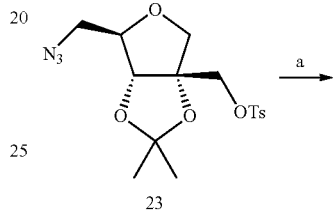

23

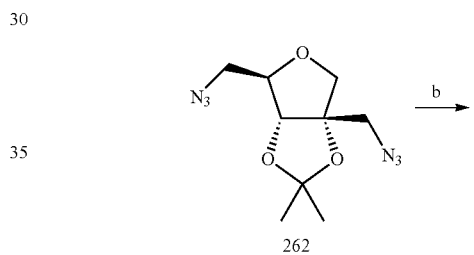

262

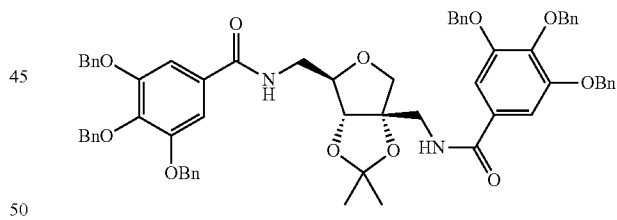

263

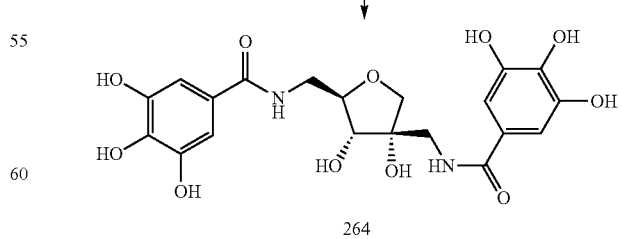

264

(a) NaN₃, DMF, 80° C., overnight, 86%; (b) [i] PMe₃, THF, H₂O, [ii] RCOOH, EDC·HCl, DMF, DMAP, HOBt; (c) [i] H₂, Pd/C, MeOH, 2 h, [ii] 35% TFA, H₂O, 3 h.

Scheme 10:

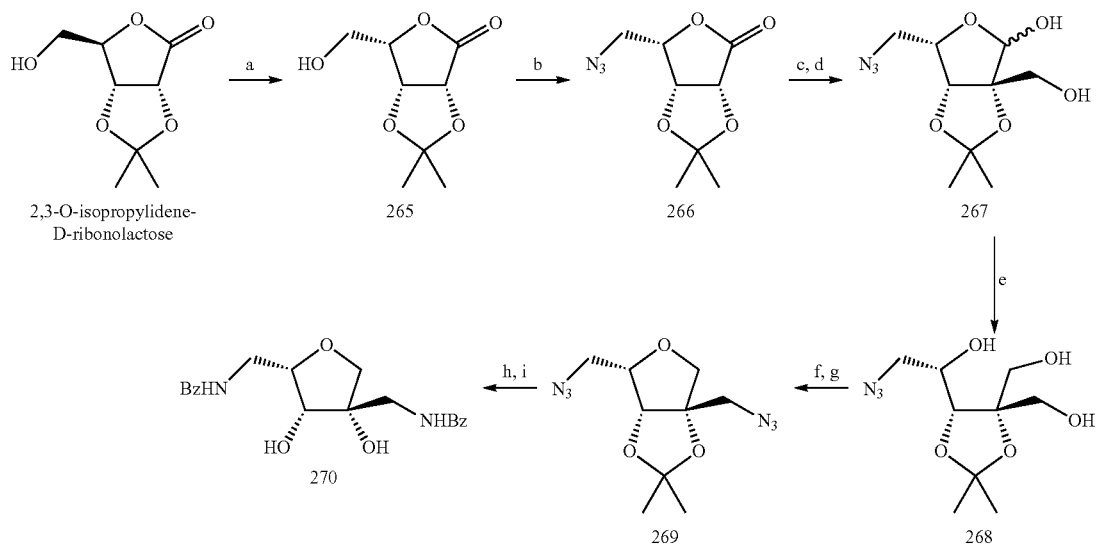

2,3-O-isopropylidene-
D-ribonolactose (a) [i] MsCl, Et₃N, CH₂Cl₂, rt, 3 h, [ii] KOH, dioxane/H₂O, [iii] dil. aq. HCl, 65%; (b) [i] MsCl, Et₃N, CH₂Cl₂, rt, 3 h, [ii] NaN₃, DMF, 90° C., overnight, 81%; (c) DIBALH, CH₂Cl₂, -78° C., 4 h; [d] aq. CH₂O, K₂CO₃, MeOH, 50° C., 24 h, 46% over two steps; (e) NaBH₄, MeOH, 0° C., overnight, 24% (82% borsm); (f) [i] TsCl, pyridine, rt, 3 h, [ii] 60° C., overnight; (g) NaN₃, DMF, 80° C., overnight 29%; (h) [i] PMe₃, THF, 3 h [ii] H₂O, 45 min [iii] PhCOOH, EDC•HCl, DIPEA, HOBt, DMF, rt, overnight; (i) 35% TFA, H₂O, rt, overnight, 74.3% over two steps.

Compound Synthesis—Experimental Methods

General Procedure 1: Synthesis of Protected Homodibenzamides 8-14 from Bisazide 7.

To a solution of bisazide 7 in THF (0.2 M) was added Me₃P (1M in THF, 10 eq.) and the mixture was stirred for 2 h at rt. Water (100 µL per mmol bisazide) was added and stirring was continued for 15 minutes. The mixture was taken to dryness and co-evaporated twice with toluene. The crude bisamine was taken up in DMF (to a concentration of 0.1 M). EDC.HCl (3.0 eq.), DMAP (1.0 eq.) HOBt (1.0 eq.) and the appropriate carboxylic acid (2.5 eq.) were added and the mixture was stirred overnight. The mixture was taken to dryness, the residue was redissolved in EtOAc, transferred to a separatory funnel and washed successively with HCl (1M, twice) and NaHCO₃ (sat. aq., twice). The organic layer was dried (Na₂SO₄) and concentrated in vacuo. The residue was purified by silica gel chromatography (CH₂Cl₂/MeOH system) to yield the homobisbenzamide as a pale yellow foam (yields 85-95%).

General Procedure 2: Full Deprotection of the Homobisbenzamide Derivatives 8-14 to Compounds 15-21.

A solution of bisbenzamide (8-14) (0.05 M) in HOAc was placed under a N₂ atmosphere. Palladium black (20 mg/mmol bisbenzamide) was added and the reaction vessel was purged again with N₂. Hydrogen gas was bubbled through the solution for 5 h until all benzylethers were cleaved (MS analysis). The vessel was purged with nitrogen gas and the reaction mixture was filtered over a Whatman fiberglass filter. The filtrate was concentrated in vacuo, the residue redissolved in TFA (35% aq. solution) and stirred for 3 h. The solution was concentrated and the residue was dissolved in a mixture of water and tBuOH (4:1 v/v). The mixture was frozen and lyophilized overnight yielding the product as an off white amorphous solid (yields 90%-quant.).

General Procedure 3: Staudinger Reduction

A solution of compounds 26-32 or azide 149 (0.4 to 0.6 mmol) in THF (10 mL/mmol) was treated with Me₃P (1 M solution, 5 eq.) and the reaction mixture was stirred for 3 h. Water (13 eq.) was added and the solution was stirred for another hour, after which it was concentrated. The residue was co-evaporated with toluene. The obtained crude amine was used without further purification.

General Procedure 4: EDC-mediated Amide Formation.

To a solution of amine 25, crude amine 33, the crude amines obtained after reduction of azides 27-32, amines 117-118, or the crude amines obtained after reduction of azide 149 in DMF (25 mL/mmol) were added the appropriate organic acid (1.5 eq.), EDC.HCl (2 eq.), diisopropylethylamine (4 eq.) and a catalytic amount of 1-hydroxybenzotriazole and the reaction mixture was stirred overnight at rt. The reaction mixture was concentrated and partioned between water and EtOAc. The organic layer was dried over sodium sulphate, filtered and evaporated. The products were then purified by column chromatography with appropriate eluents.

General Procedure 5: Formation of 5-sulfonamide Derivatives 94-103 from Amine 33.

A solution of the crude amine 33 in CH₂Cl₂ (20 mL/mmol) was cooled in an ice-bath, treated with triethylamine (2 eq.) and the appropriate sulfonyl chloride (1 eq.) and the reaction mixture was stirred for 3 h. When TLC indicated that the reaction was finished, the reaction mixture was concentrated under reduced pressure. The residue was taken up in EtOAc and washed with 0.1 M aq. HCl and sat. aq. NaHCO₃ solution. The organic layer was dried over sodium sulphate, filtered and concentrated. The residue was purified by column chromatography.

General Procedure 6: One-pot Staudinger Reduction and Amide Formation from Phthalimide 24.

To a solution of phthalimide 24 in THF (10 mL/mmol) was added the appropriate acid chloride (2 eq.), followed by PMe$_3$ (1M solution in THF, 4 eq). Flocculation was observed upon addition, after which the reaction mixture turned yellow. The RM was stirred overnight at rt. TLC analysis (toluene/EtOAc 1:1) showed complete consumption of starting material. The RM was concentrated in vacuo and adsorbed onto celite. Purification via FCC (toluene/EtOAc 1:0→1:1) afforded compounds 115 and 116.

General Procedure 7: Ing-Manske Procedure for Cleavage of Phthalimides 115 and 116

To a solution of phthalimides 115-116 in EtOH (12 to 20 mL/mmol) was added hydrazine monohydrate (2 eq.). The RM was heated to 60° C. for 5 h. When the reaction was complete (TLC toluene/EtOAc 1:1 and CH$_2$Cl$_2$/MeOH 9:1), the RM was concentrated in vacuo and the residue adsorbed onto celite. Purification via FCC (CH$_2$Cl$_2$/MeOH/NH$_4$OH 100:0:1→85:15:1) afforded compounds 117 and 118.

General Procedure 8: Deprotection—Cleavage of Acetonide.

A known amount of the isopropylidene protected compound was treated with a 35% aq. CF$_3$COOH solution (30 mL/mmol) overnight at room temperature. For the more lipophilic derivatives the reaction mixture was put at ultra sound for 2-3 h. When TLC indicated that the deprotection was complete, the reaction mixture was concentrated and, if required, purified by column chromatography.

(3aR,6R,6aR)-6-(Azidomethyl)-2,2-dimethyldihydrofuro[3,4-d][1,3]dioxol-4(3aH)-one (1)

To a solution of 2,3-O-isopropylidene-D-ribonolactone (15.1 g, 80.0 mmol) and triethylamine (22.3 mL, 160.0 mmol) in CH$_2$Cl$_2$ (400 mL) stirred at 0° C., methanesulfonyl chloride (7.4 mL, 96.0 mmol) was added dropwise under nitrogen atmosphere. The reaction mixture was allowed to attain ambient temperature. After 3 hours, TLC analysis (toluene/EtOAc 3:2) showed complete consumption of the starting material. The reaction mixture was washed with saturated sodium bicarbonate solution and water. The organic layer was dried over sodium sulphate, filtered and concentrated in vacuo to afford the mesylate as a yellow to orange colored oil. To this crude mesylate, dissolved in DMF (400 mL), was added sodium azide (26.0 g, 400.0 mmol). After overnight reaction at 60° C., TLC analysis (toluene/EtOAc 3:2) showed the presence of one major product. The solvent was evaporated and the residue was taken up in EtOAc (350 mL). The resulting solution was washed with saturated sodium bicarbonate solution and water. The organic layer was dried over sodium sulphate, filtered and concentrated in vacuo. This crude material was purified by flash column chromatography (toluene/EtOAc 3:2) to afford azidolactone 1 as a pale yellow oil (93.9% over two steps). $^1$H NMR (300 MHz, CDCl$_3$) δ ppm 1.38 (s, 3 H) 1.47 (s, 3 H) 3.67 (dd, J=13.2, 2.3 Hz, 1 H) 3.79 (dd, J=13.2, 3.2 Hz, 1 H) 4.64 (app. d, J=5.9 Hz, 1 H) 4.67 (app. t, J=2.8 Hz, 1 H) 4.85 (d, J=5.6 Hz, 1 H). $^{13}$C NMR (75 MHz, CDCl$_3$) δ ppm 25.6, 26.8, 52.7, 75.3, 78.2, 80.2, 113.8, 173.5.

(3aR,6R,6aR)-6-(Azidomethyl)-2,2-dimethyltetrahydrofuro[3,4-d][1,3]dioxol-4-ol (2)

Azidolactone 1 (13.9 g, 65.3 mmol) was dissolved in CH$_2$Cl$_2$ (170 mL) and cooled to −78° C. This solution was flushed with nitrogen gas, after which a solution of diisobutylaluminium hydride (1M in toluene, 71.8 mL, 71.8 mmol) was added dropwise. The cooled solution was allowed to react for 4 hours under nitrogen. The reaction was quenched by adding EtOAc (11 mL) and the mixture was allowed to come to room temperature over 30 min, after which a saturated Na$^+$/K$^+$ tartrate solution (450 mL) was added. The mixture was stirred for another hour and extracted with EtOAc (4×250 mL). The combined organic layers were dried (sodium sulphate), filtered and concentrated in vacuo. The residue was purified by flash column chromatography (hexane/EtOAc 3:1) to afford 13.7 g of azidolactole 2 as a pale oil (97.5%). Anomeric ratio=82:18. Major anomer: $^1$H NMR (300 MHz, CDCl$_3$) δ ppm 1.33 (s, 3 H) 1.49 (s, 3 H) 3.39 (dd, J=12.6, 5.9 Hz, 1 H) 3.57 (dd, J=12.6, 7.3 Hz, 1 H) 4.05 (d, J=4.4 Hz, 1 H) 4.32 (ddd, J=7.3, 5.9, 0.9 Hz, 1 H) 4.61-4.72 (m, 2 H) 5.47 (d, J=4.7 Hz, 1 H). $^{13}$C NMR (75 MHz, CDCl$_3$) δ ppm 24.9, 26.4, 54.0, 82.2, 85.5, 86.0, 103.3, 112.8.

(3aR,6R,6aR)-6-(Azidomethyl)-3a-(hydroxymethyl)-2,2-dimethyltetrahydrofuro[3,4-d][1,3]dioxol-4-ol (3)

To a stirred solution of 2 (13.7 g, 63.7 mmol) in MeOH (400 mL) was added K$_2$CO$_3$ (4.4 g, 31.8 mmol) and an aqueous solution of formaldehyde (38% aqueous solution, 130 mL). The solution was heated under reflux. After 24 h, TLC analysis (CH$_2$Cl$_2$/MeOH 97:3) showed complete consumption of the starting material and the presence of a major product. The reaction mixture was cooled to ambient temperature and the MeOH was evaporated under reduced pressure. The residual aqueous solution was extracted with EtOAc (3×250 mL). The organic layers were combined, dried over sodium sulphate, filtered and concentrated. The residue was purified by flash chromatography (CH$_2$Cl$_2$/MeOH 98:2) to afford compound 3 as a colorless syrup in 83.5% yield, along with a significant amount of triol 22 (11.5%). Anomeric ratio=56:44. Major anomer: $^1$H NMR (300 MHz, CDCl$_3$) δ ppm 1.43 (s, 3 H) 1.50 (s, 3 H) 2.64 (t, J=6.9 Hz, 1 H) 3.37 (dd, J=12.6, 5.9 Hz, 1 H) 3.60 (dd, J=12.6, 7.9 Hz, 1 H) 3.74-3.98 (m, 3 H) 4.28-4.36 (m, 1 H) 4.52 (app. s, 1 H) 5.49 (d, J=4.4 Hz, 1 H). $^{13}$C NMR (75 MHz, CDCl$_3$) δ ppm 27.7, 28.1, 53.6, 63.41, 84.8, 85.5, 91.6, 105.2, 114.1. Minor anomer: $^1$H NMR (300 MHz, CDCl$_3$) δ ppm 1.48 (s, 3 H) 1.60 (s, 3 H) 2.17 (t, J=5.7 Hz, 1 H) 3.46 (dd, J=12.9, 4.7 Hz, 1 H) 3.53 (dd, J=13.0, 4.5 Hz, 1 H) 3.74-3.98 (m, 3 H) 4.28-4.36 (m, 1 H) 4.53 (d, J=0.9 Hz, 1 H) 5.22 (d, J=8.5 Hz, 1 H). $^{13}$C NMR (75 MHz, CDCl$_3$) δ ppm 27.3, 27.4, 52.6, 63.35, 80.8, 83.7, 93.7, 98.2, 115.5.

(3aR,6R,6aR)-6-(Azidomethyl)-3a-(((tert-butyldimethylsilyl)oxy)methyl)-2,2-dimethyl tetrahydrofuro[3,4-d][1,3]dioxol-4-ol (4)

5-Azido-5-deoxy-2,3-O-isopropylidene-D-hamamelose (5.6 g, 22.8 mmol) was taken up in DMF (250 mL). The solution was placed under a nitrogen atmosphere and cooled to 0° C. Imidazole (2.4 g, 35 mmol) and tert-butylchlorodimethylsilane (4.1 g, 27 mmol) were added and the mixture was stirred for 16 h allowing the temperature to rise to rt. The mixture was taken to dryness and the residue was redissolved in EtOAc (200 mL) and water (200 mL) and transferred to a separatory funnel. The layers were separated and the aqueous layer was extracted with ethyl acetate (3×100 mL). All organic fractions were pooled, dried (Na$_2$SO$_4$), filtered and concentrated in vacuo. The residue was purified by silica gel chromatography (toluene/EtOAc 95:5) yielding the title product 4 (5.2 g, 14.5 mmol, 63.4%) as a colorless oil alongside significant amounts of starting material, anomeric- and bis-silylether. The abovementioned side products could be recycled into the starting material via a TBAF mediated deprotection. Anomeric ratio=29:71. Major anomer: $^1$H NMR (300 MHz, CDCl$_3$) δ ppm 0.07 (s, 6 H), 0.90 (m, 9 H), 1.42 (s, 3 H), 1.53 (s, 3 H), 3.30-3.42 (m, 2 H) 3.72 (dd J=12.8 Hz, J=10.5 Hz, 2H), 3.80 (d, J=9.7 Hz 1 H) 3.90-3.95 (m, 1 H) 4.17-4.24 (m, 1 H), 4.51 (d, J=1.93 Hz, 1 H) 5.11 (d, J=9.7 Hz, 1 H). $^{13}$C NMR (75 MHz, CDCl$_3$) d ppm −5.6, −5.4, 18.3, 25.9, 27.9, 28.0, 53.4, 63.6, 84.4, 84.6, 93.20, 105.5, 114.0. Minor anomer: $^1$H NMR (300 MHz, CDCl$_3$) δ ppm 0.08 (s, 3 H) 0.09 (s, 3 H) 0.89 (s, 9 H) 1.38 (s, 3 H), 1.44 (s, 3 H), 3.29 (dd J=11.8 Hz, J=6.8 Hz, 1H) 3.53 (dd J=11.8 Hz, J=6.8 Hz 1 H) 3.79 (d, J=10.9 Hz, 1 H) 3.93 d, J=10.9 Hz, 1 H) 4.17-4.24 (m, 1 H) 4.32 (d, J=6.32 Hz, 1 H) 4.48 (d, J=1.40 Hz, 1 H), 5.34 (d, J=6.32 Hz, 1 H). $^{13}$C NMR (75 MHz, CDCl$_3$) d ppm −5.6, −5.5, 18.4, 25.9, 27.3, 27.4, 51.7, 63.2, 80.5, 83.7, 90.8, 97.8, 114.3, 114.9. HRMS (ESI-TOF) m/z: [M+H]$^+$ Calcd for C$_{15}$H$_{30}$N$_3$O$_5$Si$^+$ 360.19492; Found 360.1953.

((3aR,4R,6R,6aR)-6-(Azidomethyl)-4-(benzyloxy)-2,2-dimethyldihydrofuro[3,4-d][1,3]dioxol-3a(4H)-yl)methanol and ((3aR,4S,6R,6aR)-6-(Azidomethyl)-4-(benzyloxy)-2,2-dimethyldihydrofuro[3,4-d][1,3]dioxol-3a(4H)-yl)methanol (5)

Silylether 4 (14.5 g, 40 mmol) was taken up in DMF (400 mL) and benzyl bromide (5.3 mL, 7.5 g, 44 mmol) was added. The reaction mixture was placed under a N$_2$ atmosphere and cooled to 0° C. on ice. Sodium hydride (60% in mineral oil, 2.0 g, 50 mmol) was added in portions. The mixture was stirred overnight allowing the temperature to rise to rt. MeOH (5 mL) was added and stirring was continued for 1 h. The reaction mixture was poured into a separatory funnel containing water (1.0 L) and the resulting liquid has extracted with diethylether (4×300 mL). All organic extracts were pooled, dried (Na$_2$SO$_4$) and taken to dryness. The crude intermediate was dissolved in THF (300 mL) and TBAF (50 mL 1.0 M in THF, 50 mmol) was added. After 4 h the reaction mixture was concentrated in vacuo and the residue was redissolved in EtOAc (400 mL) and water (400 mL). The biphasic mixture was transferred to a separatory funnel and separated. The aqueous phase was extracted with ethyl acetate (2×250 mL). All organic fractions were pooled, dried (Na$_2$SO$_4$) and taken to dryness. The residue was purified by silica gel chromatography to yield a higher running (5.7 g, 17.0 mmol, 42.5%) and a lower running anomer (5.6 g, 16.7 mmol, 41.8%) both as colorless oils. Top anomer: $^1$H NMR (300 MHz, CDCl$_3$) δ ppm 1.40 (s, 3 H) 1.48 (s, 3 H) 2.58 (br. s., 1 H) 3.27 (dd, J=12.6, 6.4 Hz, 1 H) 3.48 (dd, J=12.6, 8.4 Hz, 1 H) 3.77 (d, J=12.2 Hz, 1 H) 3.89 (d, J=12.2 Hz, 1 H) 4.33 (ddd, J=8.4, 6.4, 1.10 Hz, 1 H) 4.46-4.56 (m, 2 H) 4.80 (d, J=11.6 Hz, 1 H) 5.20 (s, 1 H) 7.23-7.39 (m, 5 H). $^{13}$C NMR (75 MHz, CDCl$_3$) δ ppm 27.6, 28.0, 53.4, 62.9, 70.2, 84.7, 85.6, 93.7, 109.5, 113.8, 127.9, 128.1, 128.6, 136.6. Bottom anomer: $^1$H NMR (300 MHz, CDCl$_3$) δ ppm 1.38 (s, 3 H) 1.54 (s, 3 H) 2.80 (br. s., 1 H) 3.37 (dd, J=13.20, 4.70 Hz, 1 H) 3.51 (dd, J=13.20, 3.80 Hz, 1 H) 3.64 (d, J=12.00 Hz, 1 H) 3.76 (d, J=12.00 Hz, 1 H) 4.32 (m, J=3.70, 3.70, 3.70 Hz, 1 H) 4.37 (d, J=3.20 Hz, 1 H) 4.58 (d, J=12.01 Hz, 1 H) 4.81 (d, J=12.01 Hz, 1 H) 4.86 (s, 1 H) 7.16-7.44 (m, 5 H). $^{13}$C NMR (75 MHz, CDCl$_3$) d ppm 26.4, 27.3, 52.1, 63.4, 69.6, 80.9, 81.8, 92.5, 102.1, 116.3, 127.5, 127.6, 128.2, 137.6. HRMS (ESI-TOF) m/z: [M+H]$^+$ Calcd for C$_{16}$H$_{22}$N$_3$O$_5^+$ 336.15540; Found 336.1561.

((3aR,4R,6R,6aR)-6-(azidomethyl)-4-(benzyloxy)-2,2-dimethyldihydrofuro[3,4-d][1,3]dioxol-3a(4H)-yl)methyl methanesulfonate (6)

A solution of the top anomer of 5 (500 mg, 1.5 mmol) in CH$_2$Cl$_2$ (15 mL) containing triethylamine (280 μL, 2 mmol) was placed under a nitrogen atmosphere and cooled to 0° C. on ice. Methanesulfonyl chloride (132 μL, 1.7 mmol) was added. After stirring for 2 h the mixture was transferred to a separatory funnel, diluted with EtOAc (50 mL) and washed with HCl (1M, 40 mL), NaHCO$_3$ (sat. aq., 40 mL). The organic layer was separated, dried (Na$_2$SO$_4$), concentrated in vacuo and purified by silica gel chromatography (toluene/EtOAc 1:4) to yield the title compound (590 mg, 1.42 mmol, 94.7%) as a colorless oil. $^1$H NMR (300 MHz, CDCl$_3$) δ ppm 1.45 (s, 3 H) 1.49 (s, 3 H) 2.95 (s, 3 H) 3.31 (dd, J=12.6, 6.7 Hz, 1 H) 3.51 (dd, J=12.6, 8.1 Hz, 1 H) 4.28-4.35 (m, 1 H) 4.39-4.56 (m, 4 H) 4.78 (d, J=11.7 Hz, 1 H) 5.17 (s, 1 H) 7.23-7.43 (m, 5 H). $^{13}$C NMR (75 MHz, CDCl$_3$) δ ppm 27.7, 27.8, 37.4, 53.5, 68.6, 70.1, 84.7, 85.4, 92.2, 107.8, 114.9, 128.16, 128.17, 128.6, 136.4. HRMS (ESI-TOF) m/z: [M+Na]$^+$ Calcd for C$_{17}$H$_{23}$N$_3$NaO$_7$S$^+$ 436.11489; Found 436.1159.

(3aR,4R,6R,6aR)-3a,6-bis(azidomethyl)-4-(benzyloxy)-2,2-dimethyltetrahydrofuro[3,4-d][1,3]dioxole (7)

Methanesulfonic ester 6 (590 mg, 1.42 mmol) was taken up in DMF (50 mL) and NaN$_3$ (1.4 g, 21.3 mmol) was added. The mixture was stirred at 90° C. for 48 h. The mixture was allowed to cool to rt and taken to dryness. The residue was dissolved in Et$_2$O (30 mL) and water (30 mL) and transferred to a separatory funnel. The layers were separated and the aqueous layer was extracted once with Et$_2$O (30 mL). All ether fractions were pooled, dried (Na$_2$SO$_4$) and concentrated in vacuo. The residue was purified by silica gel chromatography (hexane/EtOAc 100:0→90:10) yielding the compound (356 mg, 1.0 mmol, 70%) as a colorless viscous oil. $^1$H NMR (300 MHz, CDCl$_3$) δ ppm 1.49 (s, 3 H) 1.50 (s, 3 H) 3.27 (dd, J=12.6, 6.7 Hz, 1 H) 3.44-3.56 (m, 2 H) 3.66 (d, J=13.2, 1 H) 4.30 (t, J=7.18 Hz, 1 H) 4.38 (s, 1 H) 4.54 (d, J=11.6 Hz, 1 H) 4.79 (d, J=11.6 Hz, 1 H) 5.19 (s, 1 H) 7.24-7.42 (m, 5 H). $^{13}$C NMR (75 MHz, CDCl$_3$) δ ppm 27.8, 28.2, 53.0, 53.8, 70.3, 85.4, 93.9, 108.2, 114.9, 128.20, 128.23, 128.7, 136.7. HRMS (ESI-TOF) m/z: [M+H−N$_2$]$^+$ Calcd for C$_{16}$H$_{21}$N$_4$O$_4^+$ 333.15573; Found 333.1568.

N,N'-(((3aR,4R,6R,6aR)-4-(benzyloxy)-2,2-dimethyldihydrofuro[3,4-d][1,3]dioxole-3a,6(4H)-diyl)bis(methylene))bis(3,4,5-tris(benzyloxy)benzamide) (8)

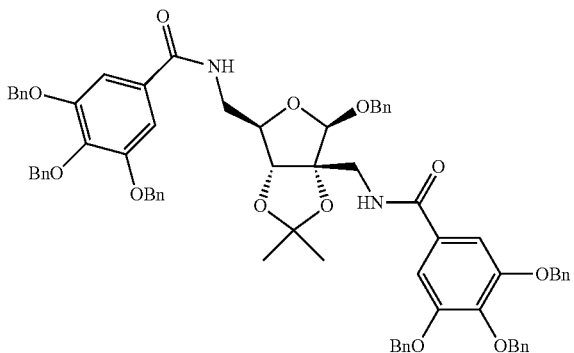 [SMILES: CC1(C)O[C@@H]2[C@@H](CNC(=O)c3cc(OCc4ccccc4)c(OCc4ccccc4)c(OCc4ccccc4)c3)O[C@@H](OCc3ccccc3)[C@]2(CNC(=O)c2cc(OCc3ccccc3)c(OCc3ccccc3)c(OCc3ccccc3)c2)O1]

General procedure 1. White foam. $^1$H NMR (300 MHz, CDCl$_3$) δ ppm 1.38 (s, 3 H) 1.50 (s, 3 H) 3.58-3.70 (m, 1 H) 3.70-3.82 (m, 2 H) 4.08 (dd, J=14.6, 6.7 Hz, 1 H) 4.44-4.54 (m, 2 H) 4.63 (s, 1 H) 4.76 (d, J=11.8 Hz, 1 H) 4.98-5.08 (m, 12 H) 5.19 (s, 1 H) 6.53 (t, J=6.0 Hz, 1 H) 6.99 (t, J=5.9 Hz, 1 H) 7.03 (s, 2 H) 7.17 (s, 2 H) 7.17-7.27 (m, 12 H) 7.27-7.38 (m, 23 H). $^{13}$C NMR (75 MHz, CDCl$_3$) δ ppm 27.7, 28.0, 41.4, 42.5, 70.5, 71.3, 71.4, 75.2, 75.3, 84.9, 85.0, 93.9, 106.9, 107.1, 109.1, 113.5, 127.6, 127.7, 127.9, 127.96, 128.04, 128.1, 128.22, 128.24, 128.3, 128.57, 128.60, 128.7, 129.4, 129.5, 136.6, 136.7, 136.8 137.5, 137.6, 141.4, 141.6, 152.8, 153.0, 167.3, 167.6. HRMS (ESI-TOF) m/z: [M+H]$^+$ Calcd for C$_{72}$H$_{69}$N$_2$O$_{12}$$^+$ 1153.4845; Found: 1153.4854.

N,N'-(((3aR,4R,6R,6aR)-4-(benzyloxy)-2,2-dimethyldihydrofuro[3,4-d][1,3]dioxole-3a,6(4H)-diyl)bis(methylene))bis(3,4,5-trimethoxybenzamide) (9)

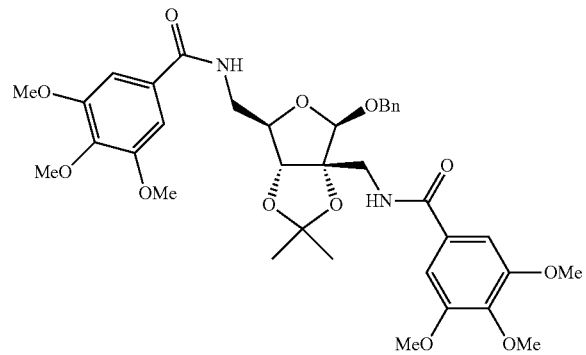 [SMILES: COc1cc(C(=O)NC[C@H]2O[C@@H](OCc3ccccc3)[C@]3(CNC(=O)c4cc(OC)c(OC)c(OC)c4)OC(C)(C)O[C@H]23)cc(OC)c1OC]

General procedure 1. White foam. $^1$H NMR (300 MHz, CDCl$_3$) δ ppm 1.43 (s, 3 H) 1.50 (s, 3 H) 3.54-3.79 (m, 3 H) 3.81 (s, 6 H) 3.82 (s, 6 H) 3.86 (s, 3 H) 3.87 (s, 3 H) 4.15 (dd, J=14.7, 7.2 Hz, 1 H) 4.47-4.59 (m, 2 H) 4.62 (s, 1 H) 4.83 (d, J=11.6 Hz, 1 H) 5.23 (s, 1 H) 6.67 (t, J=6.1 Hz, 1 H) 6.94 (s, 2 H) 7.04 (s, 2 H) 7.09 (t, J=5.7 Hz, 1 H) 7.23-7.31 (m, 5 H). $^{13}$C NMR (75 MHz, CDCl$_3$) δ ppm 27.6, 28.0, 41.3, 42.44, 56.30, 56.31, 60.9, 61.0, 70.5, 84.7, 84.9, 94.0, 104.4, 104.6, 109.2, 113.4, 127.9, 128.2, 128.7, 129.5, 129.6, 136.8, 141.0, 141.2, 153.1, 153.3, 167.5, 167.8. HRMS (ESI-TOF) m/z: [M+Na]$^+$ Calcd for C$_{36}$H$_{44}$N$_2$NaO$_{12}$ 719,27865; Found: 719,2809.

N,N'-(((3aR,4R,6R,6aR)-4-(benzyloxy)-2,2-dimethyldihydrofuro[3,4-d][1,3]dioxole-3a,6(4H)-diyl)bis(methylene))bis(3,4-bis(benzyloxy)benzamide) (10)

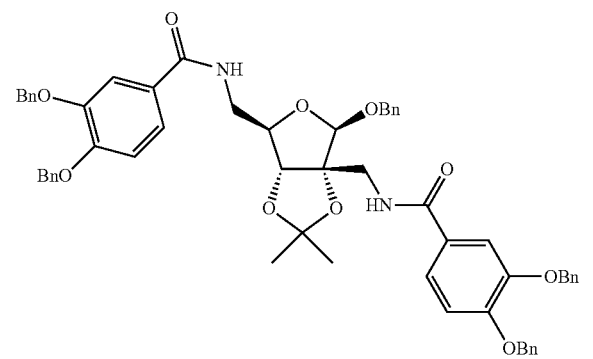 [SMILES: CC1(C)O[C@@H]2[C@@H](CNC(=O)c3ccc(OCc4ccccc4)c(OCc4ccccc4)c3)O[C@@H](OCc3ccccc3)[C@]2(CNC(=O)c2ccc(OCc3ccccc3)c(OCc3ccccc3)c2)O1]

General procedure 1. White foam. $^1$H NMR (300 MHz, CDCl$_3$) δ ppm 1.38 (s, 3 H) 1.47 (s, 3 H) 3.48-3.59 (m, 1 H) 3.73-3.85 (m, 2 H) 3.98 (dd, J=14.5, 6.3 Hz, 1 H) 4.45 (t, J=6.8 Hz, 1 H) 4.52 (d, J=11.6 Hz, 1 H) 4.57 (s, 1 H) 4.78 (d, J=11.6 Hz, 1 H) 5.09 (s, 2 H) 5.10-5.12 (m, 4 H) 5.15 (s, 2 H) 5.20 (s, 1 H) 6.56 (t, J=5.5 Hz, 1 H) 6.78 (d, J=2.3 Hz, 1 H) 6.81 (d, J=2.3 Hz, 1 H) 6.89 (t, J=5.7 Hz, 1 H) 7.05 (d, J=8.36 Hz, 1 H) 7.18-7.43 (m, 26 H) 7.47 (d, J=1.6 Hz, 1 H) 7.53 (d, J=2.0 Hz, 1 H). $^{13}$C NMR (75 MHz, CDCl3) δ ppm 27.7, 28.0, 41.4, 42.3, 70.5, 71.9, 71.0, 71.2, 71.3, 84.9, 85.0, 93.9, 109.1, 113.4, 113.6, 113.8, 114.0, 114.1, 120.0, 120.3, 127.0, 127.1, 127.19, 127.23, 127.5, 127.9, 127.99, 128.02, 128.06, 128.2, 128.5, 128.6, 128.7, 128.8, 136.71, 136.80 (br), 137.0, 148.8, 148.9, 151.7, 151.9, 167.0, 167.2. HRMS (ESI-TOF) m/z: [M+H]$^+$ Calcd for C$_{58}$H$_{57}$N$_2$O$_{10}$$^+$ 941, 40077; Found: 941,4030.

N,N'-(((3aR,4R,6R,6aR)-4-(benzyloxy)-2,2-dimethyldihydrofuro[3,4-d][1,3]dioxole-3a,6(4H)-diyl)bis(methylene))bis(3,5-bis(benzyloxy)benzamide) (11)

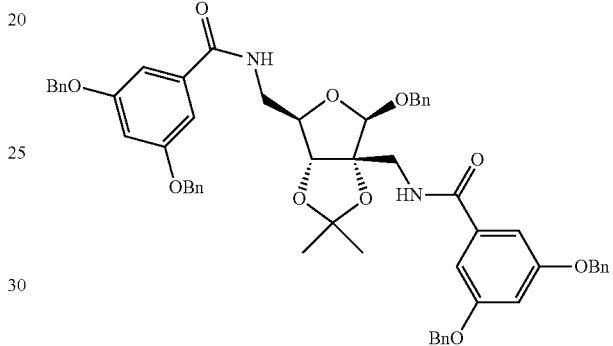

General procedure 1. White foam. $^1$H NMR (300 MHz, CDCl$_3$) δ ppm 1.40 (s, 3 H) 1.48 (s, 3 H) 3.58-3.76 (m, 2 H) 3.81 (dd, J=14.5, 5.7 Hz, 1 H) 4.04 (dd, J=14.5, 6.6 Hz, 1 H) 4.45 (t, J=7.0 Hz, 1 H) 4.54 (d, J=12.0 Hz, 1 H) 4.58 (s, 1 H) 4.78 (d, J=11.7 Hz, 1 H) 4.96 (s, 4 H) 4.98 (s, 4 H) 5.19 (s, 1 H) 6.58 (t, J=6.0 Hz, 1 H) 6.68 (t, J=2.1 Hz, 1 H) 6.70 (t, J=2.1 Hz, 1 H) 6.88 (t, J=5.7 Hz, 1 H) 6.93 (d, J=2.1 Hz, 2 H) 7.04 (d, J=2.1 Hz, 2 H) 7.14-7.38 (m, 25 H); $^{13}$C NMR (75 MHz, CDCl$_3$) δ ppm 27.7, 28.0, 41.6, 42.5, 70.3, 70.4, 70.5, 84.9, 85.1, 93.9, 105.4, 105.6, 106.1, 106.2, 109.0, 113.6, 127.6, 127.7, 128.0, 128.1, 128.24, 128.28, 128.66, 128.71, 128.8, 136.3, 136.4, 136.5, 136.6, 136.8, 160.1, 160.2, 167.3, 167.6. HRMS (ESI-TOF) m/z: [M+H]$^+$ Calcd for C$_{58}$H$_{57}$N$_2$O$_{10}$$^+$ 941,40077; Found: 941,4005.

N,N'-(((3aR,4R,6R,6aR)-4-(benzyloxy)-2,2-dimethyldihydrofuro[3,4-d][1,3]dioxole-3a,6(4H)-diyl)bis(methylene))bis(3-(benzyloxy)benzamide) (12)

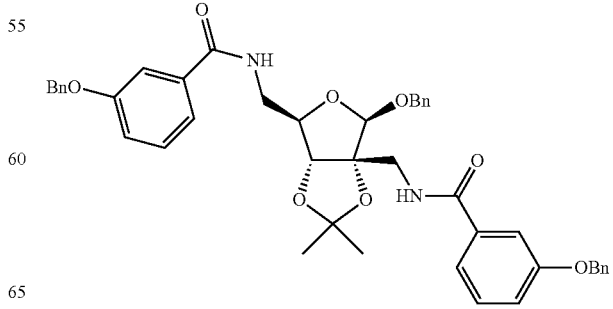

General procedure 1. White foam. $^1$H NMR (300 MHz, CDCl$_3$) δ ppm 1.41 (s, 3 H) 1.49 (s, 3 H) 3.53-3.67 (m, 1 H) 3.74-3.89 (m, 2 H) 4.04 (dd, J=14.4, 6.6 Hz, 1 H) 4.02-4.02 (m, 1 H) 4.48 (t, J=7.0 Hz, 1 H) 4.52-4.60 (m, 2 H) 4.81 (d, J=11.5 Hz, 1 H) 5.04 (s, 2 H) 5.05 (s, 2 H) 5.22 (s, 1 H) 6.63 (t, J=6.1 Hz, 1 H) 6.90 (t, J=5.9 Hz, 1 H) 7.03-7.11 (m, 2 H) 7.12-7.17 (m, 1 H) 7.22-7.43 (m, 19 H) 7.45-7.51 (m, 1 H). $^{13}$C NMR (75 MHz, CDCl$_3$) δ ppm 27.7, 28.0, 41.5, 42.4, 70.2, 70.3, 70.6, 84.9, 85.0, 93.9, 109.2, 113.47, 113.54, 113.57, 118.7, 118.8, 118.9, 119.2, 127.67, 127.69, 128.15, 128.24, 128.28, 128.35, 128.70, 128.74, 128.86, 129.7, 129.9, 135.5, 135.6, 136.6, 136.7, 136.8, 159.1, 159.2, 167.4, 167.5. HRMS (ESI-TOF) m/z: [M+Na]$^+$ Calcd for C$_{44}$H$_{44}$N$_2$NaO$_8$$^+$ 751.29899; Found: 751.3020.

N,N'-(((3aR,4R,6R,6aR)-4-(benzyloxy)-2,2-dimethyldihydrofuro[3,4-d][1,3]dioxole-3a,6(4H)-diyl)bis(methylene))bis(4-(benzyloxy)benzamide) (13)

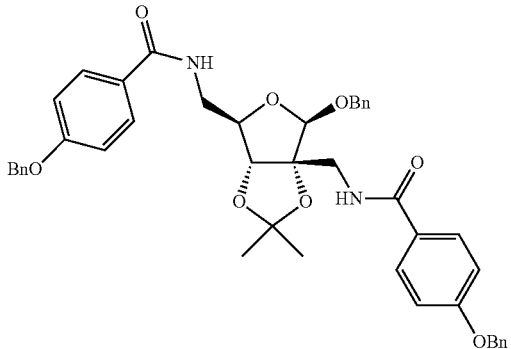 [SMILES: CC1(C)O[C@@H]2[C@@H](CNC(=O)c3ccc(OCc4ccccc4)cc3)O[C@@H](OCc3ccccc3)[C@]2(CNC(=O)c2ccc(OCc3ccccc3)cc2)O1]

General procedure 1. White foam. $^1$H NMR (300 MHz, CDCl$_3$) δ ppm 1.39 (s, 3 H) 1.47 (s, 3 H) 3.47-3.60 (m, 1 H) 3.77-3.91 (m, 2 H) 4.00 (dd, J=14.5, 6.3 Hz, 1 H) 4.47 (t, J=7.0 Hz, 1 H) 4.54 (d, J=11.4 Hz, 1 H) 4.59 (s, 1 H) 4.80 (d, J=11.6 Hz, 1 H) 5.05 (s, 2 H) 5.07 (s, 2 H) 5.22 (s, 1 H) 6.70 (t, J=6.2 Hz, 1 H) 6.92 (t, J=7.7 Hz, 4 H) 7.04 (t, J=5.8 Hz, 1 H) 7.24-7.44 (m, 15 H) 7.63 (d, J=8.7 Hz, 2 H) 7.72 (d, J=8.9 Hz, 2 H). $^{13}$C NMR (75 MHz, CDCl$_3$) δ ppm 27.7, 27.9, 41.3, 42.2, 70.08, 70.14, 70.4, 84.88, 84.89, 93.9, 109.2, 113.4, 114.6, 114.8, 126.5, 126.6, 127.50, 127.53, 128.19, 128.24, 128.3, 128.69, 128.72, 128.75, 128.76, 128.78, 129.0, 129.1, 136.3, 136.4, 136.9, 161.4, 161.5, 167.0, 167.1. HRMS (ESI-TOF) m/z: [M+Na]$^+$ Calcd for C$_{44}$H$_{44}$N$_2$NaO$_8$$^+$ 751.29899, found: 751.3013.

N,N'-(((3aR,4R,6R,6aR)-4-(benzyloxy)-2,2-dimethyldihydrofuro[3,4-d][1,3]dioxole-3a,6(4H)-diyl)bis(methylene))dibenzamide (14)

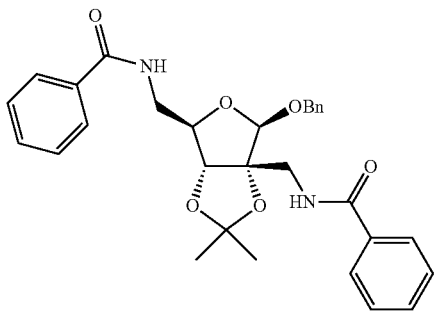 [SMILES: CC1(C)O[C@@H]2[C@@H](CNC(=O)c3ccccc3)O[C@@H](OCc3ccccc3)[C@]2(CNC(=O)c2ccccc2)O1]

General procedure 1. White foam. $^1$H NMR (300 MHz, CDCl$_3$) δ ppm 1.41 (s, 3 H) 1.49 (s, 3 H) 3.53-3.64 (m, 1 H) 3.78-3.89 (m, 2 H) 4.03 (dd, J=14.4, 6.4 Hz, 1 H) 4.49 (t, J=7.0 Hz, 1 H) 4.54-4.61 (m, 2 H) 4.82 (d, J=11.3 Hz, 1 H) 5.24 (s, 1 H) 6.71 (t, J=6.0 Hz, 1 H) 6.98 (t, J=5.4 Hz, 1 H) 7.27-7.52 (m, 11 H) 7.63-7.71 (m, 2 H) 7.71-7.80 (m, 2 H). $^{13}$C NMR (75 MHz, CDCl$_3$) δ ppm 27.7, 28.0, 41.5, 42.4, 70.6, 85.0, 94.0, 109.2, 113.5, 127.0, 127.1, 128.35, 128.36, 128.6, 128.8, 128.9, 131.6, 131.8, 134.0, 134.1, 136.8, 167.6, 167.7. HRMS (ESI-TOF) m/z: [M+Na]$^+$ Calcd for C$_{30}$H$_{32}$N$_2$NaO$_6$$^+$ 539.21526, found: 539.2169.

N,N'-(((2R,3R,4R)-3,4,5-trihydroxytetrahydrofuran-2,4-diyl)bis(methylene))bis(3,4,5-trihydroxybenzamide) (15)

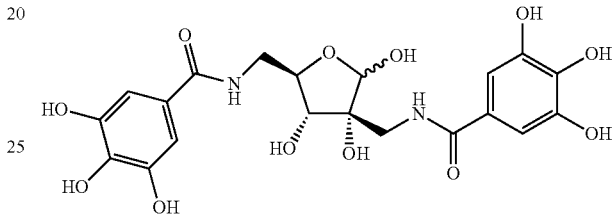

General procedure 2. White foam. (56:44 mixture of anomers)$^1$H NMR (300 MHz, D$_2$O) δ 3.38-3.55 (m, 2.56 H), 3.71-3.88 (m, 2 H), 4.00 (d, J=8.1 Hz, 0.44 H), 4.01-4.16 (m, 1 H), 6.63 (s, 1.12 H), 6.65 (s, 1.12 H), 6.73 (s, 0.88 H); $^{13}$C NMR (75 MHz, D$_2$O) δ ppm 39.4, 40.7, 41.1, 41.7, 70.6, 71.6, 77.5, 79.1, 79.9, 80.0, 97.7, 101.6, 106.96, 107.00, 107.11, 107.18, 123.9, 124.1, 124.5, 124.6, 136.2 (br.), 136.3 (br.), 144.3, 144.5, 169.9, 170.1, 170.2, 170.3. HRMS (ESI-TOF) m/z: [M+H]$^+$ Calcd for C$_{20}$H$_{23}$N$_2$O$_{12}$$^+$ 483, 12455; Found: 483,1250.

N,N'-(((2R,3R,4R)-3,4,5-trihydroxytetrahydrofuran-2,4-diyl)bis(methylene))bis(3,4,5-trimethoxybenzamide) (16)

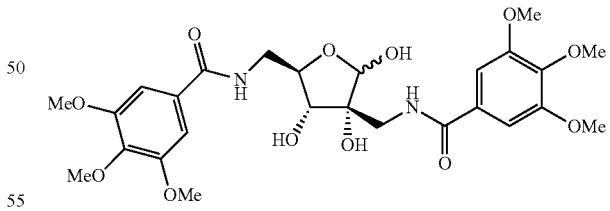

General procedure 2. White foam. (70:30 mixture of anomers)$^1$H NMR (300 MHz, CD$_3$OD) δ 3.50-3.90 (m, 22.30 H), 4.08-4.19 (m, 1.70H), 5.14 (s, 0.70 H), 5.22 (s 0.30 H), 7.12-7.18 (m, 4 H). $^{13}$C NMR (75 MHz, CD$_3$OD) δ ppm 42.7, 43.0, 44.9, 45.9, 56.8 (br.), 61.2 (br.), 74.8, 75.3, 79.2, 81.3, 81.7, 82.4, 99.7, 103.1, 105.9, 106.12, 106.15, 106.18, 130.7, 130.8, 130.9, 131.0, 142.0, 142.1, 142.2, 142.3, 154.3, 154.4, 154.5, 154.6, 169.9, 170.0, 170.5, 170.8. HRMS (ESI-TOF) m/z: [M+H]$^+$ Calcd for C$_{26}$H$_{35}$N$_2$O$_{12}$$^+$ 567,21845; Found: 483,1250.

N,N'-(((2R,3R,4R)-3,4,5-trihydroxytetrahydrofuran-2,4-diyl)bis(methylene))bis(3,4-dihydroxybenzamide) (17)

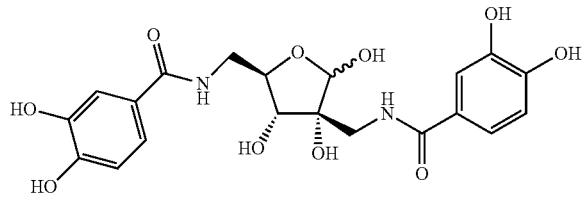 [SMILES: O=C(NC[C@H]1OC(O)[C@@](O)(CNC(=O)c2ccc(O)c(O)c2)[C@@H]1O)c1ccc(O)c(O)c1]

General procedure 2. White foam. (55:45 mixture of anomers)$^1$H NMR (300 MHz, $D_2O$) δ ppm 3.37-3.57 (m, 2.58 H) 3.69-3.88 (m, 2 H) 4.01 (d, J=7.9 Hz, 0.45 H) 4.09-4.18 (m, 1 H) 5.23 (s, 0.45 H) 5.28 (s, 0.55 H) 6.62-6.81 (m, 2 H) 6.92-7.04 (m, 2.70 H) 7.06-7.15 (m, 1.30 H). $^{13}$C NMR (75 MHz, $D_2O$) δ ppm 29.5, 39.4, 40.6, 41.2, 41.6, 70.7, 71.5, 77.5, 79.1, 79.8, 80.0, 97.6, 101.6, 114.3, 114.4, 114.5, 114.6, 115.1, 115.2, 115.30, 115.4, 120.0, 120.1, 120.2, 120.3, 124.7, 124.8, 125.1, 125.2, 143.43 (br.), 143.5, 143.6, 147.7 (br.), 147.8, 169.9, 170.0, 170.1, 170.2. HRMS (ESI-TOF) m/z: [M+H]+ Calcd for $C_{20}H_{23}N_2O_{10}^+$ 451,13472; Found: 451,1346.

N,N'-(((2R,3R,4R)-3,4,5-trihydroxytetrahydrofuran-2,4-diyl)bis(methylene))bis(3,5-dihydroxybenzamide) (18)

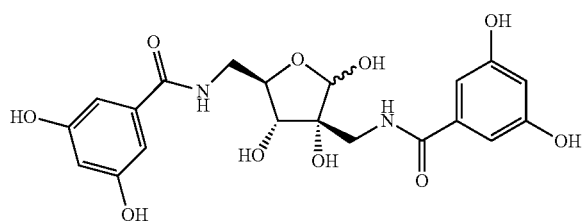 [SMILES: O=C(NC[C@H]1OC(O)[C@@](O)(CNC(=O)c2cc(O)cc(O)c2)[C@@H]1O)c1cc(O)cc(O)c1]

General procedure 2. White foam. (54:46 mixture of anomers)$^1$H NMR (300 MHz, $D_2O$) δ 3.37-3.60 (m, 2.54 H), 3.74-3.88 (m, 2 H), 4.00 (d, J=7.91 Hz, 0.46 H), 5.23 (s, 0.46 H), 5.30 (s, 0.54 H); 6.35 (s, 0.54 H), 6.39 (s, 0.54 H), 6.41 (s, 0.46H), 6.44 (s, 0.46 H), 6.52 (s, 1.08 H), 6.53 (s, 1.08 H), 6.58 (s, 0.92 H), 6.64 (s, 0.92 H). $^{13}$C NMR (75 MHz, $D_2O$) δ ppm 39.5, 40.6, 41.3, 41.7, 70.7, 71.4, 77.4, 79.0, 79.8, 80.0, 97.6, 101.6, 105.9 (v br.), 106.0, 135.0, 135.2, 135.5, 135.7, 156.75, 156.77, 156.80, 156.84, 170.0, 170.2, 170.3, 170.4. HRMS (ESI-TOF) m/z: [M+H]+ Calcd for $C_{20}H_{23}N_2O_{10}^+$ 451,13472; Found: 451,1344.

N,N'-(((2R,3R,4R)-3,4,5-trihydroxytetrahydrofuran-2,4-diyl)bis(methylene))bis(3-hydroxybenzamide) (19)

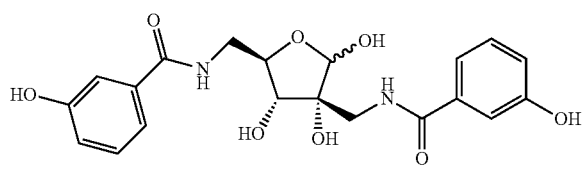 [SMILES: O=C(NC[C@H]1OC(O)[C@@](O)(CNC(=O)c2cccc(O)c2)[C@@H]1O)c1cccc(O)c1]

General procedure 2. White foam. (51:49 mixture of anomers)$^1$H NMR (300 MHz, $D_2O$) δ ppm 3.38-3.59 (m, 2.51 H) 3.68-3.82 (m, 2 H) 4.03 (d, J=7.9 Hz, 0.49 H) 4.09-4.20 (m, 1 H) 5.21 (s, 0.51 H) 5.27 (s, 0.49 H) 6.85-6.99 (m, 3 H) 7.02-7.25 (m, 5 H). $^{13}$C NMR (75 MHz, $D_2O$) d ppm 39.9, 40.9, 41.8, 42.0, 71.4, 72.0, 77.4, 79.1, 79.9, 78.0, 97.6, 101.3, 113.49, 113.50, 113.58, 113.61, 118.70, 118.78, 118.97, 119.03, 129.88, 129.91, 129.96 (br), 134.25, 134.38, 134.61 (br), 155.42, 155.44, 155.5 (br), 170.2, 170.4, 170.51, 170.53. HRMS (ESI-TOF) m/z: [M+H]+ Calcd for $C_{20}H_{23}N_2O_8^+$ 419,14489; Found: 419, 1447.

N,N'-(((2R,3R,4R)-3,4,5-trihydroxytetrahydrofuran-2,4-diyl)bis(methylene))bis(4-hydroxybenzamide) (20)

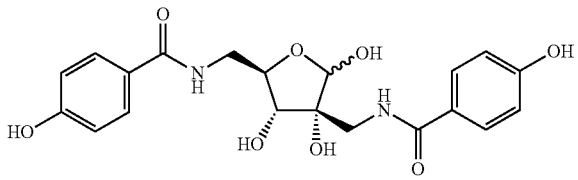 [SMILES: O=C(NC[C@H]1OC(O)[C@@](O)(CNC(=O)c2ccc(O)cc2)[C@@H]1O)c1ccc(O)cc1]

General procedure 2. White foam. (68:32 mixture of anomers)$^1$H NMR (300 MHz, $CD_3OD$) δ ppm 3.48-3.63 (m, 2.32 H) 3.65-3.79 (m, 2 H) 4.05 (d, J=7.6 Hz, 0.68 H) 4.08-4.16 (m, 1 H) 5.11 (s, 0.68 H) 5.19 (s, 0.32 H) 6.76-6.86 (m, 4 H) 7.64-7.77 (m, 4 H). $^{13}$C NMR (75 MHz, $CD_3OD$) δ ppm 42.8 (br.), 44.5, 45.9, 74.8, 75.3, 79.3, 81.3, 81.7, 82.3, 99.7, 103.2, 116.2, 116.3 (br.), 126.2 (br.), 126.37, 126.42, 130.4, 130.5 (br.), 130.6, 162.18, 162.24, 162.3 (br.), 170.3, 170.5, 171.0, 171.2. HRMS (ESI-TOF) m/z: [M+H]+ Calcd for $C_{20}H_{23}N_2O_8^+$ 419,14489; Found: 419,1455.

N,N'-(((2R,3R,4R)-3,4,5-trihydroxytetrahydrofuran-2,4-diyl)bis(methylene))dibenzamide (21)

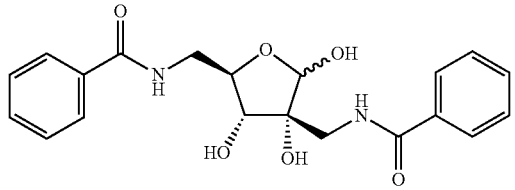 [SMILES: O=C(NC[C@H]1OC(O)[C@@](O)(CNC(=O)c2ccccc2)[C@@H]1O)c1ccccc1]

General procedure 2. White foam. (67:33 mixture of anomers)$^1$H NMR (300 MHz, $CD_3OD$) δ ppm 3.52-3.72 (m, 2.67 H) 3.72-3.87 (m, 2 H) 4.11 (d, J=7.6 Hz, 0.68 H) 4.14-4.22 (m, 1 H) 5.19 (s, 0.68 H) 5.26 (s, 0.32 H) 7.35-7.52 (m, 6 H) 7.75-7.88 (m, 4 H). $^{13}$C NMR (75 MHz, $CD_3OD$) δ ppm 42.8, 42.9, 44.5, 45.8, 74.9, 75.3, 79.0, 81.0, 81.5, 82.1, 99.6, 103.1, 128.31, 128.36, 128.41, 128.43, 129.55, 129.60, 129.62, 129.64, 132.70, 132.79, 132.83 (br.), 135.34, 135.37, 135.45, 135.52, 170.3, 170.5, 171.0, 171.1. HRMS (ESI-TOF) m/z: [M+H]+ Calcd for $C_{20}H_{23}N_2O_6^+$ 387,15506; Found: 387,1549.

((R)-5-((R)-2-azido-1-hydroxyethyl)-2,2-dimethyl-1,3-dioxolane-4,4-diyl)dimethanol (22)

Sodium borohydride (5.0 g, 133.1 mmol) was added to a stirred and cooled (0° C.) solution of compound 3 (13.1 g, 53.2 mmol) in MeOH (400 mL). The reaction mixture was allowed to attain ambient temperature and was stirred for 12 h, at which time TLC (CH$_2$Cl$_2$/MeOH 94:6) showed the consumption of starting material. Ammonium chloride (25.0 g) was added to quench the excess of borohydride. The resulting suspension was stirred for 2 h, concentrated and adsorbed onto celite. Purification by flash chromatography (CH$_2$Cl$_2$/MeOH 95:5) afforded triol 22 as a white powder in 92.7% yield. $^1$H NMR (300 MHz, CD$_3$OD) δ ppm 1.36 (s, 3 H) 1.39 (s, 3 H) 3.29-3.38 (m, 1 H) 3.46 (dd, J=12.6, 2.1 Hz, 1 H) 3.59-3.76 (m, 4 H) 3.90-3.99 (m, 2 H). $^{13}$C NMR (75 MHz, CD$_3$OD) δ ppm 26.8, 28.6, 56.0, 62.2, 64.6, 70.0, 79.4, 85.7, 109.6. HRMS (ESI-TOF) m/z: [M+NH$_4$]$^+$ Calcd for C$_3$H$_{21}$N$_4$O$_5$$^+$ 265.15065; Found 265.1501.

((3aR,6R,6aR)-6-(Azidomethyl)-2,2-dimethyldihydrofuro[3,4-d][1,3]dioxol-3a(4H)-yl)methyl 4-methylbenzenesulfonate (23)

To a stirred solution of triol 22 (5.0 g, 20.1 mmol) in pyridine (100 mL) was added p-toluenesulfonylchloride (8.4 g, 44.1 mmol). The reaction mixture was stirred at room temperature for 3 h and then heated to 60° C. overnight, after which time TLC analysis (hexane/EtOAc 3:1) showed the presence of a major product. The resulting suspension was filtered and the residue was concentrated under reduced pressure. The crude material was then purified by flash column chromatography (hexane/EtOAc 4:1) to afford tosylate 23 as a colorless oil in 71.5% yield. $^1$H NMR (300 MHz, CDCl$_3$) δ ppm 1.34 (s, 3 H) 1.49 (s, 3 H) 2.46 (s, 3 H) 3.37 (app. d, J=5.0 Hz, 2 H) 3.83 (app. s, 2 H) 4.11 (d, J=10.3 Hz, 1 H) 4.17 (app. td, J=5.1, 2.1 Hz, 1 H) 4.22 (d, J=10.5 Hz, 1 H) 4.41 (d, J=2.1 Hz, 1 H) 7.34-7.41 (m, 2 H) 7.79-7.85 (m, 2 H). $^{13}$C NMR (75 MHz, CDCl$_3$) δ ppm 21.5, 27.1, 27.7, 51.4, 69.2, 74.5, 83.9, 84.3, 90.1, 115.0, 127.9, 129.9, 132.2, 145.3. HRMS (ESI-TOF) m/z: [M+H]$^+$ Calcd for C$_{16}$H$_{22}$N$_3$O$_6$S$^+$ 384.12238; Found 384.1229.

2-(((3aS,6R,6aR)-6-(Azidomethyl)-2,2-dimethyldihydrofuro[3,4-d][1,3]dioxol-3a(4H)-yl)methyl)isoindoline-1,3-dione (24)

To a solution of compound 23 (4.1 g, 10.7 mmol) in DMF (100 mL) was added a catalytic amount of NaI, followed by potassium phthalimide (4.0 g, 21.4 mmol). The reaction mixture was heated to 90° C. and stirred overnight, after which TLC analysis (toluene/EtOAc 4:1) showed the formation of a major product. The solvent was evaporated under reduced pressure and the residue was taken up in EtOAc and washed with water. The organic layer was dried over sodium sulphate, filtered and concentrated in vacuo. The crude material was purified by flash chromatography (toluene/EtOAc 95:5) to afford compound 24 as a pale yellow oil, which solidified on standing (86.2%). $^1$H NMR (300 MHz, CDCl$_3$) δ ppm 1.29 (s, 3 H) 1.49 (s, 3 H) 3.42-3.55 (m, 2 H) 3.96 (d, J=10.3 Hz, 1 H) 4.06 (app. s, 2 H) 4.10 (d, J=10.3 Hz, 1 H) 4.17 (app. td, J=5.3, 2.1 Hz, 1 H) 4.63 (d, J=2.1 Hz, 1 H) 7.72-7.79 (m, 2 H) 7.86-7.92 (m, 2 H). $^{13}$C NMR (75 MHz, CDCl$_3$) δ ppm 27.5, 27.6, 41.0, 51.9, 75.8, 84.0, 85.6, 91.6, 114.2, 123.3, 131.6, 134.1, 168.2. HRMS (ESI-TOF) m/z: [M+NH4]$^+$ Calcd for C$_{17}$H$_{22}$N$_5$O$_5$$^+$ 376.16155; Found 376.1601.

((3aS,6R,6aR)-6-(Azidomethyl)-2,2-dimethyldihydrofuro[3,4-d][1,3]dioxol-3a(4H)-yl)methanamine (25)

Hydrazine monohydrate (0.54 mL, 11.2 mmol) was added dropwise to a stirred solution of compound 24 (1.60 g, 4.46 mmol) in 50 mL of EtOH. The solution was heated to reflux for 4 h, after which time TLC analysis (CH$_2$Cl$_2$/MeOH 9:1 or toluene/EtOAc 4:1) showed complete consumption of starting material and the presence of a major product. The mixture was allowed to attain room temperature, concentrated and adsorbed onto celite. Purification by flash chromatography (CH$_2$Cl$_2$/MeOH/20% NH$_4$OH 92:8:0.1) afforded compound 25 as a colorless oil in 93.3% yield. $^1$H NMR (300 MHz, CDCl$_3$) δ ppm 1.43 (s, 3 H) 1.53 (m, 5 H) 2.91-3.04 (m, 2 H) 3.42 (d, J=5.3 Hz, 2 H) 3.92 (s, 2 H) 4.21 (td, J=5.1, 2.1 Hz, 1 H) 4.35 (d, J=2.3 Hz, 1 H). $^{13}$C NMR (75 MHz, CDCl$_3$) δ ppm 27.8, 27.9, 45.7, 51.7, 75.9, 84.1, 84.8, 93.3, 113.7.

N-(((3aS,6R,6aR)-6-(Azidomethyl)-2,2-dimethyldihydrofuro[3,4-d][1,3]dioxol-3a(4H)-yl)methyl)benzamide (26)

To a cooled (0° C.) solution of compound 25 (1.8 g, 7.9 mmol) in 100 mL of CH$_2$Cl$_2$ were added triethylamine (2.2 mL, 15.8 mmol) and benzoyl chloride (1.0 mL, 8.7 mmol) and the reaction mixture was stirred for 3 hours. The solvent was evaporated, after which the residue was taken up in EtOAc and washed with 0.1 M aq. HCl and sat. aq. NaHCO$_3$ solution. The organic layer was dried over sodium sulphate, filtered and concentrated. The residue was purified by flash column chromatography (toluene/EtOAc 7:3) to afford compound 26 as a colorless syrup (98.3%). $^1$H NMR (300 MHz, CDCl$_3$) δ ppm 1.43 (s, 3 H) 1.55 (s, 3 H) 3.40-3.56 (m, 2 H) 3.75 (dd, J=14.1, 5.6 Hz, 1 H) 3.92 (dd, J=14.1, 6.4 Hz, 1 H) 3.96 (s, 2 H) 4.23 (ddd, J=6.4, 4.6, 1.9 Hz, 1 H) 4.39 (d, J=2.1 Hz, 1 H) 6.59 (t, J=5.1 Hz, 1 H) 7.42-7.56 (m, 3 H) 7.77-7.83 (m, 2 H). $^{13}$C NMR (75 MHz, CDCl$_3$) δ ppm 27.9, 28.1, 43.5, 52.1, 76.0, 84.3, 85.3, 92.2, 114.3, 127.0, 128.9, 132.0, 134.0, 167.8. HRMS (ESI-TOF) m/z: [M+H]$^+$ Calcd for C$_{16}$H$_{21}$N$_4$O$_4$$^+$ 333.15573; Found 333.1554.

N-(((3aS,6R,6aR)-6-(azidomethyl)-2,2-dimethyldihydrofuro[3,4-d][1,3]dioxol-3a(4H)-yl)methyl)-2-chlorobenzamide (27)

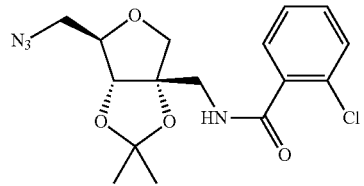 [SMILES: CC1(C)O[C@@H]2[C@@H](CN=[N+]=[N-])OC[C@]2(CNC(=O)c2ccccc2Cl)O1]

General procedure 4. Colourless oil, 69.2% $^1$H NMR (300 MHz, CDCl$_3$) δ ppm 1.41 (s, 3 H) 1.54 (s, 3 H) 3.44 (dd, J=12.9, 5.0 Hz, 1 H) 3.53 (dd, J=13.1, 6.3 Hz, 1 H) 3.85 (app. dd, J=6.2, 1.8 Hz, 2 H) 3.99 (app. s, 2 H) 4.24 (ddd, J=6.4, 4.8, 2.1 Hz, 1 H) 4.41 (d, J=2.1 Hz, 1 H) 6.60 (t, J=6.0 Hz, 1 H) 7.31-7.45 (m, 3 H) 7.65-7.69 (m, 1 H). $^{13}$C NMR (75 MHz, CDCl$_3$) δ ppm 27.9, 28.0, 43.7, 51.9, 75.9, 84.2, 85.4, 92.0, 114.3, 127.2, 130.0, 130.4, 130.7, 131.6, 134.8, 167.0. HRMS (ESI-TOF) m/z: Calcd for C$_{16}$H$_{20}$ClN$_4$O$_4$$^+$ 367.11676; Found 367.1167.

N-(((3aS,6R,6aR)-6-(azidomethyl)-2,2-dimethyldihydrofuro[3,4-d][1,3]dioxol-3a(4H)-yl)methyl)-[1,1'-biphenyl]-4-carboxamide (28)

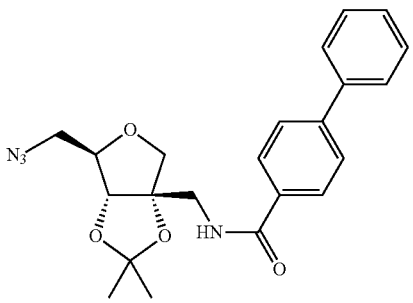 [SMILES: CC1(C)O[C@@H]2[C@@H](CN=[N+]=[N-])OC[C@]2(CNC(=O)c2ccc(-c3ccccc3)cc2)O1]

General procedure 4. Colourless oil, 80.1% $^1$H NMR (300 MHz, CDCl$_3$) δ ppm 1.45 (s, 3 H) 1.56 (s, 3 H) 3.46 (dd, J=12.9, 5.0 Hz, 1 H) 3.55 (dd, J=13.0, 6.3 Hz, 1 H) 3.77 (dd, J=14.1, 5.6 Hz, 1 H) 3.89-4.01 (m, 3 H) 4.20-4.28 (m, 1 H) 4.40 (d, J=2.1 Hz, 1 H) 6.58 (t, J=6.0 Hz, 1 H) 7.37-7.50 (m, 3 H) 7.58-7.64 (m, 2 H) 7.65-7.71 (m, 2 H) 7.84-7.90 (m, 2 H). $^{13}$C NMR (75 MHz, CDCl$_3$) δ ppm 27.9, 28.0, 43.4, 51.9, 75.8, 84.2, 85.2, 92.2, 114.2, 127.2, 127.4, 127.5, 128.1, 129.0, 132.6, 139.9, 144.7, 167.5. HRMS (ESI-TOF) m/z: [M+H]$^+$ Calcd for C$_{17}$H$_{23}$N$_4$O$_4^+$ 409.18703; Found 409.1856.

N-(((3aS,6R,6aR)-6-(azidomethyl)-2,2-dimethyldihydrofuro[3,4-d][1,3]dioxol-3a(4H)-yl)methyl)pyridazine-4-carboxamide (29)

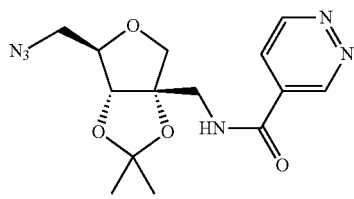 [SMILES: CC1(C)O[C@@H]2[C@@H](CN=[N+]=[N-])OC[C@]2(CNC(=O)c2ccnnc2)O1]

General procedure 4. Colourless oil, 83.3% $^1$H NMR (300 MHz, CDCl$_3$) δ ppm 1.39 (s, 3 H) 1.53 (s, 3 H) 3.44-3.57 (m, 2 H) 3.82-4.03 (m, 4 H) 4.23 (app. td, J=5.1, 2.2 Hz, 1 H) 4.45 (d, J=2.1 Hz, 1 H) 7.89 (t, J=6.0 Hz, 1 H) 7.96 (dd, J=5.3, 2.3 Hz, 1 H) 9.36 (dd, J=5.3, 1.5 Hz, 1 H) 9.61 (dd, J=2.3, 1.2 Hz, 1 H). $^{13}$C NMR (75 MHz, CDCl$_3$) δ ppm 27.8, 27.9, 43.8, 52.1, 75.8, 84.1, 85.3, 91.9, 114.5, 124.4, 131.8, 148.6, 152.0, 164.1. HRMS (ESI-TOF) m/z: [M+H]$^+$ Calcd for C$_{14}$H$_{13}$N$_6$O$_4^+$ 335.14623; Found 335.1459.

N-(((3aS,6R,6aR)-6-(azidomethyl)-2,2-dimethyldihydrofuro[3,4-d][1,3]dioxol-3a(4H)-yl)methyl)-2-phenylacetamide (30)

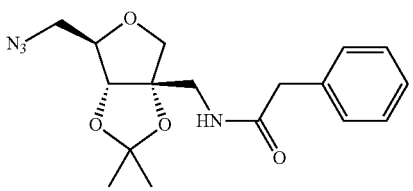 [SMILES: CC1(C)O[C@@H]2[C@@H](CN=[N+]=[N-])OC[C@]2(CNC(=O)Cc2ccccc2)O1]

General procedure 4. Colourless oil, 79.9% $^1$H NMR (300 MHz, CDCl$_3$) δ ppm 1.14 (s, 3 H) 1.46 (s, 3 H) 3.28-3.45 (m, 3 H) 3.61 (s, 2 H) 3.71-3.87 (m, 3 H) 4.13-4.21 (m, 2 H) 5.89 (t, J=6.0 Hz, 1 H) 7.23-7.39 (m, 5 H). $^{13}$C NMR (75 MHz, CDCl$_3$) δ ppm 27.6, 27.8, 42.6, 43.9, 51.8, 75.7, 84.2, 84.9, 92.0, 113.8, 127.6, 129.2, 129.5, 134.5, 171.4. HRMS (ESI-TOF) m/z: [M+H]$^+$ Calcd for C$_{17}$H$_{23}$N$_4$O$_4^+$ 347.17138; Found 347.1710.

N-(((3aS,6R,6aR)-6-(azidomethyl)-2,2-dimethyldihydrofuro[3,4-d][1,3]dioxol-3a(4H)-yl)methyl)-3-phenylpropanamide (31)

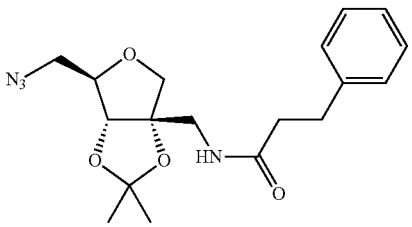 [SMILES: CC1(C)O[C@@H]2[C@@H](CN=[N+]=[N-])OC[C@]2(CNC(=O)CCc2ccccc2)O1]

General procedure 4. Colourless oil, 79.6% $^1$H NMR (300 MHz, CDCl$_3$) δ ppm 1.32 (s, 3 H) 1.49 (s, 3 H) 2.52 (t, J=7.5 Hz, 2 H) 2.98 (t, J=7.3 Hz, 2 H) 3.30-3.67 (m, 4 H) 3.74-3.84 (m, 2 H) 4.14-4.20 (m, 2 H) 5.86 (t, J=5.6 Hz, 1 H) 7.16-7.32 (m, 5 H). $^{13}$C NMR (75 MHz, CDCl$_3$) δ ppm 27.8, 27.9, 31.6, 38.4, 42.9, 51.8, 75.7, 84.1, 85.1, 92.0, 114.0, 126.4, 128.4, 128.7, 140.7, 172.4. HRMS (ESI-TOF) m/z: [M+H]$^+$ Calcd for C$_{18}$H$_{25}$N$_4$O$_4^+$ 361.18703; Found 361.1878.

N-(((3aS,6R,6aR)-6-(azidomethyl)-2,2-dimethyldihydrofuro[3,4-d][1,3]dioxol-3a(4H)-yl)methyl)-N-methylbenzamide (32)

A flask containing a solution of azide 26 (0.15 g, 0.45 mmol) in THF (5 mL) was purged with nitrogen gas and treated with NaH (60% dispersion in mineral oil, 22 mg, 0.54 mmol). After 1 hour, MeI (56 μL, 0.90 mmol) was added and the RM was stirred at RT overnight, after which mass spectrometry (ESI-TOF) analysis indicated incomplete consumption of SM and the formation of the desired compound. Further NaH (18 mg, 0.45 mmol) and MeI (56 μL, 0.90 mmol) were added and the mixture was stirred for 24 h. Solid particles were separated by filtration and the filtrate was adsorbed onto celite. Purification via flash column chromatography (toluene/EtOAc 100:0→70:30) gave the title compound in 68.4% yield (colourless oil). $^1$H NMR (300 MHz, CDCl$_3$) δ ppm 1.46 (s, 3 H) 1.55 (s, 3 H) 3.13 (s, 3 H) 3.43 (dd, J=12.9, 4.7 Hz, 1 H) 3.61 (dd, J=12.7, 7.8 Hz, 1 H) 3.81 (d, J=14.4 Hz, 1 H) 3.91-4.09 (m, 3 H) 4.25 (br. s., 1 H) 4.53 (app. s, 1 H) 7.38-7.44 (m, 5 H). $^{13}$C NMR (75 MHz, CDCl$_3$) δ ppm 27.6, 27.9, 40.6, 51.3, 51.5, 75.7, 84.4, 85.2, 93.4, 113.7, 126.8, 128.6, 129.8, 136.0, 172.5. HRMS (ESI-TOF) m/z: [M+H]$^+$ Calcd for C$_{17}$H$_{23}$N$_4$O$_4^+$ 347.17138; Found 347.1700.

N-(((3aS,6R,6aR)-6-(Aminomethyl)-2,2-dimethyldihydrofuro[3,4-d][1,3]dioxol-3a(4H)-yl)methyl)benzamide (33)

Azide 26 was subjected to general procedure 3. Crude amine was used without further purification.

N-(((3aR,4R,6aS)-6a-(benzamidomethyl)-2,2-dimethyltetrahydrofuro[3,4-d][1,3]dioxol-4-yl)methyl)-4-methylbenzamide (34)

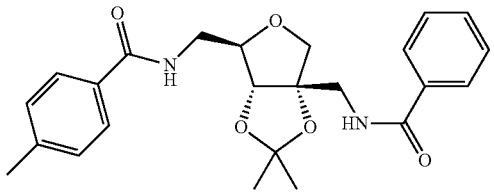 [SMILES: Cc1ccc(C(=O)NC[C@H]2OC[C@]3(CNC(=O)c4ccccc4)OC(C)(C)O[C@H]23)cc1]

General procedure 4. White foam, 79.9% ¹H NMR (300 MHz, CDCl₃) δ ppm 1.35 (s, 3 H) 1.50 (s, 3 H) 2.36 (s, 3 H) 3.42 (ddd, J=13.9, 6.7, 5.1 Hz, 1 H) 3.73 (app. td, J=14.4, 6.6 Hz, 2 H) 3.83-4.00 (m, 3 H) 4.27 (app. t, J=7.0 Hz, 1 H) 4.53 (d, J=1.2 Hz, 1 H) 7.18 (d, J=7.9 Hz, 2 H) 7.32 (dd, J=6.4, 5.6 Hz, 1 H) 7.36-7.58 (m, 4 H) 7.75 (d, J=8.2 Hz, 2 H) 7.85-7.94 (m, 2 H). ¹³C NMR (75 MHz, CDCl₃) δ ppm 21.5, 27.7, 27.8, 39.7, 43.1, 74.9, 83.7, 85.1, 92.3, 113.3, 127.25 (2C), 128.7, 129.2, 131.2, 131.8, 133.8, 142.1, 168.06, 168.12. HRMS (ESI-TOF) m/z: [M+H]⁺ Calcd for $C_{24}H_{29}N_2O_5^+$ 425.20710; Found 425.2072.

N-(((3aR,4R,6aS)-6a-(benzamidomethyl)-2,2-dimethyltetrahydrofuro[3,4-d][1,3]dioxol-4-yl)methyl)-4-fluorobenzamide (35)

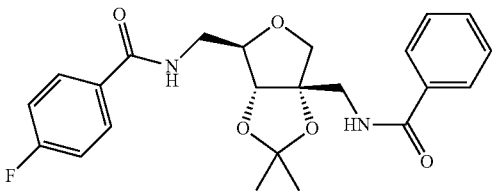 [SMILES: CC1(C)O[C@@H]2[C@@H](CNC(=O)c3ccc(F)cc3)OC[C@]2(CNC(=O)c2ccccc2)O1]

General procedure 4. White foam, 81.8% ¹H NMR (300 MHz, CDCl₃) δ ppm 1.36 (s, 3 H) 1.51 (s, 3 H) 3.46 (ddd, J=14.1, 6.6, 5.1 Hz, 1 H) 3.63-3.81 (m, 2 H) 3.85-3.98 (m, 3 H) 4.29 (app. td, J=6.9, 0.9 Hz, 1 H) 4.51 (d, J=1.2 Hz, 1 H) 7.01-7.09 (m, 2 H) 7.39-7.47 (m, 3 H) 7.48-7.56 (m, 2 H) 7.83-7.94 (m, 4 H). ¹⁹F NMR (282 MHz, CDCl3) δ ppm −108.5 (m). ¹³C NMR (75 MHz, CDCl₃) δ ppm 27.7, 27.8, 39.9, 43.2, 75.0, 83.6, 84.9, 92.3, 113.5, 115.5 (d, J=21.6 Hz), 127.2, 128.7, 129.7 (d, J=8.9 Hz), 130.2 (d, J=2.8 Hz), 132.0, 133.7, 164.8 (d, J=252.1 Hz), 167.0, 168.3. HRMS (ESI-TOF) m/z: [M+H]⁺ Calcd for $C_{23}H_{26}FN_2O_5^+$ 429.18203; Found 429.1828.

N-(((3aR,4R,6aS)-6a-(benzamidomethyl)-2,2-dimethyltetrahydrofuro[3,4-d][1,3]dioxol-4-yl)methyl)-4-chlorobenzamide (36)

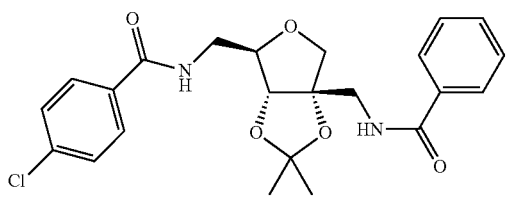 [SMILES: CC1(C)O[C@@H]2[C@@H](CNC(=O)c3ccc(Cl)cc3)OC[C@]2(CNC(=O)c2ccccc2)O1]

General procedure 4. White foam, 74.6% ¹H NMR (300 MHz, CDCl₃) δ ppm 1.36 (s, 3 H) 1.50 (s, 3 H) 3.46 (ddd, J=14.1, 6.6, 5.1 Hz, 1 H) 3.62-3.82 (m, 2 H) 3.84-3.98 (m, 3 H) 4.29 (app. t, J=6.6, 1 H) 4.51 (d, J=1.5 Hz, 1 H) 7.31-7.37 (m, 2 H) 7.39-7.55 (m, 4 H) 7.62 (t, J=6.0 Hz, 1 H) 7.77-7.91 (m, 4 H). ¹³C NMR (75 MHz, CDCl₃) δ ppm 27.7, 27.8, 39.9, 43.1, 75.0, 83.5, 84.9, 92.2, 113.5, 127.2, 128.70, 128.72, 128.8, 132.0, 132.4, 133.6, 137.8, 167.1, 168.3. HRMS (ESI-TOF) m/z: [M+H]⁺ Calcd for $C_{23}H_{26}ClN_2O_5^+$ 445.15248; Found 445.1537.

N-(((3aR,4R,6aS)-6a-(benzamidomethyl)-2,2-dimethyltetrahydrofuro[3,4-d][1,3]dioxol-4-yl)methyl)-4-methoxybenzamide (37)

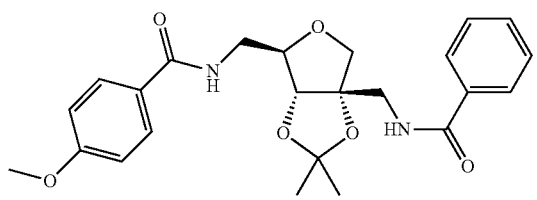 [SMILES: COc1ccc(C(=O)NC[C@H]2OC[C@]3(CNC(=O)c4ccccc4)OC(C)(C)O[C@H]23)cc1]

General procedure 4. White foam, 72.3% ¹H NMR (300 MHz, CDCl₃) δ ppm 1.35 (s, 3 H) 1.50 (s, 3 H) 3.42 (ddd, J=14.1, 6.6, 5.1 Hz, 1 H) 3.66-3.79 (m, 2 H) 3.81 (s, 3 H) 3.85-3.97 (m, 3 H) 4.27 (app. t, J=7.2 Hz, 1 H) 4.54 (d, J=1.2 Hz, 1 H) 6.83-6.91 (m, 2 H) 7.34 (t, J=5.9 Hz, 1 H) 7.38-7.53 (m, 3 H) 7.56 (t, J=6.2 Hz, 1 H) 7.80-7.87 (m, 2 H) 7.87-7.94 (m, 2 H). ¹³C NMR (75 MHz, CDCl₃) δ ppm 27.7, 27.8, 39.7, 43.1, 55.4, 74.9, 83.7, 85.1, 92.2, 113.3, 113.7, 126.3, 127.2, 128.6, 129.1, 131.9, 133.7, 162.3, 167.6, 168.2. HRMS (ESI-TOF) m/z: [M+H]⁺ Calcd for $C_{24}H_{29}N_2O_6^+$ 441.20201; Found 441.2027.

N-(((3aR,4R,6aS)-6a-(benzamidomethyl)-2,2-dimethyltetrahydrofuro[3,4-d][1,3]dioxol-4-yl)methyl)-4-cyanobenzamide (38)

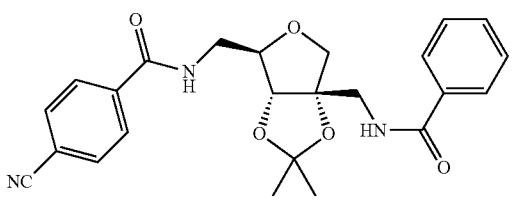 [SMILES: CC1(C)O[C@@H]2[C@@H](CNC(=O)c3ccc(C#N)cc3)OC[C@]2(CNC(=O)c2ccccc2)O1]

General procedure 4. White foam, 90.7% ¹H NMR (300 MHz, CDCl₃) δ ppm 1.37 (s, 3 H) 1.52 (s, 3 H) 3.53 (app. dt, J=14.1, 5.9 Hz, 1 H) 3.63 (dd, J=14.4, 5.6 Hz, 1 H) 3.76-3.98 (m, 4 H) 4.32 (app. t, J=6.4 Hz, 1 H) 4.48 (d, J=1.5 Hz, 1 H) 7.25-7.34 (m, 1 H) 7.42-7.49 (m, 2 H) 7.51-7.57 (m, 1 H) 7.68 (app. d, J=8.5 Hz, 2 H) 7.79-7.88 (m, 3 H) 8.02 (app. d, J=8.5 Hz, 2 H). ¹³C NMR (75 MHz, CDCl₃) δ ppm 27.9, 28.1, 40.3, 43.3, 75.3, 83.5, 84.8, 92.4, 113.8, 115.1, 118.4, 127.3, 128.3, 129.0, 132.4, 132.5, 133.6, 138.2, 166.4, 168.5. HRMS (ESI-TOF) m/z: [M+H]⁺ Calcd for $C_{24}H_{26}N_3O_5^+$ 436.18670; Found 436.1869.

N-(((3aR,4R,6aS)-6a-(benzamidomethyl)-2,2-dimethyltetrahydrofuro[3,4-d][1,3]dioxol-4-yl)methyl)-4-(dimethylamino)benzamide (39)

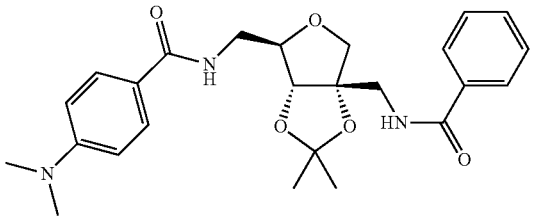 [SMILES: CN(C)c1ccc(C(=O)NC[C@H]2OC[C@]3(CNC(=O)c4ccccc4)OC(C)(C)O[C@H]23)cc1]

General procedure 4. White foam, 72.2% ¹H NMR (300 MHz, CDCl₃) δ ppm 1.35 (s, 3 H) 1.50 (s, 3 H) 2.99 (s, 6 H) 3.37 (ddd, J=14.0, 6.2, 5.3 Hz, 1 H) 3.69-3.80 (m, 2 H) 3.86-3.97 (m, 3 H) 4.25 (app. t, J=7.2 Hz, 1 H) 4.56 (d, J=0.9 Hz, 1 H) 6.63 (app. d, J=8.8 Hz, 2 H) 6.92 (t, J=6.0 Hz, 1 H) 7.38-7.53 (m, 3 H) 7.58 (t, J=6.2 Hz, 1 H) 7.72-7.79 (m, 2 H) 7.89-7.97 (m, 2 H). ¹³C NMR (75 MHz, CDCl₃) δ ppm 27.7, 27.8, 39.6, 40.2, 43.1, 75.0, 84.1, 85.3, 92.3, 111.1, 113.2, 120.6, 127.4, 128.6, 128.7, 131.8, 133.9, 152.7, 168.0, 168.1. HRMS (ESI-TOF) m/z: [M+H]⁺ Calcd for $C_{25}H_{32}N_3O_5^+$ 454.23365; Found 454.2357.

N-(((3aR,4R,6aS)-6a-(benzamidomethyl)-2,2-dimethyltetrahydrofuro[3,4-d][1,3]dioxol-4-yl)methyl)-4-(trifluoromethyl)benzamide (40)

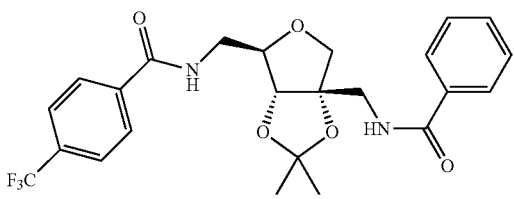

General procedure 4. White foam, 83.9% ¹H NMR (300 MHz, CDCl₃) δ ppm 1.37 (s, 3 H) 1.52 (s, 3 H) 3.53 (ddd, J=14.1, 6.5, 5.1 Hz, 1 H) 3.65 (dd, J=14.4, 5.6 Hz, 1 H) 3.77-3.98 (m, 4 H) 4.33 (app. td, J=6.7, 1.2 Hz, 1 H) 4.49 (d, J=1.5 Hz, 1 H) 7.22 (t, J=6.3 Hz, 1 H) 7.41-7.48 (m, 2 H) 7.50-7.56 (m, 1 H) 7.60-7.69 (m, 3 H) 7.82-7.88 (m, 2 H) 8.00 (d, J=8.2 Hz, 2 H). ¹⁹F NMR (282 MHz, CDCl₃) δ ppm −63.3 (s). ¹³C NMR (75 MHz, CDCl₃) δ ppm 27.8, 27.9, 40.1, 43.2, 75.1, 83.4, 84.8, 92.3, 113.7, 125.6 (q, J=3.7 Hz), 125.6 (q, J=272.6 Hz) (weak), 127.1, 127.9, 128.8, 132.2, 133.3 (q, J=32.8 Hz), 133.6, 137.4, 166.8, 168.3. HRMS (ESI-TOF) m/z: [M+H]⁺ Calcd for $C_{24}H_{26}F_3N_2O_5^+$ 479.17883; Found 479.1777.

N-(((3aR,4R,6aS)-6a-(benzamidomethyl)-2,2-dimethyltetrahydrofuro[3,4-d][1,3]dioxol-4-yl)methyl)isonicotinamide (41)

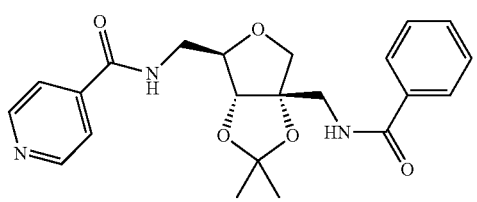

General procedure 4. White foam, 73.3% ¹H NMR (300 MHz, CDCl₃) δ ppm 1.36 (s, 3 H) 1.52 (s, 3 H) 3.50-3.67 (m, 2 H) 3.77-3.97 (m, 4 H) 4.32 (app. td, J=6.6, 1.2 Hz, 1 H) 4.48 (d, J=1.5 Hz, 1 H) 7.38-7.57 (m, 4 H) 7.73-7.80 (m, 2 H) 7.82-7.89 (m, 2 H) 7.96 (t, J=5.9 Hz, 1 H) 8.63-8.72 (m, 2 H). ¹³C NMR (75 MHz, CDCl₃) δ ppm 27.7, 27.9, 40.0, 43.1, 75.1, 83.3, 84.6, 92.3, 113.6, 121.4, 127.1, 128.8, 132.1, 133.5, 141.3, 150.4, 166.1, 168.4. HRMS (ESI-TOF) m/z: [M+H]⁺ Calcd for $C_{22}H_{26}N_3O_5^+$ 412.18670; Found 412.1876.

N-(((3aR,4R,6aS)-6a-(benzamidomethyl)-2,2-dimethyltetrahydrofuro[3,4-d][1,3]dioxol-4-yl)methyl)-[1,1'-biphenyl]-4-carboxamide (42)

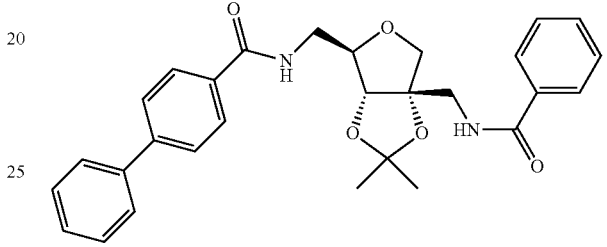

General procedure 4. White foam, 65.3% ¹H NMR (300 MHz, CDCl₃) δ ppm 1.36 (s, 3 H) 1.51 (s, 3 H) 3.49 (ddd, J=14.0, 6.7, 5.1 Hz, 1 H) 3.67-3.85 (m, 2 H) 3.88-4.00 (m, 3 H) 4.32 (app. t, J=6.9 Hz, 1 H) 4.54 (d, J=1.2 Hz, 1 H) 7.31-7.54 (m, 8 H) 7.54-7.65 (m, 4 H) 7.84-7.99 (m, 4 H). ¹³C NMR (75 MHz, CDCl₃) δ ppm 27.8, 27.9, 39.9, 43.2, 75.0, 83.7, 85.1, 92.3, 113.5, 127.2, 127.26 (2C), 127.9, 128.1, 128.7, 129.0, 132.0, 132.7, 133.8, 140.1, 144.4, 167.8, 168.2. HRMS (ESI-TOF) m/z: [M+H]⁺ Calcd for $C_{29}H_{31}N_2O_5^+$ 487.22275; Found 487.2219.

N-(((3aR,4R,6aS)-6a-(benzamidomethyl)-2,2-dimethyltetrahydrofuro[3,4-d][1,3]dioxol-4-yl)methyl)-3-methylbenzamide (43)

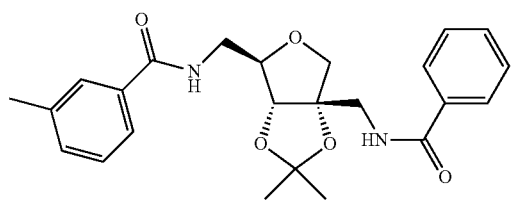 [SMILES: Cc1cccc(C(=O)NC[C@H]2OC[C@]3(CNC(=O)c4ccccc4)OC(C)(C)O[C@H]23)c1]

General procedure 4. White foam, 97.0% ¹H NMR (300 MHz, CDCl₃) δ ppm 1.36 (s, 3 H) 1.51 (s, 3 H) 2.35 (s, 3 H) 3.44 (ddd, J=14.0, 7.0, 5.1 Hz, 1 H) 3.66-3.80 (m, 2 H) 3.83-4.01 (m, 3 H) 4.29 (app. t, J=7.2 Hz, 1 H) 4.52 (d, J=1.2 Hz, 1 H) 7.23-7.32 (m, 3 H) 7.36-7.56 (m, 4 H) 7.58-7.71 (m, 2 H) 7.83-7.94 (m, 2 H). ¹³C NMR (75 MHz, CDCl₃) δ ppm 21.4, 27.7, 27.8, 39.7, 43.2, 75.0, 83.7, 85.1, 92.3, 113.4, 124.3, 127.2, 127.9, 128.4, 128.7, 131.9, 132.4, 133.7, 134.0, 138.4, 168.1, 168.3. HRMS (ESI-TOF) m/z: [M+H]⁺ Calcd for $C_{24}H_{29}N_2O_5^+$ 425.20710; Found 425.2079.

N-(((3aR,4R,6aS)-6a-(benzamidomethyl)-2,2-dimethyltetrahydrofuro[3,4-d][1,3]dioxol-4-yl)methyl)-3-fluorobenzamide (44)

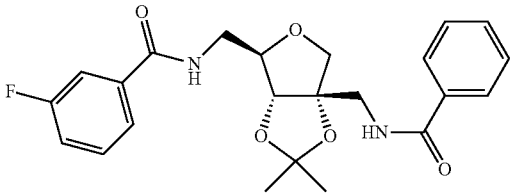 [SMILES: CC1(C)O[C@@H]2[C@@H](CNC(=O)c3cccc(F)c3)OC[C@]2(CNC(=O)c2ccccc2)O1]

General procedure 4. White foam, 78.8% $^1$H NMR (300 MHz, CDCl$_3$) δ ppm 1.37 (s, 3 H) 1.51 (s, 3 H) 3.51 (ddd, J=14.1, 6.7, 5.3 Hz, 1 H) 3.63-3.82 (m, 2 H) 3.85-4.00 (m, 3 H) 4.31 (app. td, J=7.0, 1.0 Hz, 1 H) 4.49 (d, J=1.2 Hz, 1 H) 7.13-7.27 (m, 2 H) 7.32-7.56 (m, 5 H) 7.58-7.69 (m, 2 H) 7.82-7.91 (m, 2 H). $^{19}$F NMR (282 MHz, CDCl$_3$) δ ppm −112.4 (m). $^{13}$C NMR (75 MHz, CDCl$_3$) δ ppm 27.8, 27.9, 39.9, 43.2, 75.1, 83.5, 84.8, 92.3, 113.6, 114.7 (d, J=22.7 Hz), 118.7 (d, J=21.6 Hz), 122.9 (d, J=3.3 Hz), 127.2, 128.8, 130.2 (d, J=7.7 Hz), 132.1, 133.6, 136.4 (d, J=7.2 Hz), 162.8 (d, J=247.7 Hz), 166.7 (d, J=2.2 Hz), 168.3. HRMS (ESI-TOF) m/z: [M+H]$^+$ Calcd for C$_{23}$H$_{26}$FN$_2$O$_5$$^+$ 429.18203; Found 429.1837.

N-(((3aR,4R,6aS)-6a-(benzamidomethyl)-2,2-dimethyltetrahydrofuro[3,4-d][1,3]dioxol-4-yl)methyl)-3-chlorobenzamide (45)

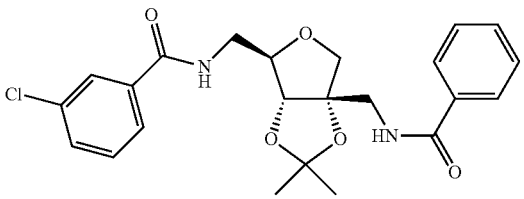 [SMILES: CC1(C)O[C@@H]2[C@@H](CNC(=O)c3cccc(Cl)c3)OC[C@]2(CNC(=O)c2ccccc2)O1]

General procedure 4. White foam, 83.9% $^1$H NMR (300 MHz, CDCl$_3$) δ ppm 1.37 (s, 3 H) 1.52 (s, 3 H) 3.51 (ddd, J=14.0, 6.8, 5.0 Hz, 1 H) 3.65 (dd, J=14.4, 5.3 Hz, 1 H) 3.77 (app. dt, J=14.1, 7.1 Hz, 1 H) 3.85-4.02 (m, 3 H) 4.31 (app. td, J=7.0, 1.0 Hz, 1 H) 4.48 (d, J=1.2 Hz, 1 H) 7.18 (t, J=6.2 Hz, 1 H) 7.30-7.56 (m, 6 H) 7.76 (app. dt, J=7.9, 1.3 Hz, 1 H) 7.84-7.89 (m, 3 H). $^{13}$C NMR (75 MHz, CDCl$_3$) δ ppm 27.8, 27.9, 39.9, 43.2, 75.2, 83.4, 84.8, 92.4, 113.6, 125.5, 127.2, 127.7, 128.9, 129.9, 131.7, 132.1, 133.6, 134.7, 135.9, 166.7, 168.3. HRMS (ESI-TOF) m/z: [M+H]$^+$ Calcd for C$_{23}$H$_{26}$ClN$_2$O$_5$$^+$ 445.15248; Found 445.1537.

N-(((3aR,4R,6aS)-6a-(benzamidomethyl)-2,2-dimethyltetrahydrofuro[3,4-d][1,3]dioxol-4-yl)methyl)-3-methoxybenzamide (46)

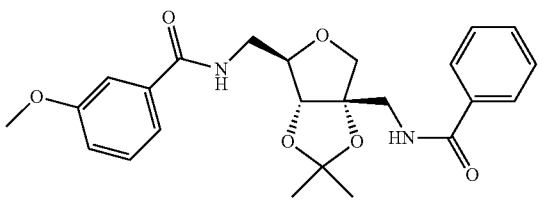 [SMILES: COc1cccc(C(=O)NC[C@H]2OC[C@]3(CNC(=O)c4ccccc4)OC(C)(C)O[C@H]23)c1]

General procedure 4. White foam, 80.7% $^1$H NMR (300 MHz, CDCl$_3$) δ ppm 1.36 (s, 3 H) 1.50 (s, 3 H) 3.45 (ddd, J=14.1, 6.7, 5.3 Hz, 1 H) 3.63-3.82 (m, 5 H) 3.85-3.99 (m, 3 H) 4.29 (app. td, J=7.0, 0.9 Hz, 1 H) 4.51 (d, J=1.2 Hz, 1 H) 7.01 (ddd, J=8.2, 2.6, 0.9 Hz, 1 H) 7.26-7.54 (m, 8 H) 7.83-7.93 (m, 2 H). $^{13}$C NMR (75 MHz, CDCl$_3$) δ ppm 27.9, 28.0, 40.0, 43.4, 55.6, 75.2, 83.8, 85.2, 92.4, 112.7, 113.6, 118.1, 119.4, 127.4, 128.9, 129.7, 132.1, 133.9, 135.6, 160.0, 168.1, 168.3. HRMS (ESI-TOF) m/z: [M+H]$^+$ Calcd for C$_{24}$H$_{29}$N$_2$O$_6$$^+$ 441.20201; Found 441.2015.

N-(((3aR,4R,6aS)-6a-(benzamidomethyl)-2,2-dimethyltetrahydrofuro[3,4-d][1,3]dioxol-4-yl)methyl)-3-cyanobenzamide (47)

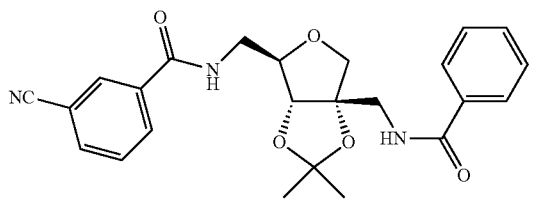 [SMILES: CC1(C)O[C@@H]2[C@@H](CNC(=O)c3cccc(C#N)c3)OC[C@]2(CNC(=O)c2ccccc2)O1]

General procedure 4. White foam, 82.3% $^1$H NMR (300 MHz, CDCl$_3$) δ ppm 1.37 (s, 3 H) 1.51 (s, 3 H) 3.51-3.67 (m, 2 H) 3.74-4.00 (m, 4 H) 4.33 (app. td, J=6.6, 0.8 Hz, 1 H) 4.50 (d, J=1.5 Hz, 1 H) 7.36 (t, J=6.3 Hz, 1 H) 7.41-7.58 (m, 4 H) 7.75 (app. dt, J=7.8, 1.4 Hz, 1 H) 7.82-7.99 (m, 3 H) 8.17 (app. dt, J=7.9, 1.5 Hz, 1 H) 8.27 (app. t, J=1.5 Hz, 1 H). $^{13}$C NMR (75 MHz, CDCl$_3$) δ ppm 27.7, 27.9, 39.9, 43.1, 75.1, 83.2, 84.5, 92.3, 112.6, 113.6, 118.2, 127.1, 128.8, 129.4, 131.3, 131.9, 132.1, 133.4, 134.7, 135.2, 165.8, 168.4. HRMS (ESI-TOF) m/z: [M+Na]$^+$ Calcd for C$_{24}$H$_{25}$N$_3$NaO$_5$$^+$ 458.16864; Found 458.1709.

N-(((3aR,4R,6aS)-6a-(benzamidomethyl)-2,2-dimethyltetrahydrofuro[3,4-d][1,3]dioxol-4-yl)methyl)-3-(dimethylamino)benzamide (48)

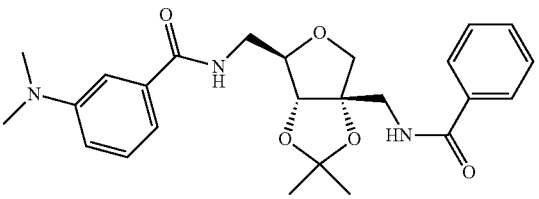 [SMILES: CN(C)c1cccc(C(=O)NC[C@H]2OC[C@]3(CNC(=O)c4ccccc4)OC(C)(C)O[C@H]23)c1]

General procedure 4. White foam, 68.8% $^1$H NMR (300 MHz, CDCl$_3$) δ ppm 1.36 (s, 3 H) 1.51 (s, 3 H) 2.95 (s, 6 H) 3.43 (ddd, J=14.1, 6.9, 5.1 Hz, 1 H) 3.67-3.82 (m, 2 H) 3.85-4.00 (m, 3 H) 4.27 (app. td, J=7.0, 0.9 Hz, 1 H) 4.52 (d, J=1.5 Hz, 1 H) 6.83 (app. dd, J=7.9, 2.6 Hz, 1 H) 6.99-7.13 (m, 2 H) 7.21-7.28 (m, 2 H) 7.31 (t, J=6.2 Hz, 1 H) 7.37-7.54 (m, 3 H) 7.82-7.94 (m, 2 H). $^{13}$C NMR (75 MHz, CDCl$_3$) δ ppm 27.78, 27.85, 39.9, 40.6, 43.2, 75.0, 83.8, 85.2, 92.3, 111.4, 113.4, 114.5, 115.5, 127.3, 128.7, 129.2, 131.9, 133.8, 134.9, 150.7, 168.0, 168.9. HRMS (ESI-TOF) m/z: [M+H]$^+$ Calcd for C$_{25}$H$_{32}$N$_3$O$_5$$^+$ 454.23365; Found 454.2343.

N-(((3aR,4R,6aS)-6a-(benzamidomethyl)-2,2-dimethyltetrahydrofuro[3,4-d][1,3]dioxol-4-yl)methyl)-3-(trifluoromethyl)benzamide (49)

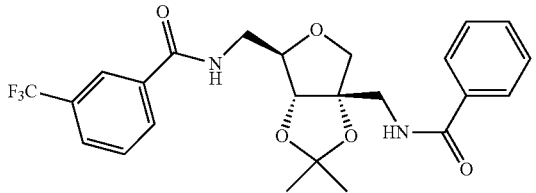

General procedure 4. White foam, 38.4% $^1$H NMR (300 MHz, CDCl$_3$) δ ppm 1.37 (s, 3 H) 1.52 (s, 3 H) 3.53 (ddd, J=14.1, 6.2, 5.1 Hz, 1 H) 3.63 (dd, J=14.4, 5.6 Hz, 1 H) 3.80-4.00 (m, 4 H) 4.33 (app. td, J=6.7, 1.0 Hz, 1 H) 4.50 (d, J=1.5 Hz, 1 H) 7.18 (t, J=6.3 Hz, 1 H) 7.40-7.48 (m, 2 H) 7.49-7.58 (m, 2 H) 7.65 (t, J=6.0 Hz, 1 H) 7.73 (app. d, J=7.9 Hz, 1 H) 7.80-7.90 (m, 2 H) 8.09 (app. d, J=7.9 Hz, 1 H) 8.20 (app. s, 1 H). $^{19}$F NMR (282 MHz, CDCl$_3$) δ ppm −63.1 (s). $^{13}$C NMR (75 MHz, CDCl$_3$) δ ppm 27.8, 28.0, 40.1, 43.1, 75.2, 83.4, 84.7, 92.3, 113.6, 123.9 (q, J=272.6 Hz) (weak), 124.52 (q, J=3.9 Hz), 127.1, 128.2 (q, J=3.9 Hz), 128.9, 129.2, 130.8, 131.1 (q, J=32.8), 132.2, 133.5, 135.0, 166.6, 168.4. HRMS (ESI-TOF) m/z: [M+H]$^+$ Calcd for C$_{24}$H$_{26}$F$_3$N$_2$O$_5^+$ 479.17883; Found 479.1787.

N-(((3aR,4R,6aS)-6a-(benzamidomethyl)-2,2-dimethyltetrahydrofuro[3,4-d][1,3]dioxol-4-yl)methyl) nicotinamide (50)

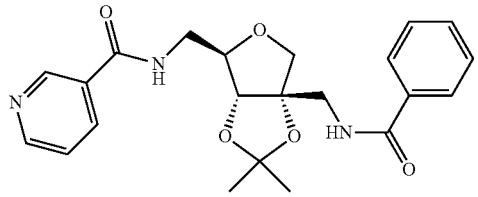 [SMILES: CC1(C)O[C@@H]2[C@@H](CNC(=O)c3cccnc3)OC[C@]2(CNC(=O)c2ccccc2)O1]

General procedure 4. White foam, 84.5% $^1$H NMR (300 MHz, CDCl$_3$) δ ppm 1.37 (s, 3 H) 1.53 (s, 3 H) 3.51-3.67 (m, 2 H) 3.82-4.02 (m, 4 H) 4.34 (app. td, J=6.4, 1.5 Hz, 1 H) 4.47 (d, J=1.5 Hz, 1 H) 6.96 (t, J=6.3 Hz, 1 H) 7.37 (ddd, J=8.0, 4.9, 0.9 Hz, 1 H) 7.40-7.58 (m, 4 H) 7.78-7.89 (m, 2 H) 8.19-8.27 (m, 1 H) 8.72 (app. dd, J=5.0, 1.8 Hz, 1 H) 9.14 (dd, J=2.3, 0.6 Hz, 1 H). $^{13}$C NMR (75 MHz, CDCl$_3$) δ ppm 27.8, 28.0, 40.1, 43.2, 75.2, 83.5, 84.7, 92.4, 113.8, 123.5, 127.1, 129.0, 129.9, 132.2, 133.6, 135.4, 148.7, 152.4, 166.2, 168.3. HRMS (ESI-TOF) m/z: [M+H]$^+$ Calcd for C$_{22}$H$_{26}$N$_3$O$_5^+$ 412.18670; Found 412.1866.

N-(((3aR,4R,6aS)-6a-(benzamidomethyl)-2,2-dimethyltetrahydrofuro[3,4-d][1,3]dioxol-4-yl)methyl)-[1,1'-biphenyl]-3-carboxamide (51)

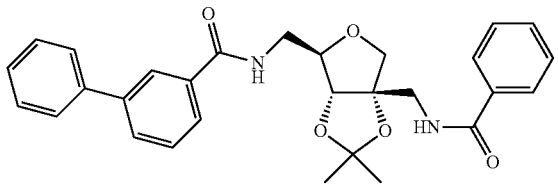 [SMILES: CC1(C)O[C@@H]2[C@@H](CNC(=O)c3cccc(-c4ccccc4)c3)OC[C@]2(CNC(=O)c2ccccc2)O1]

General procedure 4. White foam, 67.5% $^1$H NMR (300 MHz, CDCl$_3$) δ ppm 1.36 (s, 3 H) 1.51 (s, 3 H) 3.50 (ddd, J=14.1, 6.6, 5.1 Hz, 1 H) 3.66 (dd, J=14.4, 5.6 Hz, 1 H) 3.77-4.01 (m, 4 H) 4.32 (app. td, J=6.7, 0.9 Hz, 1 H) 4.52 (d, J=1.5 Hz, 1 H) 7.20 (t, J=6.2 Hz, 1 H) 7.30-7.53 (m, 8 H) 7.56-7.64 (m, 2 H) 7.67-7.74 (m, 1 H) 7.79-7.89 (m, 3 H) 8.13 (app. t, J=1.6 Hz, 1 H). $^{13}$C NMR (75 MHz, CDCl$_3$) δ ppm 27.8, 27.9, 40.0, 43.2, 75.2, 83.7, 85.0, 92.3, 113.5, 126.2, 126.2, 127.2, 127.3, 127.8, 128.8, 129.0, 129.1, 130.4, 132.0, 133.7, 134.7, 140.4, 141.7, 168.0, 168.2. HRMS (ESI-TOF) m/z: [M+H]$^+$ Calcd for C$_{29}$H$_{31}$N$_2$O$_5^+$ 487.22275; Found 487.2245.

N-(((3aR,4R,6aS)-6a-(benzamidomethyl)-2,2-dimethyltetrahydrofuro[3,4-d][1,3]dioxol-4-yl)methyl)-2-methylbenzamide (52)

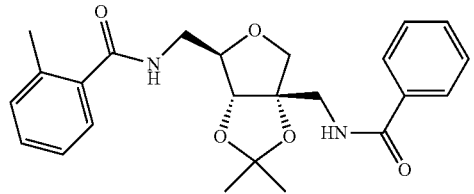 [SMILES: Cc1ccccc1C(=O)NC[C@H]1OC[C@]2(CNC(=O)c3ccccc3)OC(C)(C)O[C@H]12]

General procedure 4. White foam, 65.3% $^1$H NMR (300 MHz, CDCl$_3$) δ ppm 1.38 (s, 3 H) 1.52 (s, 3 H) 2.42 (s, 3 H) 3.31 (ddd, J=14.0, 7.5, 4.8 Hz, 1 H) 3.62-3.76 (m, 2 H) 3.83-3.99 (m, 3 H) 4.22 (app. td, J=7.4, 1.0 Hz, 1 H) 4.49 (d, J=1.2 Hz, 1 H) 6.75 (dd, J=6.9, 5.1 Hz, 1 H) 7.12-7.23 (m, 2 H) 7.25-7.52 (m, 6 H) 7.80-7.88 (m, 2 H). $^{13}$C NMR (75 MHz, CDCl$_3$) δ ppm 19.9, 27.78, 27.79, 39.5, 43.2, 74.8, 83.9, 85.3, 92.2, 113.5, 125.8, 126.9, 127.2, 128.6, 130.1, 131.1, 131.8, 133.7, 135.9, 136.1, 168.0, 170.8. HRMS (ESI-TOF) m/z: [M+H]$^+$ Calcd for C$_{24}$H$_{29}$N$_2$O$_5^+$ 425.20710; Found 425.2089.

N-(((3aR,4R,6aS)-6a-(benzamidomethyl)-2,2-dimethyltetrahydrofuro[3,4-d][1,3]dioxol-4-yl)methyl)-2-fluorobenzamide (53)

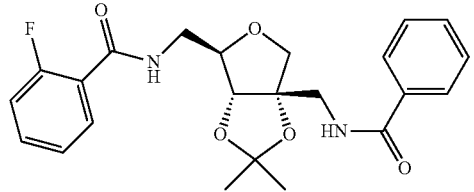 [SMILES: CC1(C)O[C@@H]2[C@@H](CNC(=O)c3ccccc3F)OC[C@]2(CNC(=O)c2ccccc2)O1]

General procedure 4. White foam, 59.1% $^1$H NMR (300 MHz, CDCl$_3$) δ ppm 1.39 (s, 3 H) 1.52 (s, 3 H) 3.40-3.50 (m, 1 H) 3.72-3.85 (m, 2 H) 3.88-3.98 (m, 3 H) 4.28 (app. t, J=7.3 Hz, 1 H) 4.50 (d, J=1.5 Hz, 1 H) 7.10 (app. dd, J=11.1, 8.2 Hz, 1 H) 7.19-7.32 (m, 3 H) 7.38-7.52 (m, 4 H) 7.84-7.90 (m, 2 H) 8.04 (app. td, J=7.9, 1.8 Hz, 1 H). $^{19}$F NMR (282 MHz, CDCl$_3$) δ ppm −113.4 (m). $^{13}$C NMR (75 MHz, CDCl$_3$) δ ppm 27.79, 27.85, 39.8, 43.3, 74.9, 83.8, 85.3, 92.3, 113.6, 116.2 (d, J=24.3 Hz), 120.9 (d, J=11.6 Hz), 124.8 (d, J=2.8 Hz), 127.2, 128.6, 131.8, 131.9 (d, J=1.7 Hz), 133.5 (d, J=9.4 Hz), 133.9, 162.6 (d, J=248.2 Hz), 164.0 (d, J=2.8 Hz), 167.9. HRMS (ESI-TOF) m/z: [M+H]$^+$ Calcd for C$_{23}$H$_{26}$FN$_2$O$_5^+$ 429.18203; Found 429.1832.

N-(((3aR,4R,6aS)-6a-(benzamidomethyl)-2,2-dimethyltetrahydrofuro[3,4-d][1,3]dioxol-4-yl)methyl)-2-chlorobenzamide (54)

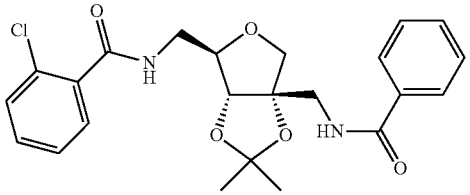 [SMILES: CC1(C)O[C@@H]2[C@@H](CNC(=O)c3ccccc3Cl)OC[C@]2(CNC(=O)c2ccccc2)O1]

General procedure 4. White foam, 71.1% $^1$H NMR (300 MHz, CDCl$_3$) δ ppm 1.38 (s, 3 H) 1.52 (s, 3 H) 3.38 (ddd, J=14.1, 7.3, 5.0 Hz, 1 H) 3.67-3.80 (m, 2 H) 3.85-3.95 (m, 3 H) 4.25 (app. td, J=7.2, 1.2 Hz, 1 H) 4.51 (d, J=1.5 Hz, 1 H) 7.12 (dd, J=6.7, 5.0 Hz, 1 H) 7.23-7.57 (m, 8 H) 7.79-7.86 (m, 2 H). $^{13}$C NMR (75 MHz, CDCl$_3$) δ ppm 27.7, 27.8, 39.8, 43.2, 74.9, 83.6, 85.2, 92.2, 113.6, 127.0, 127.2, 128.6, 129.7, 130.3, 130.9, 131.3, 131.8, 133.7, 135.1, 167.5, 168.0. HRMS (ESI-TOF) m/z: [M+H]$^+$ Calcd for $C_{23}H_{26}ClN_2O_5^+$ 445.15248; Found 445.1539.

N-(((3aR,4R,6aS)-6a-(benzamidomethyl)-2,2-dimethyltetrahydrofuro[3,4-d][1,3]dioxol-4-yl)methyl)-2-methoxybenzamide (55)

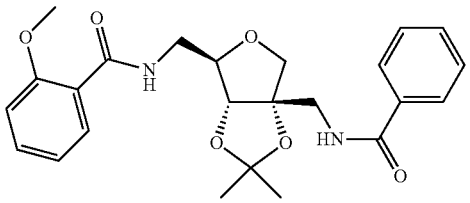 [SMILES: COc1ccccc1C(=O)NC[C@H]1OC[C@]2(CNC(=O)c3ccccc3)OC(C)(C)O[C@H]12]

General procedure 4. White foam, 64.6% $^1$H NMR (300 MHz, CDCl$_3$) δ ppm 1.38 (s, 3 H) 1.53 (s, 3 H) 3.41 (ddd, J=13.9, 6.8, 5.1 Hz, 1 H) 3.72-3.85 (m, 2 H) 3.86-4.00 (m, 6 H) 4.22-4.28 (app. t, J=7.3 Hz, 1 H) 4.56 (d, J=1.4 Hz, 1 H) 6.96-7.00 (m, 1 H) 7.04-7.11 (m, 1 H) 7.38-7.53 (m, 5 H) 7.87-7.95 (m, 2 H) 8.21 (dd, J=7.8, 1.9 Hz, 1 H) 8.27 (t, J=6.0 Hz, 1 H). $^{13}$C NMR (75 MHz, CDCl$_3$) δ ppm 27.78, 27.81, 39.5, 43.3, 56.1, 74.9, 84.2, 85.6, 92.2, 111.5, 113.4, 120.9, 121.3, 127.3, 128.6, 131.7, 132.3, 133.3, 134.1, 157.7, 166.1, 167.8. HRMS (ESI-TOF) m/z: [M+H]$^+$ Calcd for $C_{24}H_{29}N_2O_6^+$ 441.20201; Found 441.2026.

N-(((3aR,4R,6aS)-6a-(benzamidomethyl)-2,2-dimethyltetrahydrofuro[3,4-d][1,3]dioxol-4-yl)methyl)-2-cyanobenzamide (56)

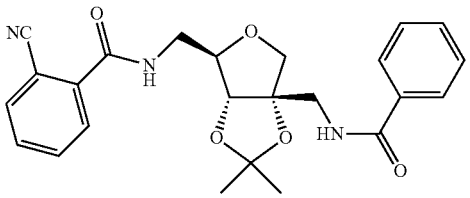 [SMILES: CC1(C)O[C@@H]2[C@@H](CNC(=O)c3ccccc3C#N)OC[C@]2(CNC(=O)c2ccccc2)O1]

General procedure 4. White foam, 65.5% $^1$H NMR (300 MHz, CDCl$_3$) δ ppm 1.40 (s, 3 H) 1.49 (s, 3 H) 3.72-3.89 (m, 2 H) 3.92-4.01 (m, 2 H) 4.03-4.14 (m, 2 H) 4.51 (app. t, J=7.8 Hz, 1 H) 4.61 (app. s, 1 H) 7.39-7.85 (m, 9 H) 7.87-7.93 (m, 2 H). $^{13}$C NMR (75 MHz, CDCl$_3$) δ ppm 27.5, 28.0, 37.9, 43.2, 74.7, 82.4, 85.8, 92.5, 113.3, 121.4, 123.4, 127.2, 128.6, 130.7, 131.7, 132.6, 133.3, 134.0, 137.5 (weak), 160.6, 168.0, 168.2. HRMS (ESI-TOF) m/z: [M+H]$^+$ Calcd for $C_{24}H_{26}N_3O_5^+$ 436.18670; Found 436.1870.

N-(((3aR,4R,6aS)-6a-(benzamidomethyl)-2,2-dimethyltetrahydrofuro[3,4-d][1,3]dioxol-4-yl)methyl)-2-(dimethylamino)benzamide (57)

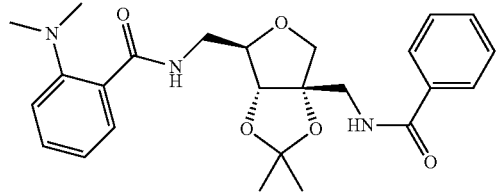 [SMILES: CN(C)c1ccccc1C(=O)NC[C@H]1OC[C@]2(CNC(=O)c3ccccc3)OC(C)(C)O[C@H]12]

General procedure 4. White foam, 64.5% $^1$H NMR (300 MHz, CDCl$_3$) δ ppm 1.38 (s, 3 H) 1.52 (s, 3 H) 2.72 (s, 6 H) 3.33 (ddd, J=13.8, 7.3, 5.0 Hz, 1 H) 3.71-3.84 (m, 2 H) 3.89-4.05 (m, 3 H) 4.18-4.28 (app. t, J=7.8 Hz, 1 H) 4.57 (app. s, 1 H) 7.12-7.26 (m, 2 H) 7.38-7.51 (m, 4 H) 7.65 (t, J=5.9 Hz, 1 H) 7.88-7.99 (m, 2 H) 8.13 (dd, J=7.8, 1.6 Hz, 1 H) 10.15 (dd, J=6.7, 5.3 Hz, 1 H). $^{13}$C NMR (75 MHz, CDCl$_3$) δ ppm 27.7, 27.8, 39.2, 43.2, 45.4, 74.8, 84.2, 85.7, 92.2, 113.3, 120.1, 124.4, 126.9, 127.3, 128.5, 131.3, 131.6, 132.3, 134.0, 152.6, 167.3, 167.8. HRMS (ESI-TOF) m/z: [M+H]$^+$ Calcd for $C_{25}H_{32}N_3O_5^+$ 454.23365; Found 454.2347.

N-(((3aR,4R,6aS)-6a-(benzamidomethyl)-2,2-dimethyltetrahydrofuro[3,4-d][1,3]dioxol-4-yl)methyl)-2-(trifluoromethyl)benzamide (58)

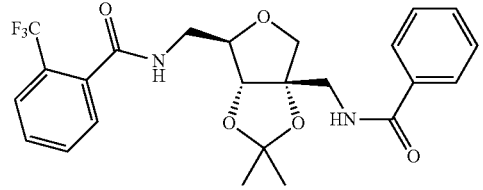 [SMILES: CC1(C)O[C@@H]2[C@@H](CNC(=O)c3ccccc3C(F)(F)F)OC[C@]2(CNC(=O)c2ccccc2)O1]

General procedure 4. White foam, 73.7% $^1$H NMR (300 MHz, CDCl$_3$) δ ppm 1.36 (s, 3 H) 1.50 (s, 3 H) 3.28 (ddd, J=13.9, 7.0, 4.8 Hz, 1 H) 3.60-3.77 (m, 2 H) 3.80-3.94 (m, 3 H) 4.20 (app. td, J=7.2, 0.9 Hz, 1 H) 4.49 (d, J=1.2 Hz, 1 H) 7.17 (dd, J=7.0, 5.0 Hz, 1 H) 7.33-7.56 (m, 7 H) 7.61-7.69 (m, 1 H) 7.75-7.83 (m, 2 H). $^{19}$F NMR (282 MHz, CDCl$_3$) δ ppm −59.3 (s). $^{13}$C NMR (75 MHz, CDCl$_3$) δ ppm 27.6, 27.7, 39.7, 43.0, 74.7, 83.5, 85.1, 92.1, 113.5, 123.6 (q, J=273.7 Hz), 126.5 (q, J=5.0 Hz), 127.1, 127.3 (q, J=32.1 Hz), 128.4, 128.6, 129.9, 131.8, 132.0, 133.5, 135.4 (q, J=2.2 Hz), 168.0, 168.8. HRMS (ESI-TOF) m/z: [M+H]$^+$ Calcd for $C_{24}H_{26}F_3N_2O_5^+$ 479.17883; Found 479.1797.

N-(((3aR,4R,6aS)-6a-(benzamidomethyl)-2,2-dimethyltetrahydrofuro[3,4-d][1,3]dioxol-4-yl)methyl)picolinamide (59)

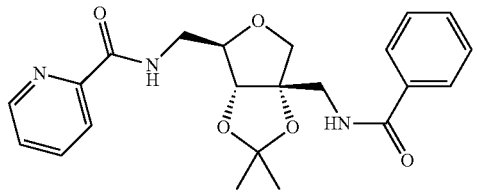

General procedure 4. White foam, 82.0% $^1$H NMR (300 MHz, CDCl$_3$) δ ppm 1.38 (s, 3 H) 1.52 (s, 3 H) 3.45 (ddd, J=13.6, 7.8, 5.6 Hz, 1 H) 3.71-3.84 (m, 2 H) 3.89-4.03 (m, 3 H) 4.28 (app. td, J=7.3, 0.9 Hz, 1 H) 4.54 (d, J=1.5 Hz, 1 H) 7.38-7.52 (m, 5 H) 7.82 (app. td, J=7.8, 1.8 Hz, 1 H) 7.89-7.95 (m, 2 H) 8.16 (app. dt, J=7.8, 1.0 Hz, 1 H) 8.48 (t, J=6.4 Hz, 1 H) 8.52-8.58 (m, 1 H). $^{13}$C NMR (75 MHz, CDCl$_3$) δ ppm 27.7, 27.8, 39.2, 43.2, 74.8, 84.0, 85.5, 92.2, 113.4, 122.2, 126.4, 127.2, 128.5, 131.6, 133.9, 137.3, 148.2, 149.4, 164.9, 167.8. HRMS (ESI-TOF) m/z: [M+H]$^+$ Calcd for C$_{22}$H$_{26}$N$_3$O$_5$$^+$ 412.18670; Found 412.1878.

N-(((3aR,4R,6aS)-6a-(benzamidomethyl)-2,2-dimethyltetrahydrofuro[3,4-d][1,3]dioxol-4-yl)methyl)-[1,1'-biphenyl]-2-carboxamide (60)

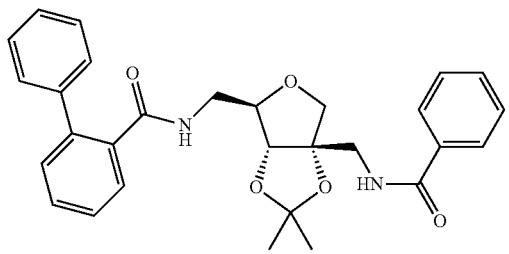 [SMILES: CC1(C)O[C@@H]2[C@@H](CNC(=O)c3ccccc3-c3ccccc3)OC[C@]2(CNC(=O)c2ccccc2)O1]

General procedure 4. White foam, 69.0% $^1$H NMR (300 MHz, CDCl$_3$) δ ppm 1.36 (s, 3 H) 1.47 (s, 3 H) 2.89-3.00 (m, 1 H) 3.42-3.65 (m, 3 H) 3.74-3.89 (m, 3 H) 4.27 (d, J=1.2 Hz, 1 H) 6.13 (dd, J=7.3, 4.7 Hz, 1 H) 7.27-7.53 (m, 12 H) 7.58-7.64 (m, 1 H) 7.77-7.85 (m, 2 H). $^{13}$C NMR (75 MHz, CDCl$_3$) δ ppm 27.7, 27.9, 39.4, 43.1, 74.5, 83.4, 85.3, 92.1, 113.3, 127.2, 127.52 (2 C), 127.7, 128.56, 128.63, 128.66 (2 C), 130.3, 131.7, 133.8, 135.4, 139.8, 140.1, 167.7, 170.3. HRMS (ESI-TOF) m/z: [M+H]$^+$ Calcd for C$_{29}$H$_{31}$N$_2$O$_5$$^+$ 487.22275; Found 487.2243.

N-(((3aR,4R,6aS)-6a-(benzamidomethyl)-2,2-dimethyltetrahydrofuro[3,4-d][1,3]dioxol-4-yl)methyl)-2-bromobenzamide (61)

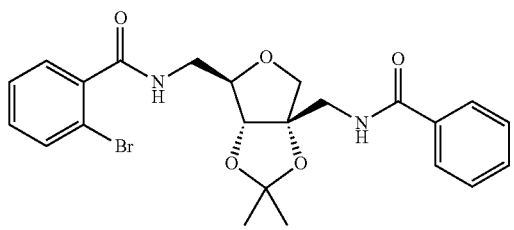 [SMILES: CC1(C)O[C@@H]2[C@@H](CNC(=O)c3ccccc3Br)OC[C@]2(CNC(=O)c2ccccc2)O1]

General procedure 4. White foam, 52.8% $^1$H NMR (300 MHz, CDCl$_3$) δ ppm 1.38 (s, 3 H) 1.52 (s, 3 H) 3.35 (ddd, J=14.1, 7.2, 4.8 Hz, 1 H) 3.64-3.81 (m, 2 H) 3.85-3.97 (m, 3 H) 4.25 (app. td, J=7.2, 1.2 Hz, 1 H) 4.53 (d, J=1.5 Hz, 1 H) 6.96 (dd, J=7.2, 4.8 Hz, 1 H) 7.20-7.34 (m, 3 H) 7.36-7.59 (m, 5 H) 7.79-7.85 (m, 2 H). $^{13}$C NMR (75 MHz, CDCl$_3$) δ ppm 27.76, 27.84, 39.8, 43.3, 74.9, 83.6, 85.2, 92.2, 113.6, 119.4, 127.2, 127.5, 128.7, 129.3, 131.3, 131.8, 133.4, 133.7, 137.7, 167.9, 168.5. HRMS (ESI-TOF) m/z: [M+H]$^+$ Calcd for C$_{23}$H$_{26}$BrN$_2$O$_5$$^+$ 489,10196; Found 489.1030.

N-(((3aR,4R,6aS)-6a-(benzamidomethyl)-2,2-dimethyltetrahydrofuro[3,4-d][1,3]dioxol-4-yl)methyl)-2-iodobenzamide (62)

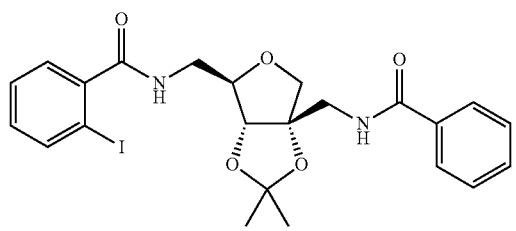 [SMILES: CC1(C)O[C@@H]2[C@@H](CNC(=O)c3ccccc3I)OC[C@]2(CNC(=O)c2ccccc2)O1]

General procedure 4. White powder, 73.9% $^1$H NMR (300 MHz, CDCl$_3$) δ ppm 1.37 (s, 3 H) 1.51 (s, 3 H) 3.32 (ddd, J=14.0, 7.3, 4.8 Hz, 1 H) 3.64-3.80 (m, 2 H) 3.85-3.97 (m, 3 H) 4.25 (app. td, J=7.1, 1.0 Hz, 1 H) 4.56 (d, J=1.5 Hz, 1 H) 6.94 (dd, J=7.2, 4.8 Hz, 1 H) 7.06 (ddd, J=8.0, 6.7, 2.3 Hz, 1 H) 7.29-7.43 (m, 5 H) 7.45-7.52 (m, 1 H) 7.79-7.86 (m, 3 H). $^{13}$C NMR (75 MHz, CDCl$_3$) δ ppm 27.76, 27.82, 39.7, 43.2, 74.9, 83.6, 85.2, 92.2, 92.6, 113.5, 127.2, 128.16, 128.22, 128.7, 131.2, 131.8, 133.7, 139.9, 141.8, 167.9, 170.2. HRMS (ESI-TOF) m/z: [M+H]$^+$ Calcd for C$_{23}$H$_{26}$IN$_2$O$_5$$^+$ 537,08809; Found 537.0892.

N-(((3aR,4R,6aS)-6a-(benzamidomethyl)-2,2-dimethyltetrahydrofuro[3,4-d][1,3]dioxol-4-yl)methyl)-3,4-dimethylbenzamide (63)

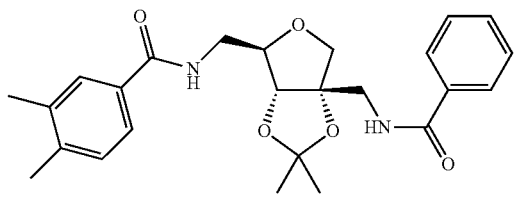 [SMILES: Cc1ccc(C(=O)NC[C@H]2OC[C@]3(CNC(=O)c4ccccc4)OC(C)(C)O[C@H]23)cc1C]

General procedure 4. White foam, 66.4% $^1$H NMR (300 MHz, CDCl$_3$) δ ppm 1.36 (s, 3 H) 1.50 (s, 3 H) 2.25 (s, 3 H) 2.27 (s, 3 H) 3.42 (ddd, J=14.1, 6.7, 5.3 Hz, 1 H) 3.66-3.80 (m, 2 H) 3.84-3.99 (m, 3 H) 4.27 (app. t, J=7.2 Hz, 1 H) 4.53 (d, J=1.2 Hz, 1 H) 7.14 (d, J=7.9 Hz, 1 H) 7.20-7.27 (m, 1 H) 7.37-7.60 (m, 5 H) 7.63 (app. s, 1 H) 7.85-7.96 (m, 2 H). $^{13}$C NMR (75 MHz, CDCl$_3$) δ ppm 19.7, 19.8, 27.7, 27.8, 39.7, 43.2, 75.0, 83.8, 85.1, 92.3, 113.3, 124.6, 127.3, 128.5, 128.6, 129.7, 131.5, 131.8, 133.8, 136.9, 140.8, 168.1, 168.2. HRMS (ESI-TOF) m/z: [M+H]$^+$ Calcd for C$_{25}$H$_{31}$N$_2$O$_5$$^+$ 439.22275; Found 439.2233.

N-(((3aR,4R,6aS)-6a-(benzamidomethyl)-2,2-dimethyltetrahydrofuro[3,4-d][1,3]dioxol-4-yl)methyl)-3,4-difluorobenzamide (64)

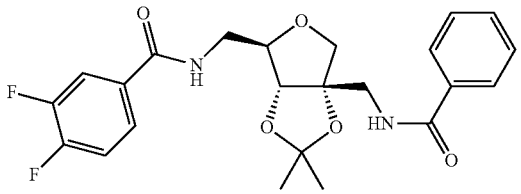 [SMILES: CC1(C)O[C@@H]2[C@@H](CNC(=O)c3ccc(F)c(F)c3)OC[C@]2(CNC(=O)c2ccccc2)O1]

General procedure 4. White foam, 93.1% $^1$H NMR (300 MHz, CDCl$_3$) δ ppm 1.37 (s, 3 H) 1.52 (s, 3 H) 3.53 (ddd, J=14.1, 6.2, 5.1 Hz, 1 H) 3.63 (dd, J=14.5, 5.4 Hz, 1 H) 3.72-4.00 (m, 4 H) 4.31 (app. td, J=6.6, 1.2 Hz, 1 H) 4.47 (d, J=1.5 Hz, 1 H) 7.13-7.23 (m, 2 H) 7.42-7.59 (m, 4 H) 7.65-7.72 (m, 1 H) 7.76-7.89 (m, 3 H). $^{19}$F NMR (282 MHz, CDCl$_3$) δ ppm −136.9 (m), −133.2 (m). $^{13}$C NMR (75 MHz, CDCl$_3$) δ ppm 27.8, 27.9, 40.0, 43.2, 75.2, 83.3, 84.7, 92.3, 113.6, 117.4 (dd, J=17.7, 3.0 Hz), 117.3 (dd, J=18.2, 6.0 Hz), 124.1 (dd, J=6.9, 3.6 Hz), 127.1, 128.9, 131.3 (dd, J=4.7, 3.6 Hz), 132.2, 133.5, 150.4 (dd, J=249.6, 13.0 Hz), 152.72 (dd, J=254.3, 12.7 Hz), 165.9 (d, J=6.0 Hz), 168.4. HRMS (ESI-TOF) m/z: [M+Na]$^+$ Calcd for C$_{23}$H$_{24}$F$_2$N$_2$NaO$_5^+$ 469.15455; Found 469.1563.

N-(((3aR,4R,6aS)-6a-(benzamidomethyl)-2,2-dimethyltetrahydrofuro[3,4-d][1,3]dioxol-4-yl)methyl)-3,4-dichlorobenzamide (65)

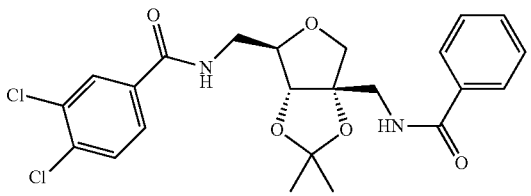 [SMILES: CC1(C)O[C@@H]2[C@@H](CNC(=O)c3ccc(Cl)c(Cl)c3)OC[C@]2(CNC(=O)c2ccccc2)O1]

General procedure 4. White foam, 76.3% $^1$H NMR (300 MHz, CDCl$_3$) δ ppm 1.36 (s, 3 H) 1.52 (s, 3 H) 3.47-3.57 (m, 1 H) 3.62 (dd, J=14.5, 5.4 Hz, 1 H) 3.74-4.00 (m, 4 H) 4.31 (app. td, J=6.7, 0.9 Hz, 1 H) 4.48 (d, J=1.2 Hz, 1 H) 7.23 (t, J=6.2 Hz, 1 H) 7.39-7.57 (m, 4 H) 7.68 (t, J=6.0 Hz, 1 H) 7.74 (dd, J=8.5, 2.1 Hz, 1 H) 7.81-7.92 (m, 2 H) 8.04 (d, J=2.1 Hz, 1 H). $^{13}$C NMR (75 MHz, CDCl$_3$) δ ppm 27.8, 27.9, 40.0, 43.1, 75.2, 83.3, 84.6, 92.3, 113.6, 126.7, 127.2, 128.9, 129.7, 130.5, 132.2, 132.9, 133.5, 133.9, 136.0, 165.9, 168.4. HRMS (ESI-TOF) m/z: [M+Na]$^+$ Calcd for C$_{23}$H$_{24}$Cl$_2$N$_2$NaO$_5^+$ 501.09545; Found 501.0978.

N-(((3aR,4R,6aS)-6a-(benzamidomethyl)-2,2-dimethyltetrahydrofuro[3,4-d][1,3]dioxol-4-yl)methyl)-3,4-dimethoxybenzamide (66)

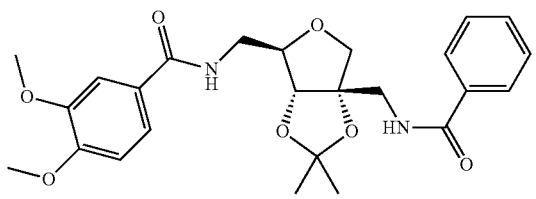 [SMILES: COc1ccc(C(=O)NC[C@H]2OC[C@]3(CNC(=O)c4ccccc4)OC(C)(C)O[C@H]23)cc1OC]

General procedure 4. White foam, 82.3% $^1$H NMR (300 MHz, CDCl$_3$) δ ppm 1.36 (s, 3 H) 1.51 (s, 3 H) 3.46 (ddd, J=14.1, 6.4, 5.3 Hz, 1 H) 3.66-3.99 (m, 11 H) 4.29 (app. td, J=6.7, 0.9 Hz, 1 H) 4.52 (d, J=1.2 Hz, 1 H) 6.84 (d, J=8.2 Hz, 1 H) 7.23-7.34 (m, 2 H) 7.37-7.57 (m, 5 H) 7.82-7.93 (m, 2 H). $^{13}$C NMR (75 MHz, CDCl$_3$) δ ppm 27.7, 27.8, 39.9, 43.1, 56.03 (2 C), 75.0, 83.8, 85.1, 92.3, 110.4, 110.7, 113.5, 120.2, 126.6, 127.2, 128.7, 132.0, 133.7, 148.9, 151.9, 167.6, 168.1. HRMS (ESI-TOF) m/z: [M+H]$^+$ Calcd for C$_{25}$H$_{31}$N$_2$O$_7^+$ 471.21258; Found 471.2130.

N-(((3aR,4R,6aS)-6a-(benzamidomethyl)-2,2-dimethyltetrahydrofuro[3,4-d][1,3]dioxol-4-yl)methyl)-1-naphthamide (67)

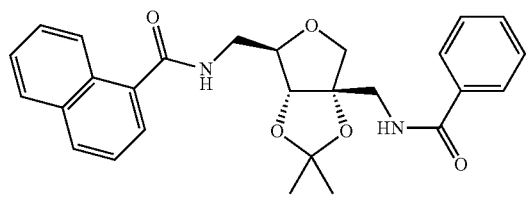 [SMILES: CC1(C)O[C@@H]2[C@@H](CNC(=O)c3cccc4ccccc34)OC[C@]2(CNC(=O)c2ccccc2)O1]

General procedure 4. White foam, 67.5% $^1$H NMR (300 MHz, CDCl$_3$) (major conformer) δ ppm 1.34 (s, 3 H) 1.49 (s, 3 H) 3.32 (ddd, J=13.9, 7.5, 5.0 Hz, 1 H) 3.57 (dd, J=14.2, 5.4 Hz, 1 H) 3.73 (app. dt, J=14.0, 7.2 Hz, 1 H) 3.79-3.91 (m, 3 H) 4.24 (app. t, J=7.2 Hz, 1 H) 4.51 (d, J=1.2 Hz, 1 H) 7.19-7.25 (m, 1 H) 7.27-7.37 (m, 3 H) 7.38-7.55 (m, 5 H) 7.74-7.85 (m, 4 H) 8.18-8.26 (m, 1 H). $^{13}$C NMR (75 MHz, CDCl$_3$) δ ppm 27.66, 27.74, 39.6, 43.0, 74.7, 83.7, 85.2, 92.1, 113.4, 124.6, 125.2, 125.3, 126.3, 127.0, 127.2, 128.3, 128.5, 130.0, 130.7, 131.7, 133.58, 133.64, 133.8, 168.0, 170.3. HRMS (ESI-TOF) m/z: [M+H]$^+$ Calcd for C$_{27}$H$_{29}$N$_2$O$_5^+$ 461.20710; Found 461.2088.

N-(((3aR,4R,6aS)-6a-(benzamidomethyl)-2,2-dimethyltetrahydrofuro[3,4-d][1,3]dioxol-4-yl)methyl)-2-naphthamide (68)

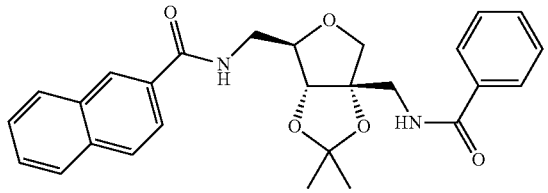 [SMILES: CC1(C)O[C@@H]2[C@@H](CNC(=O)c3ccc4ccccc4c3)OC[C@]2(CNC(=O)c2ccccc2)O1]

General procedure 4. White foam, 94.5% $^1$H NMR (300 MHz, CDCl$_3$) δ ppm 1.36 (s, 3 H) 1.51 (s, 3 H) 3.53 (ddd, J=14.0, 6.8, 5.2 Hz, 1 H) 3.71 (dd, J=14.4, 5.7 Hz, 1 H) 3.77-3.99 (m, 4 H) 4.35 (app. td, J=7.0, 1.0 Hz, 1 H) 4.56 (d, J=1.2 Hz, 1 H) 7.30-7.59 (m, 7 H) 7.76-7.98 (m, 6 H) 8.34-8.44 (app. d, J=1.4 Hz, 1 H). $^{13}$C NMR (75 MHz, CDCl$_3$) δ ppm 27.8, 27.9, 39.9, 43.2, 75.1, 83.7, 85.1, 92.3, 113.5, 123.9, 126.7, 127.2, 127.74, 127.76, 127.9, 128.4, 128.7, 129.1, 131.3, 132.0, 132.7, 133.8, 134.9, 168.15, 168.18. HRMS (ESI-TOF) m/z: [M+H]$^+$ Calcd for C$_{27}$H$_{29}$N$_2$O$_5^+$ 461.20710; Found 461.2085.

N-(((3aR,4R,6aS)-6a-(benzamidomethyl)-2,2-dimethyltetrahydrofuro[3,4-d][1,3]dioxol-4-yl)methyl)-1-methyl-1H-indole-2-carboxamide (69)

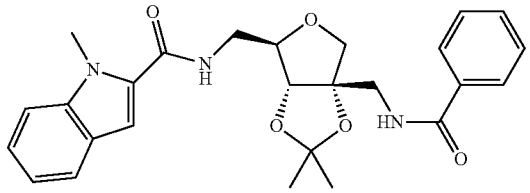 [SMILES: Cn1c(C(=O)NC[C@H]2OC[C@]3(CNC(=O)c4ccccc4)OC(C)(C)O[C@H]23)cc2ccccc21]

General procedure 4. Pink foam, 57.5% $^1$H NMR (300 MHz, CDCl$_3$) δ ppm 1.37 (s, 3 H) 1.52 (s, 3 H) 3.44 (ddd, J=14.1, 6.7, 5.3 Hz, 1 H) 3.64-3.80 (m, 2 H) 3.85-4.05 (m, 6 H) 4.30 (app. td, J=7.0, 1.2 Hz, 1 H) 4.49 (d, J=1.2 Hz, 1 H) 7.01 (app. s, 1 H) 7.09-7.22 (m, 3 H) 7.27-7.54 (m, 5 H) 7.56-7.62 (m, 1 H) 7.81-7.91 (m, 2 H). $^{13}$C NMR (75 MHz, CDCl$_3$) δ ppm 27.8, 27.9, 31.7, 39.4, 43.3, 75.1, 83.7, 85.1, 92.3, 104.7, 110.2, 113.5, 120.5, 122.0, 124.2, 126.1, 127.2, 128.8, 131.5, 132.0, 133.8, 139.2, 163.2, 168.1. HRMS (ESI-TOF) m/z: [M+H]$^+$ Calcd for C$_{26}$H$_{30}$N$_3$O$_5^+$ 464.21800; Found 464.2188.

N-(((3aR,4R,6aS)-6a-(benzamidomethyl)-2,2-dimethyltetrahydrofuro[3,4-d][1,3]dioxol-4-yl)methyl)-1-methyl-1H-indole-3-carboxamide (70)

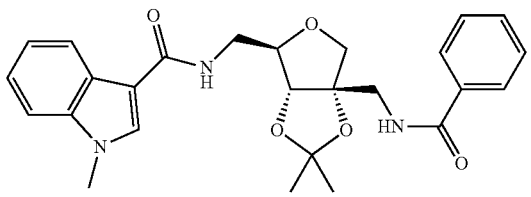 [SMILES: Cn1cc(C(=O)NC[C@H]2OC[C@]3(CNC(=O)c4ccccc4)OC(C)(C)O[C@H]23)c2ccccc21]

General procedure 4. White foam, 71.7% $^1$H NMR (300 MHz, CDCl$_3$) δ ppm 1.34 (s, 3 H) 1.50 (s, 3 H) 3.42 (app. dt, J=13.9, 5.6 Hz, 1 H) 3.68 (s, 3 H) 3.71-3.96 (m, 5 H) 4.28 (app. t, J=6.9 Hz, 1 H) 4.57-4.63 (d, J=0.9 Hz, 1 H) 6.92 (t, J=5.9 Hz, 1 H) 7.14-7.34 (m, 3 H) 7.37-7.51 (m, 3 H) 7.64 (t, J=6.2 Hz, 1 H) 7.73 (s, 1 H) 7.88-7.98 (m, 2 H) 8.11-8.17 (m, 1 H). $^{13}$C NMR (75 MHz, CDCl$_3$) δ ppm 27.8, 27.9, 33.5, 39.3, 43.3, 75.1, 84.3, 85.3, 92.3, 110.1, 110.3, 113.6, 120.9, 121.7, 122.8, 125.9, 127.3, 128.8, 131.9, 132.3, 134.0, 137.4, 165.8, 168.0. HRMS (ESI-TOF) m/z: [M+H]$^+$ Calcd for C$_{26}$H$_{30}$N$_3$O$_5^+$ 464.21800; Found 464.2202.

N,N'-(((3aS,6R,6aR)-2,2-dimethyldihydrofuro[3,4-d][1,3]dioxole-3a, 6(4H)-diyl)bis(methylene))dibenzamide (71)

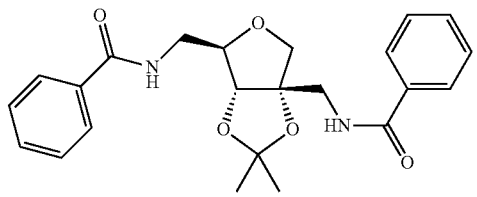 [SMILES: CC1(C)O[C@@H]2[C@@H](CNC(=O)c3ccccc3)OC[C@]2(CNC(=O)c2ccccc2)O1]

General procedure 4. White foam, 82.7% $^1$H NMR (300 MHz, CDCl$_3$) δ ppm 1.37 (s, 3 H) 1.51 (s, 3 H) 3.46 (ddd, J=14.0, 7.0, 5.1 Hz, 1 H) 3.66-3.82 (m, 2 H) 3.85-4.00 (m, 3 H) 4.29 (app. td, J=7.0, 0.9 Hz, 1 H) 4.51 (d, J=1.2 Hz, 1 H) 7.23 (t, J=6.0 Hz, 1 H) 7.32 (t, J=6.2 Hz, 1 H) 7.36-7.56 (m, 6 H) 7.77-7.95 (m, 4 H). $^{13}$C NMR (75 MHz, CDCl$_3$) δ ppm 27.8, 27.9, 39.8, 43.3, 75.0, 83.7, 85.1, 92.3, 113.5, 127.2, 127.3, 128.6, 128.8, 131.7, 132.0, 133.8, 134.1, 168.05, 168.10. HRMS (ESI-TOF) m/z: [M+H]$^+$ Calcd for C$_{23}$H$_{27}$N$_2$O$_5^+$ 411.19145; Found 411.1920.

N-(((3aS,6R,6aR)-2,2-dimethyl-6-((2-phenylacetamido)methyl)dihydrofuro[3,4-d][1,3]dioxol-3a (4H)-yl)methyl)benzamide (72)

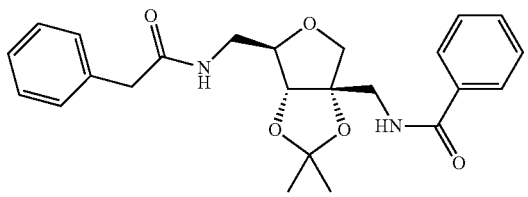 [SMILES: CC1(C)O[C@@H]2[C@@H](CNC(=O)Cc3ccccc3)OC[C@]2(CNC(=O)c2ccccc2)O1]

General procedure 4. White foam, 81.1% $^1$H NMR (300 MHz, CDCl$_3$) δ ppm 1.35 (s, 3 H) 1.49 (s, 3 H) 3.18 (ddd, J=14.1, 6.7, 5.2 Hz, 1 H) 3.51-3.66 (m, 4 H) 3.75-3.88 (m, 3 H) 4.10 (app. td, J=6.4, 1.3 Hz, 1 H) 4.37 (d, J=1.5 Hz, 1 H) 6.66 (dd, J=6.7, 5.3 Hz, 1 H) 7.20-7.33 (m, 6 H) 7.37-7.54 (m, 3 H) 7.78-7.89 (m, 2 H). $^{13}$C NMR (75 MHz, CDCl$_3$) δ ppm 27.7, 27.9, 39.7, 43.0, 43.7, 75.0, 83.8, 84.9, 92.1, 113.6, 127.2, 127.3, 128.7, 128.9, 129.4, 131.9, 133.8, 135.0, 168.0, 172.0. HRMS (ESI-TOF) m/z: [M+H]$^+$ Calcd for C$_{24}$H$_{29}$N$_2$O$_5^+$ 425.20710; Found 425.2075.

N-(((3aS,6R,6aR)-2,2-dimethyl-6-((3-phenylpropanamido)methyl)dihydrofuro[3,4-d][1,3]dioxol-3a (4H)-yl)methyl)benzamide (73)

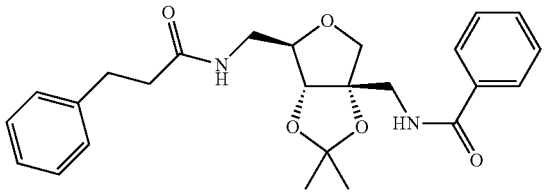 [SMILES: CC1(C)O[C@@H]2[C@@H](CNC(=O)CCc3ccccc3)OC[C@]2(CNC(=O)c2ccccc2)O1]

General procedure 4. White foam, 68.8% $^1$H NMR (300 MHz, CDCl$_3$) δ ppm 1.36 (s, 3 H) 1.51 (s, 3 H) 2.57 (t, J=7.6 Hz, 2 H) 2.98 (t, J=7.6 Hz, 2 H) 3.18-3.23 (m, 1 H) 3.56 (dd, J=14.4, 5.6 Hz, 1 H) 3.66 (ddd, J=14.1, 7.5, 6.4 Hz, 1 H) 3.74-3.91 (m, 3 H) 4.10 (app. td, J=6.1, 1.3 Hz, 1 H) 4.32 (d, J=1.5 Hz, 1 H) 6.47 (dd, J=6.7, 5.0 Hz, 1 H) 7.07 (t, J=6.2 Hz, 1 H) 7.12-7.32 (m, 5 H) 7.39-7.58 (m, 3 H) 7.78-7.91 (m, 2 H). $^{13}$C NMR (75 MHz, CDCl$_3$) δ ppm 27.8, 28.0, 31.7, 38.4, 39.5, 42.9, 75.0, 83.9, 84.8, 92.2, 113.7, 126.3, 127.2, 128.56, 128.59, 128.8, 132.0, 133.7, 141.1, 168.0, 173.0. HRMS (ESI-TOF) m/z: [M+H]$^+$ Calcd for C$_{25}$H$_{31}$N$_2$O$_5^+$ 439.22275; Found 439.2229.

N-(((3aS,6R,6aR)-6-(cyclohexanecarboxamidomethyl)-2,2-dimethyldihydrofuro[3,4-d][1,3]dioxol-3a(4H)-yl)methyl)benzamide (74)

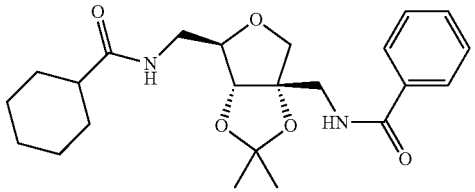 [SMILES: CC1(C)O[C@@H]2[C@@H](CNC(=O)C3CCCCC3)OC[C@]2(CNC(=O)c2ccccc2)O1]

General procedure 4. Light brown colored foam, 76.7% $^1$H NMR (300 MHz, CDCl$_3$) δ ppm 1.18-1.52 (m, 11 H) 1.63-1.89 (m, 5 H) 2.16 (tt, J=11.6, 3.4 Hz, 1 H) 3.17 (ddd, J=14.0, 6.7, 4.8 Hz, 1 H) 3.58 (app. dt, J=14.2, 7.3 Hz, 1 H) 3.71 (dd, J=14.2, 5.7 Hz, 1 H) 3.82-3.98 (m, 3 H) 4.13 (app. td, J=6.9, 0.8 Hz, 1 H) 4.43 (d, J=1.2 Hz, 1 H) 6.57 (dd, J=6.7, 5.0 Hz, 1 H) 7.38-7.59 (m, 4 H) 7.85-7.94 (m, 2 H). $^{13}$C NMR (75 MHz, CDCl$_3$) δ ppm 25.69 (2 C), 25.8, 27.7, 27.8, 29.6, 29.7, 39.1, 43.1, 45.3, 74.8, 83.8, 85.0, 92.1, 113.4, 127.3, 128.6, 131.8, 133.8, 168.0, 177.2. HRMS (ESI-TOF) m/z: [M+H]$^+$ Calcd for C$_{23}$H$_{33}$N$_2$O$_5$$^+$ 417.23840; Found 417.2396.

N-(((3aR,4R,6aS)-6a-(benzamidomethyl)-2,2-dimethyltetrahydrofuro[3,4-d][1,3]dioxol-4-yl)methyl)-2,6-dichlorobenzamide (75)

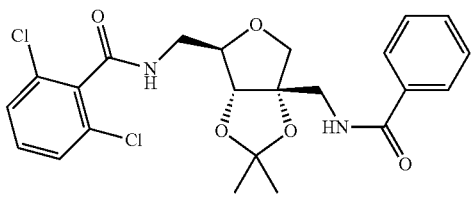

General procedure 4. White foam, 27.9% $^1$H NMR (300 MHz, CDCl$_3$) δ ppm 1.37 (s, 3 H) 1.53 (s, 3 H) 3.39 (ddd, J=14.1, 6.7, 4.7 Hz, 1 H) 3.68 (dd, J=14.4, 5.6 Hz, 1 H) 3.81-4.01 (m, 4 H) 4.28 (app. td, J=6.9, 1.2 Hz, 1 H) 4.55 (d, J=1.5 Hz, 1 H) 6.91 (dd, J=7.3, 4.7 Hz, 1 H) 7.13-7.32 (m, 4 H) 7.35-7.45 (m, 2 H) 7.47-7.53 (m, 1 H) 7.75-7.83 (m, 2 H). $^{13}$C NMR (75 MHz, CDCl$_3$) δ ppm 27.7, 27.9, 39.8, 43.2, 75.0, 83.5, 85.0, 92.1, 113.7, 127.2, 128.1, 128.7, 130.8, 132.0, 132.3, 133.6, 135.9, 165.4, 167.9. HRMS (ESI-TOF) m/z: [M+H]$^+$ Calcd for C$_{23}$H$_{25}$Cl$_2$N$_2$O$_5$$^+$ 479.11350; Found 479.1126.

N-(((3aR,4R,6aS)-6a-(benzamidomethyl)-2,2-dimethyltetrahydrofuro[3,4-d][1,3]dioxol-4-yl)methyl)-2,4-dichlorobenzamide (76)

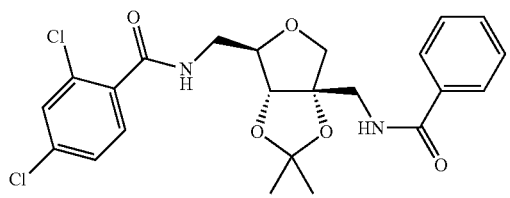 [SMILES: CC1(C)O[C@@H]2[C@@H](CNC(=O)c3ccc(Cl)cc3Cl)OC[C@]2(CNC(=O)c2ccccc2)O1]

General procedure 4. White foam, 77.3% $^1$H NMR (300 MHz, CDCl$_3$) δ ppm 1.38 (s, 3 H) 1.52 (s, 3 H) 3.42 (ddd, J=14.1, 7.3, 5.0 Hz, 1 H) 3.64-3.82 (m, 2 H) 3.85-3.94 (m, 3 H) 4.26 (app. td, J=7.0, 1.3 Hz, 1 H) 4.47 (d, J=1.5 Hz, 1 H) 7.12-7.28 (m, 3 H) 7.36-7.54 (m, 5 H) 7.76-7.82 (m, 2 H). $^{13}$C NMR (75 MHz, CDCl$_3$) δ ppm 27.95, 28.04, 40.2, 43.4, 75.2, 83.7, 85.2, 92.4, 113.9, 127.3, 127.6, 128.9, 130.2, 131.0, 132.0, 132.1, 133.7, 133.8, 136.9, 166.6, 168.2. HRMS (ESI-TOF) m/z: [M+H]$^+$ Calcd for C$_{23}$H$_{25}$Cl$_2$N$_2$O$_5$$^+$ 479.11350; Found 479.1135.

N-(((3aR,4R,6aS)-6a-(benzamidomethyl)-2,2-dimethyltetrahydrofuro[3,4-d][1,3]dioxol-4-yl)methyl)-2,4,6-trichlorobenzamide (77)

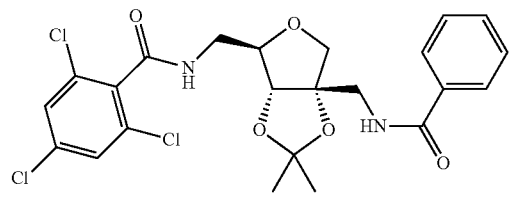 [SMILES: CC1(C)O[C@@H]2[C@@H](CNC(=O)c3c(Cl)cc(Cl)cc3Cl)OC[C@]2(CNC(=O)c2ccccc2)O1]

General procedure 4. White foam, 37.9% $^1$H NMR (300 MHz, CDCl$_3$) δ ppm 1.36 (s, 3 H) 1.53 (s, 3 H) 3.42 (ddd, J=14.1, 6.2, 4.5 Hz, 1 H) 3.66 (dd, J=14.4, 5.6 Hz, 1 H) 3.80-3.99 (m, 4 H) 4.29 (app. td, J=6.5, 1.4 Hz, 1 H) 4.50 (d, J=1.5 Hz, 1 H) 7.13 (t, J=6.2 Hz, 1 H) 7.22 (dd, J=6.9, 4.5 Hz, 1 H) 7.30 (s, 2 H) 7.39-7.55 (m, 3 H) 7.73-7.79 (m, 2 H). $^{13}$C NMR (75 MHz, CDCl$_3$) δ ppm 27.8, 28.1, 40.1, 43.3, 75.2, 83.4, 84.9, 92.2, 113.9, 127.2, 128.3, 128.9, 132.2, 133.1, 133.5, 134.6, 135.9, 164.8, 168.3. HRMS (ESI-TOF) m/z: [M+H]$^+$ Calcd for C$_{23}$H$_{24}$Cl$_3$N$_2$O$_5$$^+$ 513.07453; Found 513.0757.

N-(((3aR,4R,6aS)-6a-(benzamidomethyl)-2,2-dimethyltetrahydrofuro[3,4-d][1,3]dioxol-4-yl)methyl)-3,5-dichloroisonicotinamide (78)

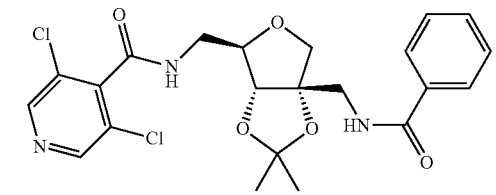 [SMILES: CC1(C)O[C@@H]2[C@@H](CNC(=O)c3c(Cl)cncc3Cl)OC[C@]2(CNC(=O)c2ccccc2)O1]

General procedure 4. White foam, 53.8% $^1$H NMR (300 MHz, CDCl$_3$) δ ppm 1.35 (s, 3 H) 1.52 (s, 3 H) 3.41 (ddd, J=14.1, 5.8, 4.4 Hz, 1 H) 3.58 (dd, J=14.4, 5.3 Hz, 1 H) 3.83-3.97 (m, 4 H) 4.28 (app. td, J=6.2, 1.5 Hz, 1 H) 4.46 (d, J=1.8 Hz, 1 H) 7.21 (t, J=6.3 Hz, 1 H) 7.35-7.42 (m, 2 H) 7.47-7.53 (m, 1 H) 7.68-7.73 (m, 2 H) 7.87 (dd, J=7.6, 4.4 Hz, 1 H) 8.44 (s, 2 H). $^{13}$C NMR (75 MHz, CDCl3) δ ppm 27.5, 28.0, 39.9, 42.9, 75.0, 83.1, 84.4, 92.1, 113.8, 127.0, 128.7, 129.0, 132.1, 133.3, 142.5, 147.6, 163.0, 168.2. HRMS (ESI-TOF) m/z: [M+H]$^+$ Calcd for C$_{22}$H$_{24}$Cl$_2$N$_3$O$_5$$^+$ 480.10875; Found 480.1098.

N-(((3aR,4R,6aS)-6a-(benzamidomethyl)-2,2-dimethyltetrahydrofuro[3,4-d][1,3]dioxol-4-yl)methyl)-2,4-dichloronicotinamide (79)

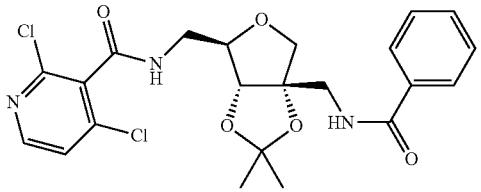 [SMILES: CC1(C)O[C@@H]2[C@@H](CNC(=O)c3c(Cl)ccnc3Cl)OC[C@]2(CNC(=O)c2ccccc2)O1]

General procedure 4. White foam, 51.5% ¹H NMR (300 MHz, CDCl₃) δ ppm 1.35 (s, 3 H) 1.51 (s, 3 H) 3.39 (ddd, J=14.1, 5.9, 4.5 Hz, 1 H) 3.61 (dd, J=14.4, 5.6 Hz, 1 H) 3.82-3.97 (m, 4 H) 4.27 (app. td, J=6.2, 1.3 Hz, 1 H) 4.49 (d, J=1.8 Hz, 1 H) 7.22-7.28 (m, 2 H) 7.36-7.43 (m, 2 H), 7.46-7.52 (m, 1 H) 7.71-7.76 (m, 2 H) 7.85 (dd, J=7.6, 4.4 Hz, 1 H) 8.22 (d, J=5.3 Hz, 1 H). ¹³C NMR (75 MHz, CDCl₃) δ ppm 27.5, 27.9, 39.9, 43.0, 74.9, 83.2, 84.6, 92.0, 113.7, 123.7, 127.1, 128.7, 132.0, 132.3, 133.3, 143.1, 148.8, 149.8, 163.8, 168.1. HRMS (ESI-TOF) m/z: [M+H]⁺ Calcd for $C_{22}H_{24}Cl_2N_3O_5^+$ 480.10875; Found 480.1087.

N-(((3aR,4R,6aS)-6a-(benzamidomethyl)-2,2-dimethyltetrahydrofuro[3,4-d][1,3]dioxol-4-yl)methyl)-2,6-dichloronicotinamide (80)

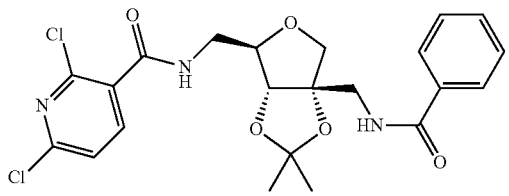 [SMILES: CC1(C)O[C@@H]2[C@@H](CNC(=O)c3ccc(Cl)nc3Cl)OC[C@]2(CNC(=O)c2ccccc2)O1]

General procedure 4. White foam, 86.1% ¹H NMR (300 MHz, CDCl₃) δ ppm 1.37 (s, 3 H) 1.52 (s, 3 H) 3.47 (ddd, J=14.1, 6.7, 4.7 Hz, 1 H) 3.64 (dd, J=14.4, 5.6 Hz, 1 H) 3.76-3.93 (m, 4 H) 4.28 (app. t, J=6.5 Hz, 1 H) 4.43 (d, J=1.5 Hz, 1 H) 7.10 (t, J=6.2 Hz, 1 H) 7.29 (d, J=7.9 Hz, 1 H) 7.38-7.46 (m, 2 H) 7.48-7.56 (m, 1 H) 7.65 (dd, J=7.0, 4.7 Hz, 1 H) 7.72-7.79 (m, 2 H) 7.93 (d, J=8.2 Hz, 1 H). ¹³C NMR (75 MHz, CDCl₃) δ ppm 27.7, 27.9, 40.3, 43.1, 75.0, 83.3, 84.6, 92.2, 113.8, 123.2, 127.0, 128.8, 130.3, 132.0, 133.4, 141.3, 146.7, 151.4, 164.9, 168.1. HRMS (ESI-TOF) m/z: [M+H]⁺ Calcd for $C_{22}H_{24}Cl_2N_3O_5^+$ 480.10875; Found 480.1090.

N-(((3aR,4R,6aS)-6a-(benzamidomethyl)-2,2-dimethyltetrahydrofuro[3,4-d][1,3]dioxol-4-yl)methyl)-4,6-dichloronicotinamide (81)

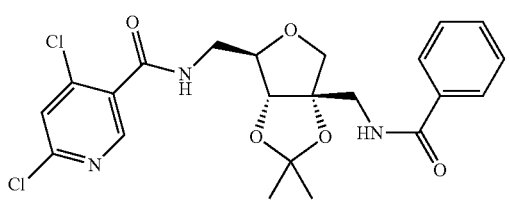 [SMILES: CC1(C)O[C@@H]2[C@@H](CNC(=O)c3cnc(Cl)cc3Cl)OC[C@]2(CNC(=O)c2ccccc2)O1]

General procedure 4. White foam, 80.9% ¹H NMR (300 MHz, CDCl₃) δ ppm 1.37 (s, 3 H) 1.52 (s, 3 H) 3.44 (ddd, J=14.1, 6.7, 4.7 Hz, 1 H) 3.63 (dd, J=14.4, 5.6 Hz, 1 H) 3.77-3.92 (m, 4 H) 4.27 (app. td, J=6.4, 1.5 Hz, 1 H) 4.45 (d, J=1.8 Hz, 1 H) 7.26-7.53 (m, 5 H) 7.72-7.78 (m, 2 H) 7.83 (dd, J=7.0, 4.7 Hz, 1 H) 8.52 (s, 1 H). ¹³C NMR (75 MHz, CDCl₃) δ ppm 27.6, 27.9, 40.1, 43.0, 74.9, 83.2, 84.6, 92.1, 113.7, 125.0, 127.0, 128.6, 130.2, 131.9, 133.3, 143.0, 149.8, 152.9, 164.2, 168.1. HRMS (ESI-TOF) m/z: [M+H]⁺ Calcd for $C_{22}H_{24}Cl_2N_3O_5^+$ 480.10875; Found 480.1100.

N-(((3aR,4R,6aS)-6a-(benzamidomethyl)-2,2-dimethyltetrahydrofuro[3,4-d][1,3]dioxol-4-yl)methyl)-2-chloronicotinamide (82)

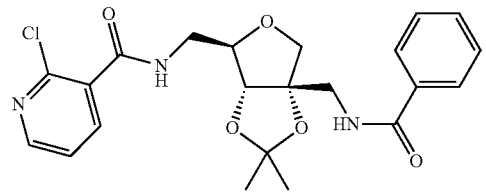 [SMILES: CC1(C)O[C@@H]2[C@@H](CNC(=O)c3cccnc3Cl)OC[C@]2(CNC(=O)c2ccccc2)O1]

General procedure 4. White foam ¹H NMR (300 MHz, CDCl₃) δ ppm 1.37 (s, 3 H) 1.51 (s, 3 H) 3.42 (ddd, J=14.0, 7.1, 4.7 Hz, 1 H) 3.66 (dd, J=14.4, 5.6 Hz, 1 H) 3.73-3.93 (m, 4 H) 4.27 (app. td, J=6.7, 0.9 Hz, 1 H) 4.48 (d, J=1.5 Hz, 1 H) 7.26 (dd, J=7.6, 4.7 Hz, 1 H) 7.33-7.52 (m, 4 H) 7.69 (dd, J=6.9, 4.8 Hz, 1 H) 7.75-7.81 (m, 2 H) 7.91 (dd, J=7.6, 2.1 Hz, 1 H) 8.37 (dd, J=4.8, 1.9 Hz, 1 H). ¹³C NMR (75 MHz, CDCl₃) δ ppm 27.6, 27.8, 40.0, 43.1, 74.9, 83.3, 84.8, 92.1, 113.6, 122.5, 127.0, 128.6, 131.7, 131.8, 133.5, 138.7, 147.4, 150.6, 165.8, 168.0. HRMS (ESI-TOF) m/z: [M+H]⁺ Calcd for $C_{22}H_{25}ClN_3O_5^+$ 446.14773; Found 446.1489.

N-(((3aR,4R,6aS)-6a-(benzamidomethyl)-2,2-dimethyltetrahydrofuro[3,4-d][1,3]dioxol-4-yl)methyl)-3-chloroisonicotinamide (83)

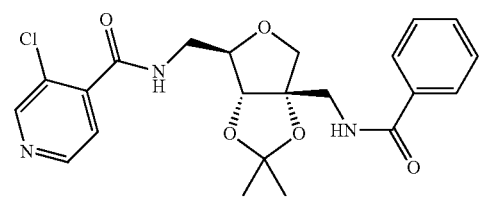 [SMILES: CC1(C)O[C@@H]2[C@@H](CNC(=O)c3ccncc3Cl)OC[C@]2(CNC(=O)c2ccccc2)O1]

General procedure 4. White foam ¹H NMR (300 MHz, CDCl₃) δ ppm 1.37 (s, 3 H) 1.52 (s, 3 H) 3.44 (ddd, J=14.1, 6.9, 4.8 Hz, 1 H) 3.63 (dd, J=14.4, 5.9 Hz, 1 H) 3.75-3.92 (m, 4 H) 4.27 (app. t, J=6.6 Hz, 1 H) 4.45 (d, J=1.2 Hz, 1 H) 7.28-7.35 (m, 1 H) 7.36-7.53 (m, 4 H) 7.69 (dd, J=6.7, 5.0 Hz, 1 H) 7.73-7.80 (m, 2 H) 8.47 (app. d, J=5.0 Hz, 1 H) 8.56 (app. s, 1 H). ¹³C NMR (75 MHz, CDCl₃) δ ppm 27.7, 27.9, 40.0, 43.1, 74.9, 83.2, 84.6, 92.1, 113.7, 123.0, 127.0, 128.1, 128.6, 131.9, 133.5, 142.0, 148.0, 150.2, 165.2, 168.1. HRMS (ESI-TOF) m/z: [M+H]⁺ Calcd for $C_{22}H_{25}ClN_3O_5^+$ 446.14773; Found 446.1493.

N-(((3aR,4R,6aS)-6a-(benzamidomethyl)-2,2-dimethyltetrahydrofuro[3,4-d][1,3]dioxol-4-yl)methyl)-4-chloronicotinamide (84)

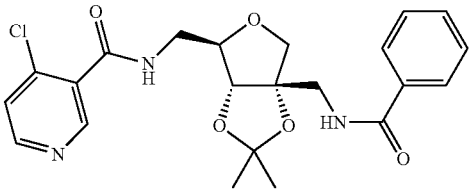

General procedure 4. White foam $^{1}$H NMR (300 MHz, CDCl$_3$) δ ppm 1.37 (s, 3 H) 1.52 (s, 3 H) 3.45 (ddd, J=14.0, 7.0, 4.8 Hz, 1 H) 3.65 (dd, J=14.2, 5.7 Hz, 1 H) 3.77-3.93 (m, 4 H) 4.28 (app. t, J=6.6 Hz, 1 H) 4.47 (d, J=1.5 Hz, 1 H) 7.25-7.34 (m, 2 H) 7.37-7.44 (m, 2 H) 7.46-7.53 (m, 1 H) 7.67 (dd, J=6.7, 5.0 Hz, 1 H) 7.74-7.81 (m, 2 H) 8.45 (app. d, J=5.6 Hz, 1 H) 8.73 (app. s, 1 H). $^{13}$C NMR (75 MHz, CDCl$_3$) δ ppm 27.7, 27.9, 40.1, 43.1, 74.9, 83.4, 84.8, 92.1, 113.7, 125.0, 127.1, 128.7, 131.3, 131.9, 133.5, 141.2, 150.1, 151.4, 165.1, 168.1. HRMS (ESI-TOF) m/z: [M+H]$^+$ Calcd for C$_{22}$H$_{25}$ClN$_3$O$_5$$^+$ 446.14773; Found 446.1476.

N-(((3aR,4R,6aS)-6a-(benzamidomethyl)-2,2-dimethyltetrahydrofuro[3,4-d][1,3]dioxol-4-yl)methyl)-6-chloronicotinamide (85)

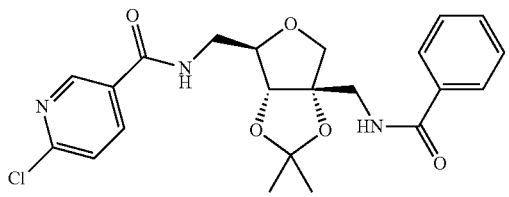

General procedure 4. White foam, 57.6% $^{1}$H NMR (300 MHz, CDCl$_3$) δ ppm 1.36 (s, 3 H) 1.51 (s, 3 H) 3.51 (app. dt, J=14.4, 5.2 Hz, 1 H) 3.61 (dd, J=14.4, 5.6 Hz, 1 H) 3.82-3.96 (m, 4 H) 4.30 (app. td, J=6.2, 1.2 Hz, 1 H) 4.48 (d, J=1.5 Hz, 1 H) 7.31-7.57 (m, 5 H) 7.80-7.87 (m, 2 H) 8.06 (dd, J=6.9, 4.8 Hz, 1 H) 8.18-8.24 (m, 1 H) 8.94 (app. dd, J=2.6, 0.6 Hz, 1 H). $^{13}$C NMR (75 MHz, CDCl$_3$) δ ppm 27.6, 27.9, 40.1, 43.0, 75.1, 83.3, 84.5, 92.2, 113.7, 124.1, 127.1, 128.77, 128.80, 132.2, 133.4, 138.2, 149.0, 154.1, 165.3, 168.5. HRMS (ESI-TOF) m/z: [M+H]$^+$ Calcd for C$_{22}$H$_{25}$ClN$_3$O$_5$$^+$ 446.14773; Found 446.1460.

N-(((3aR,4R,6aS)-6a-(benzamidomethyl)-2,2-dimethyltetrahydrofuro[3,4-d][1,3]dioxol-4-yl)methyl)pyrimidine-2-carboxamide (86)

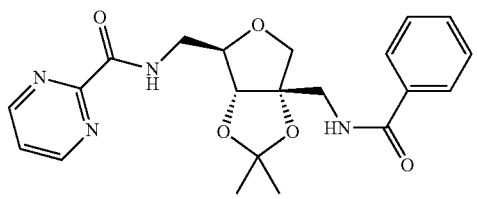

General procedure 4. Pale yellow foam, 50.8% $^{1}$H NMR (300 MHz, CDCl$_3$) δ ppm 1.39 (s, 3 H) 1.52 (s, 3 H) 3.47 (ddd, J=13.9, 7.2, 5.6 Hz, 1 H) 3.71-3.89 (m, 2 H) 3.94-4.04 (m, 3 H) 4.27 (app. td, J=7.3, 1.2 Hz, 1 H) 4.54 (d, J=1.2 Hz, 1 H) 7.34 (t, J=6.2 Hz, 1 H) 7.39-7.53 (m, 4 H) 7.88-7.94 (m, 2 H) 8.46 (t, J=6.3 Hz, 1 H) 8.89 (d, J=4.7 Hz, 2 H). $^{13}$C NMR (75 MHz, CDCl$_3$) δ ppm 27.7, 27.8, 39.6, 43.3, 74.8, 84.1, 85.8, 92.3, 113.6, 122.8, 127.3, 128.7, 131.8, 133.8, 157.3, 157.6, 163.0, 167.9. HRMS (ESI-TOF) m/z: [M+H]$^+$ Calcd for C$_{21}$H$_{25}$N$_4$O$_5$$^+$ 413.18195; Found 413.1826.

N-(((3aR,4R,6aS)-6a-(benzamidomethyl)-2,2-dimethyltetrahydrofuro[3,4-d][1,3]dioxol-4-yl)methyl)pyrimidine-4-carboxamide (87)

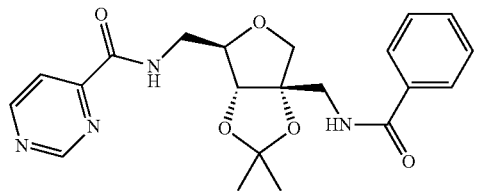 [SMILES: CC1(C)O[C@@H]2[C@@H](CNC(=O)c3ccncn3)OC[C@]2(CNC(=O)c2ccccc2)O1]

General procedure 4. Pale yellow foam, 52.8% $^{1}$H NMR (300 MHz, CDCl$_3$) δ ppm 1.41 (s, 3 H) 1.53 (s, 3 H) 3.54 (ddd, J=13.9, 8.1, 5.6 Hz, 1 H) 3.72-3.82 (m, 2 H) 3.89-3.99 (m, 3 H) 4.26-4.34 (m, 1 H) 4.45 (d, J=1.5 Hz, 1 H) 6.99 (t, J=6.0 Hz, 1 H) 7.41-7.56 (m, 3 H) 7.82-7.89 (m, 2 H) 8.10 (dd, J=5.0, 1.5 Hz, 1 H) 8.41 (t, J=6.2 Hz, 1 H) 8.97 (d, J=5.3 Hz, 1 H) 9.25 (d, J=1.2 Hz, 1 H). $^{13}$C NMR (75 MHz, CDCl$_3$) δ ppm 27.8, 28.0, 39.7, 43.5, 75.1, 83.8, 85.4, 92.3, 113.9, 118.7, 127.1, 128.7, 131.9, 133.9, 156.0, 157.9, 159.3, 163.2, 167.9. HRMS (ESI-TOF) m/z: [M+H]$^+$ Calcd for C$_{21}$H$_{25}$N$_4$O$_5$$^+$ 413.18195; Found 413.1816.

N-(((3aR,4R,6aS)-6a-(benzamidomethyl)-2,2-dimethyltetrahydrofuro[3,4-d][1,3]dioxol-4-yl)methyl)pyrimidine-5-carboxamide (88)

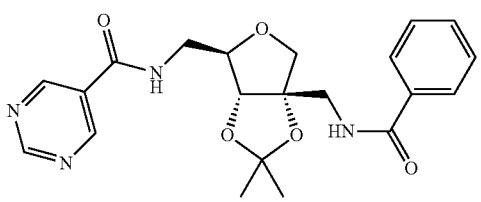

General procedure 4. Pale yellow foam, 71.3% $^{1}$H NMR (300 MHz, CDCl$_3$) δ ppm 1.36 (s, 3 H) 1.52 (s, 3 H) 3.50-3.61 (m, 2 H) 3.83-3.99 (m, 4 H) 4.32 (app. td, J=5.8, 1.6 Hz, 1 H) 4.47 (d, J=1.8 Hz, 1 H) 7.38 (dd, J=6.7, 5.9 Hz, 1 H) 7.41-7.57 (m, 3 H) 7.79-7.87 (m, 2 H) 8.34 (dd, J=7.0, 4.7 Hz, 1 H) 9.27 (app. s, 1 H) 9.29 (app. s, 2 H). $^{13}$C NMR (75 MHz, CDCl$_3$) δ ppm 27.6, 28.0, 40.2, 42.9, 75.1, 83.2, 84.3, 92.2, 113.9, 127.1, 127.7, 128.9, 132.3, 133.2, 156.3, 160.4 (weak), 164.3, 168.6. HRMS (ESI-TOF) m/z: [M+H]$^+$ Calcd for C$_{21}$H$_{25}$N$_4$O$_5$$^+$ 413.18195; Found 413.1828.

N-(((3aR,4R,6aS)-6a-(benzamidomethyl)-2,2-dimethyltetrahydrofuro[3,4-d][1,3]dioxol-4-yl)methyl)pyridazine-3-carboxamide (89)

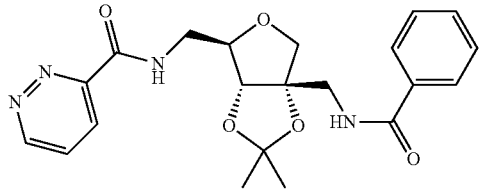

General procedure 4. White foam, 75.8% $^1$H NMR (300 MHz, CDCl$_3$) δ ppm 1.40 (s, 3 H) 1.53 (s, 3 H) 3.56 (ddd, J=13.8, 8.1, 5.6 Hz, 1 H) 3.72-3.87 (m, 2 H) 3.91-4.03 (m, 3 H) 4.33 (app. t, J=7.3 Hz, 1 H) 4.53 (d, J=1.5 Hz, 1 H) 7.18 (t, J=6.0 Hz, 1 H) 7.39-7.53 (m, 3 H) 7.67 (dd, J=8.5, 5.0 Hz, 1 H) 7.82-7.91 (m, 2 H) 8.29 (dd, J=8.5, 1.8 Hz, 1 H) 8.65 (t, J=6.2 Hz, 1 H) 9.29 (dd, J=5.0, 1.8 Hz, 1 H). $^{13}$C NMR (75 MHz, CDCl$_3$) δ ppm 27.8, 28.0, 39.6, 43.3, 74.9, 83.9, 85.5, 92.3, 113.7, 125.8, 127.1, 127.7, 128.6, 131.7, 133.9, 152.4, 152.9, 163.1, 167.8. HRMS (ESI-TOF) m/z: [M+H]$^+$ Calcd for C$_{21}$H$_{25}$N$_4$O$_5^+$ 413.18195; Found 413.1825.

N-(((3aR,4R,6aS)-6a-(benzamidomethyl)-2,2-dimethyltetrahydrofuro[3,4-d][1,3]dioxol-4-yl)methyl)pyridazine-4-carboxamide (90)

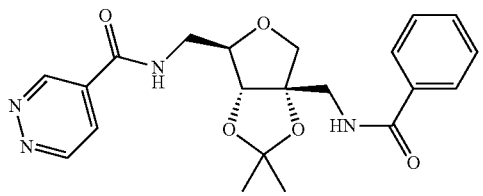 [SMILES: CC1(C)O[C@@H]2[C@@H](CNC(=O)c3ccnnc3)OC[C@]2(CNC(=O)c2ccccc2)O1]

General procedure 4. Yellow foam, 77.4% $^1$H NMR (300 MHz, CDCl$_3$) δ ppm 1.36 (s, 3 H) 1.51 (s, 3 H) 3.51-3.64 (m, 2 H) 3.82-3.99 (m, 4 H) 4.33 (app. td, J=5.9, 1.4 Hz, 1 H) 4.49 (d, J=1.8 Hz, 1 H) 7.40-7.57 (m, 4 H) 7.82-7.89 (m, 2 H) 8.07 (dd, J=5.3, 2.3 Hz, 1 H) 8.74 (dd, J=6.9, 4.8 Hz, 1 H) 9.30 (dd, J=5.3, 1.2 Hz, 1 H) 9.73 (dd, J=2.2, 1.3 Hz, 1 H). $^{13}$C NMR (75 MHz, CDCl$_3$) δ ppm 27.6, 28.0, 40.3, 43.0, 75.1, 83.1, 84.4, 92.2, 113.8, 124.5, 127.1, 128.8, 131.7, 132.2, 133.3, 149.2, 151.8, 164.2, 168.6. HRMS (ESI-TOF) m/z: [M+H]$^+$ Calcd for C$_{21}$H$_{25}$N$_4$O$_5^+$ 413.18195; Found 413.1819.

N-(((3aR,4R,6aS)-6a-(benzamidomethyl)-2,2-dimethyltetrahydrofuro[3,4-d][1,3]dioxol-4-yl)methyl)pyrazine-2-carboxamide (91)

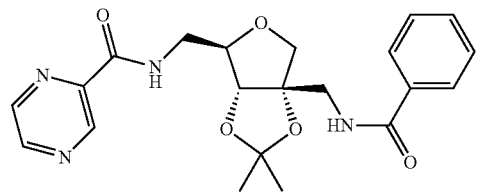

General procedure 4. White foam, 83.1% $^1$H NMR (300 MHz, CDCl$_3$) δ ppm 1.40 (s, 3 H) 1.53 (s, 3 H) 3.53 (ddd, J=13.8, 7.8, 5.7 Hz, 1 H) 3.72-3.82 (m, 2 H) 3.87-4.00 (m, 3 H) 4.29 (app. t, J=7.0 Hz, 1 H) 4.48 (d, J=1.2 Hz, 1 H) 7.15 (t, J=6.00 Hz, 1 H) 7.40-7.54 (m, 3 H) 7.82-7.91 (m, 2 H) 8.26 (t, J=6.2 Hz, 1 H) 8.50-8.57 (m, 1 H) 8.75 (d, J=2.3 Hz, 1 H) 9.39 (d, J=1.2 Hz, 1 H). $^{13}$C NMR (75 MHz, CDCl$_3$) δ ppm 27.8, 27.9, 39.4, 43.3, 74.9, 83.9, 85.3, 92.3, 113.7, 127.1, 128.6, 131.8, 133.8, 142.7, 144.2, 144.4, 147.4, 163.6, 167.9. HRMS (ESI-TOF) m/z: [M+H]$^+$ Calcd for C$_{21}$H$_{25}$N$_4$O$_5^+$ 413.18195; Found 413.1831.

N-(((3aR,4R,6aS)-6a-(benzamidomethyl)-2,2-dimethyltetrahydrofuro[3,4-d][1,3]dioxol-4-yl)methyl)-1-methyl-1H-pyrazole-5-carboxamide (92)

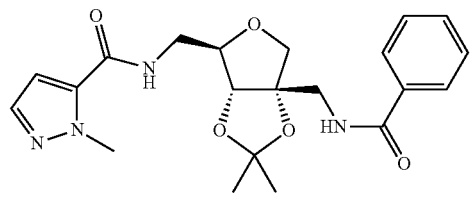 [SMILES: Cn1nccc1C(=O)NC[C@H]1OC[C@]2(CNC(=O)c3ccccc3)OC(C)(C)O[C@H]12]

General procedure 4. White foam, 87.2% $^1$H NMR (300 MHz, CDCl$_3$) δ ppm 1.36 (s, 3 H) 1.51 (s, 3 H) 3.40 (app. dt, J=14.1, 5.7 Hz, 1 H) 3.63 (dd, J=14.4, 5.6 Hz, 1 H) 3.71-3.98 (m, 4 H) 4.14 (s, 3 H) 4.28 (app. t, J=6.2 Hz, 1 H) 4.48 (d, J=1.2 Hz, 1 H) 6.80 (d, J=2.1 Hz, 1 H) 7.38-7.56 (m, 5 H) 7.63 (dd, J=6.9, 5.4 Hz, 1 H) 7.82-7.91 (m, 2 H). $^{13}$C NMR (75 MHz, CDCl$_3$) δ ppm 27.6, 27.8, 39.26, 39.33, 42.9, 75.0, 83.3, 84.7, 92.1, 107.1, 113.4, 127.1, 128.6, 132.0, 133.5, 135.0, 137.5, 160.5, 168.3. HRMS (ESI-TOF) m/z: [M+H]$^+$ Calcd for C$_{21}$H$_{27}$N$_4$O$_5^+$ 415.19760; Found 415.1985.

N-(((3aR,4R,6aS)-6a-(benzamidomethyl)-2,2-dimethyltetrahydrofuro[3,4-d][1,3]dioxol-4-yl)methyl)-1-methyl-1H-imidazole-5-carboxamide (93)

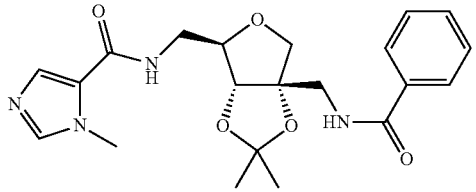 [SMILES: Cn1cncc1C(=O)NC[C@H]1OC[C@]2(CNC(=O)c3ccccc3)OC(C)(C)O[C@H]12]

General procedure 4. White foam, 94.6% $^1$H NMR (300 MHz, CDCl$_3$) δ ppm 1.36 (s, 3 H) 1.51 (s, 3 H) 3.37 (app. dt, J=14.1, 5.6 Hz, 1 H) 3.61 (dd, J=14.4, 5.3 Hz, 1 H) 3.70-4.00 (m, 7 H) 4.26 (app. t, J=6.3 Hz, 1 H) 4.50 (d, J=1.2 Hz, 1 H) 7.36-7.53 (m, 4 H) 7.63-7.75 (m, 2 H) 7.83-7.98 (m, 3 H). $^{13}$C NMR (75 MHz, CDCl$_3$) δ ppm 27.8, 28.0, 34.4, 39.3, 43.1, 75.4, 83.6, 84.8, 92.4, 113.7, 126.1, 127.1, 128.9, 132.2, 132.5, 133.6, 141.9, 161.0, 168.3. HRMS (ESI-TOF) m/z: [M+H]$^+$ Calcd for C$_{21}$H$_{27}$N$_4$O$_5^+$ 415.19760; Found 415.1991.

N-(((3aS,6R,6aR)-2,2-dimethyl-6-(methylsulfonamidomethyl)dihydrofuro[3,4-d][1,3]dioxol-3a(4H)-yl)methyl)benzamide (94)

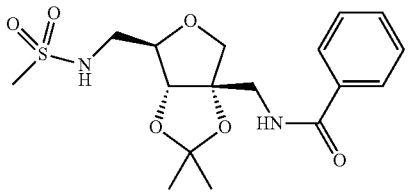 [SMILES: CC1(C)O[C@@H]2[C@@H](CNS(C)(=O)=O)OC[C@]2(CNC(=O)c2ccccc2)O1]

General procedure 5. White foam, 77.3% $^1$H NMR (300 MHz, CDCl$_3$) δ ppm 1.37 (s, 3 H) 1.51 (s, 3 H) 2.96 (s, 3 H) 3.25-3.40 (m, 2 H) 3.74 (dd, J=14.4, 6.2 Hz, 1 H) 3.82-3.94 (m, 3 H) 4.19 (app. td, J=5.6, 1.6 Hz, 1 H) 4.45 (d, J=1.8 Hz, 1 H) 5.96 (t, J=6.3 Hz, 1 H) 7.02 (t, J=6.3 Hz, 1 H) 7.40-7.54 (m, 3 H) 7.77-7.84 (m, 2 H). $^{13}$C NMR (75 MHz, CDCl$_3$) δ ppm 27.9, 28.1, 40.7, 43.1, 43.7, 75.4, 84.1, 84.6, 92.4, 114.1, 127.3, 128.9, 132.2, 133.8, 168.5. HRMS (ESI-TOF) m/z: [M−H]$^-$ Calcd for C$_{17}$H$_{23}$N$_2$O$_6$S$^-$ 383.12823; Found 383.1270.

N-(((3aS,6R,6aR)-6-(ethylsulfonamidomethyl)-2,2-dimethyldihydrofuro[3,4-d][1,3]dioxol-3a(4H)-yl)methyl)benzamide (95)

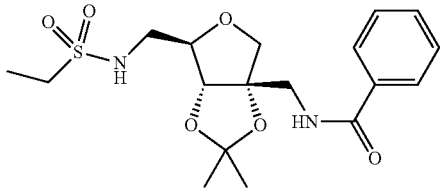 [SMILES: CCS(=O)(=O)NC[C@H]1OC[C@]2(CNC(=O)c3ccccc3)OC(C)(C)O[C@H]12]

General procedure 5. White foam, 77.9% $^1$H NMR (300 MHz, CDCl$_3$) δ ppm 1.32 (t, J=7.3 Hz, 3 H) 1.37 (s, 3 H) 1.51 (s, 3 H) 3.03 (q, J=7.3 Hz, 2 H) 3.20-3.35 (m, 2 H) 3.74 (dd, J=14.4, 6.2 Hz, 1 H) 3.80-3.96 (m, 3 H) 4.17 (app. td, J=5.8, 1.3 Hz, 1 H) 4.48 (d, J=1.5 Hz, 1 H) 5.89 (t, J=6.3 Hz, 1 H) 7.15 (t, J=6.3 Hz, 1 H) 7.39-7.53 (m, 3 H) 7.77-7.86 (m, 2 H). $^{13}$C NMR (75 MHz, CDCl$_3$) δ ppm 8.2, 27.6, 27.8, 42.9, 43.4, 47.1, 75.1, 84.0, 84.4, 92.1, 113.7, 127.1, 128.6, 131.9, 133.6, 168.2. HRMS (ESI-TOF) m/z: [M−H]$^-$ Calcd for C$_{18}$H$_{25}$N$_2$O$_6$S$^-$ 397.14388; Found 397.1423.

N-(((3aS,6R,6aR)-2,2-dimethyl-6-(((1-methylethyl)sulfonamido)methyl)dihydrofuro[3,4-d][1,3]dioxol-3a(4H)-yl)methyl)benzamide (96)

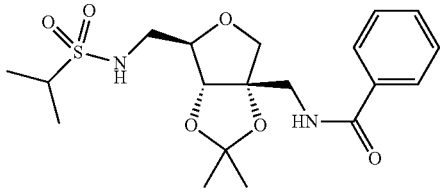 [SMILES: CC(C)S(=O)(=O)NC[C@H]1OC[C@]2(CNC(=O)c3ccccc3)OC(C)(C)O[C@H]12]

General procedure 5. White foam, 36.0% $^1$H NMR (300 MHz, CDCl$_3$) δ ppm 1.28-1.42 (m, 9 H) 1.52 (s, 3 H) 3.18 (sep, J=6.9 Hz, 1 H) 3.25-3.41 (m, 2 H) 3.74 (dd, J=14.5, 6.0 Hz, 1 H) 3.84-3.96 (m, 3 H) 4.18 (app. td, J=5.7, 1.5 Hz, 1 H) 4.46 (d, J=1.5 Hz, 1 H) 5.52 (dd, J=7.3, 5.3 Hz, 1 H) 6.93 (t, J=6.3 Hz, 1 H) 7.41-7.55 (m, 3 H) 7.77-7.86 (m, 2 H). $^{13}$C NMR (75 MHz, CDCl$_3$) δ ppm 16.66, 16.71, 27.7, 27.9, 43.0, 44.0, 53.8, 75.3, 84.2, 84.4, 92.3, 113.8, 127.1, 128.8, 132.0, 133.7, 168.2. HRMS (ESI-TOF) m/z: [M−H]$^-$ Calcd for C$_{19}$H$_{27}$N$_2$O$_6$S$^-$ 411.15953; Found 411.1585.

N-(((3aS,6R,6aR)-2,2-dimethyl-6-((((trifluoromethyl)sulfonamido)methyl)dihydrofuro[3,4-d][1,3]dioxol-3a(4H)-yl)methyl)benzamide (97)

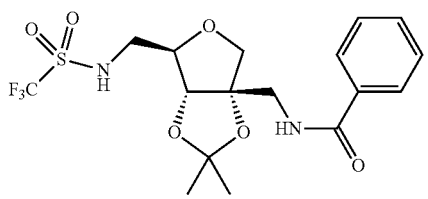 [SMILES: CC1(C)O[C@@H]2[C@@H](CNS(=O)(=O)C(F)(F)F)OC[C@]2(CNC(=O)c2ccccc2)O1]

General procedure 5. White foam, 16.4% $^1$H NMR (300 MHz, CDCl$_3$) δ ppm 1.33 (s, 3 H) 1.54 (s, 3 H) 3.43-3.57 (m, 2 H) 3.60-3.70 (m, 1 H) 3.90 (q, J=9.7 Hz, 2 H) 4.10 (dd, J=14.9, 7.9 Hz, 1 H) 4.24 (app. td, J=4.3, 1.8 Hz, 1 H) 4.36 (d, J=1.8 Hz, 1 H) 6.84 (t, J=6.3 Hz, 1 H) 7.44-7.59 (m, 3 H) 7.76-7.85 (m, 2 H) 7.92 (br.s., 1 H). $^{19}$F NMR (282 MHz, CDCl$_3$) δ ppm −77.9 (s). $^{13}$C NMR (75 MHz, CDCl$_3$) δ ppm 27.5, 28.3, 42.6, 45.2, 75.7, 82.9, 83.7, 92.3, 114.2, 120.0 (q, J=321.2 Hz), 127.2, 129.1, 132.6, 133.1, 169.1. HRMS (ESI-TOF) m/z: [M−H]$^-$ Calcd for C$_{17}$H$_{20}$F$_3$N$_2$O$_6$S$^-$ 437.09997; Found 437.0984.

N-(((3aS,6R,6aR)-2,2-dimethyl-6-(phenylsulfonamidomethyl)dihydrofuro[3,4-d][1,3]dioxol-3a(4H)-yl)methyl)benzamide (98)

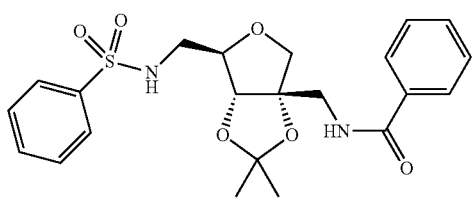 [SMILES: CC1(C)O[C@@H]2[C@@H](CNS(=O)(=O)c3ccccc3)OC[C@]2(CNC(=O)c2ccccc2)O1]

General procedure 5. White foam, 60.0% $^1$H NMR (300 MHz, CDCl$_3$) δ ppm 1.35 (s, 3 H) 1.48 (s, 3 H) 3.07 (app. dt, J=13.6, 5.6 Hz, 1 H) 3.21 (ddd, J=13.6, 8.0, 5.4 Hz, 1 H) 3.65-3.88 (m, 4 H) 4.13 (app. td, J=5.6, 1.5 Hz, 1 H) 4.44 (d, J=1.8 Hz, 1 H) 6.11 (dd, J=7.8, 5.1 Hz, 1 H) 6.96 (t, J=6.2 Hz, 1 H) 7.34-7.59 (m, 6 H) 7.72-7.93 (m, 4 H). $^{13}$C NMR (75 MHz, CDCl$_3$) δ ppm 27.7, 27.9, 43.0, 43.6, 75.3, 83.6, 84.5, 92.2, 113.8, 127.0, 127.1, 128.8, 129.2, 132.0, 132.7, 133.7, 140.1, 168.3. HRMS (ESI-TOF) m/z: [M−H]$^-$ Calcd for C$_{22}$H$_{25}$N$_2$O$_6$S$^-$ 445.14388; Found 445.1421.

N-(((3aS,6R,6aR)-2,2-dimethyl-6-(((4-methylphenyl)sulfonamido)methyl)dihydrofuro[3,4-d][1,3]dioxol-3a(4H)-yl)methyl)benzamide (99)

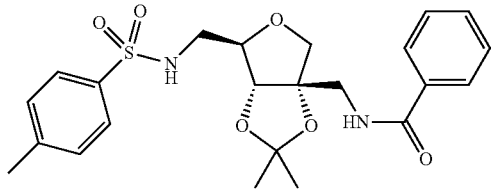 [SMILES: Cc1ccc(S(=O)(=O)NC[C@H]2OC[C@]3(CNC(=O)c4ccccc4)OC(C)(C)O[C@H]23)cc1]

General procedure 5. White powder, 86.4% ¹H NMR (300 MHz, CDCl₃) δ ppm 1.34 (s, 3 H) 1.47 (s, 3 H) 2.38 (s, 3 H) 2.98-3.21 (m, 2 H) 3.67-3.85 (m, 4 H) 4.12 (app. td, J=5.9, 1.3 Hz, 1 H) 4.47 (d, J=1.5 Hz, 1 H) 6.10 (dd, J=7.6, 5.3 Hz, 1 H) 7.09 (t, J=6.2 Hz, 1 H) 7.23 (d, J=8.2 Hz, 2 H) 7.35-7.43 (m, 2 H) 7.45-7.52 (m, 1 H) 7.70 (d, J=8.2 Hz, 2 H) 7.76-7.83 (m, 2 H). ¹³C NMR (75 MHz, CDCl₃) δ ppm 21.6, 27.8, 27.9, 43.2, 43.7, 75.4, 83.6, 84.6, 92.3, 113.9, 127.14 (2 C), 128.8, 129.9, 132.0, 133.8, 137.1, 143.5, 168.2. HRMS (ESI-TOF) m/z: [M+H]⁺ Calcd for $C_{23}H_{29}N_2O_6S^+$ 461.17408; Found 461.1738.

N-(((3aS,6R,6aR)-6-(((4-chlorophenyl)sulfonamido)methyl)-2,2-dimethyldihydrofuro[3,4-d][1,3]dioxol-3a(4H)-yl)methyl)benzamide (100)

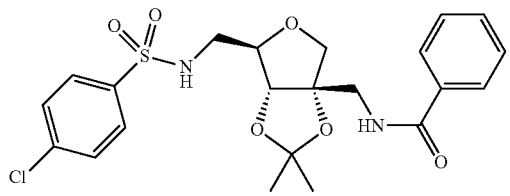 [SMILES: CC1(C)O[C@@H]2[C@@H](CNS(=O)(=O)c3ccc(Cl)cc3)OC[C@]2(CNC(=O)c2ccccc2)O1]

General procedure 5. White foam, 90.6% ¹H NMR (300 MHz, CDCl₃) δ ppm 1.35 (s, 3 H) 1.48 (s, 3 H) 3.09 (app. dt, J=13.7, 5.5 Hz, 1 H) 3.22 (ddd, J=13.6, 8.0, 5.4 Hz, 1 H) 3.69 (dd, J=14.4, 6.2 Hz, 1 H) 3.75-3.90 (m, 3 H) 4.13 (app. td, J=5.5, 1.6 Hz, 1 H) 4.42 (d, J=1.8 Hz, 1 H) 6.37 (dd, J=7.8, 5.1 Hz, 1 H) 6.95 (t, J=6.2 Hz, 1 H) 7.36-7.56 (m, 5 H) 7.71-7.86 (m, 4 H). ¹³C NMR (75 MHz, CDCl₃) δ ppm 27.7, 27.9, 43.0, 43.7, 75.3, 83.5, 84.4, 92.2, 113.9, 127.1, 128.5, 128.8, 129.4, 132.1, 133.6, 138.8, 139.0, 168.4. HRMS (ESI-TOF) m/z: [M−H]⁻ Calcd for $C_{22}H_{24}ClN_2O_6S^-$ 479.10491; Found 479.1047.

N-(((3aS,6R,6aR)-6-(((2-chlorophenyl)sulfonamido)methyl)-2,2-dimethyldihydrofuro[3,4-d][1,3]dioxol-3a(4H)-yl)methyl)benzamide (101)

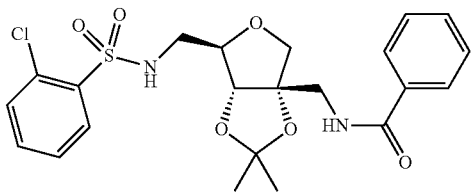 [SMILES: CC1(C)O[C@@H]2[C@@H](CNS(=O)(=O)c3ccccc3Cl)OC[C@]2(CNC(=O)c2ccccc2)O1]

General procedure 5. White foam, 76.4% ¹H NMR (300 MHz, CDCl₃) δ ppm 1.34 (s, 3 H) 1.46 (s, 3 H) 3.04 (ddd, J=13.7, 7.0, 5.1 Hz, 1 H) 3.17 (ddd, J=13.6, 7.8, 5.6 Hz, 1 H) 3.68 (dd, J=14.4, 6.2 Hz, 1 H) 3.75-3.89 (m, 3 H) 4.12 (app. t, J=6.3 Hz, 1 H) 4.45 (d, J=1.5 Hz, 1 H) 6.23 (dd, J=7.6, 5.0 Hz, 1 H) 7.04 (t, J=6.2 Hz, 1 H) 7.30-7.53 (m, 6 H) 7.73-7.83 (m, 2 H) 7.96-8.03 (m, 1 H). ¹³C NMR (75 MHz, CDCl₃) δ ppm 27.6, 27.8, 43.0, 43.3, 75.1, 83.3, 84.4, 92.1, 113.7, 127.0, 127.2, 128.6, 131.0, 131.4, 131.6, 131.8, 133.6, 133.8, 137.1, 168.1. HRMS (ESI-TOF) m/z: [M−H]⁻ Calcd for $C_{22}H_{24}ClN_2O_6S^-$ 479.10491; Found 479.1055.

N-(((3aS,6R,6aR)-6-(([1,1'-biphenyl]-4-sulfonamido)methyl)-2,2-dimethyldihydrofuro[3,4-d][1,3]dioxol-3a(4H)-yl)methyl)benzamide (102)

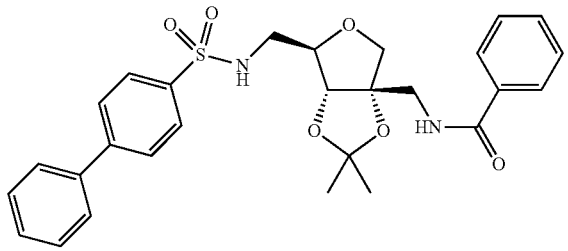 [SMILES: CC1(C)O[C@@H]2[C@@H](CNS(=O)(=O)c3ccc(-c4ccccc4)cc3)OC[C@]2(CNC(=O)c2ccccc2)O1]

General procedure 5. White foam, 66.6% ¹H NMR (300 MHz, CDCl₃) δ ppm 1.35 (s, 3 H) 1.48 (s, 3 H) 3.13 (dt, J=13.8, 5.6 Hz, 1 H) 3.25 (ddd, J=13.6, 7.8, 5.3 Hz, 1 H) 3.73 (dd, J=14.4, 6.2 Hz, 1 H) 3.78-3.91 (m, 3 H) 4.16 (app. td, J=5.6, 1.5 Hz, 1 H) 4.47 (d, J=1.8 Hz, 1 H) 6.22 (dd, J=7.3, 5.3 Hz, 1 H) 6.98 (t, J=6.3 Hz, 1 H) 7.31-7.52 (m, 6 H) 7.52-7.60 (m, 2 H) 7.61-7.71 (m, 2 H) 7.75-7.85 (m, 2 H) 7.85-7.96 (m, 2 H). ¹³C NMR (75 MHz, CDCl₃) δ ppm 27.7, 27.9, 43.1, 43.7, 75.3, 83.6, 84.5, 92.2, 113.8, 127.1, 127.4, 127.6, 127.8, 128.5, 128.7, 129.1, 132.0, 133.7, 138.7, 139.4, 145.5, 168.3. HRMS (ESI-TOF) m/z: [M−H]⁻ Calcd for $C_{28}H_{23}N_2O_6S^-$ 521.17518; Found 521.1768.

N-(((3aS,6R,6aR)-6-(((2-bromophenyl)sulfonamido)methyl)-2,2-dimethyldihydrofuro[3,4-d][1,3]dioxol-3a(4H)-yl)methyl)benzamide (103)

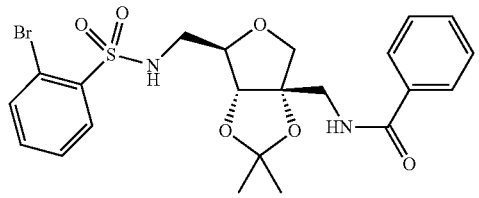 [SMILES: CC1(C)O[C@@H]2[C@@H](CNS(=O)(=O)c3ccccc3Br)OC[C@]2(CNC(=O)c2ccccc2)O1]

General procedure 5. White foam, 79.2% ¹H NMR (300 MHz, CDCl₃) δ ppm 1.34 (s, 3 H) 1.46 (s, 3 H) 2.97-3.07 (m, 1 H) 3.15 (ddd, J=13.6, 7.7, 5.7 Hz, 1 H) 3.68 (dd, J=14.2, 6.0 Hz, 1 H) 3.74-3.91 (m, 3 H) 4.12 (app. t, J=6.3, 1 H) 4.45 (d, J=1.8 Hz, 1 H) 6.20 (dd, J=7.6, 5.0 Hz, 1 H) 7.04 (t, J=6.2 Hz, 1 H) 7.31-7.53 (m, 5 H) 7.64-7.71 (m, 1 H) 7.73-7.85 (m, 2 H) 7.99-8.06 (m, 1 H). ¹³C NMR (75 MHz, CDCl₃) δ ppm 27.66, 27.74, 43.0, 43.2, 75.0, 83.3, 84.4, 92.1, 113.6, 119.7, 127.0, 127.8, 128.6, 131.3, 131.8, 133.6, 133.7, 135.1, 138.6, 168.0. HRMS (ESI-TOF) m/z: [M−H]⁻ Calcd for C₂₂H₂₄BrN₂O₆S⁻ 523.05439; Found 523.0547.

N-(((3aS,6R,6aR)-6-(([1,1'-biphenyl]-2-sulfonamido)methyl)-2,2-dimethyldihydrofuro[3,4-d][1,3]dioxol-3a(4H)-yl)methyl)benzamide (104)

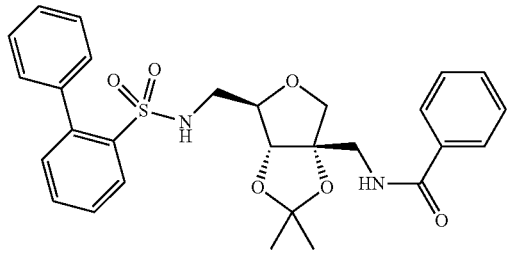 [SMILES: CC1(C)O[C@@H]2[C@@H](CNS(=O)(=O)c3ccccc3-c3ccccc3)OC[C@]2(CNC(=O)c2ccccc2)O1]

To a solution of compound 103 (0.33 g, 0.63 mmol) in a 10:1 mixture of DMF and H₂O were added K₂CO₃ (0.24 g, 1.76 mmol) and phenyl boronic acid (0.12 g, 0.95 mmol) and the flask was flushed with nitrogen gas. After addition of a catalytic amount of Pd(PPh₃)₄ the reaction mixture was stirred at 110° C. overnight. The reaction mixture was concentrated under reduced pressure and purified by flash column chromatography (toluene/EtOAc 100:0→70:30). The title compound was obtained as a white foam in 45.6% yield. ¹H NMR (300 MHz, CDCl₃) δ ppm 1.34 (s, 3 H) 1.45 (s, 3 H) 2.64-2.75 (m, 1 H) 2.84 (ddd, J=13.4, 8.0, 5.6 Hz, 1 H) 3.60-3.80 (m, 4 H) 3.93 (ddd, J=7.0, 5.6, 1.5 Hz, 1 H) 4.22 (app. dd, J=7.9, 5.3 Hz, 1 H) 4.28 (d, J=1.8 Hz, 1 H) 6.75 (t, J=6.2 Hz, 1 H) 7.32 (dd, J=7.5, 1.3 Hz, 1 H) 7.38-7.61 (m, 10 H) 7.74-7.82 (m, 2 H) 8.05 (dd, J=7.9, 1.2 Hz, 1 H). ¹³C NMR (75 MHz, CDCl₃) δ ppm 27.8, 27.9, 43.1, 43.2, 75.0, 83.6, 84.7, 92.1, 113.9, 127.1, 128.0, 128.3, 128.6, 128.7, 129.2, 129.3, 131.9, 132.47, 132.49, 133.9, 138.1, 138.8, 140.5, 167.8. HRMS (ESI-TOF) m/z: [M−H]⁻ Calcd for C₂₈H₂₉N₂O₆S⁻ 521.17518; Found 521.1757.

N-(((3aS,6R,6aR)-2,2-dimethyl-6-((4-phenyl-1H-1,2,3-triazol-1-yl)methyl)dihydrofuro[3,4-d][1,3]dioxol-3a(4H)-yl)methyl)benzamide (105)

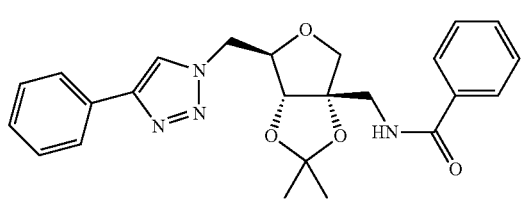 [SMILES: CC1(C)O[C@@H]2[C@@H](Cn3cc(-c4ccccc4)nn3)OC[C@]2(CNC(=O)c2ccccc2)O1]

To a solution of compound 26 (0.19 g, 0.56 mmol) in 5.5 mL of a mixture of DMF/H₂O/TEA (4:1:0.5) were added a catalytic amount of Cu(I)I and TBTA, along with phenylacetylene (0.18 mL, 1.68 mmol). The reaction mixture was stirred for 4 h at 75° C., after which time TLC (toluene/EtOAc 1:1) showed no starting material. The reaction mixture was concentrated under reduced pressure. The residue was taken up in ethyl acetate and washed with 0.1M aq. HCl and sat. aq. NHCO₃ solution. The organic layer was dried over sodium sulphate, filtered and concentrated. Purification by flash column chromatography (toluene/EtOAc 3:2) afforded triazole 105 in 83.9% yield. ¹H NMR (300 MHz, CDCl₃) δ ppm 1.36 (s, 3 H) 1.50 (s, 3 H) 3.67-3.80 (2× dd, J=14.3, 6.6 Hz, J=14.3, 6.2 Hz, 2 H) 3.87-3.97 (2× d, J=10.3 Hz, 2 H) 4.46-4.69 (m, 4 H) 6.90 (t, J=6.2 Hz, 1 H) 7.27-7.55 (m, 6 H) 7.75-7.88 (m, 4 H) 7.99 (s, 1 H). ¹³C NMR (75 MHz, CDCl₃) δ ppm 27.8, 27.9, 43.0, 50.7, 75.3, 83.5, 84.3, 92.1, 114.3, 121.3, 125.9, 127.1, 128.2, 128.8, 128.9, 130.6, 132.0, 133.7, 148.0, 168.0. HRMS (ESI-TOF) m/z: [M+H]⁺ Calcd for C₂₄H₂₇N₄O₄⁺ 435.20268; Found 435.2034.

N-(((3aS,6R,6aR)-2,2-dimethyl-6-((5-phenyl-1H-1,2,3-triazol-1-yl)methyl)dihydrofuro[3,4-d][1,3]dioxol-3a(4H)-yl)methyl)benzamide (106)

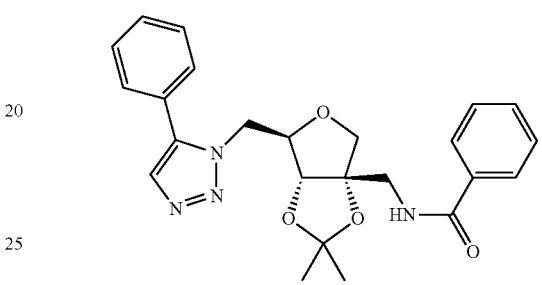

To a solution of compound 26 (0.17 g, 0.51 mmol) in 1,4-dioxane (5 mL) was added phenylacetylene (0.056 mL, 0.51 mmol). The flask was purged with nitrogen gas, sealed and heated to 60° C. A catalytic amount of CpRuCl(PPh₃)₂ was dissolved in 0.5 mL of 1,4-dioxane and added to the reaction mixture, which was further stirred for 24 hours at 60° C. The reaction mixture was concentrated under reduced pressure and adsorbed onto celite. Purification by flash column chromatography afforded the triazole 106 in 82.6% yield. ¹H NMR (300 MHz, CDCl₃) δ ppm 1.37 (s, 3 H) 1.46 (s, 3 H) 3.51-3.70 (m, 3 H) 3.78 (d, J=10.5 Hz, 1 H) 4.38-4.57 (m, 3 H) 4.66 (d, J=1.5 Hz, 1 H) 7.02 (t, J=6.2 Hz, 1 H) 7.34-7.55 (m, 8 H) 7.69 (s, 1 H) 7.78-7.89 (m, 2 H). ¹³C NMR (75 MHz, CDCl₃) δ ppm 27.74, 27.78, 42.9, 48.0, 74.9, 83.7, 84.7, 92.1, 113.9, 126.8, 127.09, 127.10, 128.7, 129.1, 129.2, 129.6, 131.8, 133.9, 139.0, 167.8. HRMS (ESI-TOF) m/z: [M+H]⁺ Calcd for C₂₄H₂₇N₄O₄⁺ 435.20268; Found 435.2037.

N-(((3aS,6R,6aR)-2,2-dimethyl-6-((3-phenylureido)methyl)dihydrofuro[3,4-d][1,3]dioxol-3a(4H)-yl)methyl)benzamide (107)

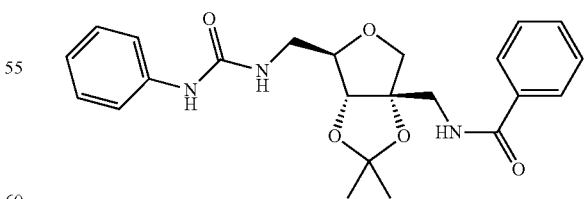

A flask containing a solution of the crude amine 33 (originating from 0.54 mmol of azide 26) in 5 mL of pyridine was purged with nitrogen gas and treated with phenylisocyanate (0.065 mL, 0.59 mmol). After 3 h TLC (CH₂Cl₂/MeOH 97:3) showed complete conversion of the starting material. Purification via flash column chromatography (CH$_2$Cl$_2$/MeOH 98:2) afforded the final compound in 76.3% yield. $^1$H NMR (300 MHz, CDCl$_3$) δ ppm 1.32 (s, 3 H) 1.49 (s, 3 H) 3.14 (app. dt, J=14.2, 4.5 Hz, 1 H) 3.62 (app. dt, J=14.3, 7.1 Hz, 1 H) 3.74 (dd, J=14.4, 5.6 Hz, 1 H) 3.81 (app. s, 2 H) 3.93 (dd, J=14.4, 7.3 Hz, 1 H) 4.11 (app. t, J=5.13 Hz, 1 H) 4.51 (d, J=1.2 Hz, 1 H) 6.39 (dd, J=7.2, 4.83 Hz, 1 H) 6.96 (app. t, J=7.3 Hz, 1 H) 7.21 (app. t, J=7.9 Hz, 2 H) 7.30-7.44 (m, 4 H) 7.46-7.54 (m, 1 H) 7.78 (t, J=6.3 Hz, 1 H) 7.85-7.95 (m, 2 H) 8.06 (s, 1 H). $^{13}$C NMR (75 MHz, CDCl$_3$) δ ppm 27.4, 27.9, 40.1, 42.6, 75.0, 84.0, 84.4, 92.0, 113.5, 119.6, 122.6, 127.3, 128.7, 128.9, 132.0, 133.5, 139.3, 156.8, 168.6. HRMS (ESI-TOF) m/z: [M+H]$^+$ Calcd for C$_{23}$H$_{28}$N$_3$O$_5^+$ 426.20235; Found 426.2041.

N-(((3aS,6R,6aR)-2,2-dimethyl-6-((3-phenylthioureido)methyl)dihydrofuro[3,4-d][1,3]dioxol-3a(4H)-34)methyl)benzamide (108)

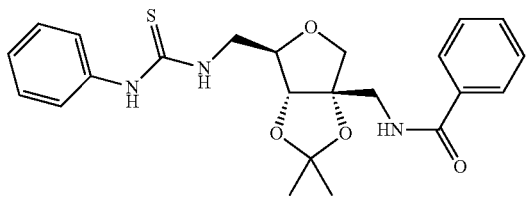 [SMILES: CC1(C)O[C@@H]2[C@@H](CNC(=S)Nc3ccccc3)OC[C@]2(CNC(=O)c2ccccc2)O1]

A flask containing a solution of the crude amine 33 (originating from 0.56 mmol of azide 26) in 5 mL of pyridine was purged with nitrogen gas and treated with phenylisothiocyanate (0.074 mL, 0.62 mmol). After 3 h TLC (CH$_2$Cl$_2$/MeOH 97:3) showed no starting material. Purification via flash column chromatography (CH$_2$Cl$_2$/MeOH 95:5) afforded the final compound in 65.2% yield. $^1$H NMR (300 MHz, CDCl$_3$) δ ppm 1.37 (s, 3 H) 1.48 (s, 3 H) 3.63-3.80 (m, 3 H) 3.83 (app. s, 2 H) 3.97-4.07 (m, 1 H) 4.30 (app. t, J=6.0 Hz, 1 H) 4.48 (d, J=1.8 Hz, 1 H) 6.84 (br. s., 1 H) 7.09 (br. s., 1 H) 7.16-7.53 (m, 8 H) 7.70-7.83 (m, 2 H) 8.61 (br. s., 1 H). $^{13}$C NMR (75 MHz, CDCl$_3$) δ ppm 27.7, 27.8, 43.1, 45.1, 75.0, 83.3, 84.4, 92.1, 113.8, 124.8, 126.6, 127.1, 128.6, 129.7, 131.9, 133.5, 136.9, 168.2, 181.2. HRMS (ESI-TOF) m/z: [M+H]$^+$ Calcd for C$_{23}$H$_{28}$N$_3$O$_4$S$^+$ 442.17950; Found 442.1802.

N-(((3aS,6R,6aR)-6-(Acetamidomethyl)-2,2-dimethyldihydrofuro[3,4-d][1,3]dioxol-3a(4H)-yl)methyl)benzamide (109)

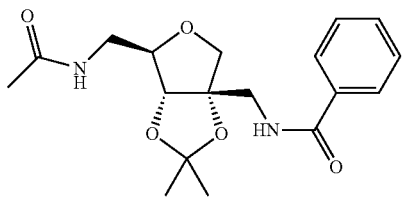 [SMILES: CC(=O)NC[C@H]1OC[C@]2(CNC(=O)c3ccccc3)OC(C)(C)O[C@H]12]

A solution of the crude amine 33 in CH$_2$Cl$_2$ (24 mL per mmol) was treated with diisopropylethylamine (2 eq.) and acetic anhydride (1.2 eq.). The reaction mixture was cooled in an ice-bath and stirred overnight. It was evaporated under reduced pressure, the residue was diluted with EtOAc and washed with 0.1 M aq. HCl and sat. aq. NaHCO$_3$. The organic layer was dried over sodium sulphate, filtered and concentrated. The residue was purified by column chromatography (CH$_2$Cl$_2$/MeOH 100:0→90:10) to afford the title compound as a white foam in 96.2% yield. $^1$H NMR (300 MHz, CDCl$_3$) δ ppm 1.37 (s, 3 H) 1.51 (s, 3 H) 2.03 (s, 3 H) 3.18 (ddd, J=14.1, 5.9, 4.9 Hz, 1 H) 3.57-3.69 (m, 2 H) 3.86 (app. s, 2 H) 3.95 (dd, J=14.2, 7.2 Hz, 1 H) 4.14 (app. td, J=6.3, 1.5 Hz, 1 H) 4.43 (d, J=1.5 Hz, 1 H) 7.02 (dd, J=7.0, 4.7 Hz, 1 H) 7.38-7.56 (m, 4 H) 7.83-7.91 (m, 2 H). $^{13}$C NMR (75 MHz, CDCl$_3$) δ ppm 23.1, 27.7, 27.8, 39.4, 42.9, 74.8, 83.8, 84.8, 92.1, 113.5, 127.2, 128.6, 131.9, 133.7, 168.2, 171.2. HRMS (ESI-TOF) m/z: [M+H]$^+$ Calcd for C$_{18}$H$_{25}$N$_2$O$_5^+$ 349.17580; Found 349.1756.

N-(((3aS,6R,6aR)-2,2-dimethyl-6-(pivalamidomethyl)dihydrofuro[3,4-d][1,3]dioxol-3a(4H)-yl)methyl)benzamide (110)

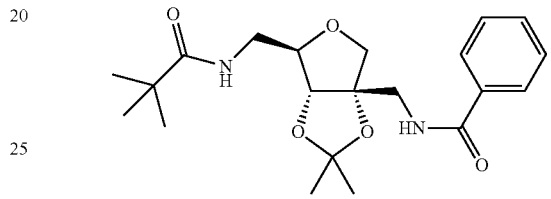

A cooled (0° C.) solution of the crude amine 33 in CH$_2$Cl$_2$ (20 mL per mmol) was treated with triethylamine (2 eq.) and pivaloyl chloride (1.1 eq.). The reaction mixture was stirred overnight and concentrated under reduced pressure. The residue was diluted with EtOAc and washed with 0.1 M aqueous hydrochloric acid and saturated sodium bicarbonate solution. The organic layer was dried over sodium sulphate, filtered and concentrated. The product was purified by column chromatography (toluene/EtOAc 100:0→20:80) and appeared as a white foam 74.10% yield. $^1$H NMR (300 MHz, CDCl$_3$) δ ppm 1.22 (s, 9 H) 1.38 (s, 3 H) 1.52 (s, 3 H) 3.24 (ddd, J=13.9, 7.3, 5.1 Hz, 1 H) 3.53 (app. dt, J=14.2, 7.3 Hz, 1 H) 3.76 (dd, J=14.4, 5.9 Hz, 1 H) 3.84-3.95 (m, 3 H) 4.15 (app. td, J=7.3, 1.2 Hz, 1 H) 4.40 (d, J=1.2 Hz, 1 H) 6.30 (t, J=5.9 Hz, 1 H) 7.33 (t, J=6.2 Hz, 1 H) 7.39-7.55 (m, 3 H) 7.84-7.92 (m, 2 H). $^{13}$C NMR (75 MHz, CDCl$_3$) δ ppm 27.6, 27.77, 27.82, 38.9, 39.4, 43.3, 74.9, 83.8, 85.1, 92.2, 113.5, 127.3, 128.7, 131.9, 133.8, 167.9, 179.4. HRMS (ESI-TOF) m/z: [M+H]$^+$ Calcd for C$_{21}$H$_{31}$N$_2$O$_5^+$ 391.22275; Found 391.2242.

N-(((3aS,6R,6aR)-6-((5-chloro-1,3-dioxoisoindolin-2-yl)methyl)-2,2-dimethyldihydrofuro[3,4-d][1,3]dioxol-3a(4H)-yl)methyl)benzamide (111)

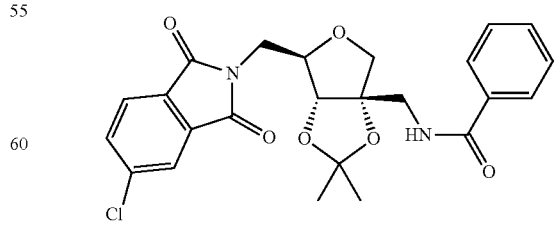

To a solution of the crude amine 33 (0.32 g, 1.04 mmol) in 10 mL of CHCl$_3$ was added 4-chlorophthalic anhydride (0.26 g, 1.40 mmol) and the reaction mixture was heated to reflux overnight. TLC analysis (toluene/EtOAc 3:2) showed consumption of starting material. The reaction mixture was concentrated under reduced pressure. The residue was taken up in EtOAc and washed with saturated sodium bicarbonate solution. The organic layer was dried over sodium sulphate, filtered and concentrated. Purification via flash column chromatography (toluene/EtOAc 100:0→60:40) afforded the title compound as a foam in 21.9% yield. $^1$H NMR (300 MHz, CDCl$_3$) δ ppm 1.42 (s, 3 H) 1.50 (s, 3 H) 3.67 (dd, J=14.1, 5.9 Hz, 1 H) 3.78 (dd, J=14.4, 5.6 Hz, 1 H) 3.86 (dd, J=14.1, 9.7 Hz, 1 H) 3.93-4.04 (m, 3 H) 4.41 (app. dd, J=9.7, 5.9 Hz, 1 H) 4.48 (d, J=0.6, 1 H) 6.83 (t, J=6.0 Hz, 1 H) 7.41-7.55 (m, 3 H) 7.64-7.70 (m, 1 H) 7.73-7.90 (m, 4 H). $^{13}$C NMR (75 MHz, CDCl$_3$) δ ppm 27.6, 28.2, 37.5, 43.4, 74.9, 82.3, 85.5, 92.7, 113.7, 124.0, 124.7, 127.1, 128.8, 130.1, 131.9, 133.7, 133.9, 134.2, 140.9, 166.9, 167.2, 167.8. HRMS (ESI-TOF) [M+H]$^+$ Calcd for C$_{24}$H$_{24}$ClN$_2$O$_6$$^+$ 471.13174; Found 471.1324.

N-(((3aS,6R,6aR)-6-((benzylamino)methyl)-2,2-dimethyldihydrofuro[3,4-d][1,3]dioxol-3a(4H)-yl)methyl)benzamide (112)

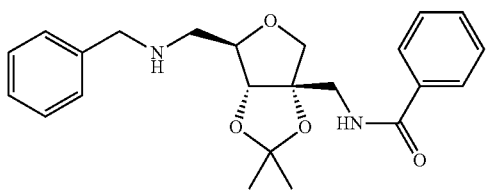 [SMILES: CC1(C)O[C@@H]2[C@@H](CNCc3ccccc3)OC[C@]2(CNC(=O)c2ccccc2)O1]

A flask containing a solution of crude amine 33 (originating from 0.60 mmol of azide 26) in MeOH (9 mL) was purged with nitrogen gas. Molecular sieves (3 Å, rods) were added and the flask was flushed again. Benzaldehyde (0.18 mL, 1.8 mmol) was added and the whole was stirred for 4 h at RT. After that, the aldimine was carefully treated with NaBH$_4$ (0.11 g, 3.0 mmol) for 30 minutes. The RM was filtered and the filtrate was adsorbed onto celite. The product was purified by column chromatography (toluene/EtOAc 100:0→60:40) and appeared as a pale yellow oil (47.3%). $^1$H NMR (300 MHz, CDCl$_3$) δ ppm 1.41 (s, 3 H) 1.54 (s, 3 H) 2.04 (br. s., 1 H) 2.71-2.79 (m, 2 H) 3.71-3.92 (m, 6 H) 4.20 (app. td, J=6.1, 1.9 Hz, 1 H) 4.36 (d, J=2.1 Hz, 1 H) 6.76 (t, J=5.7 Hz, 1 H) 7.19-7.35 (m, 5 H) 7.39-7.54 (m, 3 H) 7.75-7.81 (m, 2 H). $^{13}$C NMR (75 MHz, CDCl$_3$) δ ppm 27.9, 28.0, 43.9, 49.4, 53.8, 75.3, 84.9, 86.2, 91.9, 113.9, 127.0, 127.1, 128.2, 128.5, 128.7, 131.8, 134.2, 139.9, 167.8. HRMS (ESI-TOF) m/z: [M+H]$^+$ Calcd for C$_{23}$H$_{28}$N$_2$O$_4$$^+$ 397.21218; Found 397.2119.

N-(((3aS,6R,6aR)-6-(benzamidomethyl)-2,2-dimethyldihydrofuro[3,4-d][1,3]dioxol-3a(4H)-yl)methyl)-N-methylbenzamide (113)

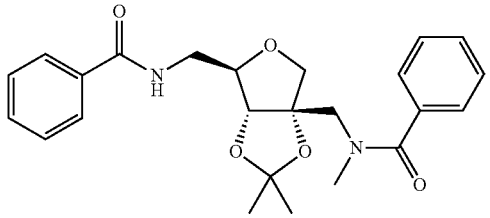 [SMILES: CN(C[C@]12CO[C@H](CNC(=O)c3ccccc3)[C@H]1OC(C)(C)O2)C(=O)c1ccccc1]

Azide 32 was subjected to general procedure 3, followed by general procedure 4 to obtain the title compound as a white foam (94.3%)$^1$H NMR (300 MHz, CDCl$_3$) δ ppm 1.43 (s, 3 H) 1.53 (s, 3 H) 3.15 (s, 3 H) 3.67-3.79 (m, 3 H) 3.89-3.99 (m, 2 H) 4.04 (d, J=14.4 Hz, 1 H) 4.40 (app. t, J=6.4 Hz, 1 H) 4.61 (app. s, 1 H) 7.33-7.46 (m, 9 H) 7.87 (app. d, J=7.3 Hz, 2 H). $^{13}$C NMR (75 MHz, CDCl$_3$) δ ppm 27.6, 27.9, 39.8, 40.7, 51.5, 75.6, 83.5, 84.9, 93.4, 113.3, 126.8, 127.3, 128.4, 128.6, 129.9, 131.4, 134.2, 135.8, 167.6, 172.7. HRMS (ESI-TOF) m/z: [M+H]$^+$ Calcd for C$_{24}$H$_{29}$N$_2$O$_5$$^+$ 425.20710; Found 425.2067.

N-(((3aS,6R,6aR)-2,2-dimethyl-6-((1-oxoisoindolin-2-yl)methyl)dihydrofuro[3,4-d][1,3]dioxol-3a(4H)-yl)methyl)benzamide (114)

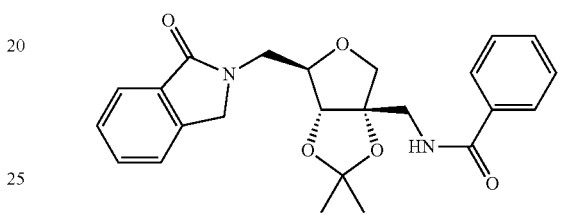

To a flask containing a solution of the crude amine 33 (originating from 0.46 mmol of azide 26) in 6 mL of MeOH was added TEA (70.9 μL, 0.51 mmol) and methyl 2-(bromomethyl)benzoate (269) (0.12 g, 0.51 mmol). The mixture was heated to reflux at 80° C. for 14 h. The reaction was monitored by mass spectrometry (ESI-TOF), which indicated the formation of the target compound. The reaction mixture was concentrated and adsorbed onto celite. Purification via flash column chromatography (toluene/EtOAc 100:0→30:70) yielded the title compound as a white foam (58.8%). $^1$H NMR (300 MHz, CDCl$_3$) δ ppm 1.38 (s, 3 H) 1.51 (s, 3 H) 3.46 (dd, J=14.4, 7.0 Hz, 1 H) 3.77 (dd, J=14.1, 5.6 Hz, 1 H) 3.85-4.05 (m, 4 H) 4.34 (app. t., J=7.5, 1 H) 4.42 (d, J=17.0 Hz, 1 H) 4.57 (d, J=17.0 Hz, 1 H) 4.61 (d, J=1.2 Hz, 1 H) 7.37-7.58 (m, 6 H) 7.66 (t, J=6.2 Hz, 1 H) 7.81-7.87 (m, 1 H) 7.91-8.04 (m, 2 H). $^{13}$C NMR (75 MHz, CDCl$_3$) δ ppm 27.7, 27.8, 42.5, 43.1, 51.2, 74.8, 83.4, 85.7, 92.3, 113.5, 122.9, 123.8, 127.4, 128.3, 128.6, 131.7, 131.8, 132.1, 133.9, 141.5, 167.8, 169.4. HRMS (ESI-TOF) m/z: [M+H]$^+$ Calcd for C$_{24}$H$_{27}$N$_2$O$_5$$^+$ 423.19145; Found 423.1908.

N-(((3aR,4R,6aS)-6a-((1,3-dioxoisoindolin-2-yl)methyl)-2,2-dimethyltetrahydrofuro[3,4-d][1,3]dioxol-4-yl)methyl)benzamide (115)

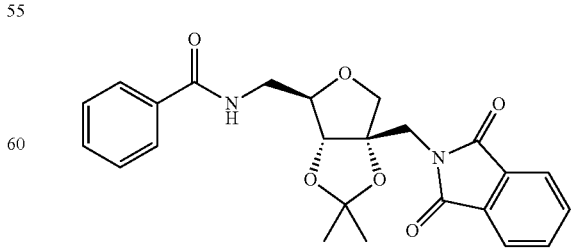

General procedure 6. White foam, 45.4% $^1$H NMR (300 MHz, CDCl$_3$) δ ppm 1.29 (s, 3 H) 1.49 (s, 3 H) 3.46 (ddd, J=14.0, 8.7, 4.3 Hz, 1 H) 3.85 (ddd, J=14.0, 7.3, 5.1, 1 H) 3.95 (d, J=10.5 Hz, 1 H) 3.98-4.06 (m, 3 H) 4.27 (ddd, J=8.6, 5.1, 1.8 Hz, 1 H) 4.59 (d, J=1.8 Hz, 1 H) 6.59 (dd, J=6.4, 4.4 Hz, 1 H) 7.39-7.53 (m, 3 H) 7.71-7.92 (m, 6 H). $^{13}$C NMR (75 MHz, CDCl$_3$) δ ppm 27.7, 27.9, 39.9, 41.7, 75.2, 83.9, 86.0, 91.8, 114.6, 123.7, 127.2, 128.7, 131.7, 131.9, 134.3, 134.5, 167.7, 168.5. HRMS (ESI-TOF) m/z: [M+H]$^+$ Calcd for $C_{24}H_{25}N_2O_6^+$ 437.17071, found 437.1712.

2-chloro-N-(((3aR,4R,6aS)-6a-((1,3-dioxoisoindolin-2-yl)methyl)-2,2-dimethyltetrahydrofuro[3,4-d][1,3]dioxol-4-yl)methyl)benzamide (116)

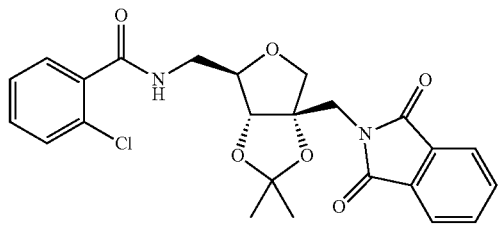 [SMILES: CC1(C)O[C@@H]2[C@@H](CNC(=O)c3ccccc3Cl)OC[C@]2(CN2C(=O)c3ccccc3C2=O)O1]

General procedure 6. White foam, 57.1% $^1$H NMR (300 MHz, CDCl$_3$) δ ppm 1.29 (s, 3 H) 1.49 (s, 3 H) 3.46 (ddd, J=14.0, 9.0, 4.3 Hz, 1 H) 3.84 (ddd, J=14.1, 7.0, 5.3 Hz, 1 H) 3.94 (d, J=10.5 Hz, 1 H) 3.98-4.12 (m, 3 H) 4.26 (ddd, J=8.8, 5.3, 1.8 Hz, 1 H) 4.59 (d, J=1.8 Hz, 1 H) 6.65 (dd, J=6.2, 4.7 Hz, 1 H) 7.27-7.42 (m, 3 H) 7.63-7.69 (m, 1 H) 7.70-7.79 (m, 2 H) 7.81-7.94 (m, 2 H). $^{13}$C NMR (75 MHz, CDCl$_3$) δ ppm 27.7, 27.9, 40.0, 41.7, 75.1, 83.7, 86.0, 91.8, 114.5, 123.7, 127.1, 130.2, 130.3, 130.8, 131.4, 131.8, 134.4, 134.9, 166.8, 168.5. HRMS (ESI-TOF) [M+H]$^+$ Calcd for $C_{24}H_{24}ClN_2O_6^+$ 471.13174, found 471.1313.

N-(((3aR,4R,6aS)-6a-(aminomethyl)-2,2-dimethyltetrahydrofuro[3,4-d][1,3]dioxol-4-yl)methyl)benzamide (117)

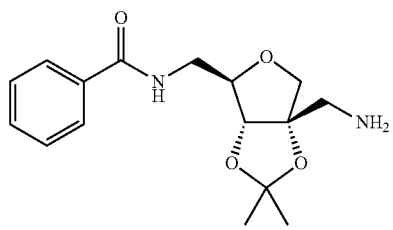 [SMILES: CC1(C)O[C@@H]2[C@@H](CNC(=O)c3ccccc3)OC[C@]2(CN)O1]

General procedure 7. Transparent oil, 95.8% $^1$H NMR (300 MHz, CDCl$_3$) δ ppm 1.42 (s, 3 H) 1.51-1.70 (m, 5 H) 2.98 (s, 2 H) 3.46 (ddd, J=14.1, 7.9, 4.4 Hz, 1 H) 3.76 (ddd, J=14.1, 6.4, 5.3 Hz, 1 H) 3.90 (d, J=10.0 Hz, 1 H) 3.95 (d, J=10.3 Hz, 1 H) 4.26 (ddd, J=7.7, 5.5, 1.8 Hz, 1 H) 4.39 (d, J=2.1 Hz, 1 H) 6.67 (br. s., 1 H) 7.39-7.54 (m, 3 H) 7.75-7.81 (m, 2 H). $^{13}$C NMR (75 MHz, CDCl$_3$) δ ppm 28.0, 28.1, 40.3, 46.6, 75.5, 84.2, 85.4, 93.3, 113.9, 127.1, 128.7, 131.8, 134.4, 167.9. HRMS (ESI-TOF) m/z: [M+H]$^+$ Calcd for $C_{16}H_{23}N_2O_4^+$ 307.16523, found 307.1658.

N-(((3aR,4R,6aS)-6a-(aminomethyl)-2,2-dimethyltetrahydrofuro[3,4-d][1,3]dioxol-4-yl)methyl)-2-chlorobenzamide (118)

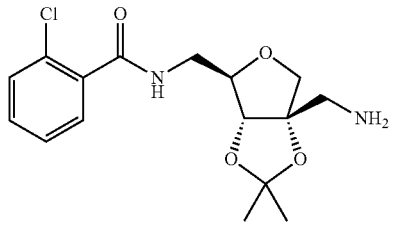 [SMILES: CC1(C)O[C@@H]2[C@@H](CNC(=O)c3ccccc3Cl)OC[C@]2(CN)O1]

General procedure 7. Transparent oil, 71.9% $^1$H NMR (300 MHz, CDCl$_3$) δ ppm 1.29-1.46 (m, 5 H) 1.54 (s, 3 H) 2.99 (s, 2 H) 3.47 (ddd, J=13.9, 7.8, 4.5 Hz, 1 H) 3.78 (ddd, J=14.0, 6.5, 5.1 Hz, 1 H) 3.90 (d, J=10.3 Hz, 1 H) 3.94 (d, J=10.0 Hz, 1 H) 4.27 (ddd, J=7.5, 5.2, 1.9 Hz, 1 H) 4.41 (d, J=1.8 Hz, 1 H) 6.86 (br. s, 1 H) 7.32-7.43 (m, 3 H) 7.62-7.66 (m, 1 H). $^{13}$C NMR (75 MHz, CDCl$_3$) δ ppm 27.9, 28.1, 40.4, 46.7, 75.5, 83.9, 85.5, 93.3, 113.9, 127.2, 130.2, 130.4, 130.8, 131.5, 135.1, 167.0. HRMS (ESI-TOF) m/z: [M+H]$^+$ Calcd for $C_{16}H_{22}ClN_2O_4^+$ 341.12626, found 341.1269.

2-chloro-N-(((3aR,4R,6aS)-2,2-dimethyl-6a-((4-methylbenzamido)methyl)tetrahydrofuro[3,4-d][1,3]dioxol-4-yl)methyl)benzamide (119)

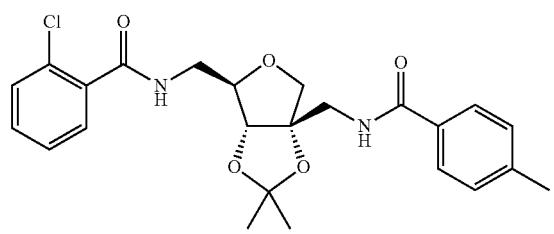 [SMILES: Cc1ccc(C(=O)NC[C@]23CO[C@H](CNC(=O)c4ccccc4Cl)[C@H]2OC(C)(C)O3)cc1]

General procedure 4. White foam, 91.1% $^1$H NMR (300 MHz, CDCl$_3$) δ ppm 1.37 (s, 3 H) 1.51 (s, 3 H) 2.37 (s, 3 H) 3.39 (ddd, J=13.9, 7.3, 4.8 Hz, 1 H) 3.64-3.80 (m, 2 H) 3.83-3.96 (m, 3 H) 4.25 (app. td, J=7.1, 1.3 Hz, 1 H) 4.51 (d, J=1.5 Hz, 1 H) 7.09-7.39 (m, 7 H) 7.54-7.59 (m, 1 H) 7.68-7.76 (m, 2 H). $^{13}$C NMR (75 MHz, CDCl$_3$) δ ppm 21.5, 27.7, 27.8, 39.8, 43.1, 74.9, 83.6, 85.1, 92.2, 113.5, 127.0, 127.2, 129.3, 129.7, 130.2, 130.8, 130.9, 131.3, 135.1, 142.3, 167.5, 167.9. HRMS (ESI-TOF) m/z: [M+H]$^+$ Calcd for $C_{24}H_{28}ClN_2O_5^+$ 459.16813, found 459.1682.

2-chloro-N-(((3aR,4R,6aS)-6a-((4-fluorobenzamido)methyl)-2,2-dimethyltetrahydrofuro[3,4-d][1,3]dioxol-4-yl)methyl)benzamide (120)

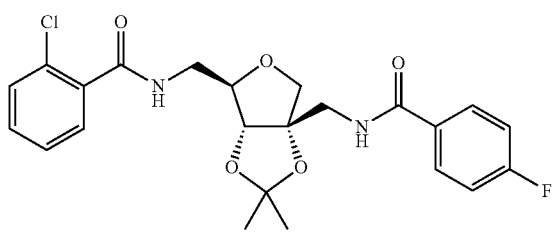 [SMILES: CC1(C)O[C@@H]2[C@@H](CNC(=O)c3ccccc3Cl)OC[C@]2(CNC(=O)c2ccc(F)cc2)O1]

General procedure 4. White foam, 98.7% $^1$H NMR (300 MHz, CDCl$_3$) δ ppm 1.38 (s, 3 H) 1.52 (s, 3 H) 3.36 (ddd, J=13.9, 7.2, 5.0 Hz, 1 H) 3.66-3.82 (m, 2 H) 3.85-3.97 (m, 3 H) 4.24 (app. td, J=7.3, 1.0 Hz, 1 H) 4.52 (d, J=1.5 Hz, 1 H) 7.00-7.14 (m, 3 H) 7.28-7.41 (m, 4 H) 7.54-7.61 (m, 1 H) 7.82-7.91 (m, 2 H). $^{13}$F NMR (282 MHz, CDCl$_3$) δ ppm –107.8 (m). $^{13}$C NMR (75 MHz, CDCl$_3$) δ ppm 27.76, 27.81, 39.8, 43.3, 74.9, 83.7, 85.3, 92.2, 113.6, 115.7 (d, J=21.9 Hz), 127.1, 129.7 (d, J=9.2 Hz), 129.8, 129.9 (d, J=3.5 Hz), 130.3, 130.9, 131.5, 135.0, 165.0 (d, J=252.2 Hz), 166.9, 167.6. HRMS (ESI-TOF) m/z: [M+H]$^+$ Calcd for C$_{23}$H$_{25}$ClFN$_2$O$_5^+$ 463.14305, found 463.1425.

2-chloro-N-(((3aR,4R,6aS)-6a-((4-chlorobenzamido)methyl)-2,2-dimethyltetrahydrofuro[3,4-d][1,3]dioxol-4-yl)methyl)benzamide (121)

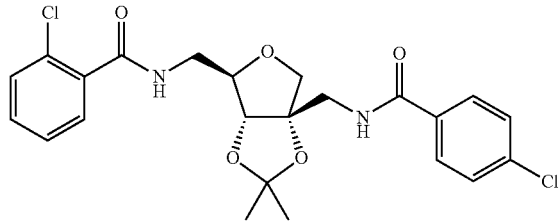 [SMILES: CC1(C)O[C@@H]2[C@@H](CNC(=O)c3ccccc3Cl)OC[C@]2(CNC(=O)c2ccc(Cl)cc2)O1]

General procedure 4. White foam, 97.5% $^1$H NMR (300 MHz, CDCl$_3$) δ ppm 1.37 (s, 3 H) 1.51 (s, 3 H) 3.34 (ddd, J=14.1, 7.2, 4.8 Hz, 1 H) 3.65-3.80 (m, 2 H) 3.84-3.96 (m, 3 H) 4.23 (app. td, J=7.3, 1.2 Hz, 1 H) 4.53 (d, J=1.5 Hz, 1 H) 7.08 (dd, J=7.2, 4.8 Hz, 1 H) 7.28-7.41 (m, 5 H) 7.46 (t, J=6.2 Hz, 1 H) 7.53-7.58 (m, 1 H) 7.76-7.81 (m, 2 H). $^{13}$C NMR (75 MHz, CDCl$_3$) δ ppm 27.7, 27.8, 39.8, 43.2, 74.8, 83.7, 85.2, 92.1, 113.6, 127.1, 128.7, 128.9, 129.7, 130.3, 130.8, 131.5, 132.1, 134.9, 138.0, 166.9, 167.6. HRMS (ESI-TOF) m/z: [M+H]$^+$ Calcd for C$_{23}$H$_{25}$Cl$_2$N$_2$O$_5^+$ 479.11350, found 479.1132.

2-chloro-N-(((3aR,4R,6aS)-6a-((4-methoxybenzamido)methyl)-2,2-dimethyltetrahydrofuro[3,4-d][1,3]dioxol-4-yl)methyl)benzamide (122)

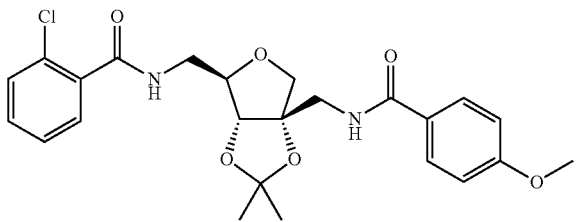 [SMILES: COc1ccc(C(=O)NC[C@]23CO[C@H](CNC(=O)c4ccccc4Cl)[C@H]2OC(C)(C)O3)cc1]

General procedure 4. White foam, 92.6% $^1$H NMR (300 MHz, CDCl$_3$) δ ppm 1.37 (s, 3 H) 1.51 (s, 3 H) 3.37 (ddd, J=13.9, 7.2, 4.8 Hz, 1 H) 3.61-3.80 (m, 2 H) 3.82 (s, 3 H) 3.86-3.96 (m, 3 H) 4.24 (app. td, J=7.2, 0.9 Hz, 1 H) 4.52 (d, J=1.5 Hz, 1 H) 6.85-6.92 (m, 2 H) 7.17 (dd, J=6.9, 5.1 Hz, 1 H) 7.24-7.38 (m, 4 H) 7.53-7.59 (m, 1 H) 7.73-7.85 (m, 2 H). $^{13}$C NMR (75 MHz, CDCl$_3$) δ ppm 27.7, 27.8, 39.8, 43.1, 55.4, 74.9, 83.6, 85.1, 92.2, 113.4, 113.8, 125.9, 127.0, 129.0, 129.6, 130.2, 130.8, 131.3, 135.1, 162.4, 167.4, 167.5. HRMS (ESI-TOF) m/z: [M+H]$^+$ Calcd for C$_{24}$H$_{28}$ClN$_2$O$_6^+$ 475.16304, found 475.1636.

2-chloro-N-(((3aR,4R,6aS)-6a-((4-cyanobenzamido)methyl)-2,2-dimethyltetrahydrofuro[3,4-d][1,3]dioxol-4-yl)methyl)benzamide (123)

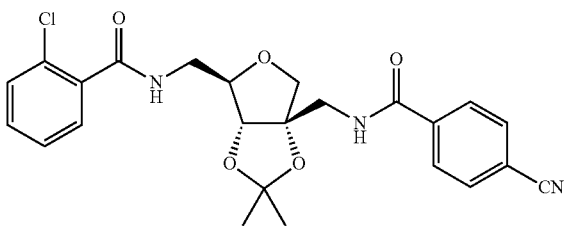 [SMILES: CC1(C)O[C@@H]2[C@@H](CNC(=O)c3ccccc3Cl)OC[C@]2(CNC(=O)c2ccc(C#N)cc2)O1]

General procedure 4. White foam, 94.7% $^1$H NMR (300 MHz, CDCl$_3$) δ ppm 1.37 (s, 3 H) 1.52 (s, 3 H) 3.31 (ddd, J=14.0, 7.1, 4.7 Hz, 1 H) 3.69-3.81 (m, 2 H) 3.85-3.99 (m, 3 H) 4.19-4.27 (m, 1 H) 4.55 (d, J=1.2 Hz, 1 H) 7.05 (dd, J=7.5, 4.5 Hz, 1 H) 7.26-7.40 (m, 3 H) 7.52-7.58 (m, 1 H) 7.65-7.71 (m, 2 H) 7.75 (t, J=6.3 Hz, 1 H) 7.94-8.02 (m, 2 H). $^{13}$C NMR (75 MHz, CDCl$_3$) δ ppm 27.70, 27.73, 39.7, 43.3, 74.7, 83.7, 85.3, 92.0, 113.6, 115.2, 118.1, 127.1, 128.1, 129.6, 130.4, 130.8, 131.6, 132.4, 134.8, 137.7, 166.2, 167.8. HRMS (ESI-TOF) m/z: [M+H]$^+$ Calcd for C$_{24}$H$_{25}$ClN$_3$O$_5^+$ 470.14773, found 470.1478.

2-chloro-N-(((3aR,4R,6aS)-6a-((4-(dimethylamino)benzamido)methyl)-2,2-dimethyltetrahydrofuro[3,4-d][1,3]dioxol-4-yl)methyl)benzamide (124)

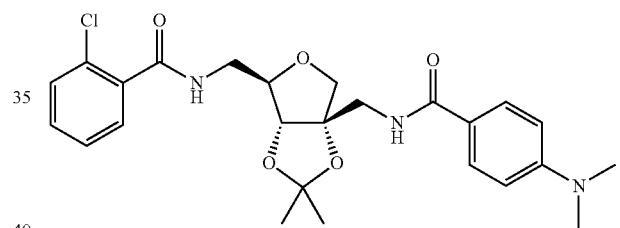

General procedure 4. White foam, 83.6% $^1$H NMR (300 MHz, CDCl$_3$) δ ppm 1.38 (s, 3 H) 1.51 (s, 3 H) 2.99 (s, 6 H) 3.41 (ddd, J=13.8, 7.3, 5.0 Hz, 1 H) 3.61 (dd, J=14.4, 5.3 Hz, 1 H) 3.69-3.79 (m, 1 H) 3.86-3.96 (m, 3 H) 4.26 (app. td, J=7.2, 1.0 Hz, 1 H) 4.51 (d, J=1.5 Hz, 1 H) 6.62 (m, 2 H) 7.04 (t, J=6.2 Hz, 1 H) 7.20 (dd, J=6.7, 5.3 Hz, 1 H) 7.23-7.38 (m, 3 H) 7.52-7.61 (m, 1 H) 7.66-7.77 (m, 2 H). $^{13}$C NMR (75 MHz, CDCl$_3$) δ ppm 27.7, 27.8, 39.8, 40.1, 42.9, 74.9, 83.4, 85.0, 92.4, 111.0, 113.3, 120.2, 126.9, 128.7, 129.7, 130.2, 130.9, 131.2, 135.2, 152.6, 167.4, 167.8. HRMS (ESI-TOF) m/z: [M+H]$^+$ Calcd for C$_{25}$H$_{31}$ClN$_3$O$_5^+$ 488.19468, found 488.1947.

2-chloro-N-(((3aR,4R,6aS)-2,2-dimethyl-6a-((4-(trifluoromethyl)benzamido)methyl)tetrahydrofuro[3,4-d][1,3]dioxol-4-yl)methyl)benzamide (125)

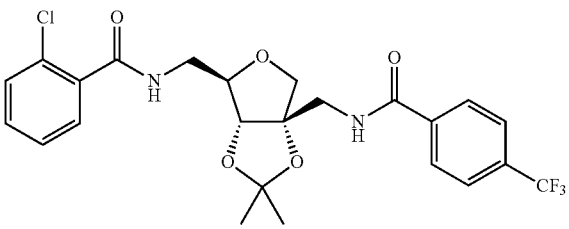 [SMILES: CC1(C)O[C@@H]2[C@@H](CNC(=O)c3ccccc3Cl)OC[C@]2(CNC(=O)c2ccc(C(F)(F)F)cc2)O1]

General procedure 4. White foam, 74.5% $^1$H NMR (300 MHz, CDCl$_3$) δ ppm 1.37 (s, 3 H) 1.52 (s, 3 H) 3.35 (ddd, J=13.9, 7.2, 4.7 Hz, 1 H) 3.68-3.82 (m, 2 H) 3.85-4.00 (m, 3 H) 4.24 (app. td, J=7.3, 0.9 Hz, 1 H) 4.56 (d, J=1.5 Hz, 1 H) 7.12 (dd, J=7.2, 4.8 Hz, 1 H) 7.24-7.39 (m, 3 H) 7.49-7.58 (m, 1 H) 7.61-7.73 (m, 3 H) 7.96 (app. d, J=7.9 Hz, 2 H). $^{19}$F NMR (282 MHz, CDCl$_3$) δ ppm −63.0 (s). $^{13}$C NMR (75 MHz, CDCl$_3$) δ ppm 27.7, 27.8, 39.8, 43.3, 74.8, 83.7, 85.3, 92.1, 113.6, 123.7 (q, J=274.9 Hz), 125.6 (q, J=3.8 Hz), 127.1, 127.8, 129.6, 130.3, 130.8, 131.5, 133.4 (q, J=32.0 Hz), 134.9, 137.0, 166.8, 167.8. HRMS (ESI-TOF) m/z: [M+H]$^+$ Calcd for C$_{24}$H$_{25}$ClF$_3$N$_2$O$_5^+$ 513.13986, found 513.1384.

N-(((3aS,6R,6aR)-6-((2-chlorobenzamido)methyl)-2,2-dimethyldihydrofuro[3,4-d][1,3]dioxol-3a(4H)-yl)methyl)isonicotinamide (126)

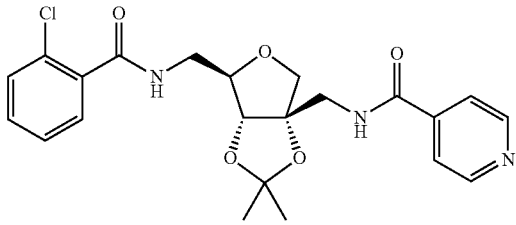 [SMILES: CC1(C)O[C@@H]2[C@@H](CNC(=O)c3ccccc3Cl)OC[C@]2(CNC(=O)c2ccncc2)O1]

General procedure 4. White foam, 83.4% $^1$H NMR (300 MHz, CDCl$_3$) δ ppm 1.37 (s, 3 H) 1.52 (s, 3 H) 3.33 (ddd, J=13.9, 7.0, 4.8 Hz, 1 H) 3.70-3.81 (m, 2 H) 3.86-4.00 (m, 3 H) 4.20-4.28 (m, 1 H) 4.56 (d, J=1.2 Hz, 1 H) 7.21 (dd, J=7.3, 5.0 Hz, 1 H) 7.29-7.42 (m, 3 H) 7.53-7.59 (m, 1 H) 7.69-7.74 (m, 2 H) 7.86 (t, J=6.3 Hz, 1 H) 8.63-8.70 (m, 2 H). $^{13}$C NMR (75 MHz, CDCl$_3$) δ ppm 27.70, 27.75, 39.8, 43.2, 74.8, 83.8, 85.3, 92.0, 113.6, 121.2, 127.1, 129.6, 130.4, 130.8, 131.6, 134.8, 141.0, 150.5, 166.1, 167.8. HRMS (ESI-TOF) m/z: [M+H]$^+$ Calcd for C$_{22}$H$_{25}$ClN$_3$O$_5^+$ 446.14773 found 446.1475.

2-chloro-N-(((3aR,4R,6aS)-6a-((3-fluorobenzamido)methyl)-2,2-dimethyltetrahydrofuro[3,4-d][1,3]dioxol-4-yl)methyl)benzamide (127)

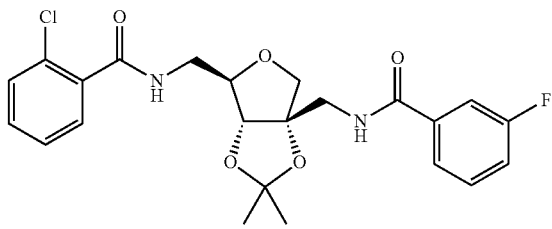 [SMILES: CC1(C)O[C@@H]2[C@@H](CNC(=O)c3ccccc3Cl)OC[C@]2(CNC(=O)c2cccc(F)c2)O1]

General procedure 4. White foam, 82.1% $^1$H NMR (300 MHz, CDCl$_3$) δ ppm 1.37 (s, 3 H) 1.52 (s, 3 H) 3.30-3.41 (m, 1 H) 3.65-3.83 (m, 2 H) 3.83-3.96 (m, 3 H) 4.24 (app. t, J=7.2 Hz, 1 H) 4.53 (d, J=1.5 Hz, 1 H) 7.06-7.65 (m, 10 H). $^{19}$F NMR (282 MHz, CDCl$_3$) δ ppm −111.7 (m). $^{13}$C NMR (75 MHz, CDCl$_3$) δ ppm 27.7, 27.8, 39.8, 43.3, 74.8, 83.6, 85.2, 92.1, 113.6, 114.7 (d, J=23.0 Hz), 118.8 (d, J=21.9 Hz), 122.7 (d, J=3.5 Hz), 127.1, 129.7, 130.285, 130.293 (d, J=8.1 Hz), 130.8, 131.4, 134.9, 136.0 (d, J=6.9 Hz), 162.8 (d, J=247.6 Hz), 166.7 (app. s), 167.6. HRMS (ESI-TOF) m/z: [M+H]$^+$ Calcd for C$_{23}$H$_{25}$ClFN$_2$O$_5^+$ 463.14305, found 463.1438.

2-chloro-N-(((3aR,4R,6aS)-6a-((3-chlorobenzamido)methyl)-2,2-dimethyltetrahydrofuro[3,4-d][1,3]dioxol-4-yl)methyl)benzamide (128)

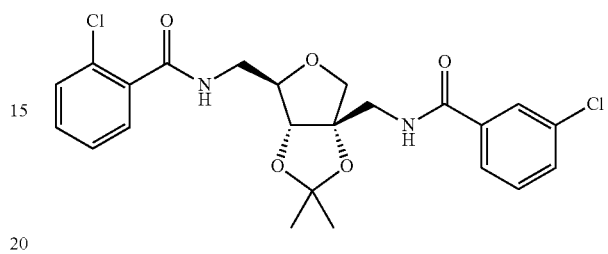

General procedure 4. White foam, 85.7% $^1$H NMR (300 MHz, CDCl$_3$) δ ppm 1.38 (s, 3 H) 1.52 (s, 3 H) 3.38 (ddd, J=14.0, 7.3, 4.8 Hz, 1 H) 3.69-3.82 (m, 2 H) 3.84-3.95 (m, 3 H) 4.25 (app. td, J=7.2, 0.9 Hz, 1 H) 4.52 (d, J=1.2 Hz, 1 H) 7.06 (dd, J=7.0, 5.0 Hz, 1 H) 7.27-7.49 (m, 6 H) 7.56-7.61 (m, 1 H) 7.71 (app. dt, J=7.9, 1.3 Hz, 1 H) 7.84 (app. t, J=1.9 Hz, 1 H). $^{13}$C NMR (75 MHz, CDCl$_3$) δ ppm 27.76, 27.81, 39.9, 43.4, 74.9, 83.7, 85.2, 92.1, 113.7, 125.3, 127.1, 127.7, 129.8, 130.0, 130.3, 130.8, 131.6, 131.9, 134.8, 134.9, 135.5, 166.8, 167.7. HRMS (ESI-TOF) m/z: [M+H]$^+$ Calcd for C$_{23}$H$_{25}$Cl$_2$N$_2$O$_5^+$ 479.11350, found 479.1144.

2-chloro-N-(((3aR,4R,6aS)-2,2-dimethyl-6a-((3-(trifluoromethyl)benzamido)methyl)tetrahydrofuro[3,4-d][1,3]dioxol-4-yl)methyl)benzamide (129)

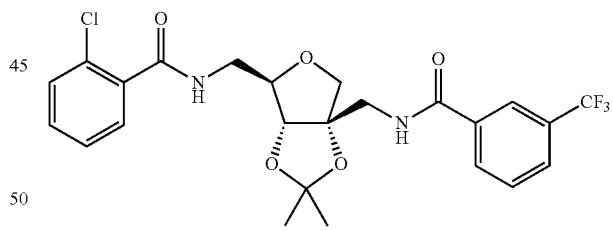

General procedure 4. White foam, 97.2% $^1$H NMR (300 MHz, CDCl$_3$) δ ppm 1.38 (s, 3 H) 1.52 (s, 3 H) 3.34 (ddd, J=14.1, 7.0, 4.7 Hz, 1 H) 3.67-3.83 (m, 2 H) 3.87-4.02 (m, 3 H) 4.25 (app. td, J=7.3, 0.9 Hz, 1 H) 4.56 (d, J=1.2 Hz, 1 H) 7.04 (dd, J=7.3, 5.0 Hz, 1 H) 7.28-7.40 (m, 3 H) 7.51-7.60 (m, 2 H) 7.65 (t, J=6.2 Hz, 1 H) 7.72-7.77 (m, 1 H) 8.05 (app. d, J=7.9 Hz, 1 H) 8.16 (app. s, 1 H). $^{19}$F NMR (282 MHz, CDCl$_3$) δ ppm −62.7 (s). $^{13}$C NMR (75 MHz, CDCl$_3$) δ ppm 27.7, 27.8, 39.8, 43.3, 74.8, 83.7, 85.3, 92.1, 113.6, 123.8 (q, J=272.5 Hz), 124.5 (q, J=3.8 Hz), 127.1, 128.4 (q, J=3.5 Hz), 129.3, 129.8, 130.3, 130.6, 130.8, 131.1 (q, J=33.0 Hz), 131.6, 134.6, 134.8, 166.6, 167.7. HRMS (ESI-TOF) m/z: [M+H]$^+$ Calcd for C$_{24}$H$_{25}$ClF$_3$N$_2$O$_5^+$ 513.13986, found 513.1387.

N-(((3aS,6R,6aR)-6-((2-chlorobenzamido)methyl)-2,2-dimethyldihydrofuro[3,4-d][1,3]dioxol-3a(4H)-yl)methyl)nicotinamide (130)

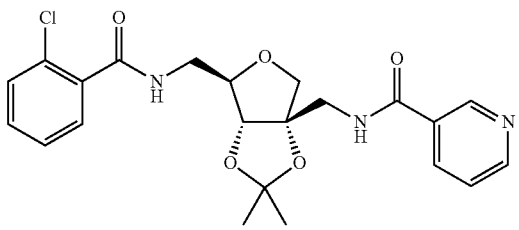

General procedure 4. White foam, 79.9% $^1$H NMR (300 MHz, CDCl$_3$) δ ppm 1.37 (s, 3 H) 1.52 (s, 3 H) 3.35 (ddd, J=13.9, 7.2, 4.7 Hz, 1 H) 3.67-3.81 (m, 2 H) 3.87-4.01 (m, 3 H) 4.24 (app. td, J=7.3, 1.2 Hz, 1 H) 4.55 (d, J=1.5 Hz, 1 H) 7.20-7.40 (m, 5 H) 7.53-7.59 (m, 1 H) 7.79 (t, J=6.2 Hz, 1 H) 8.18 (ddd, J=8.0, 2.2, 1.8 Hz, 1 H) 8.66 (app. dd, J=5.0, 1.8 Hz, 1 H) 9.06 (dd, J=2.2, 0.7 Hz, 1 H). $^{13}$C NMR (75 MHz, CDCl$_3$) δ ppm 27.75 (2 C), 39.7, 43.2, 74.8, 83.7, 85.3, 92.0, 113.6, 123.5, 127.1, 129.5, 129.7, 130.3, 130.8, 131.5, 134.9, 135.3, 148.5, 152.3, 166.2, 167.7. HRMS (ESI-TOF) m/z: [M+H]$^+$ Calcd for C$_{22}$H$_{25}$ClN$_3$O$_5$$^+$ 446.14773, found 446.1470.

2-chloro-N-(((3aR,4R,6aS)-2,2-dimethyl-6a-((2-methylbenzamido)methyl)tetrahydrofuro[3,4-d][1,3]dioxol-4-yl)methyl)benzamide (131)

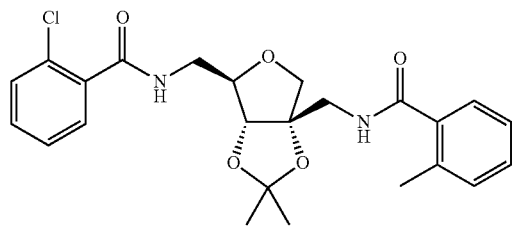

General procedure 4. White foam, 81.1% $^1$H NMR (300 MHz, CDCl$_3$) δ ppm 1.38 (s, 3 H) 1.52 (s, 3 H) 2.39 (s, 3 H) 3.43 (ddd, J=14.0, 7.7, 4.7 Hz, 1H) 3.68-3.85 (m, 3 H) 3.92 (app. s, 2 H) 4.27 (ddd, J=7.7, 6.1, 1.8 Hz, 1 H) 4.47 (d, J=1.8 Hz, 1 H) 6.61 (t, J=6.2 Hz, 1 H) 6.93 (dd, J=6.7, 5.0 Hz, 1 H) 7.14-7.39 (m, 7 H) 7.54-7.59 (m, 1 H). $^{13}$C NMR (75 MHz, CDCl$_3$) δ ppm 19.9, 27.87, 27.93, 39.9, 43.5, 75.1, 83.7, 85.3, 92.2, 113.8, 125.9, 126.7, 127.0, 129.9, 130.25 (2C), 130.8, 131.2, 131.3, 135.1, 135.7, 136.3, 167.2, 170.6. HRMS (ESI-TOF) m/z: [M+H]$^+$ Calcd for C$_{24}$H$_{28}$ClN$_2$O$_5$$^+$ 459.16813, found 459.1676.

2-chloro-N-(((3aR,4R,6aS)-6a-((2-fluorobenzamido)methyl)-2,2-dimethyltetrahydrofuro[3,4-d][1,3]dioxol-4-yl)methyl)benzamide (132)

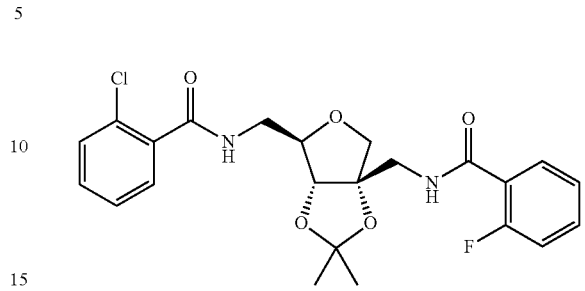

General procedure 4. White foam, 68.1% $^1$H NMR (300 MHz, CDCl$_3$) δ ppm 1.41 (s, 3 H) 1.54 (s, 3 H) 3.50 (ddd, J=14.0, 8.0, 4.8 Hz, 1 H) 3.67-3.84 (m, 2 H) 3.86-3.99 (m, 3 H) 4.31 (ddd, J=7.7, 5.9, 1.3 Hz, 1 H) 4.42 (d, J=1.5 Hz, 1 H) 6.92 (t, J=5.6 Hz, 1 H) 7.12 (app. dd, J=12.2, 8.3 Hz, 1 H) 7.20-7.40 (m, 5 H) 7.43-7.53 (m, 1 H) 7.57-7.64 (m, 1 H) 8.01 (app. td, J=7.9, 1.8 Hz, 1 H). $^{19}$F NMR (282 MHz, CDCl$_3$) δ ppm −113.2 (m). $^{13}$C NMR (75 MHz, CDCl$_3$) δ ppm 27.7, 27.9, 40.1, 43.4, 75.1, 83.6, 84.9, 92.1, 113.9, 116.2 (d, J=24.2 Hz), 120.5 (d, J=11.5 Hz), 124.9 (d, J=3.5 Hz), 127.0, 130.1 (d, J=17.3 Hz), 130.2, 130.8, 131.2, 132.1, 133.7 (d, J=9.2 Hz), 135.2, 160.7 (d, J=248.8 Hz), 164.0 (d, J=3.5 Hz), 167.0. HRMS (ESI-TOF) m/z: [M+H]$^+$ Calcd for C$_{23}$H$_{25}$ClFN$_2$O$_5$$^+$ 463.14305, found 463.1428.

N-(((3aS,6R,6aR)-6-((2-chlorobenzamido)methyl)-2,2-dimethyldihydrofuro[3,4-d][1,3]dioxol-3a(4H)-yl)methyl)furan-2-carboxamide (133)

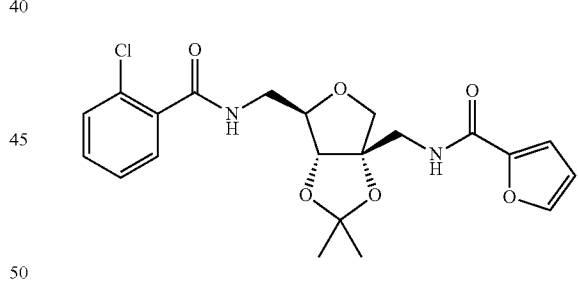

General procedure 4. White foam, 87.3% $^1$H NMR (300 MHz, CDCl$_3$) δ ppm 1.41 (s, 3 H) 1.53 (s, 3 H) 3.46 (ddd, J=14.1, 7.9, 5.0 Hz, 1 H) 3.67 (dd, J=14.4, 5.9 Hz, 1 H) 3.72-3.94 (m, 4 H) 4.28 (ddd, J=7.8, 6.2, 1.6 Hz, 1 H) 4.42 (d, J=1.5 Hz, 1 H) 6.49 (dd, J=3.4, 1.9 Hz, 1 H) 6.91 (dd, J=6.2, 5.3 Hz, 1 H) 7.03 (t, J=6.2 Hz, 1 H) 7.11 (dd, J=3.5, 0.6 Hz, 1 H) 7.26-7.40 (m, 3 H) 7.45 (dd, J=1.8, 0.9 Hz, 1 H) 7.58-7.63 (m, 1 H). $^{13}$C NMR (75 MHz, CDCl$_3$) δ ppm 27.7, 27.9, 40.0, 42.5, 75.0, 83.6, 85.1, 92.2, 112.3, 114.0, 114.9, 127.0, 129.9, 130.3, 130.8, 131.3, 135.1, 144.5, 147.5, 158.8, 167.2. HRMS (ESI-TOF) m/z: [M+H]$^+$ Calcd for C$_{21}$H$_{24}$ClN$_2$O$_6$$^+$ 435.13174, found 435.1323.

N-(((3aS,6R,6aR)-6-((2-chlorobenzamido)methyl)-2,2-dimethyldihydrofuro[3,4-d][1,3]dioxol-3a(4H)-yl)methyl)furan-3-carboxamide (134)

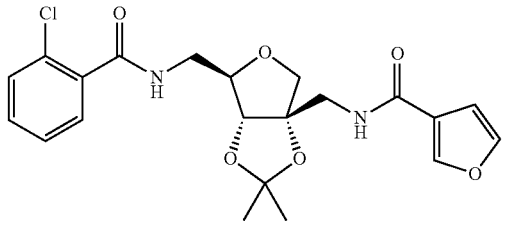 [SMILES: CC1(C)O[C@@H]2[C@@H](CNC(=O)c3ccccc3Cl)OC[C@]2(CNC(=O)c2ccoc2)O1]

General procedure 4. White foam, 88.5% $^1$H NMR (300 MHz, CDCl$_3$) δ ppm 1.38 (s, 3 H) 1.51 (s, 3 H) 3.30 (ddd, J=13.9, 6.7, 4.8 Hz, 1 H) 3.55 (dd, J=14.2, 5.1 Hz, 1 H) 3.74-4.01 (m, 4 H) 4.19-4.26 (m, 1 H) 4.53 (d, J=1.2 Hz, 1 H) 6.76 (dd, J=1.8, 0.9 Hz, 1 H) 7.10 (dd, J=7.3, 4.7 Hz, 1 H) 7.28-7.42 (m, 5 H) 7.56-7.62 (m, 1 H) 8.03 (dd, J=1.5, 0.9 Hz, 1 H). $^{13}$C NMR (75 MHz, CDCl$_3$) δ ppm 27.6, 27.7, 39.7, 42.3, 74.7, 83.8, 85.4, 92.1, 108.6, 113.4, 122.1, 127.1, 129.7, 130.4, 130.9, 131.6, 134.8, 143.8, 145.5, 163.3, 167.8. HRMS (ESI-TOF) m/z: [M+H]$^+$ Calcd for C$_{21}$H$_{24}$ClN$_2$O$_6{}^+$ 435.13174, found 435.1309.

N-(((3aS,6R,6aR)-6-((2-chlorobenzamido)methyl)-2,2-dimethyldihydrofuro[3,4-d][1,3]dioxol-3a(4H)-yl)methyl)pyrimidine-5-carboxamide (135)

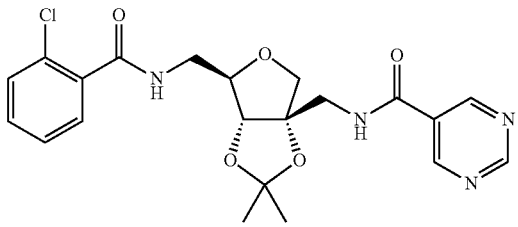

General procedure 4. White foam, 75.4% $^1$H NMR (300 MHz, CDCl$_3$) δ ppm 1.38 (s, 3 H) 1.52 (s, 3 H) 3.30 (ddd, J=14.0, 6.8, 4.7 Hz, 1 H) 3.67-3.83 (m, 2 H) 3.86-4.08 (m, 3 H) 4.23 (app. t, J=7.5 Hz, 1 H) 4.58 (app. s, 1 H) 7.09 (dd, J=7.3, 5.0 Hz, 1 H) 7.28-7.42 (m, 3 H) 7.55-7.63 (m, 1 H) 8.07 (t, J=6.2 Hz, 1 H) 9.22 (app. s, 2 H) 9.27 (app. s, 1 H). $^{13}$C NMR (75 MHz, CDCl$_3$) δ ppm 27.70, 27.75, 39.7, 43.1, 74.7, 83.8, 85.4, 91.8, 113.6, 127.2, 127.4, 129.8, 130.4, 130.8, 131.8, 134.5, 156.2, 160.6, 164.2, 168.0. HRMS (ESI-TOF) m/z: [M+H]$^+$ Calcd for C$_{21}$H$_{24}$ClN$_4$O$_5{}^+$ 447.14297, found 447.1439.

N,N'-(((3aS,6R,6aR)-2,2-dimethyldihydrofuro[3,4-d][1,3]dioxole-3a,6(4H)-diyl)bis(methylene))bis(2-chlorobenzamide) (136)

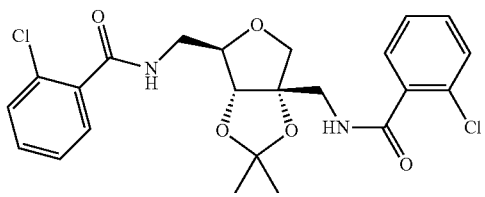 [SMILES: CC1(C)O[C@@H]2[C@@H](CNC(=O)c3ccccc3Cl)OC[C@]2(CNC(=O)c2ccccc2Cl)O1]

Azide 27 was subjected to general procedure 3, followed by general procedure 4. White powder, 76.3% $^1$H NMR (300 MHz, CDCl$_3$) δ ppm 1.39 (s, 3 H) 1.52 (s, 3 H) 3.42 (ddd, J=14.1, 7.8, 4.8 Hz, 1 H) 3.70-3.88 (m, 3 H) 3.94 (s, 2 H) 4.26 (ddd, J=7.8, 6.3, 1.5 Hz, 1 H) 4.47 (d, J=1.8 Hz, 1 H) 6.91 (dd, J=6.7, 5.0 Hz, 1 H) 7.05 (t, J=6.0 Hz, 1 H) 7.23-7.41 (m, 6 H) 7.52-7.58 (m, 2 H). $^{13}$C NMR (75 MHz, CDCl$_3$) δ ppm 27.85 (2C), 39.9, 43.7, 75.0, 83.7, 85.3, 92.0, 113.8, 127.0, 127.1, 129.7, 129.8, 130.2, 130.3, 130.7, 130.8, 131.3, 131.4, 134.9, 135.0, 167.2, 167.3. HRMS (ESI-TOF) m/z: [M+H]$^+$ Calcd for C$_{23}$H$_{25}$Cl$_2$N$_2$O$_5{}^+$ 479.11350; Found 479.1144.

N-(((3aR,4R,6aS)-6a-((2-chlorobenzamido)methyl)-2,2-dimethyltetrahydrofuro[3,4-d][1,3]dioxol-4-yl)methyl)-[1,1'-biphenyl]-4-carboxamide (137)

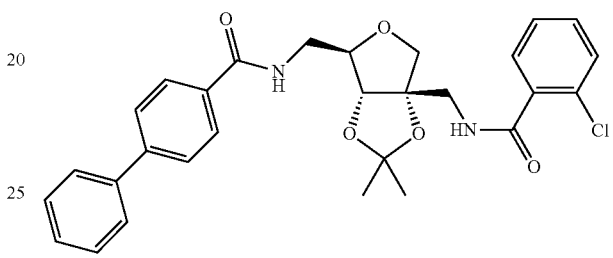

Azide 27 was subjected to general procedure 3, followed by general procedure 4. White powder, 70.5% $^1$H NMR (300 MHz, CDCl$_3$) δ ppm 1.38 (s, 3 H) 1.51 (s, 3 H) 3.52 (ddd, J=14.0, 7.3, 5.1 Hz, 1 H) 3.71-3.90 (m, 3 H) 3.92-4.01 (m, 2 H) 4.28-4.36 (app. td, J=6.9, 7.0 Hz, 1 H) 4.51 (d, J=1.5 Hz, 1 H) 7.15 (t, J=6.2 Hz, 1 H) 7.21 (t, J=5.9 Hz, 1 H) 7.26-7.47 (m, 6 H) 7.55-7.63 (m, 5 H) 7.84-7.92 (m, 2 H). $^{13}$C NMR (75 MHz, CDCl$_3$) δ ppm 27.85 (2C), 39.9, 43.7, 75.1, 83.8, 85.2, 92.1, 113.8, 127.17, 127.23, 127.8, 128.0, 128.94 (2C), 129.7, 130.4, 130.8, 131.5, 132.6, 134.9, 140.0, 144.3, 167.61, 167.64. HRMS (ESI-TOF) m/z: [M+H]$^+$ Calcd for C$_{29}$H$_{30}$ClN$_2$O$_5{}^+$ 521.18378; Found 521.1831.

N-(((3aR,4R,6aS)-6a-((2-chlorobenzamido)methyl)-2,2-dimethyltetrahydrofuro[3,4-d][1,3]dioxol-4-yl)methyl)pyridazine-4-carboxamide (138)

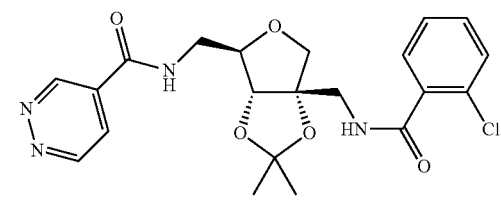 [SMILES: CC1(C)O[C@@H]2[C@@H](CNC(=O)c3ccnnc3)OC[C@]2(CNC(=O)c2ccccc2Cl)O1]

Azide 27 was subjected to general procedure 3, followed by general procedure 4. White powder, 75.4% $^1$H NMR (300 MHz, CDCl$_3$) δ ppm 1.37 (s, 3 H) 1.50 (s, 3 H) 3.48-3.59 (m, 1 H) 3.66-3.94 (m, 5 H) 4.32 (app. td, J=6.3, 1.5 Hz, 1 H) 4.49 (d, J=1.5 Hz, 1 H) 7.27-7.44 (m, 4 H) 7.54-7.60 (m, 1 H) 7.99 (dd, J=5.3, 2.3 Hz, 1 H) 8.53 (t, J=6.0 Hz, 1 H) 9.26 (dd, J=5.3, 1.2 Hz, 1 H) 9.64 (dd, J=2.3, 1.2 Hz, 1 H). $^{13}$C NMR (75 MHz, CDCl$_3$) δ ppm 27.8, 27.9, 40.2, 43.5, 75.1, 83.3, 84.7, 92.0, 113.9, 124.4, 127.2, 129.4, 130.4, 130.7, 131.6, 131.7, 134.6, 149.1, 151.8, 164.1, 168.0. HRMS (ESI-TOF) m/z: [M+H]$^+$ Calcd for C$_{21}$H$_{24}$ClN$_4$O$_5{}^+$ 447.14297; Found 447.1422.

N-(((3aS,6R,6aR)-6-((2-chlorobenzamido)methyl)-2,2-dimethyldihydrofuro[3,4-d][1,3]dioxol-3a(4H)-yl)methyl)-[1,1'-biphenyl]-4-carboxamide (139)

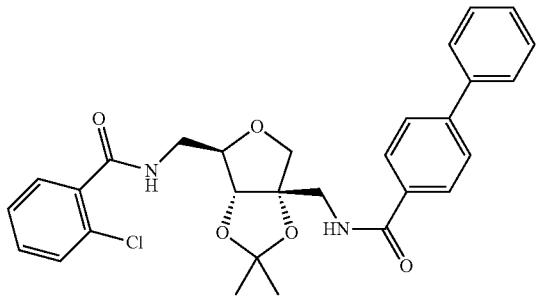 [SMILES: CC1(C)O[C@@H]2[C@@H](CNC(=O)c3ccccc3Cl)OC[C@]2(CNC(=O)c2ccc(-c3ccccc3)cc2)O1]

Azide 28 was subjected to general procedure 3, followed by general procedure 4. White powder, 59.8% $^1$H NMR (300 MHz, CDCl$_3$) δ ppm 1.40 (s, 3 H) 1.53 (s, 3 H) 3.41 (ddd, J=13.9, 7.3, 4.8 Hz, 1 H) 3.67-3.85 (m, 2 H) 3.88-4.00 (m, 3 H) 4.27 (app. td, J=7.2, 1.2 Hz, 1H) 4.54 (d, J=1.5 Hz, 1 H) 7.03 (dd, J=6.9, 4.8 Hz, 1 H) 7.26-7.49 (m, 7 H) 7.55-7.65 (m, 5 H) 7.88-7.94 (m, 2 H). $^{13}$C NMR (75 MHz, CDCl$_3$) δ ppm 27.8, 27.9, 39.9, 43.3, 74.9, 83.7, 85.3, 92.2, 113.6, 127.1, 127.2, 127.3, 127.8, 128.1, 129.0, 129.8, 130.3, 130.9, 131.4, 132.4, 135.0, 140.0, 144.6, 167.5, 167.7. HRMS (ESI-TOF) m/z: [M+H]$^+$ Calcd for C$_{29}$H$_{30}$ClN$_2$O$_5^+$ 521.18378; Found 521.1825.

N-(((3aR,4R,6aS)-6a-([1,1'-biphenyl]-4-carboxamidomethyl)-2,2-dimethyltetrahydrofuro[3,4-d][1,3]dioxol-4-yl)methyl)pyridazine-4-carboxamide (140)

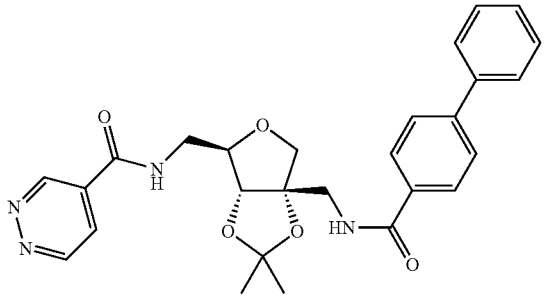 [SMILES: CC1(C)O[C@@H]2[C@@H](CNC(=O)c3ccnnc3)OC[C@]2(CNC(=O)c2ccc(-c3ccccc3)cc2)O1]

Azide 28 was subjected to general procedure 3, followed by general procedure 4. White powder, 58.0% $^1$H NMR (300 MHz, CDCl$_3$) δ ppm 1.37 (s, 3 H) 1.52 (s, 3 H) 3.52-3.64 (m, 2 H) 3.85-4.04 (m, 4 H) 4.35 (app. t, J=5.1 Hz, 1 H) 4.50 (d, J=1.8 Hz, 1 H) 7.33-7.50 (m, 4 H) 7.55-7.72 (m, 4 H) 7.92 (d, J=8.5 Hz, 2 H) 8.07 (dd, J=5.3, 2.1 Hz, 1 H) 8.56-8.67 (m, 1 H) 9.32 (app. d, J=5.0 Hz, 1 H) 9.77 (app. s, 1 H). $^{13}$C NMR (75 MHz, CDCl$_3$) δ ppm 27.7, 28.1, 40.3, 43.0, 75.2, 83.1, 84.3, 92.3, 113.9, 124.5, 127.3, 127.52, 127.53, 127.7, 128.3, 129.1, 131.7, 131.8, 139.7, 145.1, 149.2, 151.9, 164.3, 168.4. HRMS (ESI-TOF) m/z: [M+H]$^+$ Calcd for C$_{27}$H$_{29}$N$_4$O$_5^+$ 489.21325; Found 489.2127.

N-(((3aS,6R,6aR)-6-((1,3-dioxoisoindolin-2-yl)methyl)-2,2-dimethyldihydrofuro[3,4-d][1,3]dioxol-3a(4H)-yl)methyl)-[1,1'-biphenyl]-4-carboxamide (141)

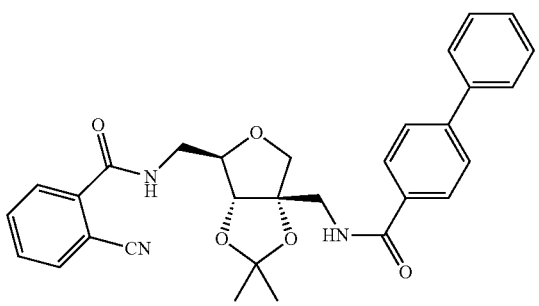 [SMILES: CC1(C)O[C@@H]2[C@@H](CNC(=O)c3ccccc3C#N)OC[C@]2(CNC(=O)c2ccc(-c3ccccc3)cc2)O1]

Azide 28 was subjected to general procedure 3, followed by general procedure 4. White foam, 48.4%. Without NMR- or HRMS analysis, this compound was deprotected. The o-cyanobenzamide moiety was converted into the corresponding phthalimide in the acidic environment of the last step.

N-(((3aS,6R,6aR)-6-((2-chlorobenzamido)methyl)-2,2-dimethyldihydrofuro[3,4-d][1,3]dioxol-3a(4H)-yl)methyl)pyridazine-4-carboxamide (142)

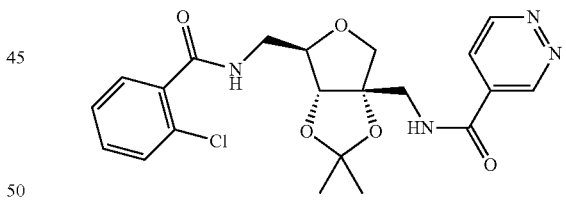

Azide 29 was subjected to general procedure 3, followed by general procedure 4. White foam, 62.7% $^1$H NMR (300 MHz, CDCl$_3$) δ ppm 1.35 (s, 3 H) 1.51 (s, 3 H) 3.31 (ddd, J=13.8, 6.8, 4.8 Hz, 1 H) 3.66-3.80 (m, 2 H) 3.87 (d, J=10.4 Hz, 1 H) 3.93 (d, J=10.4 Hz, 1 H) 4.01 (dd, J=14.4, 7.3 Hz, 1 H) 4.24 (app. t, J=7.8 Hz, 1 H) 4.60 (d, J=0.9 Hz, 1 H) 7.24-7.44 (m, 4 H) 7.51-7.59 (m, 1 H) 8.02 (dd, J=5.6, 2.3 Hz, 1 H) 8.66 (t, J=6.2 Hz, 1 H) 9.26 (dd, J=5.3, 1.2 Hz, 1 H) 9.63 (dd, J=2.3, 1.2 Hz, 1 H). $^{13}$C NMR (75 MHz, CDCl$_3$) δ ppm 27.6, 27.7, 39.6, 43.2, 74.6, 83.7, 85.3, 91.8, 113.5, 124.3, 127.1, 129.5, 130.4, 130.8, 131.3, 131.6, 134.7, 149.0, 151.8, 164.2, 168.1. HRMS (ESI-TOF) m/z: [M+H]$^+$ Calcd for C$_{21}$H$_{24}$ClN$_4$O$_5^+$ 447.14297; Found 447.1428.

N-(((3aS,6R,6aR)-6-([1,1'-biphenyl]-4-carboxamidomethyl)-2, 2-dimethyldihydro furo[3,4-d][1,3]dioxol-3a(4H)-yl)methyl)pyridazine-4-carboxamide (143)

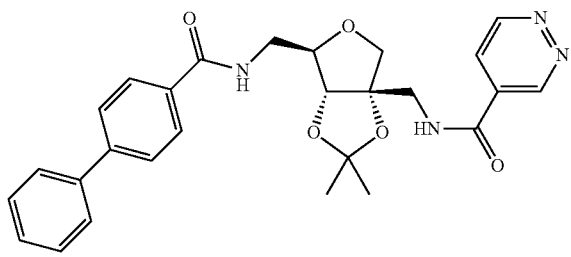 [SMILES: CC1(C)O[C@@H]2[C@@H](CNC(=O)c3ccc(-c4ccccc4)cc3)OC[C@]2(CNC(=O)c2ccnnc2)O1]

Azide 29 was subjected to general procedure 3, followed by general procedure 4. White powder, 87.7% $^1$H NMR (300 MHz, CDCl$_3$) δ ppm 1.35 (s, 3 H) 1.50 (s, 3 H) 3.32 (ddd, J=5.0, 6.5, 13.8 Hz, 1 H) 3.68-3.84 (m, 2 H) 3.89 (d, J=10.5 Hz, 1 H) 3.96 (d, J=10.5 Hz, 1 H) 4.10 (dd, J=14.1, 7.6 Hz, 1 H) 4.26 (app. dd, J=8.4, 6.9 Hz, 1 H) 4.60 (app. s, 1 H) 7.34-7.49 (m, 4 H) 7.54-7.69 (m, 4 H) 7.87-7.96 (m, 2 H) 8.08 (dd, J=5.3, 2.3 Hz, 1 H) 8.74 (dd, J=7.3, 5.3 Hz, 1 H) 9.33 (dd, J=5.3, 1.2 Hz, 1 H) 9.76 (dd, J=2.2, 1.3 Hz, 1 H). $^{13}$C NMR (75 MHz, CDCl$_3$) δ ppm 27.68, 27.75, 39.6, 43.2, 74.6, 84.1, 85.5, 91.9, 113.5, 124.5, 127.3, 127.4, 127.8, 128.3, 129.0, 131.4, 132.1, 139.8, 145.0, 149.0, 152.0, 164.3, 168.6. HRMS (ESI-TOF) m/z: [M+H]$^+$ Calcd for C$_{27}$H$_{29}$N$_4$O$_5^+$ 489.21325; Found 489.2126.

N,N'-(((3aS,6R,6aR)-2,2-dimethyldihydrofuro[3,4-d][1,3]dioxole-3a,6(4H)-diyl)bis(methylene))bis(pyridazine-4-carboxamide) (144)

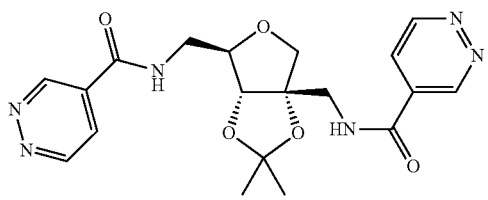 [SMILES: CC1(C)O[C@@H]2[C@@H](CNC(=O)c3ccnnc3)OC[C@]2(CNC(=O)c2ccnnc2)O1]

Azide 29 was subjected to general procedure 3, followed by general procedure 4. Yellow foam, 43.6% $^1$H NMR (300 MHz, CDCl$_3$) δ ppm 1.33 (s, 3 H) 1.48 (s, 3 H) 3.51 (app. dt, J=14.1, 5.6 Hz, 1 H) 3.70-4.00 (m, 5 H) 4.26-4.33 (m, 1 H) 4.53 (d, J=1.5 Hz, 1 H) 8.06 (app. dd, J=5.3, 2.3 Hz, 2 H) 8.60-8.73 (m, 2 H) 9.34 (app. td, J=5.4, 1.0 Hz, 2 H) 9.68 (app. dd, J=2.2, 1.3 Hz, 2 H). $^{13}$C NMR (75 MHz, CDCl$_3$) δ ppm 27.8, 27.9, 40.3, 43.5, 74.8, 83.6, 85.1, 92.0, 114.1, 124.7, 124.9, 131.6, 131.9, 148.9, 149.1, 152.07, 152.15, 164.4, 164.6. HRMS (ESI-TOF) m/z: [M+H]$^+$ Calcd for C$_{19}$H$_{23}$N$_6$O$_5^+$ 415.17244; Found 415.1736.

N-(((3aS,6R,6aR)-6-((1,3-dioxoisoindolin-2-yl)methyl)-2,2-dimethyldihydrofuro[3,4-d][1,3]dioxol-3a(4H)-yl)methyl)pyridazine-4-carboxamide (145)

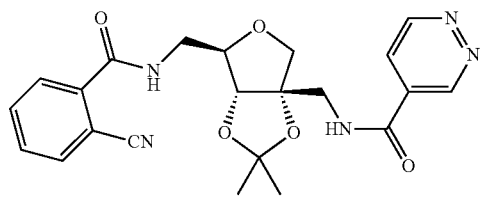 [SMILES: CC1(C)O[C@@H]2[C@@H](CNC(=O)c3ccccc3C#N)OC[C@]2(CNC(=O)c2ccnnc2)O1]

Azide 29 was subjected to general procedure 3, followed by general procedure 4. White foam, 70.2%. Without NMR- or HRMS analysis, this compound was deprotected. The o-cyanobenzamide moiety was converted into the corresponding phthalimide in the acidic environment of the last step.

2-chloro-N-(((3aR,4R,6aS)-2,2-dimethyl-6a-((2-phenylacetamido)methyl)tetrahydrofuro[3,4-d][1,3]dioxol-4-yl)methyl)benzamide (146)

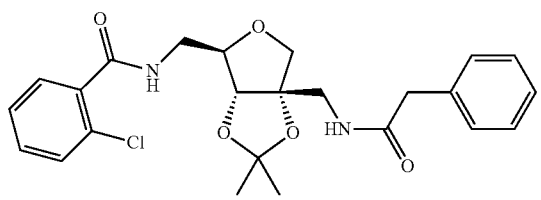 [SMILES: CC1(C)O[C@@H]2[C@@H](CNC(=O)c3ccccc3Cl)OC[C@]2(CNC(=O)Cc2ccccc2)O1]

Azide 30 was subjected to general procedure 3, followed by general procedure 4. White foam, 91.9%. $^1$H NMR (300 MHz, CDCl$_3$) δ ppm 1.20 (s, 3 H) 1.45 (s, 3 H) 3.23 (ddd, J=14.0, 7.5, 4.8 Hz, 1 H) 3.33 (dd, J=14.2, 4.8 Hz, 1 H) 3.56-3.84 (m, 6 H) 4.15-4.22 (m, 1 H) 4.31 (d, J=1.2 Hz, 1 H) 6.60 (dd, J=7.2, 4.8 Hz, 1 H) 6.93 (dd, J=7.0, 4.7 Hz, 1 H) 7.20-7.42 (m, 8 H) 7.54-7.61 (m, 1 H). $^{13}$C NMR (75 MHz, CDCl$_3$) δ ppm 27.5, 27.7, 39.7, 42.6, 43.7, 74.7, 83.6, 85.0, 92.0, 113.4, 127.1, 127.4, 129.0, 129.4, 129.8, 130.3, 130.8, 131.4, 134.7, 135.0, 167.4, 171.8. HRMS (ESI-TOF) m/z: [M+H]$^+$ Calcd for C$_{24}$H$_{28}$ClN$_2$O$_5^+$ 459.16813; Found 459.1679.

2-chloro-N-(((3aR,4R,6aS)-2,2-dimethyl-6a-((3-phenylpropanamido)methyl)tetrahydrofuro[3,4-d][1,3]dioxol-4-yl)methyl)benzamide (147)

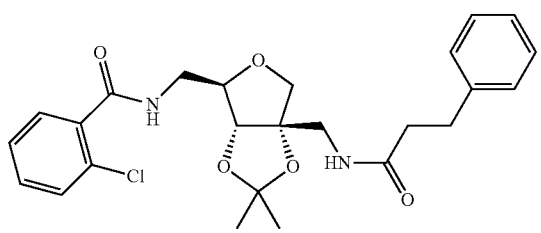 [SMILES: CC1(C)O[C@@H]2[C@@H](CNC(=O)c3ccccc3Cl)OC[C@]2(CNC(=O)CCc2ccccc2)O1]

Azide 31 was subjected to general procedure 3, followed by general procedure 4. White foam, 80.0%. $^1$H NMR (300 MHz, CDCl$_3$) δ ppm 1.31 (s, 3 H) 1.48 (s, 3 H) 2.54 (t, J=7.5 Hz, 2 H) 2.84-3.02 (m, 2 H) 3.18 (ddd, J=14.1, 7.0, 4.7 Hz, 1 H) 3.35 (dd, J=14.2, 5.1 Hz, 1 H) 3.57-3.82 (m, 4 H) 4.16 (app. t, J=7.3 Hz, 1 H) 4.31 (d, J=1.2 Hz, 1 H) 6.68 (dd, J=6.9, 5.4 Hz, 1 H) 6.94 (dd, J=7.3, 4.7 Hz, 1 H) 7.13-7.42 (m, 8 H) 7.55-7.62 (m, 1 H). $^{13}$C NMR (75 MHz, CDCl$_3$) δ ppm 27.7, 27.8, 31.5, 38.3, 39.5, 42.5, 74.6, 83.7, 85.2, 91.9, 113.5, 126.3, 127.1, 128.5, 128.6, 129.8, 130.3, 130.8, 131.5, 135.0, 140.9, 167.5, 172.8. HRMS (ESI-TOF) m/z: [M+H]$^+$ Calcd for C$_{25}$H$_{29}$ClN$_2$NaO$_5$$^+$ 495.16572; Found 495.1664.

N-(((3aR,4R,6aS)-6a-(azidomethyl)-2,2-dimethyltetrahydrofuro[3,4-d][1,3]dioxol-4-yl)methyl)benzamide (148)

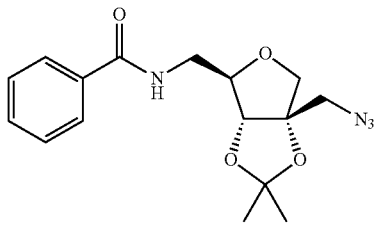 [SMILES: CC1(C)O[C@@H]2[C@@H](CNC(=O)c3ccccc3)OC[C@]2(CN=[N+]=[N-])O1]

Preparation of triflyl azide (TfN$_3$): NaN$_3$ (0.68 g, 10.45 mmol) was dissolved in water (8 mL) and cooled to 0° C. After addition of CH$_2$Cl$_2$ (8 mL) the mixture was stirred for 15 minutes. Tf$_2$O (0.352 mL, 2.09 mmol) was added dropwise over 1 minute. The RM was stirred vigorously at 0° C. and then extracted with DCM (2×3 mL) and washed with aqueous saturated Na$_2$CO$_3$ solution (2×3 mL). The organic layer was saved for the diazo transfer reaction.

Diazo transfer reaction: amine 117 (0.32 g, 1.05 mmol) was dissolved in MeOH (8 mL), giving a clear solution. Et$_3$N (0.291 mL, 2.09 mmol) was added. A freshly prepared solution of CuSO$_4$ (1.64 mg, 1 mol %) in water (3 mL) was added. The clear solution became turbid. The above-prepared TfN$_3$ solution was added and the RM was stirred vigorously for 18 h at rt. TLC analysis (toluene/EtOAc 6:4 and CH$_2$Cl$_2$/MeOH 9:1) showed complete consumption of amine and presence of 1 large higher-running spot. The RM was concentrated in vacuo and adsorbed onto celite. Purification via FCC (toluene/EtOAc 10:0→6:4) gave the title compound as a colourless oil in 89.6% yield.

$^1$H NMR (300 MHz, CDCl$_3$) δ ppm 1.45 (s, 3 H) 1.53 (s, 3 H) 3.37-3.51 (m, 2 H) 3.56 (d, J=12.9 Hz, 1 H) 3.71 (ddd, J=14.0, 6.7, 5.4 Hz, 1 H) 3.85 (d, J=10.3 Hz, 1 H) 3.93 (d, J=10.3 Hz, 1 H) 4.23 (ddd, J=7.7, 5.5, 1.8 Hz, 1 H) 4.39 (d, J=1.8 Hz, 1 H) 6.67 (t, J=5.3 Hz, 1 H) 7.37-7.53 (m, 3 H) 7.74-7.81 (m, 2 H). $^{13}$C NMR (75 MHz, CDCl$_3$) δ ppm 27.6, 28.0, 39.9, 54.8, 74.9, 84.2, 85.4, 91.8, 114.9, 127.0, 128.7, 131.8, 134.1, 167.9. HRMS (ESI-TOF) m/z: [M+H]$^+$ Calcd for C$_{16}$H$_{21}$N$_4$O$_4$$^+$ 333.15573; Found 333.1568.

N-(((3aR,4R,6aS)-6a-(azidomethyl)-2,2-dimethyltetrahydrofuro[3,4-d][1,3]dioxol-4-yl)methyl)-N-methylbenzamide (149)

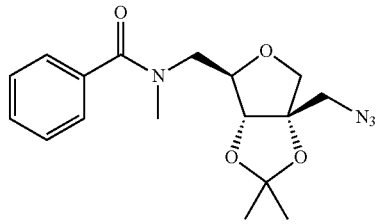 [SMILES: CN(C[C@H]1OC[C@]2(CN=[N+]=[N-])OC(C)(C)O[C@H]12)C(=O)c1ccccc1]

A flask containing a solution of azide 148 (0.30 g, 0.90 mmol) in THF (9 mL) was purged with nitrogen gas, treated with NaH (60% dispersion in mineral oil, 72 mg, 1.81 mmol) and backflushed. After 1 hour, MeI (112 µL, 1.81 mmol) was added and the whole was stirred at rt overnight. The reaction was monitored by mass spectrometry (ESI-TOF), which showed complete consumption of SM and presence of the desired compound. The RM was concentrated in vacuo and adsorbed onto celite. Purification via flash column chromatography (toluene/EtOAc 100:0→70:30) gave the title compound in 88.3% yield (transparent oil that solidifies on standing). HRMS (ESI-TOF) m/z: [M+H]$^+$ Calcd for C$_{17}$H$_{23}$N$_4$O$_4$$^+$ 347.17138; Found 347.1722.

N-(((3aR,4R,6aS)-6a-(benzamidomethyl)-2,2-dimethyltetrahydrofuro[3,4-d][1,3]dioxol-4-yl)methyl)-N-methylbenzamide (150)

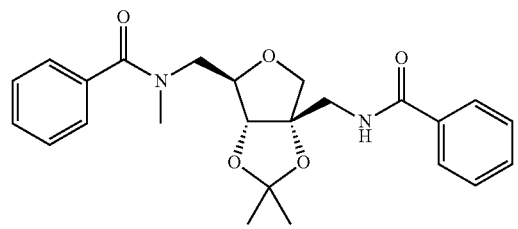 [SMILES: CN(C[C@H]1OC[C@]2(CNC(=O)c3ccccc3)OC(C)(C)O[C@H]12)C(=O)c1ccccc1]

Azide 149 was subjected to general procedure 3, followed by procedure 4. White foam, 93.3% HRMS (ESI-TOF) m/z: [M+H]$^+$ Calcd for C$_{24}$H$_{23}$N$_2$O$_5$$^+$ 425.20710; Found 425.2076.

N-(((2R,3R,4S)-4-(benzamidomethyl)-3,4-dihydroxytetrahydrofuran-2-yl)methyl)-4-methylbenzamide (151)

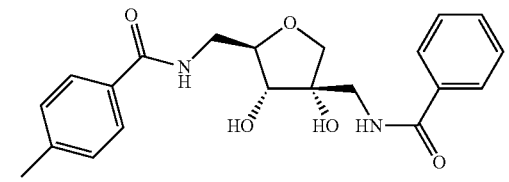 [SMILES: Cc1ccc(C(=O)NC[C@H]2OC[C@@](O)(CNC(=O)c3ccccc3)[C@@H]2O)cc1]

General procedure 8. White foam, quant. $^1$H NMR (300 MHz, DMSO-d$_6$) δ ppm 2.34 (s, 3 H) 3.29-3.48 (m, 3 H)

3.49-3.68 (m, 3 H) 3.79 (app. td, J=7.3, 3.8 Hz, 1 H) 3.87 (d, J=9.7 Hz, 1 H) 4.90 (br. s., 2 H) 7.22 (d, J=7.9 Hz, 2 H) 7.38-7.58 (m, 3 H) 7.75 (d, J=7.9 Hz, 2 H) 7.84 (app. d, J=7.0 Hz, 2 H) 8.37 (m, 2 H). $^{13}$C NMR (75 MHz, DMSO-d$_6$) δ ppm 20.9, 41.9, 44.3, 74.6, 74.7, 78.1, 80.8, 127.27, 127.31, 128.2, 128.7, 131.2, 131.7, 134.4, 140.8, 166.2, 167.1. HRMS (ESI-TOF) m/z: [M+H]$^+$ Calcd for C$_{21}$H$_{26}$N$_2$O$_6$$^+$ 385.17580; Found 385.1749.

N-(((2R,3R,4S)-4-(benzamidomethyl)-3,4-dihydroxytetrahydrofuran-2-yl)methyl)-4-fluorobenzamide (152)

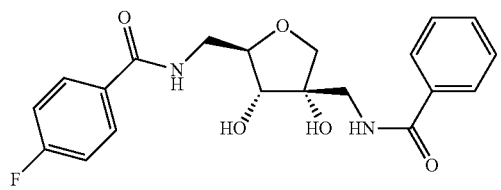 [SMILES: O=C(NC[C@H]1OC[C@@](O)(CNC(=O)c2ccccc2)[C@@H]1O)c1ccc(F)cc1]

General procedure 8. White foam, 91.9% $^1$H NMR (300 MHz, DMSO-d$_6$) δ ppm 3.37-3.47 (m, 3 H) 3.50-3.64 (m, 3 H) 3.79 (app. td, J=7.3, 3.8 Hz, 1 H) 3.87 (d, J=9.7 Hz, 1 H) 4.79 (br. s., 1 H) 4.99 (br. s., 1 H) 7.25 (app. t, J=8.9 Hz, 2 H) 7.41-7.57 (m, 3 H) 7.77-7.87 (m, 2 H) 7.91 (dd, J=8.8, 5.6 Hz, 2 H) 8.36 (t, J=5.7 Hz, 1 H) 8.52 (t, J=5.4 Hz, 1 H). $^{19}$F NMR (282 MHz, DMSO-d$_6$) δ ppm −110.2 (m). $^{13}$C NMR (75 MHz, DMSO-d$_6$) δ ppm 42.0, 44.2, 74.6, 74.7, 78.1, 80.7, 115.0 (d, J=21.6 Hz), 127.3, 128.2, 129.9 (d, J=8.9 Hz), 130.9 (d, J=2.8 Hz), 131.2, 134.4, 163.8 (d, J=248.2 Hz), 165.3, 167.1. HRMS (ESI-TOF) m/z: [M+H]$^+$ Calcd for C$_{20}$H$_{22}$FN$_2$O$_6$ 389.15073; Found 389.1496.

N-(((2R,3R,4S)-4-(benzamidomethyl)-3,4-dihydroxytetrahydrofuran-2-yl)methyl)-4-chlorobenzamide (153)

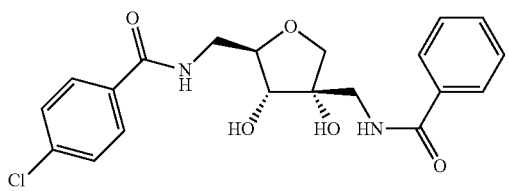 [SMILES: O=C(NC[C@H]1OC[C@@](O)(CNC(=O)c2ccccc2)[C@@H]1O)c1ccc(Cl)cc1]

General procedure 8. White foam, 89.3% $^1$H NMR (300 MHz, DMSO-d$_6$) δ ppm 3.34-3.47 (m, 3 H) 3.50-3.66 (m, 3 H) 3.79 (app. td, J=7.3, 3.7 Hz, 1 H) 3.87 (d, J=9.7 Hz, 1 H) 4.79 (s, 1 H) 4.99 (d, J=6.7 Hz, 1 H) 7.36-7.60 (m, 5 H) 7.84 (m, 4 H) 8.36 (t, J=5.7 Hz, 1 H) 8.58 (t, J=5.4 Hz, 1 H). $^{13}$C NMR (75 MHz, DMSO-d$_6$) δ ppm 42.0, 44.2, 74.6, 74.7, 78.1, 80.7, 127.3, 128.22, 128.24, 129.2, 131.2, 133.2, 134.4, 135.8, 165.3, 167.0. HRMS (ESI-TOF) m/z: [M+H]$^+$ Calcd for C$_{20}$H$_{22}$ClN$_2$O$_6$$^+$ 405.12118; Found 405.1209.

N-(((2R,3R,4S)-4-(benzamidomethyl)-3,4-dihydroxytetrahydrofuran-2-yl)methyl)-4-methoxybenzamide (154)

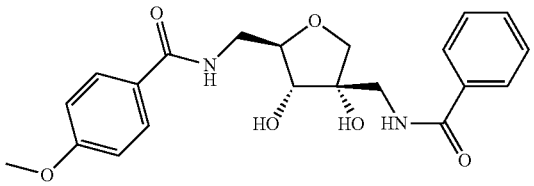 [SMILES: COc1ccc(C(=O)NC[C@H]2OC[C@@](O)(CNC(=O)c3ccccc3)[C@@H]2O)cc1]

General procedure 8. White foam, quant. $^1$H NMR (300 MHz, DMSO-d$_6$) δ ppm 3.31-3.47 (m, 3 H) 3.50-3.64 (m, 3 H) 3.72-3.83 (m, 4 H) 3.87 (d, J=9.4 Hz, 1 H) 4.88 (br. s., 2 H) 6.90-7.00 (m, 2 H) 7.41-7.57 (m, 3 H) 7.75-7.92 (m, 4 H) 8.27-8.41 (m, 2 H). $^{13}$C NMR (75 MHz, DMSO-d$_6$) δ ppm 41.9, 44.3, 55.3, 74.6, 74.7, 78.1, 80.9, 113.4, 126.7, 127.3, 128.2, 129.1, 131.2, 134.4, 161.4, 165.8, 167.1. HRMS (ESI-TOF) m/z: [M+Na]$^+$ Calcd for C$_{21}$H$_{24}$N$_2$NaO$_6$$^+$ 423.15266; Found 423.1512.

N-(((2R,3R,4S)-4-(benzamidomethyl)-3,4-dihydroxytetrahydrofuran-2-yl)methyl)-4-cyanobenzamide (155)

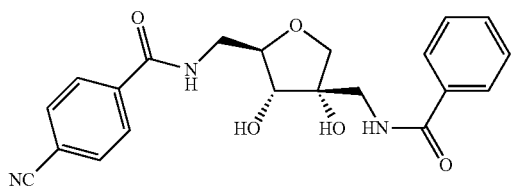 [SMILES: N#Cc1ccc(C(=O)NC[C@H]2OC[C@@](O)(CNC(=O)c3ccccc3)[C@@H]2O)cc1]

General procedure 8. White foam, 91.1% $^1$H NMR (300 MHz, DMSO-d$_6$) δ ppm 3.35-3.49 (m, 3 H) 3.50-3.66 (m, 3 H) 3.79 (app. td, J=7.3, 3.8 Hz, 1 H) 3.87 (d, J=9.7 Hz, 1 H) 4.76 (br. s., 1 H) 4.88 (br. s., 1 H) 7.37-7.57 (m, 3 H) 7.78-7.86 (m, 2 H) 7.86-7.93 (m, 2 H) 7.94-8.04 (m, 2 H) 8.36 (t, J=6.0 Hz, 1 H) 8.77 (t, J=5.6 Hz, 1 H). $^{13}$C NMR (75 MHz, DMSO-d$_6$) δ ppm 42.0, 44.1, 74.61, 74.64, 78.0, 80.6, 113.4, 118.4, 127.3, 128.1, 128.2, 131.2, 132.3, 134.4, 138.5, 165.0, 167.0. HRMS (ESI-TOF) m/z: [M+H]$^+$ Calcd for C$_{21}$H$_{22}$N$_3$O$_5$$^+$ 396.15540; Found 396.1541.

N-(((2R,3R,4S)-4-(benzamidomethyl)-3,4-dihydroxytetrahydrofuran-2-yl)methyl)-4-(dimethylamino)benzamide (156)

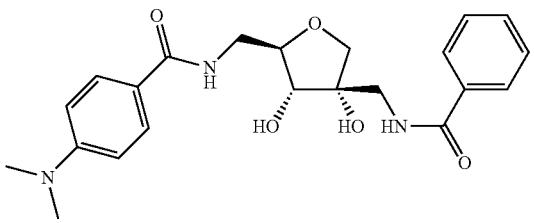 [SMILES: CN(C)c1ccc(C(=O)NC[C@H]2OC[C@@](O)(CNC(=O)c3ccccc3)[C@@H]2O)cc1]

General procedure 8. White foam, quant. $^1$H NMR (300 MHz, DMSO-d$_6$) δ ppm 2.96 (s, 6 H) 3.27-3.44 (m, 3 H) 3.47-3.62 (m, 3 H) 3.76 (app. td, J=7.3, 3.8 Hz, 1 H) 3.86 (d, J=9.4 Hz, 1 H) 6.63-6.70 (m, 2 H) 7.40-7.57 (m, 3 H) 7.68-7.75 (m, 2 H) 7.81-7.87 (m, 2 H) 8.07 (t, J=5.6 Hz, 1 H) 8.36 (t, J=5.9 Hz, 1 H). $^{13}$C NMR (75 MHz, DMSO-d$_6$) δ ppm 39.8, 41.8, 44.3, 74.5, 74.7, 78.1, 81.0, 110.8, 121.3, 127.3, 128.2, 128.6, 131.2, 134.4, 152.0, 166.2, 167.1. HRMS (ESI-TOF) m/z: [M+H]$^+$ Calcd for C$_{22}$H$_{28}$N$_3$O$_5$$^+$ 414.20235; Found 414.2032.

N-(((2R,3R,4S)-4-(benzamidomethyl)-3,4-dihydroxytetrahydrofuran-2-yl)methyl)-4-(trifluoromethyl)benzamide (157)

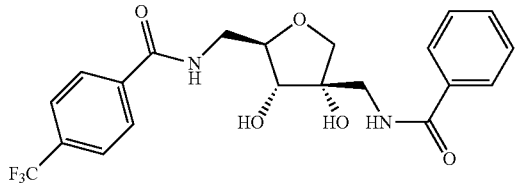 [SMILES: O=C(NC[C@H]1OC[C@@](O)(CNC(=O)c2ccccc2)[C@@H]1O)c1ccc(C(F)(F)F)cc1]

General procedure 8. White foam, 90.7% $^1$H NMR (300 MHz, DMSO-d$_6$) δ ppm 3.35-3.51 (m, 3 H) 3.51-3.69 (m, 3 H) 3.81 (app. td, J=7.3, 3.8 Hz, 1 H) 3.88 (d, J=9.4 Hz, 1 H) 4.81 (s, 1 H) 5.00 (d, J=6.7 Hz, 1 H) 7.38-7.57 (m, 3 H) 7.71-7.90 (m, 4 H) 8.02 (d, J=8.2 Hz, 2 H) 8.37 (t, J=5.9 Hz, 1 H) 8.74 (t, J=5.6 Hz, 1 H). $^{19}$F NMR (282 MHz, DMSO-d$_6$) δ ppm −61.7 (s). $^{13}$C NMR (75 MHz, DMSO-d$_6$) δ ppm 42.0, 44.1, 74.57, 74.64, 78.1, 80.6, 124.0 (q, J=272.3 Hz), 125.2 (q, J=3.7 Hz), 127.3, 128.18, 128.22, 131.0 (q, J=31.9 Hz), 131.2, 134.4, 138.3, 165.3, 167.0. HRMS (ESI-TOF) m/z: [M+Na]$^+$ Calcd for C$_{21}$H$_{21}$F$_3$N$_2$NaO$_5$$^+$ 461.12948; Found 461.1302.

N-(((2R,3R,4S)-4-(benzamidomethyl)-3,4-dihydroxytetrahydrofuran-2-yl)methyl)isonicotinamide (158)

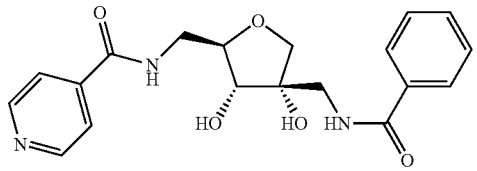

General procedure 8. White foam, quant. $^1$H NMR (300 MHz, DMSO-d$_6$) δ ppm 3.36-3.49 (m, 3 H) 3.53-3.65 (m, 3 H) 3.80 (app. td, J=7.5, 3.8 Hz, 1 H) 3.88 (d, J=9.7 Hz, 1 H) 7.41-7.57 (m, 3 H) 7.80-7.91 (m, 4 H) 8.37 (t, J=5.9 Hz, 1 H) 8.71-8.80 (m, 2 H) 8.88-8.95 (m, 1 H). $^{13}$C NMR (75 MHz, DMSO-d$_6$) δ ppm 42.0, 44.2, 74.6, 74.7, 78.0, 80.5, 122.2, 127.3, 128.2, 131.2, 134.4, 143.2, 148.5, 164.3, 167.1. HRMS (ESI-TOF) m/z: [M+H]$^+$ Calcd for C$_{19}$H$_{22}$N$_3$O$_5$$^+$ 372.15540; Found 372.1552.

N-(((2R,3R,4S)-4-(benzamidomethyl)-3,4-dihydroxytetrahydrofuran-2-yl)methyl)-[1,1'-biphenyl]-4-carboxamide (159)

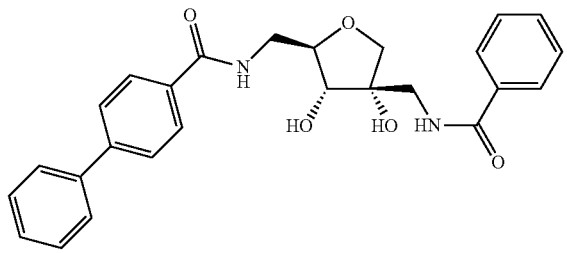 [SMILES: O=C(NC[C@H]1OC[C@@](O)(CNC(=O)c2ccccc2)[C@@H]1O)c1ccc(-c2ccccc2)cc1]

General procedure 8. White foam, quant. $^1$H NMR (300 MHz, DMSO-d$_6$) δ ppm 3.36-3.48 (m, 3 H) 3.52-3.67 (m, 3 H) 3.81 (app. td, J=7.3, 4.1 Hz, 1 H) 3.88 (d, J=9.4 Hz, 1 H) 4.80 (s, 1 H) 5.01 (d, J=6.7 Hz, 1 H) 7.35-7.57 (m, 6 H) 7.68-7.77 (m, 4 H) 7.81-7.87 (m, 2 H) 7.90-7.97 (m, 2 H) 8.38 (t, J=6.0 Hz, 1 H) 8.53 (t, J=5.4 Hz, 1 H). $^{13}$C NMR (75 MHz, DMSO-d$_6$) δ ppm 41.9, 44.2, 74.6, 74.7, 78.1, 80.8, 126.4, 126.8, 127.3, 127.97 (2 C), 128.2, 129.0, 131.2, 133.3, 134.4, 139.2, 142.6, 166.0, 167.1. HRMS (ESI-TOF) m/z: [M+H]$^+$ Calcd for C$_{26}$H$_{27}$N$_2$O$_5$$^+$ 447.19145; Found 447.1930.

N-(((2R,3R,4S)-4-(benzamidomethyl)-3,4-dihydroxytetrahydrofuran-2-yl)methyl)-3-methylbenzamide (160)

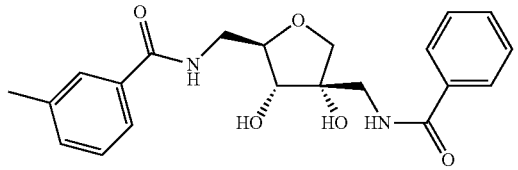 [SMILES: Cc1cccc(C(=O)NC[C@H]2OC[C@@](O)(CNC(=O)c3ccccc3)[C@@H]2O)c1]

General procedure 8. White foam, quant. $^1$H NMR (300 MHz, CD$_3$OD) δ ppm 2.36 (s, 3 H) 3.51-3.60 (m, 2 H) 3.60-3.69 (m, 2 H) 3.70-3.78 (m, 2 H) 3.90-3.97 (m, 1 H) 3.99 (d, J=10.0 Hz, 1 H) 7.24-7.36 (m, 2 H) 7.37-7.47 (m, 2 H) 7.47-7.67 (m, 3 H) 7.73-7.86 (m, 2 H). $^{13}$C NMR (75 MHz, CD$_3$OD) δ ppm 21.4, 42.9, 45.7, 76.0, 76.2, 79.8, 82.7, 125.5, 128.3, 128.9, 129.4, 129.6, 132.8, 133.3, 135.4, 135.6, 139.5, 170.8, 171.0. HRMS (ESI-TOF) m/z: [M+H]$^+$ Calcd for C$_{21}$H$_{25}$N$_2$O$_5$$^+$ 385.17580; Found 385.1776.

N-(((2R,3R,4S)-4-(benzamidomethyl)-3,4-dihydroxytetrahydrofuran-2-yl)methyl)-3-fluorobenzamide (161)

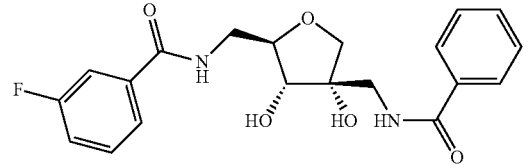 [SMILES: O=C(NC[C@H]1OC[C@@](O)(CNC(=O)c2ccccc2)[C@@H]1O)c1cccc(F)c1]

General procedure 8. White foam, quant. $^1$H NMR (300 MHz, DMSO-d$_6$) δ ppm 3.33-3.49 (m, 3 H) 3.50-3.67 (m, 3 H) 3.78 (m, 1 H) 3.88 (d, J=9.7 Hz, 1 H) 4.85 (br. s., 2 H) 7.29-7.58 (m, 5 H) 7.60-7.74 (m, 2 H) 7.84 (app. d, J=7.3 Hz, 2H) 8.36 (t, J=5.4 Hz, 1 H) 8.61 (t, J=5.0 Hz, 1 H). $^{19}$F NMR (282 MHz, DMSO-d$_6$) δ ppm −113.4 (m). $^{13}$C NMR (75 MHz, DMSO-d$_6$) δ ppm 42.0, 44.2, 74.6, 74.7, 78.1, 80.7, 114.1 (d, J=22.9 Hz), 118.0 (d, J=21.0 Hz), 123.4 (d, J=2.8 Hz), 127.3, 128.2, 130.3 (d, J=8.0 Hz), 131.2, 134.4, 136.9 (d, J=6.9 Hz), 161.9 (d, J=243.8 Hz), 165.0 (d, J=2.5 Hz), 167.1. HRMS (ESI-TOF) m/z: [M+H]$^+$ Calcd for C$_{20}$H$_{22}$FN$_2$O$_5$$^+$ 389.15073; Found 389.1522.

N-(((2R,3R,4S)-4-(benzamidomethyl)-3,4-dihydroxytetrahydrofuran-2-yl)methyl)-3-chlorobenzamide (162)

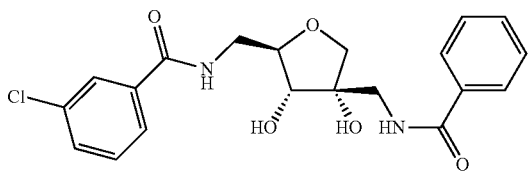 [SMILES: O=C(NC[C@H]1OC[C@@](O)(CNC(=O)c2ccccc2)[C@@H]1O)c1cccc(Cl)c1]

General procedure 8. White foam, 96.1% $^1$H NMR (300 MHz, DMSO-d$_6$) δ ppm 3.33-3.69 (m, 6 H) 3.79 (app. td, J=7.3, 4.0 Hz, 1 H) 3.87 (d, J=9.4 Hz, 1 H) 4.79 (s, 1 H) 5.01 (d, J=6.7 Hz, 1 H) 7.32-7.66 (m, 5 H) 7.70-7.99 (m, 4 H) 8.36 (t, J=5.6 Hz, 1 H) 8.65 (t, J=5.0 Hz, 1 H). $^{13}$C NMR (75 MHz, DMSO-d$_6$) δ ppm 42.1, 44.2, 74.6, 74.7, 78.1, 80.6, 126.0, 127.1, 127.3, 128.2, 130.2, 130.9, 131.2, 133.1, 134.4, 136.5, 164.9, 167.1. HRMS (ESI-TOF) m/z: [M+H]$^+$ Calcd for C$_{20}$H$_{22}$ClN$_2$O$_5$ 405.12118; Found 405.1194.

N-(((2R,3R,4S)-4-(benzamidomethyl)-3,4-dihydroxytetrahydrofuran-2-yl)methyl)-3-methoxybenzamide (163)

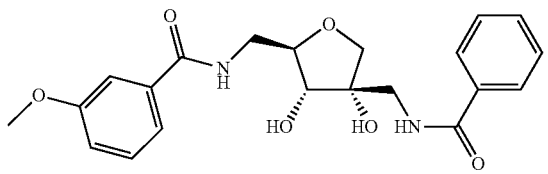

General procedure 8. White foam, quant. $^1$H NMR (300 MHz, DMSO-d$_6$) δ ppm 3.35-3.64 (m, 6 H) 3.70-3.92 (m, 5 H) 4.79 (br. s., 1 H) 5.00 (br. s., 1 H) 7.06 (app. d, J=7.9 Hz, 1 H) 7.28-7.60 (m, 6 H) 7.84 (d, J=7.3 Hz, 2 H) 8.36 (t, J=5.6 Hz, 1 H) 8.48 (t, J=4.7 Hz, 1 H). $^{13}$C NMR (75 MHz, DMSO-d$_6$) δ ppm 42.0, 44.3, 55.2, 74.6, 74.8, 78.1, 80.8, 112.3, 117.0, 119.5, 127.3, 128.2, 129.3, 131.2, 134.4, 135.9, 159.1, 166.1, 167.1. HRMS (ESI-TOF) m/z: [M+Na]$^+$ Calcd for C$_{21}$H$_{24}$N$_2$NaO$_6$$^+$ 423.15266; Found 423.1511.

N-(((2R,3R,4S)-4-(benzamidomethyl)-3,4-dihydroxytetrahydrofuran-2-yl)methyl)-3-cyanobenzamide (164)

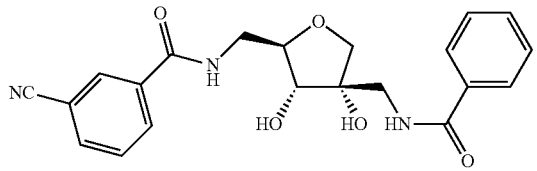 [SMILES: N#Cc1cccc(C(=O)NC[C@H]2OC[C@@](O)(CNC(=O)c3ccccc3)[C@@H]2O)c1]

General procedure 8. White foam, 80.4% $^1$H NMR (300 MHz, DMSO-d$_6$) δ ppm 3.36-3.49 (m, 3 H) 3.52-3.66 (m, 3 H) 3.79 (app. td, J=7.3, 3.5 Hz, 1 H) 3.88 (d, J=9.7 Hz, 1 H) 4.69-5.09 (br. s., 2 H) 7.40-7.48 (m, 2 H) 7.49-7.56 (m, 1 H) 7.66 (app. t, J=7.9 Hz, 1 H) 7.79-7.87 (m, 2 H) 7.98 (app. d, J=7.9 Hz, 1 H) 8.14 (app. d, J=7.9 Hz, 1 H) 8.27 (app. s, 1 H) 8.36 (t, J=5.9 Hz, 1 H) 8.74 (t, J=5.6 Hz, 1 H). $^{13}$C NMR (75 MHz, DMSO-d$_6$) δ ppm 42.1, 44.2, 74.6, 74.7, 78.0, 80.6, 111.4, 118.4, 127.3, 128.2, 129.7, 131.0, 131.2, 132.1, 134.4, 134.5, 135.4, 164.6, 167.1. HRMS (ESI-TOF) m/z: [M+H]$^+$ Calcd for C$_{21}$H$_{22}$N$_3$O$_5$$^+$ 396.15540; Found 396.1544.

N-(((2R,3R,4S)-4-(benzamidomethyl)-3,4-dihydroxytetrahydrofuran-2-yl)methyl)-3-(dimethylamino)benzamide (165)

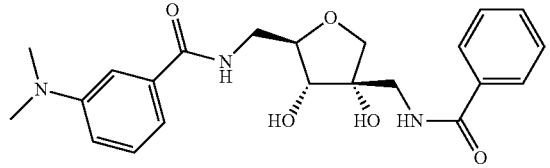

General procedure 8. White foam, quant. $^1$H NMR (300 MHz, DMSO-d$_6$) δ ppm 2.93 (s, 6 H) 3.32-3.47 (m, 3 H) 3.47-3.65 (m, 3 H) 3.78 (app. td, J=7.5, 3.8 Hz, 1 H) 3.86 (d, J=9.7 Hz, 1 H) 6.86-6.94 (m, 1 H) 7.12-7.28 (m, 3 H) 7.41-7.56 (m, 3 H) 7.79-7.87 (m, 2 H) 8.29-8.43 (m, 2 H). $^{13}$C NMR (75 MHz, DMSO-d$_6$) δ ppm 40.7, 42.0, 44.3, 74.6, 74.8, 78.1, 80.9, 111.9 (weak), 115.5 (weak), 117.7 (weak), 127.3, 128.2, 128.8, 131.2, 134.4, 135.3, 149.5 (weak), 166.8, 167.1. HRMS (ESI-TOF) m/z: [M+H]$^+$ Calcd for C$_{22}$H$_{28}$N$_3$O$_5$$^+$ 414.20235; Found 414.2022.

N-(((2R,3R,4S)-4-(benzamidomethyl)-3,4-dihydroxytetrahydrofuran-2-yl)methyl)-3-(trifluoromethyl)benzamide (166)

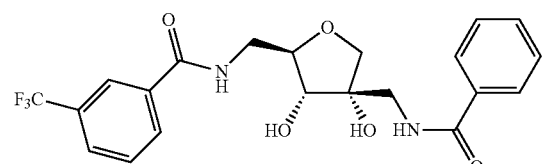

General procedure 8. White foam, 98.7% $^1$H NMR (300 MHz, DMSO-d$_6$) δ ppm 3.36-3.50 (m, 3 H) 3.53-3.66 (m, 3

H) 3.81 (app. td, J=7.5, 3.5 Hz, 1 H) 3.88 (d, J=9.7 Hz, 1 H) 4.70-5.09 (br. s., 2 H) 7.40-7.56 (m, 3 H) 7.64-7.73 (m, 1 H) 7.80-7.92 (m, 3 H) 8.15 (app. d, J=7.9 Hz, 1 H) 8.21 (app. s, 1 H) 8.37 (t, J=5.9 Hz, 1 H) 8.82 (t, J=5.4 Hz, 1 H). $^{19}$F NMR (282 MHz, DMSO-$d_6$) δ ppm −61.5 (s). $^{13}$C NMR (75 MHz, DMSO-$d_6$) δ ppm 42.2, 44.2, 74.6, 74.8, 78.1, 80.7, 123.9 (q, J=3.9 Hz), 127.3, 127.7 (q, J=272.6 Hz) (weak), 127.7 (q, J=4.2 Hz), 128.2, 129.0 (q, J=32.0 Hz), 129.5, 131.2, 131.4, 134.4, 135.3, 164.9, 167.1. HRMS (ESI-TOF) m/z: [M+Na]$^+$ Calcd for $C_{21}H_{21}F_3N_2NaO_5^+$ 461.12948; Found 461.1292.

N-(((2R,3R,4S)-4-(benzamidomethyl)-3,4-dihydroxytetrahydrofuran-2-yl)methyl)nicotinamide (167)

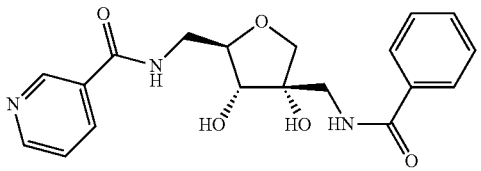

General procedure 8. White foam, quant. $^1$H NMR (300 MHz, DMSO-$d_6$) δ ppm 3.35-3.50 (m, 3 H) 3.53-3.66 (m, 3 H) 3.80 (app. td, J=7.5, 3.5 Hz, 1 H) 3.89 (d, J=9.7 Hz, 1 H) 7.42-7.56 (m, 3 H) 7.60 (dd, J=7.9, 5.0 Hz, 1 H) 7.79-7.87 (m, 2 H) 8.28-8.41 (m, 2 H) 8.76 (dd, J=5.0, 1.46 Hz, 1 H) 8.82 (t, J=5.4 Hz, 1 H) 9.05 (app. d, J=2.1 Hz, 1 H). $^{13}$C NMR (75 MHz, DMSO-$d_6$) δ ppm 42.0, 44.2, 74.6, 74.7, 78.1, 80.7, 124.1, 127.3, 128.3, 130.6, 131.2, 134.4, 136.9, 147.1, 150.1, 164.4, 167.1. HRMS (ESI-TOF) m/z: [M+H]$^+$ Calcd for $C_{19}H_{22}N_3O_6^+$ 372.15540; Found 372.1548.

N-(((2R,3R,4S)-4-(benzamidomethyl)-3,4-dihydroxytetrahydrofuran-2-yl)methyl)-[1,1'-biphenyl]-3-carboxamide (168)

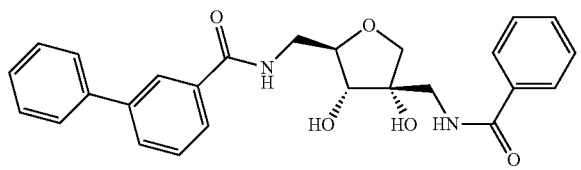 [SMILES: O=C(NC[C@H]1OC[C@@](O)(CNC(=O)c2ccccc2)[C@@H]1O)c1cccc(-c2ccccc2)c1]

General procedure 8. White foam, 78.5% $^1$H NMR (300 MHz, DMSO-$d_6$) δ ppm 3.34-3.50 (m, 3 H) 3.51-3.70 (m, 3 H) 3.76-3.94 (m, 2 H) 4.80 (br. s., 1 H) 5.03 (br. s., 1 H) 7.30-7.60 (m, 7 H) 7.66-7.91 (m, 6 H) 8.15 (app. s, 1 H) 8.37 (t, J=5.7 Hz, 1 H) 8.67 (t, J=5.3 Hz, 1 H). $^{13}$C NMR (75 MHz, DMSO-$d_6$) δ ppm 42.1, 44.3, 74.6, 74.8, 78.1, 80.9, 125.4, 126.6, 126.9, 127.3, 127.8, 128.2, 128.9, 129.0, 129.3, 131.2, 134.4, 135.1, 139.6, 140.1, 166.3, 167.1. HRMS (ESI-TOF) m/z: [M+H]$^+$ Calcd for $C_{26}H_{27}N_2O_6^+$ 447.19145; Found 447.1904.

N-(((2R,3R,4S)-4-(benzamidomethyl)-3,4-dihydroxytetrahydrofuran-2-yl)methyl)-2-methylbenzamide (169)

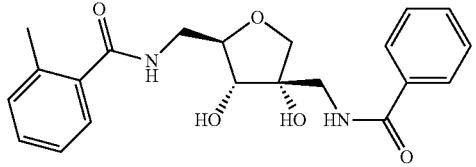

General procedure 8. White foam, quant. $^1$H NMR (300 MHz, DMSO-$d_6$) δ ppm 2.31 (s, 3 H) 3.36-3.59 (m, 5 H) 3.60-3.67 (m, 1 H) 3.73-3.80 (m, 1 H) 3.87 (d, J=9.7 Hz, 1 H) 4.79 (s, 1 H) 4.97 (d, J=6.4 Hz, 1 H) 7.10-7.23 (m, 2 H) 7.25-7.33 (m, 2 H) 7.42-7.57 (m, 3 H) 7.80-7.89 (m, 2 H) 8.22 (t, J=5.6 Hz, 1 H) 8.36 (t, J=5.9 Hz, 1 H). $^{13}$C NMR (75 MHz, DMSO-$d_6$) δ ppm 19.4, 41.4, 44.3, 74.6 (2 C), 78.1, 80.8, 125.3, 127.1, 127.3, 128.3, 129.1, 130.3, 131.2, 134.4, 135.1, 137.3, 167.1, 169.2. HRMS (ESI-TOF) m/z: [M+H]$^+$ Calcd for $C_{21}H_{25}N_2O_5^+$ 385.17580; Found 385.1776.

N-(((2R,3R,4S)-4-(benzamidomethyl)-3,4-dihydroxytetrahydrofuran-2-yl)methyl)-2-fluorobenzamide (170)

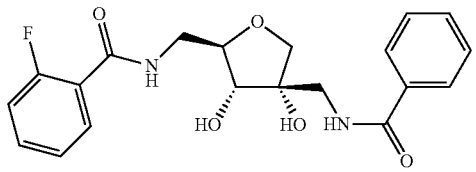

General procedure 8. White foam, quant. $^1$H NMR (300 MHz, DMSO-$d_6$) δ ppm 3.35-3.68 (m, 6 H) 3.73-3.81 (m, 1 H) 3.88 (d, J=9.4 Hz, 1 H) 4.80 (s, 1 H) 4.99 (d, J=6.7 Hz, 1 H) 7.16-7.28 (m, 2 H) 7.40-7.65 (m, 5 H) 7.84 (app. d, J=7.0 Hz, 2 H) 8.23 (br. s., 1 H) 8.36 (t, J=5.7 Hz, 1 H). $^{19}$F NMR (282 MHz, DMSO-$d_6$) δ ppm −114.6 (m). $^{13}$C NMR (75 MHz, DMSO-$d_6$) δ ppm 41.5, 44.1, 74.35, 74.72, 78.1, 80.4, 116.0 (d, J=22.4 Hz), 124.0 (d, J=14.4 Hz), 124.4 (d, J=3.3 Hz), 127.3, 128.2, 130.1 (d, J=2.8 Hz), 131.2, 132.3 (d, J=8.6 Hz), 134.4, 159.1 (d, J=253.2 Hz), 163.8 (d, J=1.4 Hz), 167.1. HRMS (ESI-TOF) m/z: [M+H]$^+$ Calcd for $C_{20}H_{22}FN_2O_5^+$ 389.15073; Found 389.1520.

N-(((2R,3R,4S)-4-(benzamidomethyl)-3,4-dihydroxytetrahydrofuran-2-yl)methyl)-2-chlorobenzamide (171)

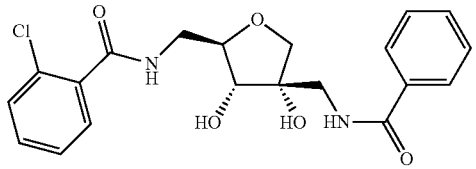

General procedure 8. White foam, quant. $^1$H NMR (300 MHz, DMSO-$d_6$) δ ppm 3.37-3.60 (m, 5 H) 3.63-3.69 (m, 1

H) 3.73-3.80 (m, 1 H) 3.88 (d, J=9.7 Hz, 1 H) 4.79 (s, 1 H) 5.01 (d, J=6.7 Hz, 1 H) 7.27-7.57 (m, 7 H) 7.82-7.89 (m, 2 H) 8.36 (t, J=5.9 Hz, 1 H) 8.46 (t, J=5.7 Hz, 1 H). $^{13}$C NMR (75 MHz, DMSO-d$_6$) δ ppm 41.3, 44.3, 74.4, 74.8, 78.1, 80.6, 126.9, 127.3, 128.3, 128.9, 129.5, 129.9, 130.6, 131.2, 134.4, 137.0, 166.5, 167.1. HRMS (ESI-TOF) m/z: [M+H]$^+$ Calcd for C$_{20}$H$_{22}$ClN$_2$O$_5$$^+$ 405.12118; Found 405.1210.

N-(((2R,3R,4S)-4-(benzamidomethyl)-3,4-dihydroxytetrahydrofuran-2-yl)methyl)-2-methoxybenzamide (172)

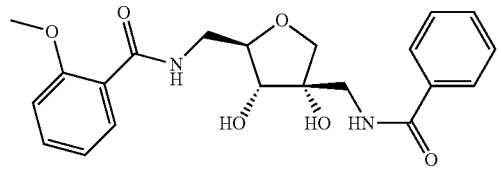 [SMILES: COc1ccccc1C(=O)NC[C@H]1OC[C@@](O)(CNC(=O)c2ccccc2)[C@@H]1O]

General procedure 8. White foam, quant. $^1$H NMR (300 MHz, DMSO-d$_6$) δ ppm 3.39-3.69 (m, 6 H) 3.72-3.87 (m, 4 H) 3.90 (d, J=9.4 Hz, 1 H) 4.83 (s, 1 H) 5.02 (d, J=6.7 Hz, 1 H) 7.00-7.11 (m, 2 H) 7.38-7.54 (m, 4 H) 7.77-7.87 (m, 3 H) 8.22 (t, J=5.3 Hz, 1 H) 8.38 (t, J=6.0 Hz, 1 H). $^{13}$C NMR (75 MHz, DMSO-d$_6$) δ ppm 41.0, 43.9, 55.9, 74.1, 74.9, 78.2, 80.2, 112.1, 120.6, 122.0, 127.3, 128.2, 130.8, 131.2, 132.5, 134.4, 157.1, 164.6, 167.1. HRMS (ESI-TOF) m/z: [M+H]$^+$ Calcd for C$_{21}$H$_{25}$N$_2$O$_6$$^+$ 401.17071; Found 401.1724.

N-(((3S,4R,5R)-5-((1,3-dioxoisoindolin-2-yl)methyl)-3,4-dihydroxytetrahydrofuran-3-yl)methyl)benzamide (173)

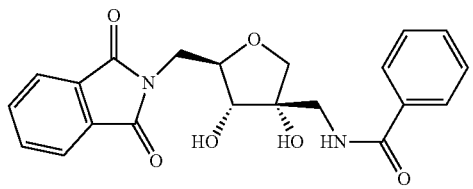 [SMILES: O=C(NC[C@]1(O)CO[C@H](CN2C(=O)c3ccccc3C2=O)[C@H]1O)c1ccccc1]

General procedure 8. White foam, quant. $^1$H NMR (300 MHz, DMSO-d$_6$) δ ppm 3.35-3.47 (m, 2 H) 3.51 (d, J=9.7 Hz, 1 H) 3.62-3.95 (m, 5 H) 4.81 (s, 1 H) 5.04 (d, J=7.0 Hz, 1 H) 7.41-7.58 (m, 3 H) 7.78-7.93 (m, 6 H) 8.36 (t, J=5.9 Hz, 1H). $^{13}$C NMR (75 MHz, DMSO-d$_6$) δ ppm 44.1, 48.6, 74.7, 75.6, 78.2, 78.6, 123.0, 127.3, 128.2, 131.2, 131.5, 134.40, 134.43, 167.1, 167.7. HRMS (ESI-TOF) m/z: [M+H]$^+$ Calcd for C$_{21}$H$_{21}$N$_2$O$_6$$^+$ 397.13941; Found 397.1400.

N-(((2R,3R,4S)-4-(benzamidomethyl)-3,4-dihydroxytetrahydrofuran-2-yl)methyl)-2-(dimethylamino)benzamide (174)

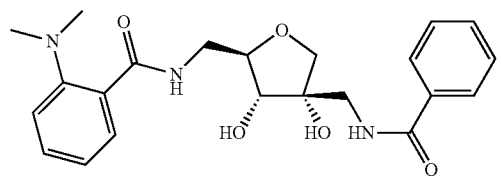 [SMILES: CN(C)c1ccccc1C(=O)NC[C@H]1OC[C@@](O)(CNC(=O)c2ccccc2)[C@@H]1O]

General procedure 8. White foam, quant. $^1$H NMR (300 MHz, DMSO-d$_6$) δ ppm 2.63 (s, 6 H) 3.37-3.67 (m, 6 H) 3.75-3.82 (m, 1 H) 3.89 (d, J=9.7 Hz, 1 H) 4.82 (s, 1 H) 5.02 (d, J=6.7 Hz, 1 H) 7.08 (app. td, J=7.5, 1.2 Hz, 1 H) 7.19 (dd, J=8.1, 1.0 Hz, 1 H) 7.37-7.55 (m, 4 H) 7.74 (dd, J=7.9, 1.8 Hz, 1 H) 7.79-7.86 (m, 2 H) 8.39 (t, J=6.0 Hz, 1 H) 9.46 (t, J=5.3 Hz, 1 H). $^{13}$C NMR (75 MHz, DMSO-d$_6$) δ ppm 41.0, 44.1, 44.5, 74.2, 74.9, 78.2, 80.4, 112.2 (weak), 119.5, 122.6, 127.3, 128.2, 130.2, 131.2, 131.5, 134.3, 147.7 (weak), 166.4, 167.1. HRMS (ESI-TOF) m/z: [M+H]$^+$ Calcd for C$_{22}$H$_{28}$N$_3$O$_5$$^+$ 414.20235; Found 414.2033.

N-(((2R,3R,4S)-4-(benzamidomethyl)-3,4-dihydroxytetrahydrofuran-2-yl)methyl)-2-(trifluoromethyl)benzamide (175)

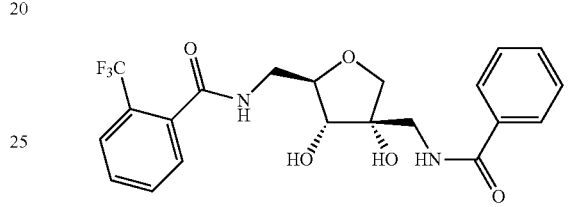

General procedure 8. White foam, quant. $^1$H NMR (300 MHz, DMSO-d$_6$) δ ppm 3.35-3.67 (m, 6 H) 3.76 (app. td, J=7.3, 3.7 Hz, 1 H) 3.88 (d, J=9.7 Hz, 1 H) 4.79 (s, 1 H) 5.01 (d, J=6.7 Hz, 1 H) 7.44-7.64 (m, 6 H) 7.72-7.77 (m, 1 H) 7.83-7.88 (m, 2 H) 8.36 (t, J=5.9 Hz, 1 H) 8.54 (t, J=5.7 Hz, 1 H). $^{13}$C NMR (75 MHz, DMSO-d$_6$) δ ppm 41.5, 44.3, 74.5, 74.7, 78.0, 80.6, 123.8 (q, J=275.9 Hz) (weak), 125.9 (q, J=31.3 Hz), 126.1 (q, J=3.3 Hz), 127.3, 128.3, 128.6, 129.5, 131.2, 132.2, 134.4, 136.5 (q, J=2.5 Hz), 167.1, 167.3. HRMS (ESI-TOF) m/z: [M+H]$^+$ Calcd for C$_{21}$H$_{22}$F$_3$N$_2$O$_5$$^+$ 439.14753; Found 439.1483.

N-(((2R,3R,4S)-4-(benzamidomethyl)-3,4-dihydroxytetrahydrofuran-2-yl)methyl)picolinamide (176)

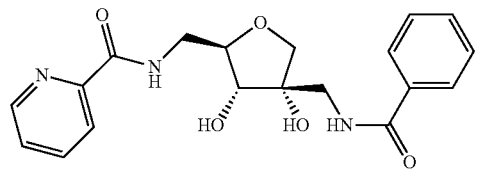

General procedure 8. White foam, quant. $^1$H NMR (300 MHz, DMSO-d$_6$) δ ppm 3.35-3.66 (m, 6 H) 3.79 (app. td, J=7.3, 4.3 Hz, 1 H) 3.88 (d, J=9.7 Hz, 1 H) 4.81 (s, 1 H) 5.03 (d, J=6.7 Hz, 1 H) 7.39-7.62 (m, 4 H) 7.77-7.84 (m, 2 H) 7.95-8.07 (m, 2 H) 8.36 (t, J=6.0 Hz, 1 H) 8.53 (t, J=5.9 Hz, 1 H) 8.56-8.61 (m, 1 H). $^{13}$C NMR (75 MHz, DMSO-d$_6$) δ ppm 41.2, 44.1, 74.5, 74.7, 78.2, 80.5, 121.7, 126.6, 127.3, 128.2, 131.2, 134.4, 137.9, 148.4, 149.6, 163.6, 167.1. HRMS (ESI-TOF) m/z: [M+H]$^+$ Calcd for C$_{19}$H$_{22}$N$_3$O$_5$$^+$ 372.15540; Found 372.1565.

N-(((2R,3R,4S)-4-(benzamidomethyl)-3,4-dihydroxytetrahydrofuran-2-yl)methyl)-[1,1'-biphenyl]-2-carboxamide (177)

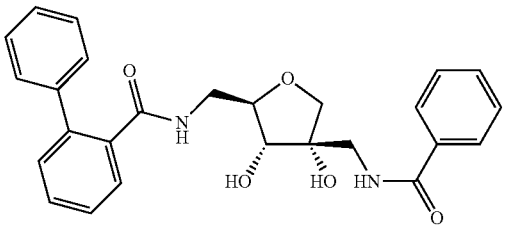 [SMILES: O=C(NC[C@]1(O)CO[C@H](CNC(=O)c2ccccc2-c2ccccc2)[C@H]1O)c1ccccc1]

General procedure 8. White foam, quant. $^1$H NMR (300 MHz, DMSO-$d_6$) δ ppm 3.20 (app. dt, J=13.6, 6.6 Hz, 1 H) 3.33-3.44 (m, 3 H) 3.52 (d, J=1.8 Hz, 1 H) 3.55 (app. s, 1 H) 3.67 (app. td, J=7.3, 3.8 Hz, 1 H) 3.84 (d, J=9.4 Hz, 1 H) 7.27-7.57 (m, 12 H) 7.81-7.88 (m, 2 H) 8.25 (t, J=5.7 Hz, 1 H) 8.34 (t, J=5.9 Hz, 1 H). $^{13}$C NMR (75 MHz, DMSO-$d_6$) δ ppm 41.5, 44.4, 74.6, 74.7, 78.0, 80.5, 126.9, 127.1, 127.3, 127.8, 128.2, 128.27, 128.32, 129.3, 129.8, 131.2, 134.4, 137.2, 139.1, 140.3, 167.1, 169.3. HRMS (ESI-TOF) m/z: [M+H]$^+$ Calcd for $C_{26}H_{27}N_2O_5^+$ 447.19145; Found 447.1901.

N-(((2R,3R,4S)-4-(benzamidomethyl)-3,4-dihydroxytetrahydrofuran-2-yl)methyl)-2-bromobenzamide (178)

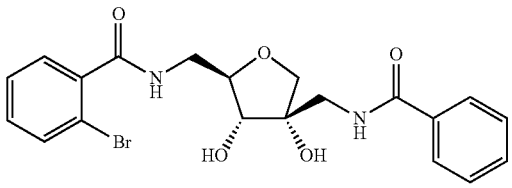 [SMILES: O=C(NC[C@]1(O)CO[C@H](CNC(=O)c2ccccc2Br)[C@H]1O)c1ccccc1]

$^1$H NMR (300 MHz, DMSO-$d_6$) δ ppm 3.33-3.59 (m, 5 H) 3.65-3.69 (m, 1 H) 3.74-3.81 (m, 1 H) 3.89 (d, J=9.7 Hz, 1 H) 4.85 (br. s., 2 H) 7.28-7.39 (m, 3 H) 7.43-7.57 (m, 3 H) 7.59-7.65 (m, 1 H) 7.83-7.89 (m, 2 H) 8.36 (t, J=6.0 Hz, 1 H) 8.45 (t, J=5.6 Hz, 1 H). $^{13}$C NMR (75 MHz, DMSO-$d_6$) δ ppm 41.3, 44.3, 74.4, 74.7, 78.1, 80.6, 118.9, 127.33 (2 C), 128.2, 128.8, 130.7, 131.2, 132.6, 134.4, 139.2, 167.0, 167.4. HRMS (ESI-TOF) m/z: [M+H]$^+$ Calcd for $C_{20}H_{22}BrN_2O_5^+$ 449.07066; Found 449.0724.

N-(((2R,3R,4S)-4-(benzamidomethyl)-3,4-dihydroxytetrahydrofuran-2-yl)methyl)-2-iodobenzamide (179)

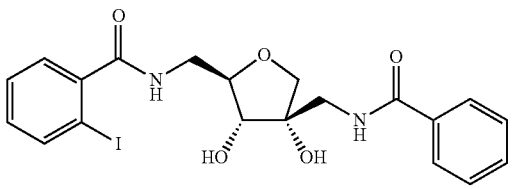 [SMILES: O=C(NC[C@]1(O)CO[C@H](CNC(=O)c2ccccc2I)[C@H]1O)c1ccccc1]

$^1$H NMR (300 MHz, DMSO-$d_6$) δ ppm 3.31-3.60 (m, 5 H) 3.66-3.70 (m, 1 H) 3.75-3.82 (m, 1 H) 3.89 (d, J=9.7 Hz, 1 H) 4.82 (br. s., 2 H) 7.13 (app. td, J=7.5, 1.9 Hz, 1 H) 7.27 (dd, J=7.6, 1.8 Hz, 1 H) 7.36 (app. td, J=7.5, 1.2 Hz, 1 H) 7.42-7.57 (m, 3 H) 7.82-7.90 (m, 3 H) 8.32-8.45 (m, 2 H). $^{13}$C NMR (75 MHz, DMSO-$d_6$) δ ppm 41.4, 44.3, 74.5, 74.8, 78.1, 80.6, 93.5, 127.3, 127.8, 128.1, 128.2, 130.6, 131.2, 134.4, 139.0, 143.1, 167.0, 169.0. HRMS (ESI-TOF) m/z: [M+H]$^+$ Calcd for $C_{20}H_{22}IN_2O_5$ 497.05679; Found 497.0583.

N-(((2R,3R,4S)-4-(benzamidomethyl)-3,4-dihydroxytetrahydrofuran-2-yl)methyl)-3,4-dimethylbenzamide (180)

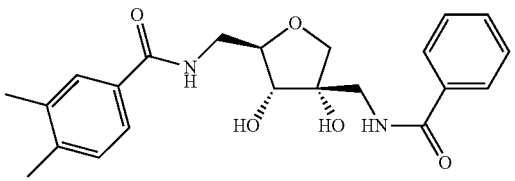 [SMILES: Cc1ccc(C(=O)NC[C@H]2OC[C@@](O)(CNC(=O)c3ccccc3)[C@@H]2O)cc1C]

General procedure 8. White foam, quant. $^1$H NMR (300 MHz, DMSO-$d_6$) δ ppm 2.18-2.32 (2×s, 6 H) 3.32-3.62 (m, 6 H) 3.78 (app. td, J=7.5, 3.8 Hz, 1 H) 3.86 (d, J=9.7 Hz, 1 H) 4.77 (br. s., 1 H) 4.99 (br. s., 1 H) 7.17 (d, J=7.9 Hz, 1 H) 7.39-7.60 (m, 4 H) 7.64 (app. s, 1 H) 7.78-7.88 (m, 2 H) 8.25-8.43 (m, 2 H). $^{13}$C NMR (75 MHz, DMSO-$d_6$) δ ppm 19.3, 19.4, 41.9, 44.3, 74.6, 74.8, 78.1, 80.9, 124.8, 127.3, 128.25, 128.35, 129.2, 131.2, 132.0, 134.4, 136.0, 139.6, 166.4, 167.1. HRMS (ESI-TOF) m/z: [M+H]$^+$ Calcd for $C_{22}H_{27}N_2O_5^+$ 399.19145; Found 399.1901.

N-(((2R,3R,4S)-4-(benzamidomethyl)-3,4-dihydroxytetrahydrofuran-2-yl)methyl)-3,4-difluorobenzamide (181)

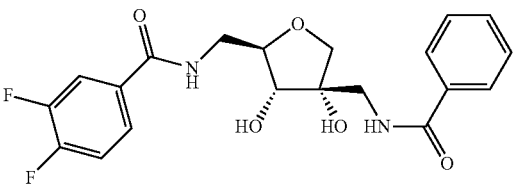 [SMILES: O=C(NC[C@H]1OC[C@@](O)(CNC(=O)c2ccccc2)[C@@H]1O)c1ccc(F)c(F)c1]

General procedure 8. White foam, 98.4% $^1$H NMR (300 MHz, DMSO-$d_6$) δ ppm 3.34-3.64 (m, 6 H) 3.78 (app. td, J=7.3, 3.5 Hz, 1 H) 3.87 (d, J=9.7 Hz, 1 H) 4.79 (s, 1 H) 4.99 (d, J=6.7 Hz, 1 H) 7.38-7.58 (m, 4 H) 7.70-7.77 (m, 1 H) 7.78-7.95 (m, 3 H) 8.36 (t, J=5.9 Hz, 1 H) 8.62 (t, J=5.6 Hz, 1 H). $^{19}$F NMR (282 MHz, DMSO-$d_6$) δ ppm −138.6 (m), −135.4 (m). $^{13}$C NMR (75 MHz, DMSO-$d_6$) δ ppm 42.1, 44.2, 74.6, 74.7, 78.1, 80.7, 117.0 (dd, J=56.3, 17.8 Hz), 117.1 (dd, J=55.8, 17.9 Hz), 124.8 (dd, J=7.3, 3.5 Hz), 127.3, 128.2, 131.2, 131.9 (dd, J=5.1, 3.5 Hz), 134.4, 149.1 (dd, J=246.0, 12.9 Hz), 152.9 (dd, J=251.0, 12.7 Hz), 164.2 (d, J=1.9 Hz), 167.1. HRMS (ESI-TOF) m/z: [M+H]$^+$ Calcd for $C_{20}H_{21}F_2N_2O_5^+$ 407.14130; Found 407.1397.

N-(((2R,3R,4S)-4-(benzamidomethyl)-3,4-dihydroxytetrahydrofuran-2-yl)methyl)-3,4-dichlorobenzamide (182)

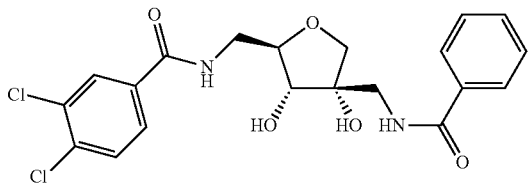 [SMILES: O=C(NC[C@H]1OC[C@@](O)(CNC(=O)c2ccccc2)[C@@H]1O)c1ccc(Cl)c(Cl)c1]

General procedure 8. White foam, 91.4% $^1$H NMR (300 MHz, DMSO-d$_6$) δ ppm 3.35-3.65 (m, 6 H) 3.78 (app. td, J=7.4, 3.7 Hz, 1 H) 3.87 (d, J=9.7 Hz, 1 H) 4.80 (s, 1 H) 5.00 (d, J=6.7 Hz, 1 H) 7.39-7.56 (m, 3 H) 7.67-7.74 (m, 1 H) 7.76-7.89 (m, 3 H) 8.08 (d, J=2.1 Hz, 1 H) 8.36 (t, J=5.7 Hz, 1 H) 8.72 (t, J=5.4 Hz, 1 H). $^{13}$C NMR (75 MHz, DMSO-d$_6$) δ ppm 42.1, 44.1, 74.6, 74.7, 78.1, 80.6, 127.3, 127.6, 128.2, 129.3, 130.6, 131.2, 131.2, 133.9, 134.4, 134.8, 164.1, 167.1. HRMS (ESI-TOF) m/z: [M+H]$^+$ Calcd for $C_{20}H_{21}Cl_2N_2O_5^+$ 439.08220; Found 439.0821.

N-(((2R,3R,4S)-4-(benzamidomethyl)-3,4-dihydroxytetrahydrofuran-2-yl)methyl)-3,4-dimethoxybenzamide (183)

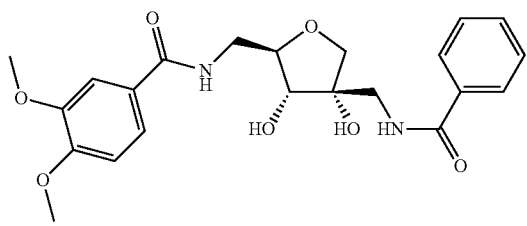 [SMILES: COc1ccc(C(=O)NC[C@H]2OC[C@@](O)(CNC(=O)c3ccccc3)[C@@H]2O)cc1OC]

General procedure 8. White foam, quant. $^1$H NMR (300 MHz, DMSO-d$_6$) δ ppm 3.30-3.48 (m, 3 H) 3.50-3.64 (m, 3 H) 3.73-3.83 (m, 7 H) 3.87 (d, J=9.4 Hz, 1 H) 6.97 (d, J=8.2 Hz, 1 H) 7.38-7.58 (m, 5 H) 7.79-7.87 (m, 2 H) 8.36 (t, J=5.9 Hz, 2 H). $^{13}$C NMR (75 MHz, DMSO-d$_6$) δ ppm 42.0, 44.3, 55.5, 55.6, 74.6, 74.7, 78.1, 81.0, 110.7, 110.8, 120.5, 126.7, 127.3, 128.2, 131.2, 134.4, 148.1, 151.1, 165.9, 167.1. HRMS (ESI-TOF) m/z: [M+H]$^+$ Calcd for $C_{22}H_{27}N_2O_7^+$ 431.18128; Found 431.1823.

N-(((2R,3R,4S)-4-(benzamidomethyl)-3,4-dihydroxytetrahydrofuran-2-yl)methyl)-1-naphthamide (184)

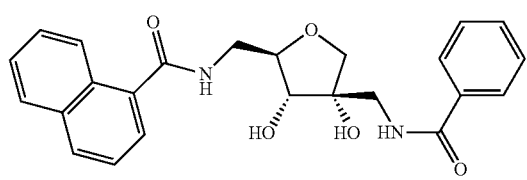 [SMILES: O=C(NC[C@]1(O)CO[C@H](CNC(=O)c2cccc3ccccc23)[C@H]1O)c1ccccc1]

General procedure 8. White foam, quant. $^1$H NMR (300 MHz, DMSO-d$_6$) (major conformer) δ ppm 3.41-3.54 (m, 3 H) 3.55-3.74 (m, 3 H) 3.85 (app. td, J=7.2, 4.1 Hz, 1 H) 3.91 (d, J=9.4 Hz, 1 H) 4.55 (br. s., 2 H) 7.37-7.65 (m, 7 H) 7.82-7.88 (m, 2 H) 7.92-8.01 (m, 2 H) 8.17-8.24 (m, 1 H) 8.38 (t, J=5.9 Hz, 1 H) 8.55 (t, J=5.7 Hz, 1 H). $^{13}$C NMR (75 MHz, DMSO-d$_6$) δ ppm 42.3, 45.0, 75.41 (2 C), 78.8, 81.4, 125.6, 125.8, 126.2, 126.8, 127.3, 128.0, 128.8, 128.9, 130.3, 130.5, 131.9, 133.8, 135.1, 135.6, 167.8, 169.4. HRMS (ESI-TOF) m/z: [M+H]$^+$ Calcd for $C_{24}H_{26}N_2O_6^+$ 421.17580; Found 421.1768.

N-(((2R,3R,4S)-4-(benzamidomethyl)-3,4-dihydroxytetrahydrofuran-2-yl)methyl)-2-naphthamide (185)

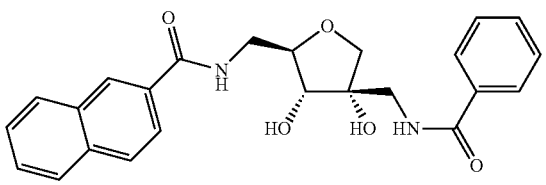 [SMILES: O=C(NC[C@H]1OC[C@@](O)(CNC(=O)c2ccccc2)[C@@H]1O)c1ccc2ccccc2c1]

General procedure 8. White foam, 94.3% $^1$H NMR (300 MHz, DMSO-d$_6$) δ ppm 3.37-3.52 (m, 3 H) 3.54-3.70 (m, 3 H) 3.79-3.93 (m, 2 H) 4.80 (s, 1 H) 5.03 (d, J=6.4 Hz, 1 H) 7.38-7.65 (m, 5 H) 7.79-7.88 (m, 2 H) 7.89-8.04 (m, 4 H) 8.37 (t, J=5.9 Hz, 1 H) 8.46 (app. s, 1 H) 8.65 (t, J=5.6 Hz, 1 H). $^{13}$C NMR (75 MHz, DMSO-d$_6$) δ ppm 42.1, 44.3, 74.6, 74.8, 78.1, 80.9, 124.3, 126.7, 127.3, 127.51 (2 C), 127.6, 127.8, 128.2, 128.9, 131.22, 131.8, 132.1, 134.1, 134.4, 166.5, 167.1. HRMS (ESI-TOF) m/z: [M+H]$^+$ Calcd for $C_{24}H_{26}N_2O_6^+$ 421.17580; Found 421.1778.

N-(((2R,3R,4S)-4-(benzamidomethyl)-3,4-dihydroxytetrahydrofuran-2-yl)methyl)-1-methyl-1H-indole-2-carboxamide (186)

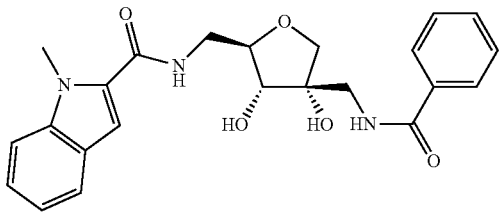 [SMILES: Cn1c(C(=O)NC[C@H]2OC[C@@](O)(CNC(=O)c3ccccc3)[C@@H]2O)cc2ccccc21]

General procedure 8. Pink foam, quant. $^1$H NMR (300 MHz, DMSO-d$_6$) δ ppm 3.33-3.48 (m, 3 H) 3.50-3.67 (m, 3 H) 3.80 (app. td, J=7.3, 3.8 Hz, 1 H) 3.89 (d, J=9.7 Hz, 1 H) 3.96 (s, 3 H) 4.88 (m, 2 H) 7.03-7.13 (m, 2 H) 7.26 (app. td, J=7.6, 1.2 Hz, 1 H) 7.38-7.56 (m, 4 H) 7.59 (app. d, J=7.9 Hz, 1 H) 7.79-7.88 (m, 2 H) 8.37 (t, J=5.9 Hz, 1 H) 8.48 (t, J=5.7 Hz, 1 H). $^{13}$C NMR (75 MHz, DMSO-d$_6$) δ ppm 31.3, 41.4, 44.3, 74.67, 74.71, 78.1, 80.8, 104.3, 110.4, 120.0, 121.5, 123.4, 125.6, 127.3, 128.2, 131.2, 132.2, 134.4, 138.4, 162.0, 167.1. HRMS (ESI-TOF) m/z: [M+Na]$^+$ Calcd for $C_{23}H_{26}N_3NaO_6^+$ 446.16864; Found 446.1708.

N-(((2R,3R,4S)-4-(benzamidomethyl)-3,4-dihydroxytetrahydrofuran-2-yl)methyl)-1-methyl-1H-indole-3-carboxamide (187)

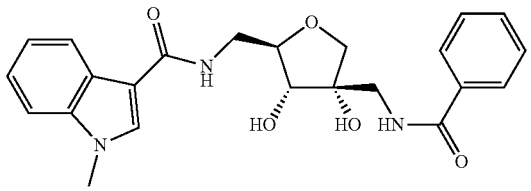 [SMILES: Cn1cc(C(=O)NC[C@H]2OC[C@@](O)(CNC(=O)c3ccccc3)[C@@H]2O)c2ccccc21]

General procedure 8. White foam, 98.9%. $^1$H NMR (300 MHz, DMSO-$d_6$) δ ppm 3.34-3.47 (m, 3 H) 3.54-3.65 (m, 3 H) 3.74-3.84 (m, 4 H) 3.88 (d, J=9.7 Hz, 1 H) 4.93 (br. s., 2 H) 7.10-7.24 (m, 2 H) 7.38-7.55 (m, 4 H) 7.78-7.87 (m, 3 H) 8.02 (s, 1 H) 8.14 (dd, J=7.6, 1.2 Hz, 1 H) 8.36 (t, J=5.9 Hz, 1 H). $^{13}$C NMR (75 MHz, DMSO-$d_6$) δ ppm 33.0, 41.1, 44.3, 74.60 (2 C), 78.1, 81.3, 109.5, 110.2, 120.6, 121.1, 121.9, 126.5, 127.3, 128.2, 131.2, 131.9, 134.4, 136.7, 164.4, 167.1. HRMS (ESI-TOF) m/z: [M+H]$^+$ Calcd for $C_{23}H_{26}N_3O_5^+$ 424.18670; Found 424.1888.

N,N'-(((2R,3R,4S)-3,4-dihydroxytetrahydrofuran-2,4-diyl)bis(methylene))dibenzamide (188)

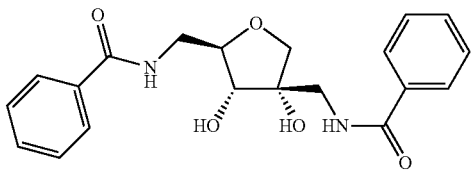

General procedure 8. White foam, quant. $^1$H NMR (300 MHz, DMSO-$d_6$) δ ppm 3.33-3.63 (m, 6 H) 3.79 (app. td, J=7.4, 4.0 Hz, 1 H) 3.87 (d, J=9.7 Hz, 1 H) 4.78 (br. s., 1 H) 4.99 (d, J=6.4 Hz, 1 H) 7.26-7.65 (m, 6 H) 7.84 (app. d, J=7.9 Hz, 4 H) 8.36 (t, J=5.9 Hz, 1 H) 8.47 (t, J=5.3 Hz, 1 H). $^{13}$C NMR (75 MHz, DMSO-$d_6$) δ ppm 42.0, 44.3, 74.6, 74.8, 78.1, 80.8, 127.27, 127.33, 128.2, 128.3, 131.1, 131.2, 134.4, 134.5, 166.4, 167.1. HRMS (ESI-TOF) m/z: [M+H]$^+$ Calcd for $C_{20}H_{23}N_2O_5^+$ 371.16015; Found 371.1595.

N-(((3S,4R,5R)-3,4-dihydroxy-5-((2-phenylacetamido)methyl)tetrahydrofuran-3-yl)methyl)benzamide (189)

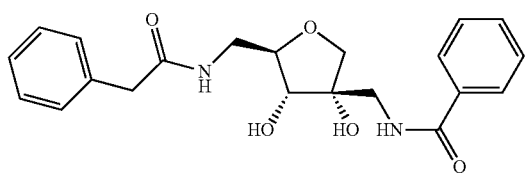 [SMILES: O=C(Cc1ccccc1)NC[C@H]1OC[C@@](O)(CNC(=O)c2ccccc2)[C@@H]1O]

General procedure 8. White foam, 94.9% $^1$H NMR (300 MHz, DMSO-$d_6$) δ ppm 3.10-3.19 (m, 1 H) 3.32-3.47 (m, 5 H) 3.49-59 (m, 2 H) 3.64 (app. td, J=7.3, 3.1 Hz, 1 H) 3.86 (d, J=9.7 Hz, 1 H) 4.78 (br. s., 1 H) 4.95 (br. s., 1 H) 7.12-7.36 (m, 5 H) 7.39-7.59 (m, 3 H) 7.79-7.94 (m, 2 H) 8.10 (t, J=5.3 Hz, 1 H) 8.34 (t, J=5.9 Hz, 1 H). $^{13}$C NMR (75 MHz, DMSO-$d_6$) δ ppm 41.0, 42.2, 44.3, 74.2, 74.8, 78.0, 81.0, 126.2, 127.3, 128.1, 128.2, 129.0, 131.2, 134.4, 136.6, 167.0, 170.2. HRMS (ESI-TOF) m/z: [M+H]$^+$ Calcd for $C_{21}H_{25}N_2O_5^+$ 385.17580; Found 385.1769.

N-(((3S,4R,5R)-3,4-dihydroxy-5-((3-phenylpropanamido)methyl)tetrahydrofuran-3-yl)methyl)benzamide (190)

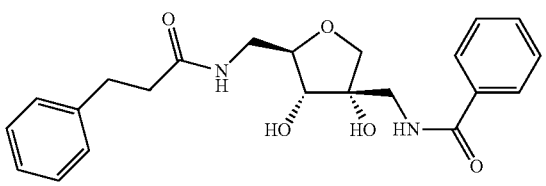 [SMILES: O=C(CCc1ccccc1)NC[C@H]1OC[C@@](O)(CNC(=O)c2ccccc2)[C@@H]1O]

General procedure 8. White foam, 98.1% $^1$H NMR (300 MHz, DMSO-$d_6$) δ ppm 2.38 (t, J=7.9 Hz, 2 H) 2.78 (t, J=7.8 Hz, 2 H) 3.06-3.20 (m, 1 H) 3.29-3.68 (m, 6 H) 3.85 (d, J=9.4 Hz, 1 H) 4.79 (br. s., 2 H) 7.03-7.35 (m, 5 H) 7.36-7.61 (m, 3 H) 7.73-8.01 (m, 3 H) 8.34 (t, J=5.4 Hz, 1 H). $^{13}$C NMR (75 MHz, DMSO-$d_6$) δ ppm 31.1, 36.8, 40.9, 44.3, 74.2, 74.7, 77.9, 81.0, 125.8, 127.3, 128.16, 128.23 (2 C), 131.2, 134.4, 141.4, 167.0, 171.5. HRMS (ESI-TOF) m/z: [M+H]$^+$ Calcd for $C_{22}H_{27}N_2O_5^+$ 399.19145; Found 399.1931.

N-(((3S,4R,5R)-5-(cyclohexanecarboxamidomethyl)-3,4-dihydroxytetrahydrofuran-3-yl)methyl)benzamide (191)

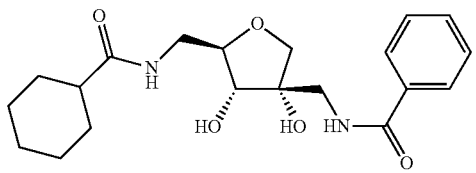 [SMILES: O=C(NC[C@]1(O)CO[C@H](CNC(=O)C2CCCCC2)[C@H]1O)c1ccccc1]

General procedure 8. White foam, quant. $^1$H NMR (300 MHz, DMSO-$d_6$) δ ppm 1.07-1.37 (m, 5 H) 1.49-1.75 (m, 5 H) 2.11 (tt, J=11.1, 2.9 Hz, 1 H) 3.12-3.22 (m, 1 H) 3.25-3.46 (m, 3 H) 3.48-3.57 (m, 2 H) 3.58-3.65 (m, 1 H) 3.84 (d, J=9.7 Hz, 1 H) 4.80 (br. s., 2 H) 7.41-7.58 (m, 3 H) 7.67 (t, J=5.6 Hz, 1 H) 7.80-7.90 (m, 2 H) 8.34 (t, J=5.9 Hz, 1 H). $^{13}$C NMR (75 MHz, DMSO-$d_6$) δ ppm 25.27, 25.31, 25.5, 29.2, 29.4, 40.5, 43.8, 44.1, 74.0, 74.6, 78.0, 80.9, 127.3, 128.3, 131.2, 134.4, 167.0, 175.4. HRMS (ESI-TOF) m/z: [M+H]$^+$ Calcd for $C_{20}H_{29}N_2O_5^+$ 377.20710; Found 377.2086.

N-(((2R,3R,4S)-4-(benzamidomethyl)-3,4-dihydroxytetrahydrofuran-2-yl)methyl)-2,6-dichlorobenzamide (192)

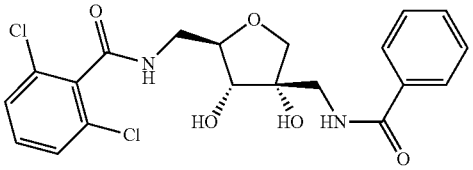 [SMILES: O=C(NC[C@]1(O)CO[C@H](CNC(=O)c2c(Cl)cccc2Cl)[C@H]1O)c1ccccc1]

General procedure 8. White foam $^1$H NMR (300 MHz, DMSO-d$_6$) δ ppm 3.33-3.49 (m, 3 H) 3.53-3.62 (m, 2 H) 3.65-3.72 (m, 1 H) 3.74-3.80 (m, 1 H) 3.88 (d, J=9.7 Hz, 1 H) 4.76 (s, 1 H) 5.04 (d, J=6.7 Hz, 1 H) 7.36-7.57 (m, 6 H) 7.81-7.89 (m, 2 H) 8.32 (t, J=5.9 Hz, 1 H) 8.74 (t, J=5.6 Hz, 1 H). $^{13}$C NMR (75 MHz, DMSO-d$_6$) δ ppm 41.1, 44.4, 74.2, 74.9, 78.0, 80.7, 127.3, 127.9, 128.2, 130.7, 131.1, 131.2, 134.4, 136.8, 163.8, 167.0. HRMS (ESI-TOF) m/z: [M+H]$^+$ Calcd for C$_{20}$H$_{21}$Cl$_2$N$_2$O$_5$$^+$ 439.08220; Found 439.0826.

N-(((2R,3R,4S)-4-(benzamidomethyl)-3,4-dihydroxytetrahydrofuran-2-yl)methyl)-2,4-dichlorobenzamide (193)

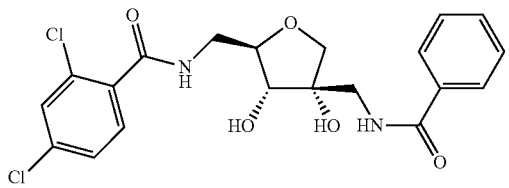 [SMILES: O=C(NC[C@]1(O)CO[C@H](CNC(=O)c2ccc(Cl)cc2Cl)[C@H]1O)c1ccccc1]

General procedure 8. White foam, quant. $^1$H NMR (300 MHz, DMSO-d$_6$) δ ppm 3.35-3.59 (m, 5 H) 3.65 (d, J=7.9 Hz, 1 H) 3.76 (app. td, J=7.1, 3.7 Hz, 1 H) 3.88 (d, J=9.7 Hz, 1 H) 4.86 (br. s., 2 H) 7.39 (app. d, J=1.2 Hz, 2 H) 7.43-7.57 (m, 3 H) 7.64 (app. t, J=1.2 Hz, 1 H) 7.82-7.88 (m, 2 H) 8.36 (t, J=5.9 Hz, 1 H) 8.54 (t, J=5.6 Hz, 1 H). $^{13}$C NMR (75 MHz, DMSO-d$_6$) δ ppm 41.3, 44.2, 74.4, 74.8, 78.1, 80.6, 127.1, 127.4, 128.3, 129.0, 130.3, 131.16, 131.24, 134.3, 134.4, 135.9, 165.6, 167.1. HRMS (ESI-TOF) m/z: [M+H]$^+$ Calcd for C$_{20}$H$_{21}$Cl$_2$N$_2$O$_5$$^+$ 439.08220; Found 439.0835.

N-(((2R,3R,4S)-4-(benzamidomethyl)-3,4-dihydroxytetrahydrofuran-2-yl)methyl)-2,4,6-trichlorobenzamide (194)

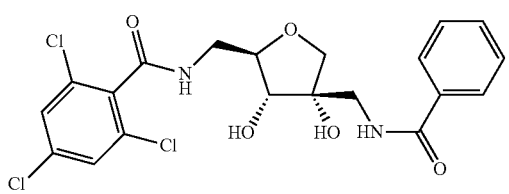 [SMILES: O=C(NC[C@]1(O)CO[C@H](CNC(=O)c2c(Cl)cc(Cl)cc2Cl)[C@H]1O)c1ccccc1]

General procedure 8. White foam, quant. $^1$H NMR (300 MHz, DMSO-d$_6$) δ ppm 3.32-3.45 (m, 3 H) 3.53-3.63 (m, 2 H) 3.67 (d, J=8.2 Hz, 1 H) 3.72-3.79 (m, 1 H) 3.88 (d, J=9.7 Hz, 1 H) 4.78 (br. s., 1 H) 5.05 (br. s., 1 H) 7.42-7.57 (m, 3 H) 7.69 (s, 2 H) 7.80-7.89 (m, 2 H) 8.32 (t, J=6.0 Hz, 1 H) 8.77 (t, J=5.6 Hz, 1 H). $^{13}$C NMR (75 MHz, DMSO-d$_6$) δ ppm 41.0, 44.4, 74.1, 74.9, 78.0, 80.6, 127.4, 127.7, 128.2, 131.2, 132.1, 134.0, 134.4, 135.8, 163.1, 167.1. HRMS (ESI-TOF) m/z: [M+H]$^+$ Calcd for C$_{20}$H$_{20}$Cl$_3$N$_2$O$_5$$^+$ 473.04323; Found 473.0438.

N-(((2R,3R,4S)-4-(benzamidomethyl)-3,4-dihydroxytetrahydrofuran-2-yl)methyl)-3,5-dichloroisonicotinamide (195)

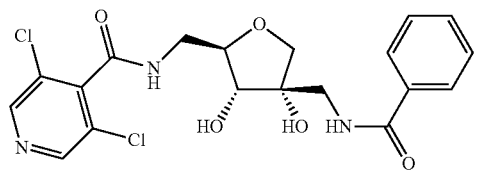

General procedure 8. White foam, quant. $^1$H NMR (300 MHz, DMSO-d$_6$) δ ppm 3.34-3.46 (m, 3 H) 3.56-3.72 (m, 3 H) 3.73-3.81 (m, 1 H) 3.90 (d, J=9.4 Hz, 1 H) 4.80 (s, 1 H) 5.07 (d, J=6.7 Hz, 1 H) 7.43-7.57 (m, 3 H) 7.81-7.89 (m, 2 H) 8.33 (t, J=5.9 Hz, 1 H) 8.66 (s, 2 H) 8.96 (t, J=5.6 Hz, 1 H). $^{13}$C NMR (75 MHz, DMSO-d$_6$) δ ppm 40.9, 44.3, 74.0, 74.9, 78.0, 80.5, 127.3, 128.17, 128.22, 131.2, 134.4, 143.2, 147.4, 161.8, 167.0. HRMS (ESI-TOF) m/z: [M+H]$^+$ Calcd for C$_{19}$H$_{20}$Cl$_2$N$_3$O$_5$$^+$ 440.07745; Found 440.0761.

N-(((2R,3R,4S)-4-(benzamidomethyl)-3,4-dihydroxytetrahydrofuran-2-yl)methyl)-2,4-dichloronicotinamide (196)

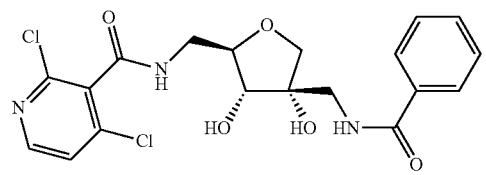 [SMILES: O=C(NC[C@]1(O)CO[C@H](CNC(=O)c2c(Cl)ccnc2Cl)[C@H]1O)c1ccccc1]

General procedure 8. White foam, 58.3% $^1$H NMR (300 MHz, DMSO-d$_6$) δ ppm 3.35-3.49 (m, 3 H) 3.55-3.71 (m, 3 H) 3.73-3.80 (m, 1 H) 3.89 (d, J=9.4 Hz, 1 H) 4.79 (br. s., 1 H) 5.06 (br. s., 1 H) 7.41-7.57 (m, 3 H) 7.64 (d, J=5.3 Hz, 1 H) 7.81-7.89 (m, 2 H) 8.33 (t, J=6.0 Hz, 1 H) 8.39 (d, J=5.3 Hz, 1 H) 8.88 (t, J=5.6 Hz, 1 H). $^{13}$C NMR (75 MHz, DMSO-d$_6$) δ ppm 41.0, 44.3, 74.1, 74.9, 78.0, 80.5, 124.0, 127.3, 128.2, 131.2, 132.8, 134.4, 142.0, 147.6, 149.9, 162.5, 167.0. HRMS (ESI-TOF) m/z: [M+H]$^+$ Calcd for C$_{19}$H$_{20}$Cl$_2$N$_3$O$_5$$^+$ 440.07745; Found 440.0767.

N-(((2R,3R,4S)-4-(benzamidomethyl)-3,4-dihydroxytetrahydrofuran-2-yl)methyl)-2,6-dichloronicotinamide (197)

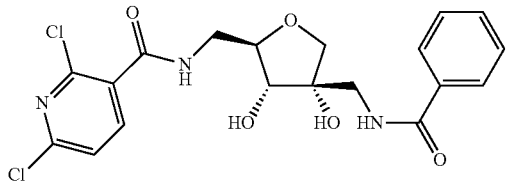 [SMILES: O=C(NC[C@]1(O)CO[C@H](CNC(=O)c2ccc(Cl)nc2Cl)[C@H]1O)c1ccccc1]

General procedure 8. White foam, 62.1% $^1$H NMR (300 MHz, DMSO-$d_6$) δ ppm 3.36-3.68 (m, 6 H) 3.72-3.79 (m, 1 H) 3.89 (d, J=9.7 Hz, 1 H) 4.81 (s, 1 H) 5.03 (d, J=7.0 Hz, 1 H) 7.42-7.59 (m, 4 H) 7.82-7.88 (m, 2 H) 7.90 (d, J=7.9 Hz, 1 H) 8.37 (t, J=5.9 Hz, 1 H) 8.71 (t, J=5.6 Hz, 1 H). $^{13}$C NMR (75 MHz, DMSO-$d_6$) δ ppm 41.3, 44.2, 74.2, 74.8, 78.0, 80.4, 123.4, 127.3, 128.2, 131.2, 132.4, 134.4, 141.1, 145.8, 148.9, 164.3, 167.0. HRMS (ESI-TOF) m/z: [M+H]$^+$ Calcd for $C_{19}H_{20}Cl_2N_3O_5^+$ 440.07745; Found 440.0777.

N-(((2R,3R,4S)-4-(benzamidomethyl)-3,4-dihydroxytetrahydrofuran-2-yl)methyl)-4,6-dichloronicotinamide (198)

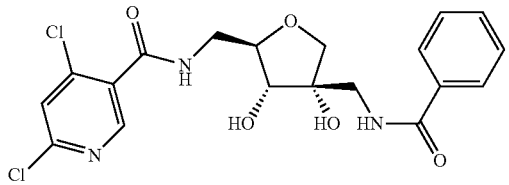 [SMILES: O=C(NC[C@]1(O)CO[C@H](CNC(=O)c2cnc(Cl)cc2Cl)[C@H]1O)c1ccccc1]

General procedure 8. White foam, 86.7% $^1$H NMR (300 MHz, DMSO-$d_6$) δ ppm 3.32-3.71 (m, 6 H) 3.71-3.81 (m, 1 H) 3.89 (d, J=9.7 Hz, 1 H) 4.81 (s, 1 H) 5.04 (d, J=6.7 Hz, 1 H) 7.41-7.59 (m, 3 H) 7.78-7.95 (m, 3 H) 8.36 (t, J=5.9 Hz, 1 H) 8.44 (s, 1 H) 8.77 (t, J=5.6 Hz, 1 H). $^{13}$C NMR (75 MHz, DMSO-$d_6$) δ ppm 41.3, 44.2, 74.3, 74.8, 78.0, 80.4, 124.6, 127.3, 128.2, 131.2, 132.0, 134.4, 142.5, 149.0, 151.0, 163.4, 167.0. HRMS (ESI-TOF) m/z: [M+H]$^+$ Calcd for $C_{19}H_{20}Cl_2N_3O_5^+$ 440.07745; Found 440.0770.

N-(((2R,3R,4S)-4-(benzamidomethyl)-3,4-dihydroxytetrahydrofuran-2-yl)methyl)-2-chloronicotinamide (199)

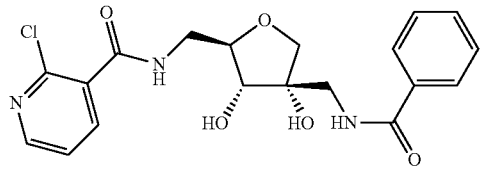 [SMILES: O=C(NC[C@]1(O)CO[C@H](CNC(=O)c2cccnc2Cl)[C@H]1O)c1ccccc1]

General procedure 8. White foam $^1$H NMR (300 MHz, DMSO-$d_6$) δ ppm 3.36-3.70 (m, 6 H) 3.74-3.81 (m, 1 H) 3.89 (d, J=9.7 Hz, 1 H) 4.81 (s, 1 H) 5.03 (d, J=6.7 Hz, 1 H) 7.38-7.57 (m, 4 H) 7.78-7.90 (m, 3 H) 8.37 (t, J=5.9 Hz, 1 H) 8.44 (dd, J=4.8, 1.9 Hz, 1 H) 8.67 (t, J=5.6 Hz, 1 H). $^{13}$C NMR (75 MHz, DMSO-$d_6$) δ ppm 41.3, 44.2, 74.3, 74.8, 78.0, 80.5, 122.9, 127.3, 128.2, 131.2, 133.3, 134.4, 138.0, 146.5, 150.0, 165.3, 167.0. HRMS (ESI-TOF) m/z: [M+H]$^+$ Calcd for $C_{19}H_{21}ClN_3O_5^+$ 406.11642; Found 406.1180.

N-(((2R,3R,4S)-4-(benzamidomethyl)-3,4-dihydroxytetrahydrofuran-2-yl)methyl)-3-chloroisonicotinamide (200)

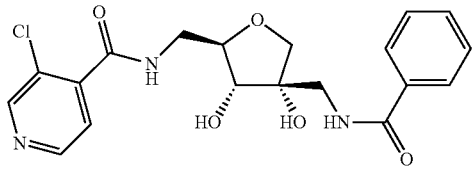 [SMILES: O=C(NC[C@]1(O)CO[C@H](CNC(=O)c2ccncc2Cl)[C@H]1O)c1ccccc1]

General procedure 8. White foam $^1$H NMR (300 MHz, DMSO-$d_6$) δ ppm 3.36-3.69 (m, 6 H) 3.73-3.80 (m, 1 H) 3.89 (d, J=9.7 Hz, 1 H) 4.81 (s, 1 H) 5.03 (d, J=6.7 Hz, 1 H) 7.39 (d, J=5.0 Hz, 1 H) 7.43-7.58 (m, 3 H) 7.81-7.91 (m, 2 H) 8.37 (t, J=5.9 Hz, 1 H) 8.50 (app. d, J=5.0 Hz, 1 H) 8.67 (app. s, 1 H) 8.74 (t, J=5.6 Hz, 1H). $^{13}$C NMR (75 MHz, DMSO-$d_6$) δ ppm 41.1, 44.2, 74.2, 74.8, 78.1, 80.4, 122.8, 127.3, 127.4, 128.2, 131.2, 134.4, 143.6, 148.1, 149.2, 164.6, 167.0. HRMS (ESI-TOF) m/z: [M+H]$^+$ Calcd for $C_{19}H_{21}ClN_3O_5^+$ 406.11642; Found 406.1170.

N-(((2R,3R,4S)-4-(benzamidomethyl)-3,4-dihydroxytetrahydrofuran-2-yl)methyl)-4-chloronicotinamide (201)

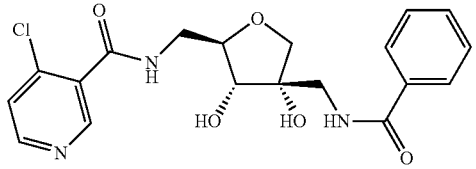

General procedure 8. White foam $^1$H NMR (300 MHz, DMSO-$d_6$) δ ppm 3.36-3.61 (m, 5 H) 3.63-3.71 (m, 1 H) 3.74-3.82 (m, 1 H) 3.89 (d, J=9.7 Hz, 1 H) 4.81 (br. s., 1 H) 5.05 (br. s., 1 H) 7.40-7.57 (m, 3 H) 7.58 (d, J=5.3 Hz, 1 H) 7.82-7.89 (m, 2 H) 8.36 (t, J=5.9 Hz, 1 H) 8.53-8.59 (m, 2 H) 8.74 (t, J=5.7 Hz, 1 H). $^{13}$C NMR (75 MHz, DMSO-$d_6$) δ ppm 41.4, 44.3, 74.4, 74.8, 78.1, 80.5, 124.7, 127.3, 128.2, 131.2, 132.7, 134.4, 140.0, 149.1, 151.1, 164.3, 167.1. HRMS (ESI-TOF) m/z: [M+H]$^+$ Calcd for $C_{19}H_{21}ClN_3O_5^+$ 406.11642; Found 406.1169.

N-(((2R,3R,4S)-4-(benzamidomethyl)-3,4-dihydroxytetrahydrofuran-2-yl)methyl)-6-chloronicotinamide (202)

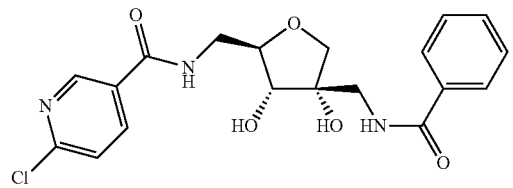

General procedure 8. White foam, quant. $^1$H NMR (300 MHz, DMSO-d$_6$) δ ppm 3.35-3.49 (m, 3 H) 3.52-3.66 (m, 3 H) 3.79 (app. td, J=7.4, 3.7 Hz, 1 H) 3.88 (d, J=9.7 Hz, 1 H) 4.80 (s, 1 H) 5.01 (d, J=6.7 Hz, 1 H) 7.40-7.49 (m, 2 H) 7.49-7.56 (m, 1 H) 7.59 (dd, J=8.4, 0.7 Hz, 1 H) 7.78-7.87 (m, 2 H) 8.21 (dd, J=8.4, 2.5 Hz, 1 H) 8.36 (t, J=5.9 Hz, 1 H) 8.75-8.87 (m, 2 H). $^{13}$C NMR (75 MHz, DMSO-d$_6$) δ ppm 41.9, 44.1, 74.5, 74.7, 78.0, 80.6, 124.0, 127.3, 128.2, 129.3, 131.2, 134.3, 138.6, 149.0, 152.4, 163.9, 167.0. HRMS (ESI-TOF) m/z: [M+H]$^+$ Calcd for C$_{19}$H$_{21}$ClN$_3$O$_5^+$ 406.11642; Found 406.1166.

N-(((2R,3R,4S)-4-(benzamidomethyl)-3,4-dihydroxytetrahydrofuran-2-yl)methyl)pyrimidine-2-carboxamide (203)

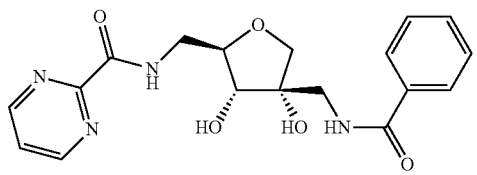 [SMILES: O=C(NC[C@]1(O)CO[C@H](CNC(=O)c2ncccn2)[C@H]1O)c1ccccc1]

General procedure 8. White foam, 54.5% $^1$H NMR (300 MHz, DMSO-d$_6$) δ ppm 3.36-3.67 (m, 6 H) 3.76-3.84 (m, 1 H) 3.89 (d, J=9.7 Hz, 1 H) 4.81 (s, 1 H) 5.04 (d, J=6.7 Hz, 1 H) 7.40-7.56 (m, 3 H) 7.66 (t, J=5.0 Hz, 1 H) 7.77-7.86 (m, 2 H) 8.36 (t, J=5.9 Hz, 1 H) 8.64 (t, J=5.7 Hz, 1 H) 8.92 (d, J=5.0 Hz, 2 H). $^{13}$C NMR (75 MHz, DMSO-d$_6$) δ ppm 41.5, 44.1, 74.5, 74.8, 78.1, 80.4, 123.0, 127.3, 128.2, 131.2, 134.4, 157.7, 157.8, 162.2, 167.1. HRMS (ESI-TOF) m/z: [M+H]$^+$ Calcd for C$_{18}$H$_{21}$N$_4$O$_5^+$ 373.15065; Found 373.1517.

N-(((2R,3R,4S)-4-(benzamidomethyl)-3,4-dihydroxytetrahydrofuran-2-yl)methyl)pyrimidine-4-carboxamide (204)

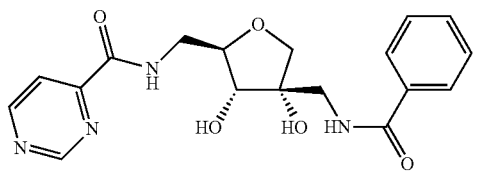

General procedure 8. White foam, 65.3% $^1$H NMR (300 MHz, DMSO-d$_6$) δ ppm 3.35-3.46 (m, 2 H) 3.47-3.67 (m, 4 H) 3.77-3.85 (m, 1 H) 3.88 (d, J=9.7 Hz, 1 H) 4.81 (s, 1 H) 5.02 (d, J=7.0 Hz, 1 H) 7.39-7.47 (m, 2 H) 7.49-7.55 (m, 1 H) 7.76-7.84 (m, 2 H) 8.01 (dd, J=5.0, 1.5 Hz, 1 H) 8.36 (t, J=6.0 Hz, 1 H) 8.74 (t, J=6.0 Hz, 1 H) 9.06 (d, J=5.0 Hz, 1 H) 9.26 (d, J=1.5 Hz, 1 H). $^{13}$C NMR (75 MHz, DMSO-d$_6$) δ ppm 41.4, 44.0, 74.5, 74.7, 78.1, 80.3, 118.4, 127.3, 128.2, 131.2, 134.4, 156.2, 157.8, 159.7, 162.5, 167.1. HRMS (ESI-TOF) m/z: [M+H]$^+$ Calcd for C$_{18}$H$_{21}$N$_4$O$_5^+$ 373.15065; Found 373.1522.

N-(((2R,3R,4S)-4-(benzamidomethyl)-3,4-dihydroxytetrahydrofuran-2-yl)methyl)pyrimidine-5-carboxamide (205)

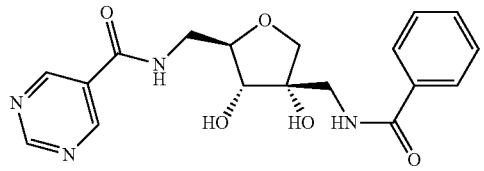 [SMILES: O=C(NC[C@H]1OC[C@@](O)(CNC(=O)c2ccccc2)[C@@H]1O)c1cncnc1]

General procedure 8. White foam, 61.1% $^1$H NMR (300 MHz, DMSO-d$_6$) δ ppm 3.36-3.51 (m, 3 H) 3.54-3.68 (m, 3 H) 3.80 (app. td, J=7.4, 3.7 Hz, 1 H) 3.89 (d, J=9.7 Hz, 1 H) 4.81 (s, 1 H) 5.03 (d, J=6.7 Hz, 1 H) 7.39-7.49 (m, 2 H) 7.49-7.56 (m, 1 H) 7.78-7.86 (m, 2 H) 8.37 (t, J=5.9 Hz, 1 H) 8.93 (t, J=5.6 Hz, 1 H) 9.14 (app. s, 2 H) 9.29 (app. s, 1 H). $^{13}$C NMR (75 MHz, DMSO-d$_6$) δ ppm 41.8, 44.2, 74.5, 74.7, 78.1, 80.6, 127.3, 127.9, 128.3, 131.3, 134.4, 155.9, 159.9, 163.3, 167.1. HRMS (ESI-TOF) m/z: [M+H]$^+$ Calcd for C$_{18}$H$_{21}$N$_4$O$_5^+$ 373.15065; Found 373.1517.

N-(((2R,3R,4S)-4-(benzamidomethyl)-3,4-dihydroxytetrahydrofuran-2-yl)methyl)pyridazine-3-carboxamide (206)

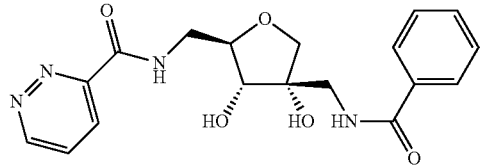 [SMILES: O=C(NC[C@]1(O)CO[C@H](CNC(=O)c2cccnn2)[C@H]1O)c1ccccc1]

General procedure 8. White foam, 58.2% $^1$H NMR (300 MHz, DMSO-d$_6$) δ ppm 3.36-3.48 (m, 2 H) 3.49-3.72 (m, 4 H) 3.79-3.92 (m, 2 H) 4.81 (s, 1 H) 5.03 (d, J=6.7 Hz, 1 H) 7.38-7.48 (m, 2 H) 7.48-7.55 (m, 1 H) 7.78-7.85 (m, 2 H) 7.90 (dd, J=8.4, 5.1 Hz, 1 H) 8.20 (dd, J=8.5, 1.8 Hz, 1 H) 8.36 (t, J=6.0 Hz, 1 H) 8.99 (t, J=6.0 Hz, 1 H) 9.40 (dd, J=5.0, 1.8 Hz, 1 H). $^{13}$C NMR (75 MHz, DMSO-d$_6$) δ ppm 41.9, 44.5, 75.0, 75.2, 78.8, 80.8, 126.3, 127.7, 129.0, 129.3, 132.1, 134.6, 153.1, 153.9, 163.5, 168.3. HRMS (ESI-TOF) m/z: [M+H]$^+$ Calcd for C$_{18}$H$_{21}$N$_4$O$_5^+$ 373.15065; Found 373.1520.

N-(((2R,3R,4S)-4-(benzamidomethyl)-3,4-dihydroxytetrahydrofuran-2-yl)methyl)pyridazine-4-carboxamide (207)

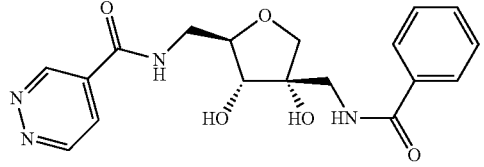

General procedure 8. White foam, 52.1% $^1$H NMR (300 MHz, DMSO-d$_6$) δ ppm 3.35-3.51 (m, 3 H) 3.52-3.67 (m, 3

H) 3.79 (app. td, J=7.5, 3.7 Hz, 1 H) 3.89 (d, J=9.7 Hz, 1 H) 4.81 (s, 1 H) 5.03 (d, J=6.7 Hz, 1 H) 7.39-7.48 (m, 2 H) 7.49-7.56 (m, 1 H) 7.78-7.87 (m, 2 H) 7.96 (dd, J=5.3, 2.3 Hz, 1 H) 8.36 (t, J=6.0 Hz, 1 H) 9.07 (t, J=5.4 Hz, 1 H) 9.38 (dd, J=5.3, 1.2 Hz, 1 H) 9.52 (dd, J=2.2, 1.3 Hz, 1 H). $^{13}$C NMR (75 MHz, DMSO-d$_6$) δ ppm 42.0, 44.1, 74.5, 74.7, 78.0, 80.5, 124.2, 127.3, 128.2, 131.2, 131.5, 134.4, 148.9, 152.0, 163.4, 167.1. HRMS (ESI-TOF) m/z: [M+H]$^+$ Calcd for $C_{18}H_{21}N_4O_5^+$ 373.15065; Found 373.1523.

N-(((2R,3R,4S)-4-(benzamidomethyl)-3,4-dihydroxytetrahydrofuran-2-yl)methyl)pyrazine-2-carboxamide (208)

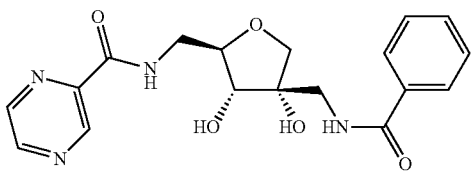

General procedure 8. White foam, 63.5% $^1$H NMR (300 MHz, DMSO-d$_6$) δ ppm 3.34-3.47 (m, 2 H) 3.48-3.67 (m, 4 H) 3.77-3.84 (m, 1 H) 3.88 (d, J=9.7 Hz, 1 H) 4.81 (s, 1 H) 5.02 (d, J=6.7 Hz, 1 H) 7.39-7.47 (m, 2 H) 7.49-7.55 (m, 1 H) 7.76-7.85 (m, 2 H) 8.35 (t, J=5.9 Hz, 1 H) 8.61 (t, J=5.9 Hz, 1 H) 8.66 (dd, J=2.6, 1.5 Hz, 1 H) 8.85 (d, J=2.3 Hz, 1 H) 9.17 (d, J=1.5 Hz, 1 H). $^{13}$C NMR (75 MHz, DMSO-d$_6$) δ ppm 41.2, 44.0, 74.5, 74.7, 78.1, 80.4, 127.3, 128.2, 131.2, 134.4, 143.3, 143.4, 144.5, 147.6, 162.7, 167.0. HRMS (ESI-TOF) m/z: [M+H]$^+$ Calcd for $C_{18}H_{21}N_4O_5^+$ 373.15065; Found 373.1514.

N-(((2R,3R,4S)-4-(benzamidomethyl)-3,4-dihydroxytetrahydrofuran-2-yl)methyl)-1-methyl-1H-pyrazole-5-carboxamide (209)

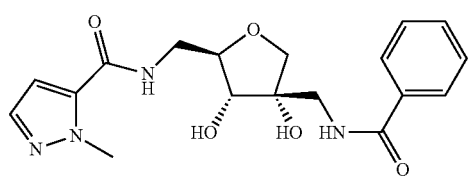 [SMILES: Cn1nccc1C(=O)NC[C@H]1OC[C@@](O)(CNC(=O)c2ccccc2)[C@@H]1O]

General procedure 8. White foam, 84.7% $^1$H NMR (300 MHz, DMSO-d$_6$) δ ppm 3.33-3.63 (m, 6 H) 3.76 (app. dt, J=7.5, 3.9 Hz, 1 H) 3.87 (d, J=9.4 Hz, 1 H) 4.03 (s, 3 H) 4.80 (s, 1 H) 5.01 (d, J=7.0 Hz, 1 H) 6.86 (d, J=2.1 Hz, 1 H) 7.41 (d, J=2.1 Hz, 1 H) 7.42-7.57 (m, 3 H) 7.80-7.88 (m, 2 H) 8.37 (t, J=6.0 Hz, 1 H) 8.49 (t, J=5.7 Hz, 1 H). $^{13}$C NMR (75 MHz, DMSO-d$_6$) δ ppm 38.9, 41.4, 44.2, 74.64 (2 C), 78.0, 80.7, 107.3, 127.3, 128.2, 131.2, 134.4, 135.2, 137.1, 159.5, 167.1. HRMS (ESI-TOF) m/z: [M+H]$^+$ Calcd for $C_{18}H_{23}N_4O_5^+$ 375.16630; Found 375.1674.

N-(((2R,3R,4S)-4-(benzamidomethyl)-3,4-dihydroxytetrahydrofuran-2-yl)methyl)-1-methyl-1H-imidazole-5-carboxamide (210)

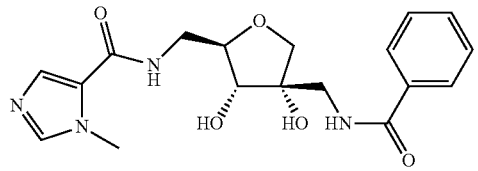 [SMILES: Cn1cncc1C(=O)NC[C@H]1OC[C@@](O)(CNC(=O)c2ccccc2)[C@@H]1O]

General procedure 8. White foam, 96.4% $^1$H NMR (300 MHz, DMSO-d$_6$) δ ppm 3.25-3.63 (m, 6 H) 3.69-3.83 (m, 4 H) 3.87 (d, J=9.7 Hz, 1 H) 4.80 (s, 1 H) 5.00 (d, J=6.7 Hz, 1 H) 7.41-7.57 (m, 3 H) 7.60 (app. s, 1 H) 7.71 (app. s, 1 H) 7.80-7.87 (m, 2 H) 8.29 (t, J=5.6 Hz, 1 H) 8.37 (t, J=5.9 Hz, 1 H). $^{13}$C NMR (75 MHz, DMSO-d$_6$) δ ppm 33.5, 41.1, 44.3, 74.65 (2 C), 78.0, 81.0, 125.8, 127.3, 128.2, 131.2, 132.0, 134.4, 141.7, 160.0, 167.1. HRMS (ESI-TOF) m/z: [M+H]$^+$ Calcd for $C_{18}H_{23}N_4O_5^+$ 375.16630; Found 375.1674.

N-(((3S,4R,5R)-3,4-dihydroxy-5-(methylsulfonamidomethyl)tetrahydrofuran-3-yl)methyl)benzamide (211)

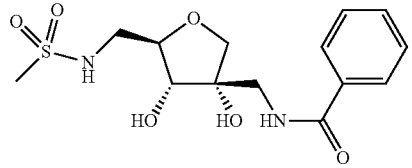 [SMILES: CS(=O)(=O)NC[C@H]1OC[C@@](O)(CNC(=O)c2ccccc2)[C@@H]1O]

General procedure 8. White foam, 81.1% $^1$H NMR (300 MHz, DMSO-d$_6$) δ ppm 2.89 (s, 3 H) 3.03 (app. dt, J=13.4, 6.6 Hz, 1 H) 3.24 (ddd, J=13.7, 5.8, 3.1 Hz, 1 H) 3.42 (m, 2 H) 3.55-3.71 (m, 3 H) 3.87 (d, J=9.7 Hz, 1 H) 4.81 (s, 1 H) 5.01 (d, J=6.7 Hz, 1 H) 7.05 (t, J=6.2 Hz, 1 H) 7.43-7.57 (m, 3 H) 7.82-7.88 (m, 2 H) 8.35 (t, J=5.9 Hz, 1 H). $^{13}$C NMR (75 MHz, DMSO-d$_6$) δ ppm 39.6, 44.2, 44.9, 73.9, 74.8, 77.9, 81.1, 127.3, 128.2, 131.2, 134.4, 167.1. HRMS (ESI-TOF) m/z: [M+H]$^+$ Calcd for $C_{14}H_{21}N_2O_6S^+$ 345.11148; Found 345.1107.

N-(((3S,4R,5R)-5-(ethylsulfonamidomethyl)-3,4-dihydroxytetrahydrofuran-3-yl)methyl)benzamide (212)

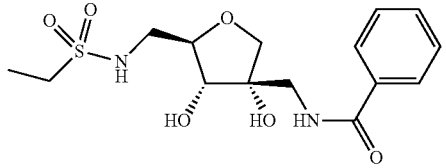

General procedure 8. White foam, 78.4% $^1$H NMR (300 MHz, DMSO-d$_6$) δ ppm 1.17 (t, J=7.3 Hz, 3 H) 2.92-3.08 (m, 3 H) 3.23 (ddd, J=13.8, 5.8, 2.9 Hz, 1 H) 3.35-3.48 (m, 2 H) 3.53-3.70 (m, 3 H) 3.87 (d, J=9.7 Hz, 1 H) 4.80 (s, 1

H) 4.99 (d, J=6.4 Hz, 1 H) 7.10 (t, J=5.9 Hz, 1 H) 7.42-7.58 (m, 3 H) 7.80-7.89 (m, 2 H) 8.35 (t, J=5.9 Hz, 1 H). $^{13}$C NMR (75 MHz, DMSO-d$_6$) δ ppm 8.1, 44.2, 44.7, 45.7, 74.0, 74.8, 78.0, 81.2, 127.3, 128.2, 131.2, 134.4, 167.1. HRMS (ESI-TOF) m/z: [M+H]$^+$ Calcd for C$_{15}$H$_{23}$N$_2$O$_6$S$^+$ 359.12713; Found 359.1285.

N-(((3S,4R,5R)-3,4-dihydroxy-5-(((1-methylethyl)sulfonamido)methyl)tetrahydrofuran-3-yl)methyl)benzamide (213)

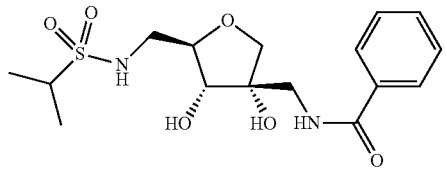

General procedure 8. White foam, 86.8% $^1$H NMR (300 MHz, DMSO-d$_6$) δ ppm 1.19 (d, J=2.1 Hz, 3 H) 1.21 (d, J=2.1, 3 H) 3.03 (app. dt, J=13.6, 6.6 Hz, 1 H) 3.12-3.30 (m, 2 H) 3.35-3.48 (m, 2 H) 3.54-3.69 (m, 3 H) 3.87 (d, J=9.4 Hz, 1 H) 4.80 (s, 1 H) 4.98 (d, J=6.7 Hz, 1 H) 7.08 (t, J=5.9 Hz, 1 H) 7.43-7.57 (m, 3 H) 7.82-7.88 (m, 2 H) 8.34 (t, J=6.0 Hz, 1 H). $^{13}$C NMR (75 MHz, DMSO-d$_6$) δ ppm 16.3 (2 C), 44.2, 45.0, 51.6, 74.0, 74.8, 78.0, 81.4, 127.3, 128.2, 131.2, 134.4, 167.1. HRMS (ESI-TOF) m/z: [M+H]$^+$ Calcd for C$_{16}$H$_{25}$N$_2$O$_6$S$^+$ 373.14278; Found 373.1445.

N-(((3S,4R,5R)-3,4-dihydroxy-5-(((trifluoromethyl)sulfonamido)methyl)tetrahydrofuran-3-yl)methyl)benzamide (214)

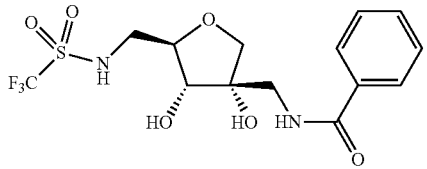 [SMILES: O=C(NC[C@]1(O)CO[C@H](CNS(=O)(=O)C(F)(F)F)[C@H]1O)c1ccccc1]

General procedure 8. White foam, 83.6% $^1$H NMR (300 MHz, DMSO-d$_6$) δ ppm 3.17-3.25 (m, 1 H) 3.36-3.48 (m, 3 H) 3.56-3.64 (m, 2 H) 3.67-3.74 (m, 1 H) 3.89 (d, J=9.7 Hz, 1 H) 4.85 (s, 1 H) 5.09 (d, J=6.6 Hz, 1 H) 7.43-7.57 (m, 3 H) 7.81-7.88 (m, 2 H) 8.36 (t, J=6.0 Hz, 1 H) 9.56 (br. s, 1 H). $^{19}$F NMR (282 MHz, DMSO-d$_6$) δ ppm −77.6 (s). $^{13}$C NMR (75 MHz, DMSO-d$_6$) δ ppm 44.1, 45.9, 73.9, 74.9, 78.0, 80.5, 119.7 (q, J=322.7 Hz), 127.3, 128.2, 131.2, 134.4, 167.1. HRMS (ESI-TOF) m/z: [M+H]$^+$ Calcd for C$_{14}$H$_{18}$F$_3$N$_2$O$_6$S$^+$ 399.08322; Found 399.0831.

N-(((3S,4R,5R)-3,4-dihydroxy-5-(phenylsulfonamidomethyl)tetrahydrofuran-3-yl)methyl)benzamide (215)

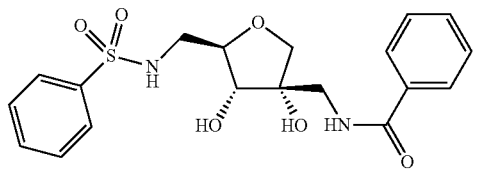 [SMILES: O=C(NC[C@]1(O)CO[C@H](CNS(=O)(=O)c2ccccc2)[C@H]1O)c1ccccc1]

General procedure 8. White foam, 92.9% $^1$H NMR (300 MHz, DMSO-d$_6$) δ ppm 2.82 (app. dt, J=13.3, 6.7 Hz, 1 H) 3.00 (ddd, J=13.0, 5.7, 2.6 Hz, 1H) 3.33-3.44 (m, 2 H) 3.48-3.65 (m, 3 H) 3.80 (d, J=9.7 Hz, 1 H) 4.76 (s, 1 H) 4.99 (d, J=6.7 Hz, 1 H) 7.36-7.68 (m, 6 H) 7.72 (t, J=6.0 Hz, 1 H) 7.75-7.90 (m, 4 H) 8.31 (t, J=5.9 Hz, 1 H). $^{13}$C NMR (75 MHz, DMSO-d$_6$) δ ppm 44.3, 45.1, 74.1, 74.8, 77.9, 80.7, 126.5, 127.3, 128.3, 129.1, 131.2, 132.3, 134.4, 140.5, 167.1. HRMS (ESI-TOF) m/z: [M+H]$^+$ Calcd for C$_{19}$H$_{23}$N$_2$O$_6$S$^+$ 407.12713; Found 407.1266.

N-(((3S,4R,5R)-3,4-dihydroxy-5-(((4-methylphenyl)sulfonamido)methyl)tetrahydrofuran-3-yl)methyl)benzamide (216)

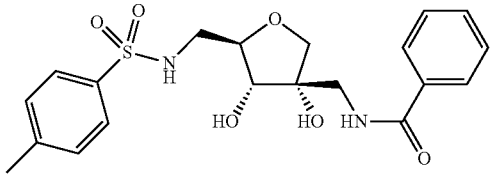 [SMILES: Cc1ccc(S(=O)(=O)NC[C@H]2OC[C@@](O)(CNC(=O)c3ccccc3)[C@@H]2O)cc1]

General procedure 8. White foam, 77.5% $^1$H NMR (300 MHz, DMSO-d$_6$) δ ppm 2.38 (s, 3 H) 2.80 (app. dt, J=13.0, 6.4 Hz, 1 H) 2.93-3.02 (m, 1 H) 3.35-3.47 (m, 2 H) 3.50-3.66 (m, 3 H) 3.82 (d, J=9.7 Hz, 1 H) 4.77 (s, 1 H) 5.00 (d, J=6.4 Hz, 1 H) 7.38 (d, J=8.2 Hz, 2 H) 7.43-7.57 (m, 3 H) 7.63 (t, J=5.6 Hz, 1 H) 7.69 (d, J=8.2 Hz, 2 H) 7.80-7.88 (m, 2 H) 8.32 (t, J=5.9 Hz, 1 H). $^{13}$C NMR (75 MHz, DMSO-d$_6$) δ ppm 21.0, 44.3, 45.1, 74.1, 74.8, 77.9, 80.7, 126.6, 127.3, 128.2, 129.5, 131.2, 134.4, 137.6, 142.5, 167.1. HRMS (ESI-TOF) m/z: [M−H]$^-$ Calcd for C$_{20}$H$_{23}$N$_2$O$_6$S$^-$ 419.12823; Found 419.1286.

N-(((3S,4R,5R)-5-(((4-chlorophenyl)sulfonamido)methyl)-3,4-dihydroxytetrahydrofuran-3-yl)methyl)benzamide (217)

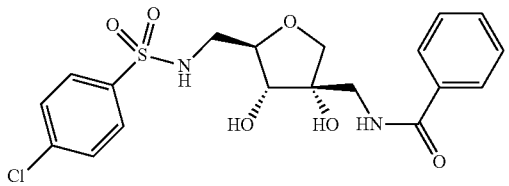 [SMILES: O=C(NC[C@]1(O)CO[C@H](CNS(=O)(=O)c2ccc(Cl)cc2)[C@H]1O)c1ccccc1]

General procedure 8. White foam, 67.1% $^1$H NMR (300 MHz, DMSO-d$_6$) δ ppm 2.83 (app. dd, J=13.0, 6.6 Hz, 1 H) 3.00-3.04 (m, 1 H) 3.33-3.46 (m, 2 H) 3.47-3.66 (m, 3 H) 3.79 (d, J=9.7 Hz, 1 H) 4.77 (s, 1 H) 4.99 (d, J=5.3 Hz, 1H) 7.40-7.49 (m, 2 H) 7.50-7.56 (m, 1 H) 7.61-7.71 (m, 2 H) 7.74-7.91 (m, 5 H) 8.31 (t, J=5.9 Hz, 1 H). $^{13}$C NMR (75 MHz, DMSO-d$_6$) δ ppm 44.3, 45.1, 74.0, 74.8, 77.9, 80.6, 127.3, 128.2, 128.5, 129.2, 131.2, 134.4, 137.1, 139.5, 167.1. HRMS (ESI-TOF) m/z: [M+H]$^+$ Calcd for C$_{19}$H$_{22}$ClN$_2$O$_6$S$^+$ 441.08816; Found 441.0902.

N-(((3S,4R,5R)-5-(((2-chlorophenyl)sulfonamido)methyl)-3,4-dihydroxytetrahydrofuran-3-yl)methyl)benzamide (218)

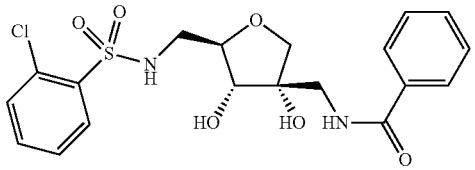 [SMILES: O=C(NC[C@]1(O)CO[C@H](CNS(=O)(=O)c2ccccc2Cl)[C@H]1O)c1ccccc1]

General procedure 8. White foam, 64.8% $^1$H NMR (300 MHz, DMSO-d$_6$) δ ppm 2.97 (app. dt, J=13.6, 6.6 Hz, 1 H) 3.17 (ddd, J=13.8, 5.6, 2.9 Hz, 1H) 3.31-3.49 (m, 3 H) 3.54 (d, J=7.9 Hz, 1 H) 3.62 (app. td, J=7.5, 2.9 Hz, 1 H) 3.72 (d, J=9.7 Hz, 1 H) 4.81 (br. s., 2 H) 7.40-7.67 (m, 6 H) 7.80-7.88 (m, 2 H) 7.89-7.99 (m, 2 H) 8.29 (t, J=6.0 Hz, 1 H). $^{13}$C NMR (75 MHz, DMSO-d$_6$) δ ppm 44.3, 45.0, 74.1, 74.8, 77.9, 80.6, 127.3, 127.5, 128.2, 130.2, 130.6, 131.2, 131.6, 133.7, 134.4, 138.3, 167.0. HRMS (ESI-TOF) m/z: [M−H]$^-$ Calcd for C$_{19}$H$_{20}$ClN$_2$O$_6$S$^-$ 439.07361; Found 439.0734.

N-(((3S,4R,5R)-5-(([1,1'-biphenyl]-4-sulfonamido)methyl)-3,4-dihydroxytetrahydrofuran-3-yl)methyl)benzamide (219)

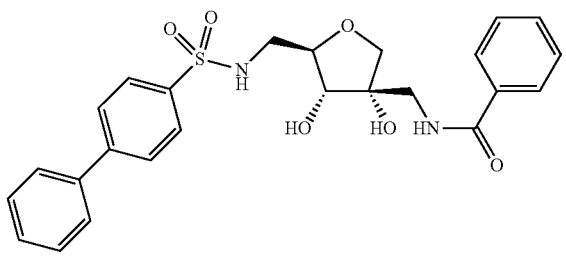 [SMILES: O=C(NC[C@]1(O)CO[C@H](CNS(=O)(=O)c2ccc(-c3ccccc3)cc2)[C@H]1O)c1ccccc1]

General procedure 8. White foam, 63.0% $^1$H NMR (300 MHz, DMSO-d$_6$) δ ppm 2.86 (app. dt, J=13.2, 6.6 Hz, 1 H) 3.05 (ddd, J=13.2, 5.6, 2.9 Hz, 1 H) 3.39 (m, 2 H) 3.50-3.69 (m, 3 H) 3.82 (d, J=9.7 Hz, 1 H) 4.77 (s, 1 H) 5.01 (d, J=6.7 Hz, 1 H) 7.38-7.57 (m, 6 H) 7.69-7.90 (m, 9 H) 8.32 (t, J=5.9 Hz, 1 H). $^{13}$C NMR (75 MHz, DMSO-d$_6$) δ ppm 45.0, 45.8, 74.7, 75.5, 78.6, 81.4, 127.8, 127.9, 128.01 (2 C), 128.9, 129.1, 129.8, 131.9, 135.1, 139.3, 140.0, 144.5, 167.8. HRMS (ESI-TOF) m/z: [M−H]$^-$ Calcd for C$_{25}$H$_{25}$N$_2$O$_6$S$^-$ 481.14388; Found 481.1446.

N-(((3S,4R,5R)-5-(([1,1'-biphenyl]-2-sulfonamido)methyl)-3,4-dihydroxytetrahydrofuran-3-yl)methyl)benzamide (220)

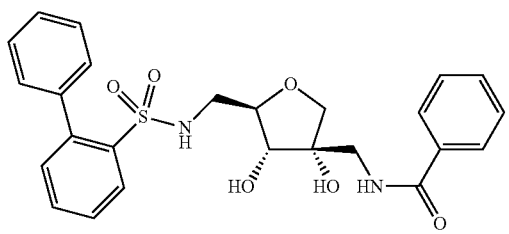 [SMILES: O=C(NC[C@]1(O)CO[C@H](CNS(=O)(=O)c2ccccc2-c2ccccc2)[C@H]1O)c1ccccc1]

General procedure 8. White foam, 92.2% $^1$H NMR (300 MHz, DMSO-d$_6$) δ ppm 2.78 (app. dt, J=13.5, 6.7 Hz, 1 H) 2.98 (ddd, J=13.4, 5.6, 3.0 Hz, 1H) 3.32-3.43 (m, 2 H) 3.48-3.61 (m, 3 H) 3.80 (d, J=9.4 Hz, 1 H) 4.82 (br. s., 2 H) 7.16 (t, J=5.9 Hz, 1 H) 7.29-7.69 (m, 11 H) 7.80-7.87 (m, 2 H) 7.96 (dd, J=7.8, 1.3 Hz, 1 H) 8.31 (t, J=5.9 Hz, 1 H). $^{13}$C NMR (75 MHz, DMSO-d$_6$) δ ppm 44.2, 45.0, 74.0, 74.8, 77.9, 80.7, 127.3, 127.4, 127.6, 127.7, 127.8, 128.2, 129.2, 131.2, 131.8, 132.7, 134.4, 139.2, 139.7, 140.6, 167.1. HRMS (ESI-TOF) m/z: [M−H]$^-$ Calcd for C$_{25}$H$_{25}$N$_2$O$_6$S$^-$ 481.14388; Found 481.1450.

N-(((3S,4R,5R)-3,4-dihydroxy-5-((4-phenyl-1H-1,2,3-triazol-1-yl)methyl)tetrahydrofuran-3-yl)methyl)benzamide (221)

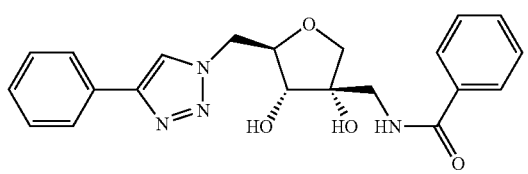 [SMILES: O=C(NC[C@]1(O)CO[C@H](Cn2cc(-c3ccccc3)nn2)[C@H]1O)c1ccccc1]

General procedure 8. White foam, 83.2% $^1$H NMR (300 MHz, DMSO-d$_6$) δ ppm 3.36 (dd, J=13.6, 6.0 Hz, 1 H) 3.44 (dd, J=13.5, 6.2 Hz, 1 H) 3.59 (d, J=9.7 Hz, 1 H) 3.65 (d, J=8.2 Hz, 1 H) 3.84 (d, J=9.7 Hz, 1 H) 4.02 (app. td, J=7.7, 3.2 Hz, 1 H) 4.52 (dd, J=14.2, 7.5 Hz, 1 H) 4.67 (dd, J=14.2, 3.1 Hz, 1 H) 7.29-7.54 (m, 6 H) 7.77-7.86 (m, 4 H) 8.37 (t, J=6.0 Hz, 1 H) 8.48 (s, 1 H). $^{13}$C NMR (75 MHz, DMSO-d$_6$) δ ppm 43.6, 51.9, 73.8, 74.9, 78.0, 80.2, 122.1, 125.2, 127.3, 127.8, 128.2, 128.9, 130.8, 131.2, 134.4, 146.3, 167.2. HRMS (ESI-TOF) m/z: [M+H]$^+$ Calcd for C$_{21}$H$_{23}$N$_4$O$_4^+$ 395.17138; Found 395.1730.

N-(((3S,4R,5R)-3,4-dihydroxy-5-((5-phenyl-1H-1,2,3-triazol-1-yl)methyl)tetrahydrofuran-3-yl)methyl)benzamide (222)

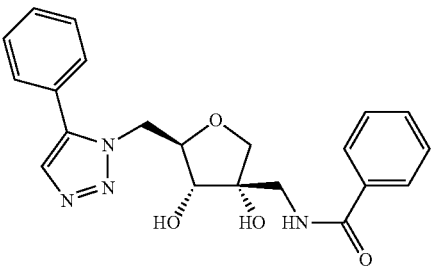 [SMILES: O=C(NC[C@]1(O)CO[C@H](Cn2nncc2-c2ccccc2)[C@H]1O)c1ccccc1]

General procedure 8. Light brown colored foam, 90.9% $^1$H NMR (300 MHz, DMSO-d$_6$) δ ppm 3.32-3.46 (m, 2 H) 3.50 (d, J=9.7 Hz, 1 H) 3.69-3.82 (m, 2 H) 4.05 (app. td, J=8.2, 2.9 Hz, 1 H) 4.42 (dd, J=14.4, 8.2 Hz, 1 H) 4.64 (dd, J=14.4, 2.9 Hz, 1 H) 4.88 (br. s., 1 H) 5.18 (br. s., 1 H) 7.41-7.64 (m, 8 H) 7.78-7.87 (m, 3 H) 8.34 (t, J=5.9 Hz, 1 H). $^{13}$C NMR (75 MHz, DMSO-d$_6$) δ ppm 44.4, 50.8, 75.0, 75.2, 78.6, 81.0, 127.1, 127.8, 129.1, 129.4, 129.7, 130.0, 132.2, 133.2, 134.6, 139.1, 168.4. HRMS (ESI-TOF) m/z: [M+H]$^+$ Calcd for C$_{21}$H$_{23}$N$_4$O$_4^+$ 395.17138; Found 395.1724.

N-(((3S,4R,5R)-3,4-dihydroxy-5-((3-phenylureido)methyl)tetrahydrofuran-3-yl)methyl)benzamide (223)

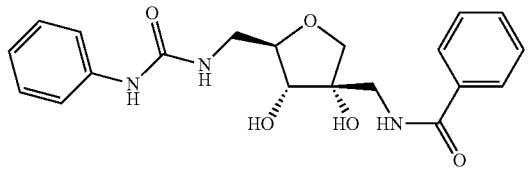 [SMILES: O=C(NC[C@H]1OC[C@@](O)(CNC(=O)c2ccccc2)[C@@H]1O)Nc1ccccc1]

General procedure 8. White foam, quant. $^1$H NMR (300 MHz, DMSO-$d_6$) δ ppm 3.19 (m, 1 H) 3.35-3.50 (m, 3 H) 3.53-3.63 (m, 2 H) 3.63-3.70 (m, 1 H) 3.89 (d, J=9.4 Hz, 1 H) 4.79 (s, 1 H) 5.00 (d, J=6.7 Hz, 1 H) 6.17 (t, J=5.4 Hz, 1 H) 6.88 (app. t, J=7.3 Hz, 1 H) 7.21 (app. t, J=7.9 Hz, 2 H) 7.30-7.58 (m, 5 H) 7.77-7.91 (m, 2 H) 8.37 (t, J=5.9 Hz, 1 H) 8.50 (s, 1 H). $^{13}$C NMR (75 MHz, DMSO-$d_6$) δ ppm 41.2, 44.2, 73.9, 74.8, 78.2, 81.2, 117.5, 121.0, 127.3, 128.3, 128.7, 131.2, 134.5, 140.5, 155.2, 167.2. HRMS (ESI-TOF) m/z: [M+H]$^+$ Calcd for $C_{20}H_{24}N_3O_5^+$ 386.17105; Found 386.1708.

N-(((3S,4R,5R)-3,4-dihydroxy-5-((3-phenylthioureido)methyl)tetrahydrofuran-3-yl)methyl)benzamide (224)

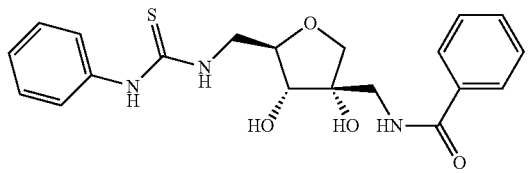

General procedure 8. White foam, 85.8% $^1$H NMR (300 MHz, DMSO-$d_6$) δ ppm 3.40-3.65 (m, 5 H) 3.76-3.93 (m, 3 H) 4.86 (br. s., 2 H) 7.04-7.13 (m, 1 H) 7.30 (app. t, J=7.8 Hz, 2 H) 7.39-7.57 (m, 5 H) 7.65 (br. s., 1 H) 7.80-7.91 (m, 2 H) 8.39 (t, J=6.0 Hz, 1 H) 9.60 (br.s., 1 H). $^{13}$C NMR (75 MHz, DMSO-$d_6$) δ ppm 44.2, 46.2, 74.3, 74.9, 78.2, 80.2, 122.9, 124.1, 127.4, 128.3, 128.5, 131.3, 134.4, 139.4, 167.2, 180.7. HRMS (ESI-TOF) m/z: [M+H]$^+$ Calcd for $C_{20}H_{24}N_3O_4S^+$ 402.14820; Found 402.1469.

N-(((3S,4R,5R)-5-(acetamidomethyl)-3,4-dihydroxytetrahydrofuran-3-yl)methyl)benzamide (225)

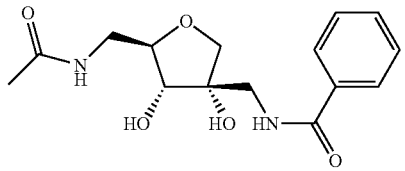 [SMILES: CC(=O)NC[C@H]1OC[C@@](O)(CNC(=O)c2ccccc2)[C@@H]1O]

General procedure 8. White foam, 91.4% $^1$H NMR (300 MHz, DMSO-$d_6$) δ ppm 1.79 (s, 3 H) 3.10 (app. dt, J=13.5, 6.4 Hz, 1 H) 3.32-3.48 (m, 3 H) 3.48-3.57 (m, 2 H) 3.61 (app. td, J=7.3, 3.3 Hz, 1 H) 3.86 (d, J=9.4 Hz, 1 H) 4.83 (br. s., 2 H) 7.40-7.57 (m, 3 H) 7.81-7.93 (m, 3 H) 8.34 (t, J=5.9 Hz, 1 H). $^{13}$C NMR (75 MHz, DMSO-$d_6$) δ ppm 22.5, 41.0, 44.3, 74.3, 74.7, 78.0, 81.0, 127.3, 128.3, 131.3, 134.4, 167.1, 169.3. HRMS (ESI-TOF) m/z: [M+H]$^+$ Calcd for $C_{15}H_{21}N_2O_5^+$ 309.14450; Found 309.1443.

N-(((3S,4R,5R)-3,4-dihydroxy-5-(pivalamidomethyl)tetrahydrofuran-3-yl)methyl)benzamide (226)

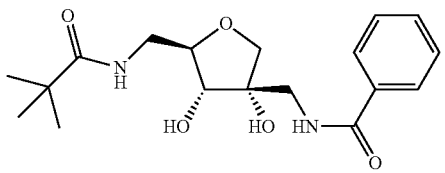 [SMILES: CC(C)(C)C(=O)NC[C@H]1OC[C@@](O)(CNC(=O)c2ccccc2)[C@@H]1O]

General procedure 8. White foam, quant. $^1$H NMR (300 MHz, DMSO-$d_6$) δ ppm 1.05 (s, 9 H) 3.17-3.44 (m, 4 H) 3.48-3.58 (m, 2 H) 3.62-3.69 (m, 1 H) 3.82 (d, J=9.4 Hz, 1 H) 4.92 (br. s., 2 H) 7.34 (t, J=5.6 Hz, 1 H) 7.42-7.57 (m, 3 H) 7.80-7.90 (m, 2 H) 8.35 (t, J=5.9 Hz, 1 H). $^{13}$C NMR (75 MHz, DMSO-$d_6$) δ ppm 27.4, 38.0, 41.3, 44.1, 74.5, 74.6, 78.1, 80.9, 127.3, 128.3, 131.3, 134.3, 167.0, 177.5. HRMS (ESI-TOF) m/z: [M+H]$^+$ Calcd for $C_{18}H_{27}N_2O_5^+$ 351.19145; Found 351.1909.

N-(((3S,4R,5R)-5-((5-chloro-1,3-dioxoisoindolin-2-yl)methyl)-3,4-dihydroxytetrahydrofuran-3-yl)methyl)benzamide (227)

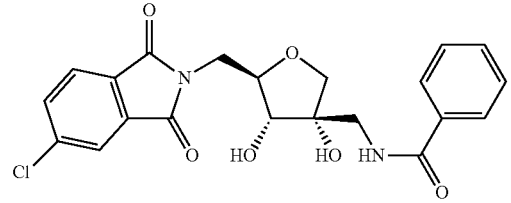 [SMILES: O=C(NC[C@]1(O)CO[C@H](CN2C(=O)c3ccc(Cl)cc3C2=O)[C@H]1O)c1ccccc1]

General procedure 8. White foam, 73.0% $^1$H NMR (300 MHz, DMSO-$d_6$) δ ppm 3.38-3.47 (m, 2 H) 3.51 (d, J=9.7 Hz, 1 H) 3.63-3.92 (m, 5 H) 4.82 (s, 1 H) 5.04 (d, J=7.0 Hz, 1 H) 7.43-7.56 (m, 3 H) 7.78-7.97 (m, 5 H) 8.36 (t, J=5.9 Hz, 1H). $^{13}$C NMR (75 MHz, DMSO-$d_6$) δ ppm 40.5, 44.0, 74.8, 75.4, 78.2, 78.6, 123.2, 124.8, 127.3, 128.2, 130.1, 131.2, 133.5, 134.2, 134.4, 139.3, 166.5, 166.8, 167.1. HRMS (ESI-TOF) m/z: [M+H]$^+$ Calcd for $C_{21}H_{20}ClN_2O_6^+$ 431.10044; Found 431.1018.

N-(((3S,4R,5R)-5-((benzylamino)methyl)-3,4-dihydroxytetrahydrofuran-3-yl)methyl)benzamide (228)

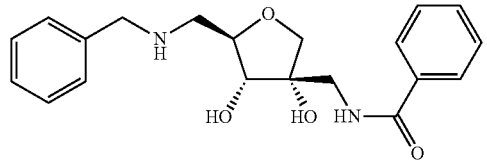 [SMILES: O=C(NC[C@]1(O)CO[C@H](CNCc2ccccc2)[C@H]1O)c1ccccc1]

General procedure 8. White foam, 83.7% $^1$H NMR (300 MHz, DMSO-d$_6$) δ ppm 2.08 (br. s., 1 H) 2.57 (dd, J=12.2, 6.3 Hz, 1 H) 2.73 (dd, J=12.2, 3.1 Hz, 1 H) 3.36-3.47 (m, 2 H) 3.54 (d, J=9.4 Hz, 1 H) 3.59-3.74 (m, 4 H) 3.85 (d, J=9.4 Hz, 1 H) 4.74 (s, 1 H) 4.90 (br. s., 1 H) 7.17-7.33 (m, 5 H) 7.42-7.57 (m, 3 H) 7.81-7.88 (m, 2 H) 8.35 (t, J=6.0 Hz, 1 H). $^{13}$C NMR (75 MHz, DMSO-d$_6$) δ ppm 44.4, 50.8, 53.1, 74.4, 74.8, 77.9, 81.8, 126.5, 127.3, 127.9, 128.1, 128.2, 131.2, 134.4, 140.8, 167.0. HRMS (ESI-TOF) m/z: [M+H]$^+$ Calcd for C$_{20}$H$_{25}$N$_2$O$_4{}^+$ 357.18088; Found 357.1804.

N-(((3S,4R,5R)-5-(benzamidomethyl)-3,4-dihydroxytetrahydrofuran-3-yl)methyl)-N-methylbenzamide (229)

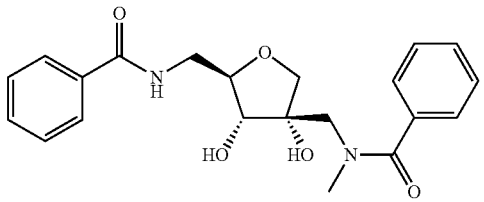 [SMILES: CN(C[C@]1(O)CO[C@H](CNC(=O)c2ccccc2)[C@H]1O)C(=O)c1ccccc1]

General procedure 8. White powder, 79.6% $^1$H NMR (300 MHz, CDCl$_3$) δ ppm 2.61 (s, 3 H) 3.26 (br. s., 2 H) 3.40 (br. s., 1 H) 3.59 (app. t., J=5.9 Hz, 2H) 3.71 (d, J=10.0 Hz, 1 H) 4.14 (d, J=10.0 Hz, 1 H) 4.22 (app. q., J=6.2 Hz, 1 H) 4.93 (d, J=6.7 Hz, 1 H) 6.21 (s, 1 H) 7.34-7.41 (m, 2 H) 7.44-7.53 (m, 3 H) 7.63-7.70 (m, 1 H) 7.73-7.78 (m, 2 H) 7.96-8.02 (m, 2 H) 8.66 (t, J=5.7 Hz, 1 H). $^{13}$C NMR (75 MHz, DMSO-d$_6$) δ ppm 34.0, 41.1, 53.9, 73.9, 76.1, 77.2, 79.4, 127.1, 128.2, 128.5, 129.3, 129.5, 131.1, 133.5, 134.2, 165.4, 166.6. HRMS (ESI-TOF) m/z: [M+H]$^+$ Calcd for C$_{21}$H$_{25}$N$_2$O$_5{}^+$ 385.17580; Found 385.1766.

N-(((3S,4R,5R)-3,4-dihydroxy-5-((1-oxoisoindolin-2-yl)methyl)tetrahydrofuran-3-yl)methyl)benzamide (230)

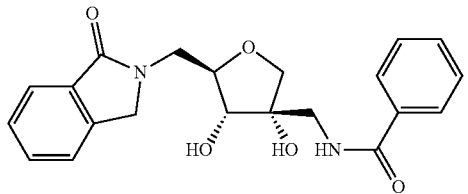 [SMILES: O=C(NC[C@]1(O)CO[C@H](CN2Cc3ccccc3C2=O)[C@H]1O)c1ccccc1]

General procedure 8. White foam, 84.3% $^1$H NMR (300 MHz, DMSO-d$_6$) δ ppm 3.34-3.49 (m, 2 H) 3.54-3.67 (m, 3 H) 3.78-3.93 (m, 3 H) 4.45-4.60 (2×d, J=18.2 Hz, 2 H) 4.77 (br. s., 2 H) 7.40-7.62 (m, 6 H) 7.65-7.71 (m, 1 H) 7.78-7.85 (m, 2 H) 8.38 (t, J=5.9 Hz, 1 H). $^{13}$C NMR (75 MHz, DMSO-d$_6$) δ ppm 44.1, 44.4, 51.0, 74.6, 74.8, 77.9, 81.0, 122.7, 123.3, 127.3, 127.7, 128.2, 131.18, 131.22, 132.1, 134.4, 142.1, 167.1, 167.4. HRMS (ESI-TOF) m/z: [M+H]$^+$ Calcd for C$_{21}$H$_{23}$N$_2$O$_5{}^+$ 383.16015; Found 383.1610.

2-chloro-N-(((2R,3R,4S)-4-((1,3-dioxoisoindolin-2-yl)methyl)-3,4-dihydroxytetrahydrofuran-2-yl)methyl)benzamide (231)

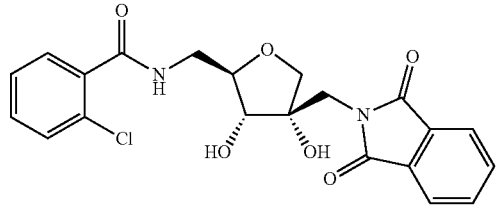 [SMILES: O=C(NC[C@H]1OC[C@@](O)(CN2C(=O)c3ccccc3C2=O)[C@@H]1O)c1ccccc1Cl]

General procedure 8. White powder, 82.2% $^1$H NMR (300 MHz, DMSO-d$_6$) δ ppm 3.35-3.64 (m, 4 H) 3.71-3.87 (m, 3 H) 3.98 (d, J=9.7 Hz, 1 H) 4.65 (s, 1 H) 5.11 (d, J=7.0 Hz, 1 H) 7.30-7.48 (m, 4 H) 7.80-7.91 (m, 4 H) 8.45 (t, J=5.6 Hz, 1 H). $^{13}$C NMR (75 MHz, DMSO-d$_6$) δ ppm 41.2, 42.3, 74.7, 75.2, 77.9, 79.9, 123.0, 126.9, 128.9, 129.5, 129.8, 130.5, 131.8, 134.3, 137.1, 166.5, 168.2. HRMS (ESI-TOF) m/z: [M+H]$^+$ Calcd for C$_{21}$H$_{20}$ClN$_2$O$_6{}^+$ 431.10044; Found 431.1005.

2-chloro-N-(((2R,3R,4S)-3,4-dihydroxy-4-((4-methylbenzamido)methyl)tetrahydrofuran-2-yl)methyl)benzamide (232)

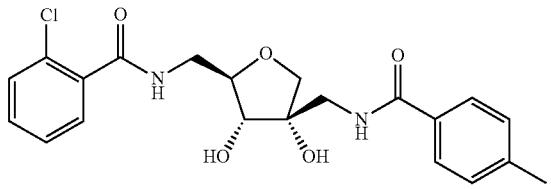 [SMILES: Cc1ccc(C(=O)NC[C@]2(O)CO[C@H](CNC(=O)c3ccccc3Cl)[C@H]2O)cc1]

General procedure 8. White foam, 77.1% $^1$H NMR (300 MHz, DMSO-d$_6$) δ ppm 2.35 (s, 3 H) 3.29-3.60 (m, 5 H) 3.65 (d, J=7.9 Hz, 1 H) 3.71-3.81 (m, 1 H) 3.87 (d, J=9.7 Hz, 1 H) 4.81 (br. s, 2 H) 7.27 (d, J=7.9 Hz, 2 H) 7.30-7.48 (m, 4 H) 7.76 (app. d, J=8.2 Hz, 2 H) 8.28 (t, J=6.0 Hz, 1 H) 8.45 (t, J=5.7 Hz, 1 H). $^{13}$C NMR (75 MHz, DMSO-d$_6$) δ ppm 20.9, 41.3, 44.2, 74.4, 74.7, 78.1, 80.6, 126.9, 127.3, 128.7, 128.9, 129.5, 129.9, 130.5, 131.5, 137.0, 141.1, 166.5, 166.9. HRMS (ESI-TOF) m/z: [M+H]$^+$ Calcd for C$_{21}$H$_{24}$ClN$_2$O$_5{}^+$ 419.13683, found 419.1368.

2-chloro-N-(((2R,3R,4S)-4-((4-fluorobenzamido)methyl)-3,4-dihydroxytetrahydrofuran-2-yl)methyl)benzamide (233)

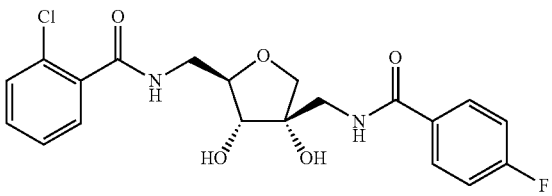 [SMILES: O=C(NC[C@]1(O)CO[C@H](CNC(=O)c2ccccc2Cl)[C@H]1O)c1ccc(F)cc1]

General procedure 8. White powder, 82.4% $^1$H NMR (300 MHz, DMSO-d$_6$) δ ppm 3.33-3.54 (m, 4 H) 3.57 (d, J=9.7 Hz, 1 H) 3.62-3.69 (m, 1 H) 3.72-3.81 (m, 1 H) 3.88 (d, J=9.7 Hz, 1 H) 4.77 (s, 1 H) 5.01 (d, J=6.7 Hz, 1 H) 7.25-7.49 (m, 6 H) 7.88-7.97 (m, 2 H) 8.40 (t, J=5.9 Hz, 1 H) 8.46 (t, J=5.7 Hz, 1 H). $^{19}$F NMR (282 MHz, DMSO-d$_6$) δ ppm −109.5 (m). $^{13}$C NMR (75 MHz, DMSO-d$_6$) δ ppm 41.3, 44.3, 74.4, 74.7, 78.0, 80.6, 115.1 (d, J=21.9 Hz), 126.9, 128.9, 129.5, 129.9, 130.0 (d, J=9.2 Hz), 130.6, 130.9 (d, J=2.3 Hz), 137.0, 163.9 (d, J=248.8 Hz), 166.0, 166.5. HRMS (ESI-TOF) m/z: [M+H]$^+$ Calcd for C$_{20}$H$_{21}$ClFN$_2$O$_6{}^+$ 423.11175, found 423.1122.

2-chloro-N-(((2R,3R,4S)-4-((4-chlorobenzamido) methyl)-3,4-dihydroxytetrahydrofuran-2-yl)methyl) benzamide (234)

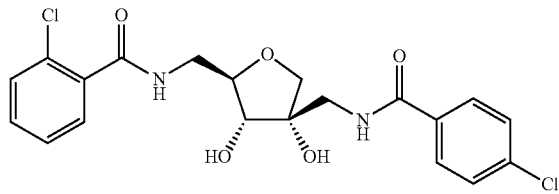 [SMILES: O=C(NC[C@]1(O)CO[C@H](CNC(=O)c2ccccc2Cl)[C@H]1O)c1ccc(Cl)cc1]

General procedure 8. White foam, 90.3% $^1$H NMR (300 MHz, DMSO-d$_6$) δ ppm 3.33-3.60 (m, 5 H) 3.61-3.69 (m, 1 H) 3.71-3.81 (m, 1 H) 3.87 (d, J=9.4 Hz, 1 H) 4.86 (br. s., 2 H) 7.29-7.48 (m, 4 H) 7.51-7.57 (m, 2 H) 7.83-7.94 (m, 2 H) 8.38-8.52 (m, 2 H). $^{13}$C NMR (75 MHz, DMSO-d$_6$) δ ppm 41.3, 44.3, 74.4, 74.7, 78.0, 80.6, 126.9, 128.3, 128.9, 129.3, 129.5, 129.9, 130.5, 133.2, 136.0, 137.0, 166.0, 166.5. HRMS (ESI-TOF) m/z: [M+H]$^+$ Calcd for C$_{20}$H$_{21}$Cl$_2$N$_2$O$_6{}^+$ 439.08220, found 439.0832.

2-chloro-N-(((2R,3R,4S)-3,4-dihydroxy-4-((4-methoxybenzamido)methyl)tetrahydrofuran-2-yl) methyl)benzamide (235)

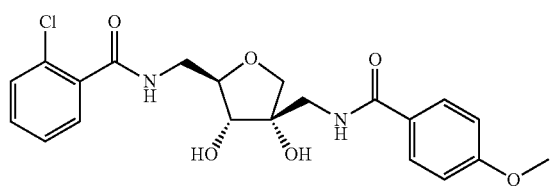 [SMILES: COc1ccc(C(=O)NC[C@]2(O)CO[C@H](CNC(=O)c3ccccc3Cl)[C@H]2O)cc1]

General procedure 8. White foam, 86.7% $^1$H NMR (300 MHz, DMSO-d$_6$) δ ppm 3.31-3.59 (m, 5 H) 3.62-3.68 (m, 1 H) 3.71-3.79 (m, 1 H) 3.81 (s, 3 H) 3.87 (d, J=9.7 Hz, 1 H) 4.73 (br. s., 2 H) 6.94-7.04 (m, 2 H) 7.27-7.50 (m, 4 H) 7.80-7.88 (m, 2 H) 8.23 (t, J=6.0 Hz, 1 H) 8.46 (t, J=5.6 Hz, 1 H). $^{13}$C NMR (75 MHz, DMSO-d$_6$) δ ppm 41.3, 44.2, 55.4, 74.4, 74.7, 78.1, 80.6, 113.4, 126.5, 126.9, 128.9, 129.2, 129.5, 129.9, 130.5, 137.0, 161.6, 166.47, 166.55. HRMS (ESI-TOF) m/z: [M+H]$^+$ Calcd for C$_{21}$H$_{24}$ClN$_2$O$_6{}^+$ 435.13174, found 435.1319.

2-chloro-N-(((2R,3R,4S)-4-((4-cyanobenzamido) methyl)-3,4-dihydroxytetrahydrofuran-2-yl)methyl) benzamide (236)

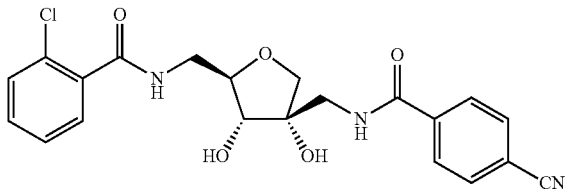 [SMILES: N#Cc1ccc(C(=O)NC[C@]2(O)CO[C@H](CNC(=O)c3ccccc3Cl)[C@H]2O)cc1]

General procedure 8. White foam, 81.2% $^1$H NMR (300 MHz, DMSO-d$_6$) δ ppm 3.34-3.55 (m, 4 H) 3.58 (d, J=9.7 Hz, 1 H) 3.62-3.70 (m, 1 H) 3.73-3.81 (m, 1 H) 3.88 (d, J=9.7 Hz, 1 H) 4.77 (s, 1 H) 5.05 (d, J=6.7 Hz, 1 H) 7.29-7.48 (m, 4 H) 7.93-7.98 (m, 2 H) 7.98-8.04 (m, 2 H) 8.46 (t, J=5.7 Hz, 1 H) 8.62 (t, J=5.9 Hz, 1H). $^{13}$C NMR (75 MHz, DMSO-d$_6$) δ ppm 41.3, 44.5, 74.4, 74.7, 77.9, 80.6, 113.5, 118.4, 126.9, 128.2, 128.9, 129.5, 129.9, 130.6, 132.3, 137.0, 138.5, 165.7, 166.5. HRMS (ESI-TOF) m/z: [M+H]$^+$ Calcd for C$_{21}$H$_{21}$ClN$_3$O$_5{}^+$ 430.11642, found 430.1175.

2-chloro-N-(((2R,3R,4S)-4-((4-(dimethylamino) benzamido)methyl)-3,4-dihydroxytetrahydrofuran-2-yl)methyl)benzamide (237)

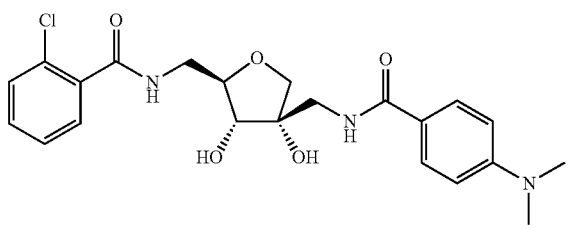 [SMILES: CN(C)c1ccc(C(=O)NC[C@]2(O)CO[C@H](CNC(=O)c3ccccc3Cl)[C@H]2O)cc1]

General procedure 8. White foam, 90.3% $^1$H NMR (300 MHz, DMSO-d$_6$) δ ppm 2.97 (s, 6 H) 3.33-3.58 (m, 5 H) 3.63 (d, J=7.9 Hz, 1 H) 3.71-3.80 (m, 1 H) 3.86 (d, J=9.7 Hz, 1 H) 5.26 (br. s., 2 H) 6.66-6.75 (m, 2 H) 7.29-7.49 (m, 4 H) 7.67-7.77 (m, 2 H) 8.05 (t, J=5.9 Hz, 1 H) 8.45 (t, J=5.7 Hz, 1 H). $^{13}$C NMR (75 MHz, DMSO-d$_6$) δ ppm 39.8, 41.4, 44.2, 74.4, 74.7, 78.2, 80.7, 110.8, 120.9, 126.9, 128.7, 128.9, 129.5, 129.9, 130.5, 137.0, 152.1, 166.5, 167.1. HRMS (ESI-TOF) m/z: [M+H]$^+$ Calcd for C$_{22}$H$_{27}$ClN$_3$O$_6{}^+$ 448.16338, found 448.1623.

2-chloro-N-(((2R,3R,4S)-3,4-dihydroxy-4-((4-(trifluoromethyl)benzamido)methyl)tetrahydrofuran-2-yl)methyl)benzamide (238)

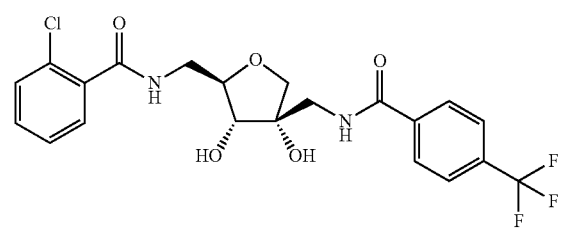 [SMILES: O=C(NC[C@]1(O)CO[C@H](CNC(=O)c2ccccc2Cl)[C@H]1O)c1ccc(C(F)(F)F)cc1]

General procedure 8. White powder, 90.5% $^1$H NMR (300 MHz, DMSO-$d_6$) δ ppm 3.34-3.56 (m, 4 H) 3.59 (d, J=9.7 Hz, 1 H) 3.64-3.70 (m, 1 H) 3.73-3.82 (m, 1 H) 3.89 (d, J=9.7 Hz, 1 H) 4.85 (br. s., 2 H) 7.26-7.49 (m, 4 H) 7.85 (app. d, J=8.2 Hz, 2 H) 8.06 (app. d, J=8.2 Hz, 2 H) 8.46 (t, J=5.6 Hz, 1 H) 8.60 (t, J=5.9 Hz, 1 H). $^{19}$F NMR (282 MHz, DMSO-$d_6$) δ ppm −61.3 (s). $^{13}$C NMR (75 MHz, DMSO-$d_6$) δ ppm 41.3, 44.4, 74.4, 74.8, 78.0, 80.6, 124.0 (q, J=272.4 Hz), 125.3 (q, J=3.46 Hz), 126.9, 128.3, 128.9, 129.5, 129.9, 130.5, 131.1 (q, J=31.7 Hz), 137.0, 138.3, 165.9, 166.5. HRMS (ESI-TOF) m/z: [M+H]$^+$ Calcd for $C_{21}H_{21}ClF_3N_2O_5^+$ 473.10856, found 473.1092.

N-(((3S,4R,5R)-5-((2-chlorobenzamido)methyl)-3,4-dihydroxytetrahydrofuran-3-yl)methyl)isonicotinamide (239)

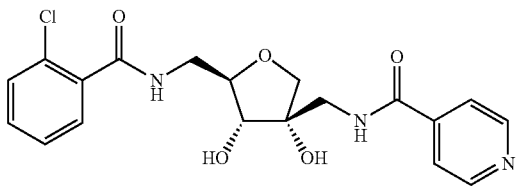

General procedure 8. White powder, 75.1% $^1$H NMR (300 MHz, DMSO-$d_6$) δ ppm 3.34-3.55 (m, 4 H) 3.58 (d, J=9.7 Hz, 1 H) 3.63-3.71 (m, 1 H) 3.73-3.82 (m, 1 H) 3.88 (d, J=9.7 Hz, 1 H) 4.77 (s, 1 H) 5.06 (d, J=6.7 Hz, 1 H) 7.28-7.48 (m, 4 H) 7.74-7.79 (m, 2 H) 8.46 (t, J=5.6 Hz, 1 H) 8.65 (t, J=5.9 Hz, 1 H) 8.69-8.76 (m, 2H). $^{13}$C NMR (75 MHz, DMSO-$d_6$) δ ppm 41.2, 44.3, 74.4, 74.7, 77.9, 80.6, 121.4, 126.9, 128.9, 129.5, 129.9, 130.6, 137.0, 141.4, 150.1, 165.4, 166.5. HRMS (ESI-TOF) m/z: [M+H]$^+$ Calcd for $C_{19}H_{21}ClN_3O_6^+$ 406.11642, found 406.1175.

2-chloro-N-(((2R,3R,4S)-4-((3-fluorobenzamido)methyl)-3,4-dihydroxytetrahydrofuran-2-yl)methyl)benzamide (240)

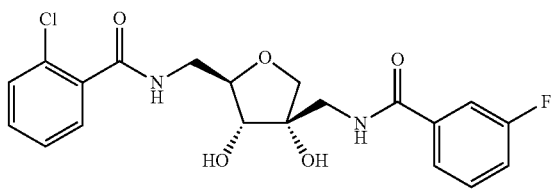 [SMILES: O=C(NC[C@]1(O)CO[C@H](CNC(=O)c2ccccc2Cl)[C@H]1O)c1cccc(F)c1]

General procedure 8. White powder, 92.2% $^1$H NMR (300 MHz, DMSO-$d_6$) δ ppm 3.35-3.55 (m, 4 H) 3.58 (d, J=9.7 Hz, 1 H) 3.63-3.70 (m, 1 H) 3.73-3.81 (m, 1 H) 3.88 (d, J=9.7 Hz, 1 H) 4.77 (s, 1 H) 5.03 (d, J=6.7 Hz, 1 H) 7.27-7.48 (m, 5 H) 7.53 (app. td, J=8.0, 6.0 Hz, 1 H) 7.63-7.75 (m, 2 H) 8.39-8.52 (m, 2 H). $^{19}$F NMR (282 MHz, DMSO-$d_6$) δ ppm −113.0 (m). $^{13}$C NMR (75 MHz, DMSO-$d_6$) δ ppm 41.3, 44.4, 74.4, 74.7, 78.0, 80.6, 114.2 (d, J=23.0 Hz), 118.1 (d, J=21.9 Hz), 123.6 (d, J=2.3 Hz), 126.9, 128.9, 129.5, 129.9, 130.4 (d, J=6.9 Hz), 130.6, 136.8 (d, J=6.9 Hz), 137.0, 161.9 (d, J=244.1 Hz), 165.7 (d, J=2.3 Hz), 166.5. HRMS (ESI-TOF) m/z: [M+H]$^+$ Calcd for $C_{20}H_{21}ClFN_2O_6^+$ 423.11175, found 423.1129.

2-chloro-N-(((2R,3R,4S)-4-((3-chlorobenzamido)methyl)-3,4-dihydroxytetrahydrofuran-2-yl)methyl)benzamide (241)

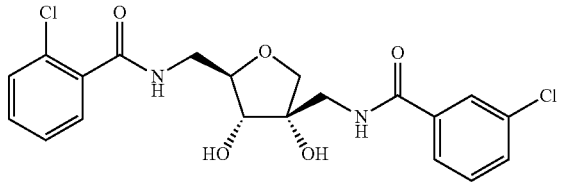 [SMILES: O=C(NC[C@]1(O)CO[C@H](CNC(=O)c2ccccc2Cl)[C@H]1O)c1cccc(Cl)c1]

General procedure 8. White powder, 59.4% $^1$H NMR (300 MHz, DMSO-$d_6$) δ ppm 3.34-3.60 (m, 5 H) 3.63-3.68 (m, 1 H) 3.72-3.81 (m, 1 H) 3.87 (d, J=9.7 Hz, 1 H) 4.82 (br. s., 2 H) 7.27-7.54 (m, 5 H) 7.58-7.64 (m, 1 H) 7.82 (app. dt, J=7.6, 1.3 Hz, 1 H) 7.91 (app. t, J=1.6 Hz, 1 H) 8.41-8.55 (m, 2 H). $^{13}$C NMR (75 MHz, DMSO-$d_6$) δ ppm 41.3, 44.4, 74.4, 74.7, 78.0, 80.6, 126.2, 126.9, 127.2, 128.9, 129.5, 129.9, 130.2, 130.5, 131.0, 133.1, 136.4, 137.0, 165.6, 166.5. HRMS (ESI-TOF) m/z: [M+H]$^+$ Calcd for $C_{20}H_{21}Cl_2N_2O_6^+$ 439.08220, found 439.0820.

2-chloro-N-(((2R,3R,4S)-3,4-dihydroxy-4-((3-(trifluoromethyl)benzamido)methyl)tetrahydrofuran-2-yl)methyl)benzamide (242)

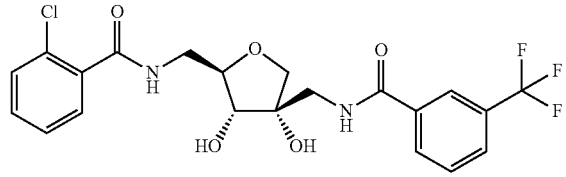 [SMILES: O=C(NC[C@]1(O)CO[C@H](CNC(=O)c2ccccc2Cl)[C@H]1O)c1cccc(C(F)(F)F)c1]

General procedure 8. White foam, 89.6% $^1$H NMR (300 MHz, DMSO-$d_6$) δ ppm 3.34-3.56 (m, 4 H) 3.59 (d, J=9.4 Hz, 1 H) 3.65-3.70 (m, 1 H) 3.74-3.82 (m, 1 H) 3.89 (d, J=9.7 Hz, 1 H) 4.82 (br. s., 2 H) 7.27-7.48 (m, 4 H) 7.73 (app. t, J=7.9 Hz, 1 H) 7.91 (app. d, J=7.9 Hz, 1 H) 8.12-8.24 (m, 2 H) 8.46 (t, J=5.7 Hz, 1H) 8.67 (t, J=5.9 Hz, 1 H). $^{19}$F NMR (282 MHz, DMSO-$d_6$) δ ppm −61.1 (s). $^{13}$C NMR (75 MHz, DMSO-$d_6$) δ ppm 41.3, 44.4, 74.4, 74.8, 78.0, 80.6, 124.02 (q, J=273.4 Hz), 124.03 (q, J=4.0 Hz), 126.9, 127.8 (q, J=3.5 Hz), 128.9, 129.03 (q, J=31.9 Hz), 129.5, 129.6, 129.9, 130.5, 131.5, 135.3, 137.0, 165.6, 166.5. HRMS (ESI-TOF) m/z: [M+H]$^+$ Calcd for $C_{21}H_{21}ClF_3N_2O_5^+$ 473.10856, found 473.1096.

N-(((3S,4R,5R)-5-((2-chlorobenzamido)methyl)-3,4-dihydroxytetrahydrofuran-3-yl)methyl)nicotinamide (243)

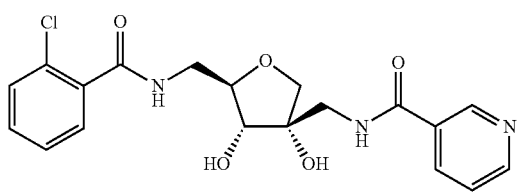 [SMILES: O=C(NC[C@]1(O)CO[C@H](CNC(=O)c2ccccc2Cl)[C@H]1O)c1cccnc1]

General procedure 8. White powder, 58.6% $^1$H NMR (300 MHz, DMSO-d$_6$) δ ppm 3.35-3.55 (m, 4 H) 3.58 (d, J=9.7 Hz, 1 H) 3.63-3.71 (m, 1 H) 3.74-3.81 (m, 1 H) 3.88 (d, J=9.7 Hz, 1 H) 4.77 (s, 1 H) 5.04 (d, J=6.7 Hz, 1 H) 7.29-7.54 (m, 5 H) 8.16-8.23 (ddd, J=8.0, 2.2, 1.8 Hz, 1 H) 8.46 (t, J=5.7 Hz, 1 H) 8.58 (t, J=6.0 Hz, 1 H) 8.71 (app. dd, J=4.8, 1.6 Hz, 1 H) 9.01 (app. dd, J=2.3, 0.9 Hz, 1 H). $^{13}$C NMR (75 MHz, DMSO-d$_6$) δ ppm 41.3, 44.3, 74.4, 74.7, 78.0, 80.6, 123.4, 126.9, 128.9, 129.5, 129.9, 130.0, 130.5, 135.1, 137.0, 148.5, 151.8, 165.6, 166.5. HRMS (ESI-TOF) m/z: [M+H]$^+$ Calcd for C$_{19}$H$_{21}$ClN$_3$O$_6^+$ 406.11642, found 406.1175.

2-chloro-N-(((2R,3R,4S)-3,4-dihydroxy-4-((2-methylbenzamido)methyl)tetrahydrofuran-2-yl)methyl)benzamide (244)

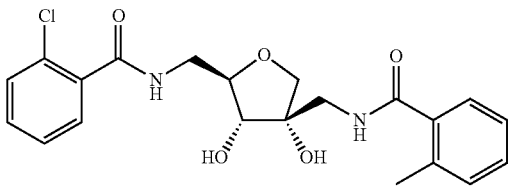 [SMILES: Cc1ccccc1C(=O)NC[C@]1(O)CO[C@H](CNC(=O)c2ccccc2Cl)[C@H]1O]

General procedure 8. White foam, 94.3% $^1$H NMR (300 MHz, DMSO-d$_6$) δ ppm 2.33 (s, 3 H) 3.33-3.43 (m, 3 H) 3.47-3.61 (m, 2 H) 3.62-3.69 (m, 1 H) 3.71-3.82 (m, 1 H) 3.91 (d, J=9.7 Hz, 1 H) 4.75 (br. s, 2 H) 7.16-7.27 (m, 2 H) 7.28-7.51 (m, 6 H) 8.14 (t, J=5.9 Hz, 1 H) 8.47 (t, J=5.6 Hz, 1 H). $^{13}$C NMR (75 MHz, DMSO-d$_6$) δ ppm 19.4, 41.4, 44.1, 74.5, 74.8, 77.9, 80.6, 125.4, 126.9, 127.1, 128.9, 129.3, 129.5, 129.9, 130.4, 130.6, 135.2, 137.0, 137.1, 166.5, 169.7. HRMS (ESI-TOF) m/z: [M+H]$^+$ Calcd for C$_{21}$H$_{24}$ClN$_2$O$_5^+$ 419.13683, found 419.1374.

2-chloro-N-(((2R,3R,4S)-4-((2-fluorobenzamido)methyl)-3,4-dihydroxytetrahydrofuran-2-yl)methyl)benzamide (245)

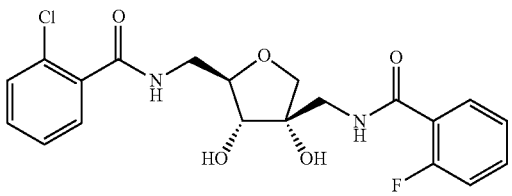 [SMILES: O=C(NC[C@]1(O)CO[C@H](CNC(=O)c2ccccc2Cl)[C@H]1O)c1ccccc1F]

General procedure 8. White foam, 95.0% $^1$H NMR (300 MHz, DMSO-d$_6$) δ ppm 3.32-3.55 (m, 4 H) 3.58 (d, J=9.7 Hz, 1 H) 3.64-3.69 (m, 1 H) 3.72-3.82 (m, 1 H) 3.87 (d, J=9.7 Hz, 1 H) 4.80 (br. s., 2 H) 7.21-7.60 (m, 7 H) 7.61-7.72 (m, 1 H) 8.15 (dd, J=9.4, 5.6 Hz, 1 H) 8.47 (t, J=5.7 Hz, 1 H). $^{19}$F NMR (282 MHz, DMSO-d$_6$) δ ppm –114.2 (m). $^{13}$C NMR (75 MHz, DMSO-d$_6$) δ ppm 41.4, 44.3, 74.5, 74.6, 77.7, 80.6, 116.1 (d, J=23.0 Hz), 123.7 (d, J=15.0 Hz), 124.5 (d, J=3.5 Hz), 126.9, 128.9, 129.5, 129.9, 130.3 (d, J=3.5 Hz), 130.6, 132.5 (d, J=9.2 Hz), 137.0, 159.2 (d, J=248.8 Hz), 164.1, 166.5. HRMS (ESI-TOF) m/z: [M+H]$^+$ Calcd for C$_{20}$H$_{21}$ClFN$_2$O$_5^+$ 423.11175, found 423.1132.

N-(((3S,4R,5R)-5-((2-chlorobenzamido)methyl)-3,4-dihydroxytetrahydrofuran-3-yl)methyl)furan-2-carboxamide (246)

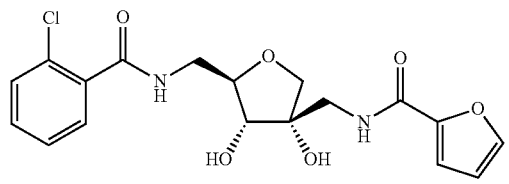 [SMILES: O=C(NC[C@]1(O)CO[C@H](CNC(=O)c2ccccc2Cl)[C@H]1O)c1ccco1]

General procedure 8. White foam, 83.1% $^1$H NMR (300 MHz, DMSO-d$_6$) δ ppm 3.33-3.57 (m, 5 H) 3.59-3.65 (m, 1 H) 3.72-3.80 (m, 1 H) 3.85 (d, J=9.7 Hz, 1 H) 4.73 (br. s., 2 H) 6.63 (dd, J=3.2, 1.8 Hz, 1 H) 7.14 (dd, J=3.5, 0.9 Hz, 1 H) 7.30-7.48 (m, 4 H) 7.84 (dd, J=1.8, 0.9 Hz, 1 H) 8.13 (t, J=6.0 Hz, 1 H) 8.45 (t, J=5.7 Hz, 1 H). $^{13}$C NMR (75 MHz, DMSO-d$_6$) δ ppm 41.2, 43.5, 74.3, 74.7, 77.9, 80.5, 111.9, 113.7, 126.9, 128.9, 129.5, 129.9, 130.5, 137.0, 145.1, 147.7, 158.3, 166.5. HRMS (ESI-TOF) m/z: [M+H]$^+$ Calcd for C$_{18}$H$_{20}$ClN$_2$O$_6^+$ 395.10044, found 395.1005.

N-(((3S,4R,5R)-5-((2-chlorobenzamido)methyl)-3,4-dihydroxytetrahydrofuran-3-yl)methyl)furan-3-carboxamide (247)

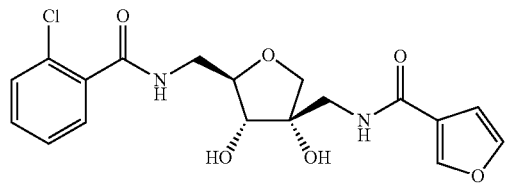 [SMILES: O=C(NC[C@]1(O)CO[C@H](CNC(=O)c2ccccc2Cl)[C@H]1O)c1ccoc1]

General procedure 8. White foam, 79.4% $^1$H NMR (300 MHz, DMSO-d$_6$) δ ppm 3.29-3.58 (m, 5 H) 3.59-3.65 (m, 1 H) 3.72-3.80 (m, 1 H) 3.85 (d, J=9.7 Hz, 1 H) 4.70 (br. s., 2 H) 6.88 (dd, J=1.9, 0.7 Hz, 1 H) 7.29-7.49 (m, 4 H) 7.72 (app. t, J=1.8 Hz, 1 H) 8.14 (t, J=6.0 Hz, 1 H) 8.22 (dd, J=1.6, 0.7 Hz, 1 H) 8.46 (t, J=5.6 Hz, 1H). $^{13}$C NMR (75 MHz, DMSO-d$_6$) δ ppm 41.3, 43.6, 74.2, 74.6, 78.1, 80.7, 109.1, 122.6, 126.9, 128.9, 129.5, 129.9, 130.6, 137.0, 143.9, 145.3, 162.3, 166.5. HRMS (ESI-TOF) m/z: [M+H]$^+$ Calcd for C$_{18}$H$_{20}$ClN$_2$O$_6^+$ 395.10044, found 395.1004.

N-(((3S,4R,5R)-5-((2-chlorobenzamido)methyl)-3,4-dihydroxytetrahydrofuran-3-yl)methyl)pyrimidine-5-carboxamide (248)

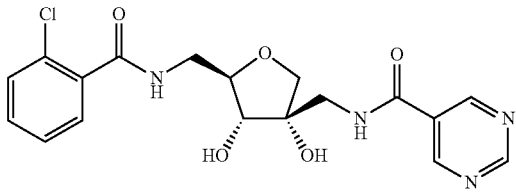 [SMILES: O=C(NC[C@]1(O)CO[C@H](CNC(=O)c2ccccc2Cl)[C@H]1O)c1cncnc1]

General procedure 8. White powder, 66.1% $^1$H NMR (300 MHz, DMSO-d$_6$) δ ppm 3.35-3.73 (m, 6 H) 3.74-3.81 (m, 1 H) 3.88 (d, J=9.7 Hz, 1 H) 4.79 (s, 1 H) 5.08 (d, J=6.7 Hz, 1 H) 7.29-7.48 (m, 4 H) 8.46 (t, J=5.7 Hz, 1 H) 8.77 (t, J=5.9 Hz, 1 H) 9.17 (app. s, 2 H) 9.31 (app. s, 1 H). $^{13}$C NMR (75 MHz, DMSO-d$_6$) δ ppm 41.2, 44.3, 74.4, 74.7, 77.9, 80.7, 126.9, 127.9, 128.9, 129.5, 129.8, 130.6, 137.0, 156.0, 160.0, 163.8, 166.5. HRMS (ESI-TOF) m/z: [M+H]$^+$ Calcd for C$_{18}$H$_{20}$ClN$_4$O$_5^+$ 407.11167, found 407.1121.

N,N'-(((2R,3R,4S)-3,4-dihydroxytetrahydrofuran-2,4-diyl)bis(methylene))bis(2-chlorobenzamide) (249)

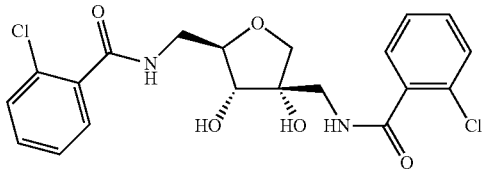 [SMILES: O=C(NC[C@H]1OC[C@@](O)(CNC(=O)c2ccccc2Cl)[C@@H]1O)c1ccccc1Cl]

General procedure 8. White foam, 94.8% $^1$H NMR (300 MHz, DMSO-d$_6$) δ ppm 3.26-3.48 (m, 3 H) 3.49-3.71 (m, 3 H) 3.74-3.82 (m, 1 H) 3.93 (d, J=9.7 Hz, 1 H) 4.62 (br. s., 2 H) 7.31-7.52 (m, 8 H) 8.39 (t, J=5.9 Hz, 1 H) 8.48 (t, J=5.6 Hz, 1 H). $^{13}$C NMR (75 MHz, DMSO-d$_6$) δ ppm 41.6, 43.9, 74.5, 74.6, 77.9, 80.6, 126.9, 127.0, 128.96, 129.02, 129.51, 129.54, 129.86, 129.91, 130.6, 130.7, 136.9, 137.0, 166.5, 166.9. HRMS (ESI-TOF) m/z: [M+H]$^+$ Calcd for C$_{20}$H$_{21}$Cl$_2$N$_2$O$_5^+$ 439.08220; Found 439.0822.

N-(((2R,3R,4S)-4-((2-chlorobenzamido)methyl)-3,4-dihydroxytetrahydrofuran-2-yl)methyl)-[1,1'-biphenyl]-4-carboxamide (250)

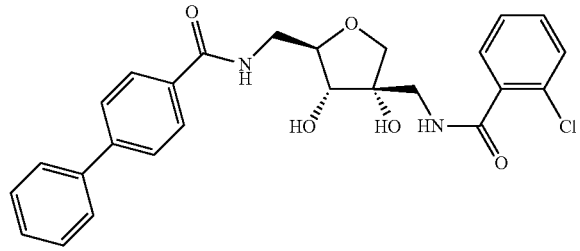 [SMILES: O=C(NC[C@H]1OC[C@@](O)(CNC(=O)c2ccccc2Cl)[C@@H]1O)c1ccc(-c2ccccc2)cc1]

General procedure 8. White powder, 94.2% $^1$H NMR (300 MHz, DMSO-d$_6$) δ ppm 3.31-3.47 (m, 3 H) 3.56-3.69 (m, 3 H) 3.83 (app. dt, J=7.5, 3.7 Hz, 1 H) 3.94 (d, J=9.7 Hz, 1 H) 4.74 (br. s., 2 H) 7.33-7.53 (m, 7 H) 7.70-7.79 (m, 4 H) 7.94-8.00 (m, 2 H) 8.41 (t, J=6.0 Hz, 1 H) 8.56 (t, J=5.7 Hz, 1 H). $^{13}$C NMR (75 MHz, DMSO-d$_6$) δ ppm 42.6, 44.2, 74.9, 75.1, 78.4, 81.1, 126.9, 127.3, 127.4, 128.4, 129.42, 129.47, 130.0, 130.3, 131.2, 133.74, 133.76, 137.3, 139.7, 143.0, 166.4, 167.3. HRMS (ESI-TOF) m/z: [M+H]$^+$ Calcd for C$_{26}$H$_{26}$ClN$_2$O$_5^+$ 481.15248; Found 481.1532.

N-(((2R,3R,4S)-4-((2-chlorobenzamido)methyl)-3,4-dihydroxytetrahydrofuran-2-yl)methyl)pyridazine-4-carboxamide (251)

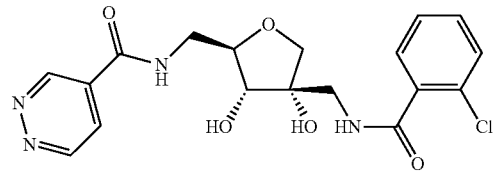 [SMILES: O=C(NC[C@H]1OC[C@@](O)(CNC(=O)c2ccccc2Cl)[C@@H]1O)c1ccnnc1]

General procedure 8. White foam, 87.9% $^1$H NMR (300 MHz, DMSO-d$_6$) δ ppm 3.34-3.49 (m, 3 H) 3.56-3.70 (m, 3 H) 3.81 (app. dt, J=7.5, 3.5 Hz, 1 H) 3.94 (d, J=9.7 Hz, 1 H) 4.73 (s, 1 H) 5.08 (d, J=6.7 Hz, 1 H) 7.32-7.51 (m, 4 H) 8.01 (dd, J=5.6, 2.3 Hz, 1 H) 8.41 (t, J=6.0 Hz, 1 H) 9.10 (t, J=5.6 Hz, 1 H) 9.41 (dd, J=5.3, 1.2 Hz, 1 H) 9.54 (dd, J=2.3, 1.2 Hz, 1 H). $^{13}$C NMR (75 MHz, DMSO-d$_6$) δ ppm 42.1, 43.6, 74.4, 74.5, 77.9, 80.4, 124.2, 127.0, 129.0, 129.5, 129.8, 130.7, 131.5, 136.9, 148.9, 152.1, 163.4, 166.9. HRMS (ESI-TOF) m/z: [M+H]$^+$ Calcd for C$_{18}$H$_{20}$ClN$_4$O$_5^+$ 407.11167; Found 407.1114.

N-(((3S,4R,5R)-5-((2-chlorobenzamido)methyl)-3,4-dihydroxytetrahydrofuran-3-yl)methyl)-[1,1'-biphenyl]-4-carboxamide (252)

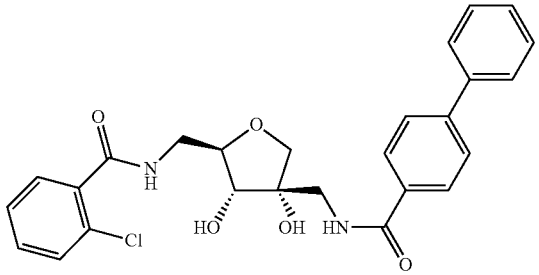 [SMILES: O=C(NC[C@]1(O)CO[C@H](CNC(=O)c2ccccc2Cl)[C@H]1O)c1ccc(-c2ccccc2)cc1]

General procedure 8. White powder, 66.1% $^1$H NMR (300 MHz, DMSO-d$_6$) δ ppm 3.33-3.70 (m, 6 H) 3.74-3.82 (m, 1 H) 3.90 (d, J=9.7 Hz, 1 H) 4.89 (br. s, 2 H) 7.28-7.54 (m, 7 H) 7.70-7.80 (m, 4 H) 7.93-8.00 (m, 2 H) 8.38-8.51 (m, 2H). $^{13}$C NMR (75 MHz, DMSO-d$_6$) δ ppm 41.3, 44.3, 74.4, 74.8, 78.1, 80.6, 126.46 (2C), 126.9, 128.03 (2C), 128.9, 129.0, 129.5, 129.9, 130.5, 133.2, 137.0, 139.2, 142.8, 166.5, 166.7. HRMS (ESI-TOF) m/z: [M+H]$^+$ Calcd for C$_{26}$H$_{26}$ClN$_2$O$_5^+$ 481.15248; Found 481.1513.

N-(((2R,3R,4S)-4-([1,1'-biphenyl]-4-carboxamidomethyl)-3,4-dihydroxytetrahydrofuran-2-yl)methyl)pyridazine-4-carboxamide (253)

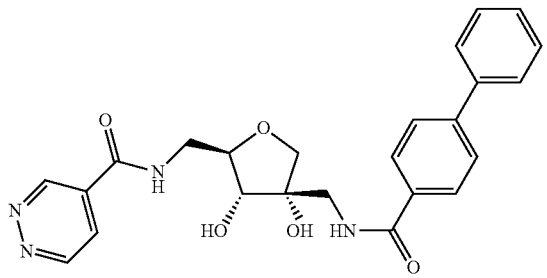 [SMILES: O=C(NC[C@H]1OC[C@@](O)(CNC(=O)c2ccc(-c3ccccc3)cc2)[C@@H]1O)c1ccnnc1]

General procedure 8. White powder, 87.4% $^1$H NMR (300 MHz, DMSO-d$_6$) δ ppm 3.38-3.53 (m, 3 H) 3.54-3.71 (m, 3 H) 3.81 (app. td, J=7.3, 3.5 Hz, 1 H) 3.91 (d, J=9.4 Hz, 1 H) 4.84 (br. s., 1 H) 5.04 (br. s., 1 H) 7.38-7.54 (m, 3 H) 7.69-7.77 (m, 4 H) 7.93 (app. d, J=8.2 Hz, 2 H) 7.97 (dd, J=5.3, 2.3 Hz, 1 H) 8.44 (t, J=5.9 Hz, 1H) 9.09 (t, J=5.6 Hz, 1 H) 9.38 (dd, J=5.3, 1.2 Hz, 1 H) 9.53 (dd, J=2.3, 1.2 Hz, 1 H). $^{13}$C NMR (75 MHz, DMSO-d$_6$) δ ppm 41.9, 44.1, 74.4, 74.7, 78.1, 80.5, 124.2, 126.4, 126.9, 127.97 (2 C), 129.0, 131.5, 133.1, 139.2, 142.8, 148.9, 152.0, 163.4, 166.7. HRMS (ESI-TOF) m/z: [M+H]$^+$ Calcd for C$_{24}$H$_{25}$N$_4$O$_5$$^+$ 449.18195; Found 449.1801.

N-(((3S,4R,5R)-5-((1,3-dioxoisoindolin-2-yl)methyl)-3,4-dihydroxytetrahydrofuran-3-yl)methyl)-[1,1'-biphenyl]-4-carboxamide (254)

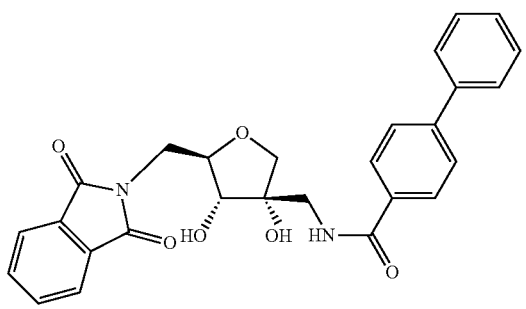 [SMILES: O=C(NC[C@]1(O)CO[C@H](CN2C(=O)c3ccccc3C2=O)[C@H]1O)c1ccc(-c2ccccc2)cc1]

General procedure 8. White powder, 81.0% $^1$H NMR (300 MHz, DMSO-d$_6$) δ ppm 3.44 (app. d, J=5.9 Hz, 2 H) 3.53 (d, J=9.7 Hz, 1 H) 3.64-3.96 (m, 5 H) 4.84 (s, 1 H) 5.06 (d, J=6.7 Hz, 1 H) 7.38-7.54 (m, 3 H) 7.70-7.80 (m, 4 H) 7.80-7.91 (m, 4 H) 7.92-7.98 (m, 2 H) 8.43 (t, J=5.9 Hz, 1 H). $^{13}$C NMR (75 MHz, DMSO-d$_6$) δ ppm 44.10 (2 C), 74.7, 75.6, 78.2, 78.6, 123.0, 126.5, 126.9, 128.0, 129.0, 131.5, 133.2, 134.3, 134.4, 139.2, 142.8, 166.7, 167.7. HRMS (ESI-TOF) m/z: [M+H]$^+$ Calcd for C$_{27}$H$_{25}$N$_2$O$_6$$^+$ 473.17071; Found 473.1718.

N-(((3S,4R,5R)-5-((2-chlorobenzamido)methyl)-3,4-dihydroxytetrahydrofuran-3-yl)methyl)pyridazine-4-carboxamide (255)

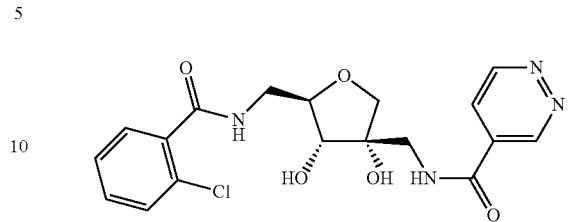

General procedure 8. White foam, 87.9% $^1$H NMR (300 MHz, DMSO-d$_6$) δ ppm 3.33-3.72 (m, 6 H) 3.72-3.82 (m, 1 H) 3.88 (d, J=9.7 Hz, 1 H) 4.80 (s, 1 H) 5.10 (d, J=6.7 Hz, 1 H) 7.27-7.50 (m, 4 H) 8.01 (dd, J=5.3, 2.3 Hz, 1 H) 8.46 (t, J=5.6 Hz, 1 H) 8.91 (t, J=5.9 Hz, 1 H) 9.43 (dd, J=5.3, 1.2 Hz, 1 H) 9.55 (dd, J=2.3, 1.5 Hz, 1H). $^{13}$C NMR (75 MHz, DMSO-d$_6$) δ ppm 41.2, 44.4, 74.4, 74.7, 77.9, 80.6, 124.3, 126.9, 128.9, 129.5, 129.8, 130.6, 131.6, 137.0, 148.9, 152.0, 163.9, 166.5. HRMS (ESI-TOF) m/z: [M+H]$^+$ Calcd for C$_{18}$H$_{20}$ClN$_4$O$_5$$^+$ 407.11167; Found 407.1100.

N-(((3S,4R,5R)-5-([1,1'-biphenyl]-4-carboxamidomethyl)-3,4-dihydroxytetrahydrofuran-3-yl)methyl)pyridazine-4-carboxamide (256)

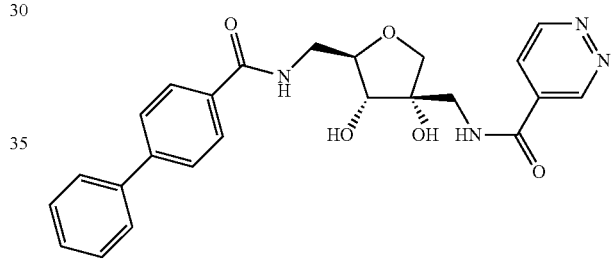

General procedure 8. White powder, 73.3% $^1$H NMR (300 MHz, DMSO-d$_6$) δ ppm 3.39-3.70 (m, 6 H) 3.83 (app. td, J=7.3, 3.7 Hz, 1 H) 3.89 (d, J=9.7 Hz, 1 H) 4.80 (s, 1 H) 5.11 (d, J=6.7 Hz, 1 H) 7.36-7.45 (m, 1 H) 7.45-7.54 (m, 2 H) 7.69-7.77 (m, 4 H) 7.94 (d, J=8.5 Hz, 2 H) 7.99 (dd, J=5.3, 2.3 Hz, 1 H) 8.54 (t, J=5.6 Hz, 1 H) 8.92 (t, J=5.9 Hz, 1 H) 9.41 (dd, J=5.3, 1.2 Hz, 1 H) 9.55 (dd, J=2.3, 1.2 Hz, 1 H). $^{13}$C NMR (75 MHz, DMSO-d$_6$) δ ppm 41.9, 44.4, 74.6, 74.8, 77.9, 80.9, 124.3, 126.4, 126.8, 127.94 (2 C), 129.0, 131.6, 133.3, 139.2, 142.6, 148.9, 152.0, 164.0, 166.0. HRMS (ESI-TOF) m/z: [M+H]$^+$ Calcd for C$_{24}$H$_{25}$N$_4$O$_5$$^+$ 449.18195; Found 449.1829.

N,N'-(((2R,3R,4S)-3,4-dihydroxytetrahydrofuran-2,4-diyl)bis(methylene))bis(pyridazine-4-carboxamide) (257)

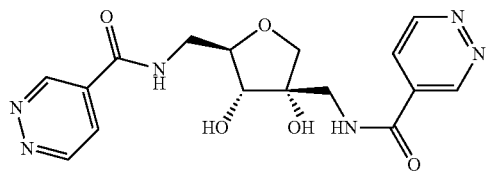 [SMILES: O=C(NC[C@H]1OC[C@@](O)(CNC(=O)c2ccnnc2)[C@@H]1O)c1ccnnc1]

General procedure 8. White powder, 77.3% $^1$H NMR (300 MHz, DMSO-$d_6$) δ ppm 3.37-3.53 (m, 3 H) 3.55-3.68 (m, 3 H) 3.76-3.84 (m, 1 H) 3.89 (d, J=9.7 Hz, 1 H) 4.82 (s, 1 H) 5.16 (d, J=6.7 Hz, 1 H) 7.97 (dd, J=2.3, 1.2 Hz, 1 H) 7.99 (dd, J=2.3, 1.2 Hz, 1 H) 8.91 (t, J=6.0 Hz, 1 H) 9.08 (t, J=5.7 Hz, 1 H) 9.38-9.43 (m, 2 H) 9.53 (app. td, J=2.5, 1.2 Hz, 2 H). $^{13}$C NMR (75 MHz, DMSO-$d_6$) δ ppm 41.9, 44.4, 74.6, 74.7, 77.8, 80.6, 124.2, 124.3, 131.5, 131.6, 148.8, 148.9, 152.03 (2 C), 163.4, 163.9. HRMS (ESI-TOF) m/z: [M+H]$^+$ Calcd for $C_{16}H_{19}N_6O_5^+$ 375.14114; Found 375.1404.

N-(((3S,4R,5R)-5-((1,3-dioxoisoindolin-2-yl)methyl)-3,4-dihydroxytetrahydrofuran-3-yl)methyl)pyridazine-4-carboxamide (258)

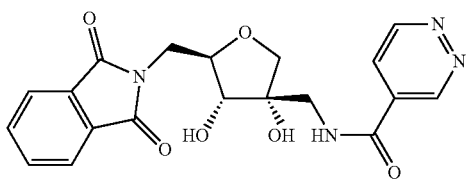 [SMILES: O=C(NC[C@]1(O)CO[C@H](CN2C(=O)c3ccccc3C2=O)[C@H]1O)c1ccnnc1]

General procedure 8. White powder, 65.7% $^1$H NMR (300 MHz, DMSO-$d_6$) δ ppm 3.37-3.56 (m, 3 H) 3.65-3.94 (m, 5 H) 4.82 (s, 1 H) 5.15 (d, J=6.7 Hz, 1 H) 7.80-7.90 (m, 4 H) 7.99 (dd, J=5.3, 2.3 Hz, 1 H) 8.90 (t, J=6.0 Hz, 1 H) 9.43 (dd, J=5.3, 1.2 Hz, 1 H) 9.54 (dd, J=2.3, 1.2 Hz, 1 H). $^{13}$C NMR (75 MHz, DMSO-$d_6$) δ ppm 40.3, 44.3, 74.7, 75.6, 78.0, 78.8, 123.0, 124.3, 131.5, 131.6, 134.4, 148.9, 152.0, 164.0, 167.7. HRMS (ESI-TOF) m/z: [M+H]$^+$ Calcd for $C_{19}H_{19}N_4O_6^+$ 399.12991; Found 399.1302.

2-chloro-N-(((2R,3R,4S)-3,4-dihydroxy-4-((2-phenylacetamido)methyl)tetrahydrofuran-2-yl)methyl)benzamide (259)

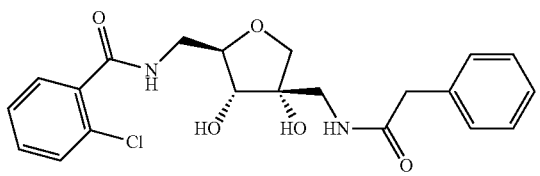 [SMILES: O=C(Cc1ccccc1)NC[C@]1(O)CO[C@H](CNC(=O)c2ccccc2Cl)[C@H]1O]

General procedure 8. White foam, 84.8% $^1$H NMR (300 MHz, DMSO-$d_6$) δ ppm 3.15 (dd, J=13.8, 5.6 Hz, 1 H) 3.20-3.59 (m, 7 H) 3.70-3.78 (m, 2 H) 4.74 (br. s., 2 H) 7.17-7.49 (m, 9 H) 8.03 (t, J=5.7 Hz, 1 H) 8.46 (t, J=5.6 Hz, 1 H). $^{13}$C NMR (75 MHz, DMSO-$d_6$) δ ppm 41.4, 42.2, 43.8, 74.4, 74.5, 77.9, 80.7, 126.3, 126.9, 128.2, 128.9, 129.0, 129.5, 129.9, 130.6, 136.5, 137.0, 166.5, 170.8. HRMS (ESI-TOF) m/z: [M+H]$^+$ Calcd for $C_{21}H_{24}ClN_2O_5^+$ 419.13683; Found 419.1366.

2-chloro-N-(((2R,3R,4S)-3,4-dihydroxy-4-((3-phenylpropanamido)methyl)tetrahydrofuran-2-yl)methyl)benzamide (260)

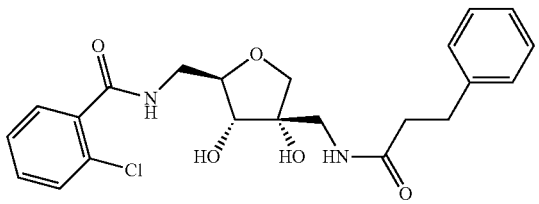 [SMILES: O=C(CCc1ccccc1)NC[C@]1(O)CO[C@H](CNC(=O)c2ccccc2Cl)[C@H]1O]

General procedure 8. White foam, 89.6% $^1$H NMR (300 MHz, DMSO-$d_6$) δ ppm 2.37-2.46 (m, 2 H) 2.75-2.85 (m, 2 H) 3.14 (dd, J=13.8, 5.6 Hz, 1 H) 3.23 (dd, J=13.8, 6.2 Hz, 1 H) 3.28-3.41 (m, 1 H) 3.42-3.57 (m, 3 H) 3.64-3.78 (m, 2 H) 4.59 (br. s., 2 H) 7.13-7.50 (m, 9 H) 7.83 (t, J=5.9 Hz, 1 H) 8.45 (t, J=5.6 Hz, 1 H). $^{13}$C NMR (75 MHz, DMSO-$d_6$) δ ppm 31.1, 36.8, 41.4, 43.7, 74.4, 74.5, 77.9, 80.7, 125.8, 126.9, 128.17, 128.24, 128.9, 129.5, 129.9, 130.6, 137.0, 141.3, 166.5, 172.0. HRMS (ESI-TOF) m/z: [M+H]$^+$ Calcd for $C_{22}H_{26}ClN_2O_5^+$ 433.15248; Found 433.1522.

N-(((2R,3R,4S)-4-(benzamidomethyl)-3,4-dihydroxytetrahydrofuran-2-yl)methyl)-N-methylbenzamide (261)

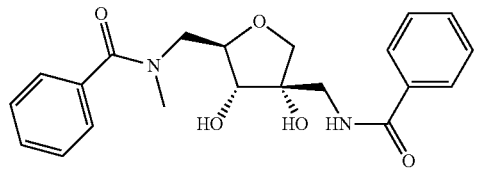 [SMILES: CN(C[C@H]1OC[C@@](O)(CNC(=O)c2ccccc2)[C@@H]1O)C(=O)c1ccccc1]

General procedure 8. White foam, 97.8% $^1$H NMR (300 MHz, DMSO-$d_6$) at 90° C. δ ppm 2.96 (s, 3 H) 3.38-3.71 (m, 6 H) 3.78-3.91 (m, 2 H) 4.36 (br. s., 2 H) 7.31-7.54 (m, 8 H) 7.78-7.84 (m, 2 H) 8.03 (br. s., 1 H). $^{13}$C NMR (75 MHz, DMSO-$d_6$) at 90° C. δ ppm 44.3, 51.7 (weak), 52.2 (weak), 74.6, 74.9, 77.4, 80.6, 126.3, 126.7, 127.6, 127.7, 128.5, 130.6, 134.3, 136.5, 166.9, 170.2. HRMS (ESI-TOF) m/z: [M+H]$^+$ Calcd for $C_{22}H_{26}ClN_2O_5^+$ 385.17580; Found 385.1770.

(3aS,6R,6aR)-3a,6-bis(azidomethyl)-2,2-dimethyltetrahydrofuro[3,4-d][1,3]dioxole (262)

To tosylate 23 (1.5 g, 4 mmol), dissolved in DMF (25 mL), was added sodium azide (1.3 g, 20 mmol). After overnight reaction at 80° C., TLC analysis (hexane/EtOAc 3:1) showed the presence of one major product. The solvent was evaporated and the residue was taken up in EtOAc (50 mL). The resulting solution was washed with saturated sodium bicarbonate solution and water. The organic layer was dried over sodium sulphate, filtered and concentrated in vacuo. This crude material was purified by flash column chromatography (hexane/EtOAc 9:1) to afford bisazide 262 as a colorless, transparent liquid in 85.5% yield. $^1$H NMR (300 MHz, CDCl$_3$) δ ppm 1.48 (s, 3 H) 1.54 (s, 3 H) 3.38-3.51 (m, 3 H) 3.61 (d, J=13.2 Hz, 1 H) 3.86-3.94 (m, 2 H) 4.21 (app. td, J=4.7, 2.3 Hz, 1 H) 4.41 (d, J=2.1 Hz, 1

H). $^{13}$C NMR (75 MHz, CDCl$_3$) δ ppm 27.5, 28.1, 52.2, 54.2, 75.8, 84.2, 85.0, 92.0, 115.2.

N,N'-(((3aS,6R,6aR)-2,2-dimethyldihydrofuro[3,4-d][1,3]dioxole-3a,6(4H)-diyl)bis(methylene))bis(3,4,5-tris(benzyloxy)benzamide) (263)

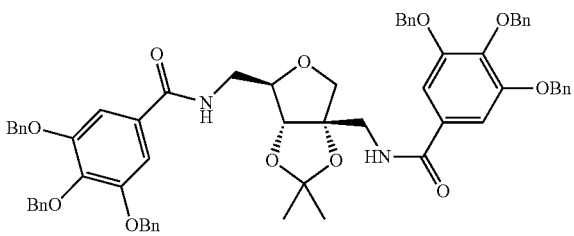 [SMILES: CC1(C)O[C@@H]2[C@@H](CNC(=O)c3cc(OCc4ccccc4)c(OCc4ccccc4)c(OCc4ccccc4)c3)OC[C@]2(CNC(=O)c2cc(OCc3ccccc3)c(OCc3ccccc3)c(OCc3ccccc3)c2)O1]

To a solution of bisazide 262 in THF (0.2 M) was added Me$_3$P (1M in THF, 10 eq.) and the mixture was stirred for 2 h at rt. Water (100 μL per mmol bisazide) was added and stirring was continued for 15 minutes. The mixture was taken to dryness and co-evaporated twice with toluene. The crude bisamine was taken up in DMF (to a concentration of 0.1 M). Added are EDC.HCl (3.0 eq.), DMAP (1.0 eq.) HOBt (1.0 eq.) and the appropriate carboxylic acid (2.5 eq.) and the mixture was stirred overnight. The mixture was taken to dryness, the residue was redissolved in EtOAc, transferred to a separatory funnel and washed successively with HCl (1M, twice) and NaHCO$_3$ (sat. aq., twice). The organic layer was dried (Na$_2$SO$_4$) and concentrated in vacuo. The residue was purified by silica gel chromatography (CH2Cl$_2$/MeOH system) to yield the homobisbenzamide as a pale yellow foam (88.5%). $^1$H NMR (300 MHz, CDCl3) δ ppm 1.32 (s, 3 H) 1.49 (s, 3 H) 3.20-3.33 (m, 1 H) 3.52 (dd, J=14.2, 4.8 Hz, 1 H) 3.81-3.96 (m, 3 H) 4.07 (dd, J=14.7, 8.2 Hz, 1 H) 4.20 (t, J=6.7 Hz, 1 H) 4.58 (s, 1 H) 4.96 (s, 2 H) 4.98 (s, 2 H) 5.00 (s, 2 H) 5.01 (s, 2 H) 5.02 (s, 2 H) 5.05 (s, 2 H) 7.19-7.37 (m, 34 H) 7.47 (t, J=6.0 Hz, 1 H) 7.56 (t, J=6.2 Hz, 1 H). $^{13}$C NMR (75 MHz, CDCl$_3$) δ ppm 27.7, 27.8, 39.9, 42.8, 71.3 (br.), 74.7, 75.2 (br.), 84.1, 85.5, 92.2, 107.0, 107.1, 113.3, 127.5, 127.6, 127.9, 128.0, 128.1, 128.2, 128.5 (v. br.), 128.8, 129.0, 136.6, 136.7, 137.5 (br.), 141.4, 141.5, 152.8, 152.9, 167.6, 167.8. HRMS (ESI-TOF) m/z: [M+H]$^+$ Calcd for C$_{65}$H$_{63}$N$_2$O$_{11}$$^+$ 1047.44264; Found 1047.4473.

N,N'-(((2R,3R,4S)-3,4-dihydroxytetrahydrofuran-2,4-diyl)bis(methylene))bis(3,4,5-trihydroxybenzamide) (264)

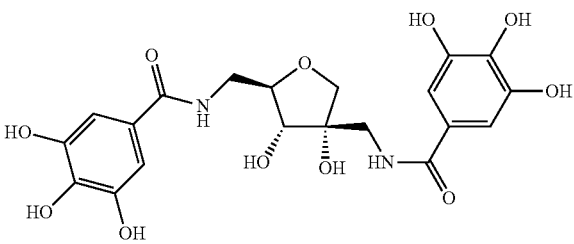 [SMILES: O=C(NC[C@H]1OC[C@@](O)(CNC(=O)c2cc(O)c(O)c(O)c2)[C@@H]1O)c1cc(O)c(O)c(O)c1]

A solution of bisbenzamide 263 (0.05 M) in MeOH was placed under a N$_2$ atmosphere. Palladium black (20 mg/mmol bisbenzamide) was added and the reaction vessel was purged again with N$_2$. Hydrogen gas was bubbled through the solution for 2 h until all benzylethers were cleaved (MS analysis). The vessel was purged with nitrogen gas, opened and the contents were filtered over a Whatman fiberglass filter. Solution was concentrated in vacuo and redissolved in TFA (35% aq. solution) and stirred for 3 h. The solution was concentrated and the residue was dissolved in a mixture of water and tBuOH (4:1 v/v). The mixture was frozen and lyophilized overnight yielding the product as an off white amorphous solid (quant.). $^1$H NMR (300 MHz, CD$_3$OD) δ ppm 3.44-3.60 (m, 3 H) 3.62-3.75 (m, 3 H) 3.87-3.94 (m, 1 H) 3.97 (d, J=9.7 Hz, 1 H) 6.86 (s, 2 H) 6.87 (s, 2H); $^{13}$C NMR (75 MHz, CD$_3$OD) δ ppm 43.2, 46.3, 76.4, 76.6, 79.9, 83.0, 108.0, 108.1, 125.9, 126.2, 138.2, 138.4, 146.7, 146.8, 170.9, 171.4. HRMS (ESI-TOF) m/z: [M+H]$^+$ Calcd for C$_{20}$H$_{22}$N$_2$O$_{11}$$^+$ 467.12964; Found 467.1300.

(3aR,6S,6aR)-6-(hydroxymethyl)-2,2-dimethyldihydrofuro[3,4-d][1,3]dioxol-4(3aH)-one (265)

To a solution of 2,3-O-isopropylidene-D-ribonolactone (24.5 g, 130.0 mmol) and triethylamine (36.2 mL, 260.0 mmol) in CH$_2$Cl$_2$ (650 mL) stirred at 0° C., methanesulfonyl chloride (12.1 mL, 156.0 mmol) was added dropwise under a nitrogen atmosphere. The reaction mixture was allowed to attain ambient temperature. After 3 hours, TLC analysis (toluene/EtOAc 3:2) showed complete consumption of the starting material. The reaction mixture was washed with saturated sodium bicarbonate solution and water. The organic layer was dried over sodium sulphate, filtered and concentrated in vacuo to afford the mesylate as a yellow to orange colored oil. To this crude mesylate, dissolved in 1,4-dioxane (600 mL), was added a solution of KOH (21.9 g, 390.0 mmol) in 300.0 mL of water. This solution was stirred vigorously for 3 h. When complete, the pH was adjusted to 3 by adding 1M HCl (270 mL). The acidic solution was concentrated in vacuo to afford a solid mass, that was triturated with acetone (250 mL) and heated to reflux (20 minutes at 70° C.). The acetone was decanted and filtered. The remaining solid mass was triturated 2 more times and each time the boiling acetone was decanted and filtered. The combined clear filtrate was concentrated in vacuo to yield 2,3-O-isopropylidene-L-Lyxonolactone as a colorless oil (64.8%). $^1$H NMR (300 MHz, (CD$_3$)$_2$CO) δ ppm 1.34 (s, 3 H) 1.37 (s, 3 H) 3.83 (dd, J=12.0, 7.0 Hz, 1 H) 3.91 (dd, J=12.0, 10.3 Hz, 1 H) 4.15 (br. s., 1 H) 4.65 (ddd, J=7.1, 4.9, 2.9 Hz, 1 H) 4.93-5.02 (m, 2 H). $^{13}$C NMR (75 MHz, CDCl$_3$) δ ppm 26.0, 27.0, 60.9, 77.2, 77.3, 80.6, 113.9, 174.6. HRMS (ESI-TOF) m/z: [M+H]$^+$ Calcd for C$_8$H$_{13}$O$_5$$^+$ 189.07575; Found 189.0766.

(3aR,6S,6aR)-6-(azidomethyl)-2,2-dimethyldihydrofuro[3,4-d][1,3]dioxol-4(3aH)-one (266)

To a dry and cooled (0° C.) solution of 2,3-O-isopropylidene-L-Lyxonolactone (4.0 g, 21.3 mmol) in CH$_2$Cl$_2$ (150 mL) were subsequently added Et$_3$N (5.9 mL, 42.5 mmol)

and MsCl (2.0 mL, 25.5 mmol). The resulting reaction mixture was stirred for 3 h, after which time TLC analysis showed completion. The reaction mixture was transferred to a sep. fun., diluted with CH$_2$Cl$_2$, washed with sat. aq. NaHCO$_3$ solution, dried (Na$_2$SO$_4$), filtered and concentrated. The residue was taken up in DMF (200 mL). Next, NaN$_3$ (5.5 g, 85.0 mmol) was added and the reaction mixture was stirred overnight at 90° C. When complete, volatile organics were evaporated. The residue was diluted with EtOAc and washed with water and brine. Purification via FCC (toluene/EtOAc 7:3) yielded the title compound as a yellow to orange colored liquid (80.8%). $^1$H NMR (300 MHz, CDCl$_3$) δ ppm 1.41 (s, 3 H) 1.49 (s, 3 H) 3.61-3.76 (m, 2 H) 4.58 (ddd, J=7.0, 6.2, 3.2 Hz, 1 H) 4.81-4.90 (m, 2 H). $^{13}$C NMR (75 MHz, CDCl$_3$) δ ppm 25.9, 26.8, 49.8, 75.8, 76.1, 77.3, 114.7, 173.1.

(3aR,6S,6aR)-6-(azidomethyl)-3a-(hydroxymethyl)-2,2-dimethyltetrahydrofuro[3,4-d][1,3]dioxol-4-ol (267)

Azidolactone 266 (10.8 g, 50.7 mmol) was dissolved in CH$_2$Cl$_2$ (130 mL) and cooled to −78° C. This solution was flushed with nitrogen gas, after which a solution of diisobutylaluminium hydride (1M in toluene, 55.5 mL, 55.5 mmol) was added dropwise. The cooled solution was allowed to react for 4 hours under nitrogen. The reaction was quenched by adding EtOAc (10 mL) and the mixture was allowed to come to room temperature over 30 min, after which a saturated Na$^+$/K$^+$ tartrate solution (300 mL) was added. The mixture was stirred for another hour and extracted with EtOAc (4×250 mL). The combined organic layers were dried (sodium sulphate), filtered and concentrated in vacuo. The residue was purified by flash column chromatography (hexane/EtOAc 3:1) to afford 10.5 g of a pale oil. The azidolactole (10.0 g, 46.5 mmol) was dissolved in 350 mL of MeOH. Potassium carbonate (3.2 g, 23.3 mmol) and an aqueous solution of formaldehyde (38%, 110 mL) were added. The reaction mixture was stirred for 24 h at 50° C. TLC analysis showed presence of a major product. The reaction mixture was cooled to ambient temperature and the MeOH was evaporated under reduced pressure. The residual aqueous solution was extracted with EtOAc (3×250 mL). The organic layers were combined, dried over sodium sulphate, filtered and concentrated. The residue was purified by flash chromatography (CH$_2$Cl$_2$/MeOH 98:2) to afford compound 267 as a white powder (46.1% over two steps). Data in accordance with Simone et al.

((R)-5-((S)-2-azido-1-hydroxyethyl)-2,2-dimethyl-1,3-dioxolane-4,4-diyl)dimethanol (268)

Sodium borohydride (0.36 g, 9.6 mmol) was added to a stirred and cooled (0° C.) solution of compound 267 (0.78 g, 3.2 mmol) in MeOH (30 mL). The reaction mixture was allowed to attain ambient temperature and was stirred overnight. Ammonium chloride (1.85 g) was added to quench the excess of borohydride. The resulting suspension was stirred for 2 h, concentrated and adsorbed onto celite. Purification by flash chromatography afforded triol 268 as a white powder in 24.2% yield (81.9% based on recovered SM). $^1$H NMR (300 MHz, CD$_3$OD) δ ppm 1.37 (s, 3 H) 1.46 (s, 3 H) 3.34-3.52 (m, 2 H) 3.58-3.70 (m, 4 H) 3.99-4.06 (m, 2 H). $^{13}$C NMR (75 MHz, CDCl$_3$) δ ppm 26.8, 28.4, 55.9, 63.0, 64.4, 69.6, 80.2, 85.1, 109.1.

(3aS,6S,6aR)-3a,6-bis(azidomethyl)-2,2-dimethyltetrahydrofuro[3,4-d][1,3]dioxole (269)

To a stirred solution of triol 268 (0.32 g, 1.3 mmol) in pyridine (15 mL) was added p-toluenesulfonylchloride (0.53 g, 2.8 mmol). The reaction mixture was stirred at room temperature for 3 h and then heated to 60° C. to let it react overnight. The resulting suspension was filtered and the residue was concentrated under reduced pressure. The crude material was then purified by flash column chromatography (hexane/EtOAc 4:1) to afford 180 mg of a colorless oil, which was subsequently taken up in DMF (10 mL). Next, NaN$_3$ was added (0.15 g, 2.35 mmol) and the reaction mixture was stirred overnight at 80° C. TLC analysis (hexane/EtOAc 3:1) showed the presence of one major product. The solvent was evaporated and the residue was taken up in EtOAc. The resulting solution was washed with saturated sodium bicarbonate solution and water. The organic layer was dried over sodium sulphate, filtered and concentrated in vacuo. This material was purified by flash column chromatography (hexane/EtOAc 9:1) to afford 269 as a pale oil (29.4% over two steps). $^1$H NMR (300 MHz, CDCl$_3$) δ ppm 1.46 (s, 3 H) 1.51 (s, 3 H) 3.42-3.61 (m, 5 H) 3.66-3.73 (m, 1 H) 3.98-4.04 (m, 2 H). $^{13}$C NMR (75 MHz, CDCl$_3$) δ ppm 27.47 (2 C), 49.7, 54.2, 76.0, 81.2, 83.8, 92.3, 114.5.

N,N'-(((2S,3R,4S)-3,4-dihydroxytetrahydrofuran-2,4-diyl)bis(methylene))dibenzamide (270)

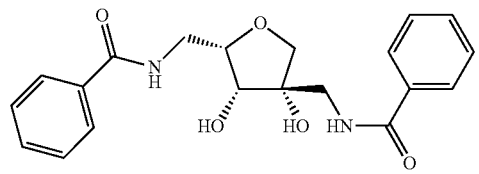 [SMILES: O=C(NC[C@@H]1OC[C@@](O)(CNC(=O)c2ccccc2)[C@@H]1O)c1ccccc1]

To a solution of bisazide 269 in THF (0.2 M) was added Me$_3$P (1M in THF, 10 eq.) and the mixture was stirred for 3 h at rt. Water (100 μL per mmol bisazide) was added and stirring was continued for 45 minutes. The mixture was taken to dryness and co-evaporated twice with toluene. The crude bisamine was taken up in DMF (to a concentration of 0.1 M). Added are EDC.HCl (3.0 eq.), DMAP (1.0 eq.) HOBt (1.0 eq.) and benzoic acid (2.5 eq.) and the mixture was stirred overnight. The mixture was taken to dryness, the residue was redissolved in EtOAc, transferred to a separatory funnel and washed successively with HCl (1M, twice) and NaHCO$_3$ (sat. aq., twice). The organic layer was dried (Na$_2$SO$_4$) and concentrated in vacuo. The residue was purified by silica gel chromatography (Toluene/EtOAc system). A solution of the obtained bisbenzamide was dissolved in TFA (35% aq. solution) and stirred for 3 h. The solution was concentrated and the residue was purified by HPLC (H$_2$O/MeCN 9:1 to 0:1) to yield homobisbenzamide 270 as a white foam (74.3% over two steps). $^1$H NMR (300 MHz, DMSO-d$_6$) δ ppm 3.33-3.69 (m, 6 H) 3.96 (app. t, J=5.0 Hz, 1 H) 4.13 (app. dt, J=7.4, 4.8 Hz, 1 H) 4.99 (s, 1 H) 5.24 (d, J=5.0 Hz, 1 H) 7.41-7.57 (m, 6 H) 7.82-7.89 (m, 4 H) 8.40-8.50 (m, 2 H). $^{13}$C NMR (75 MHz, DMSO-d$_6$) δ ppm 44.50 (2 C), 72.4, 73.2, 79.1, 79.6, 127.2, 127.3, 128.23 (2 C), 131.1, 131.2, 134.3, 134.5, 166.3, 167.1. HRMS (ESI-TOF) m/z: [M+H]$^+$ Calcd for C$_{20}$H$_{23}$N$_2$O$_6$$^+$ 371.16015; Found 371.1588.

Methyl 2-(bromomethyl)benzoate (271)

A mixture of Methyl 2-methylbenzoate (1 mL, 7.2 mmol) and NBS (1.4 g, 7.9 mmol) in CCl$_4$ (28 mL) was degassed. AIBN (24 mg, 0.14 mmol) was added and the mixture was heated to 85° C. overnight. Further NBS (0.13 g, 0.71 mmol) was added and the whole was refluxed for 1 more hour. The mixture was diluted with CH$_2$Cl$_2$ and washed with sat. aq. NaHCO$_3$ solution and water. The organic layer was dried (Na$_2$SO$_4$), filtered and concentrated in vacuo. Purification of the residue by flash chromatography (hexane/EtOAc 100: 0→95:5) gave the title compound as an orange to pink liquid that solidifies on standing (67.6%). $^1$H NMR (300 MHz, CDCl$_3$) δ ppm 3.92 (s, 3 H) 4.95 (s, 2 H) 7.30-7.39 (m, 1 H) 7.41-7.53 (m, 2 H) 7.89-8.01 (m, 1 H). $^{13}$C NMR (75 MHz, CDCl$_3$) δ ppm 31.7, 52.4, 128.7, 129.2, 131.4, 131.8, 132.7, 139.4, 167.2.

Compounds 1 to 3 were synthesized according to the procedure described in Simone, Edwards et al. 2008.

Compounds 22 and 23 were synthesized according to the procedure described in Bouisset, Gosselin et al. 2008.

C. In Vitro and In Vivo Assays

C.1. Determination of the minimal inhibitory effect:

Minimum inhibitory concentrations (MICs) of the hamamelitannin analogs were determined in triplicate according to the EUCAST broth microdilution protocol, using flat-bottom 96-well microtiter plates (TPP, Trasadingen, Switzerland). The inoculum was standardized to approximately 5×10$^5$ CFU/ml. The plates were incubated at 37° C. for 20 h, and the optical density at 590 nm was determined by using a multilabel microtiter plate reader (Envision; Perkin-Elmer LAS, Waltham, Mass.). The lowest concentration of the compounds for which a similar optical density was observed in the inoculated and the blank wells was recorded as the MIC MIC values were observed to be higher than the highest concentration tested (MIC>500 μM).

Figure 3:
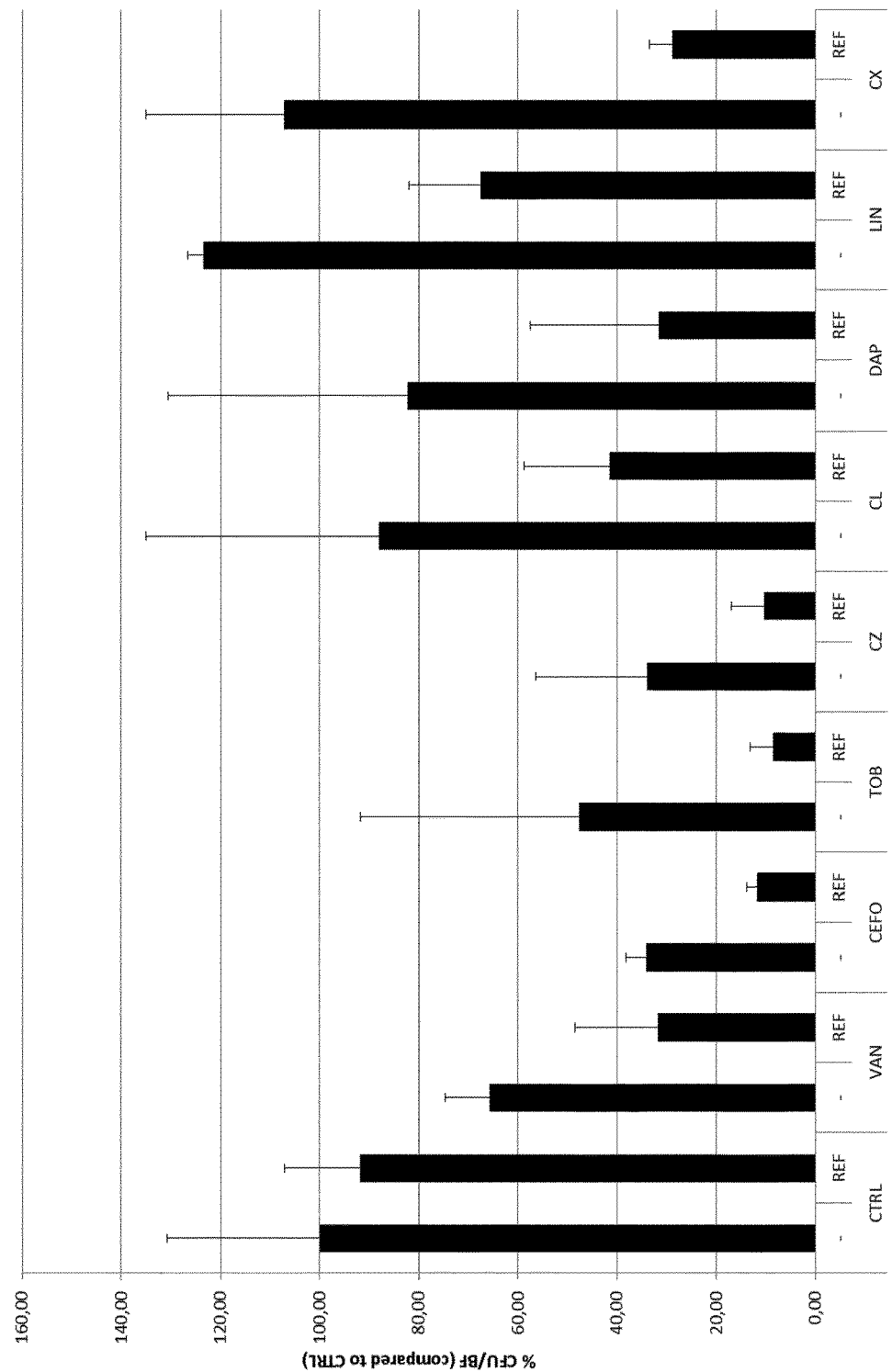
FIG. 3: Percentage CFU/BF (compared to untreated control) for 24 h old biofilms receiving a treatment with an antibiotic alone or in combination with the REF (250 μM). VAN: vancomycin (20 μg/ml), cefo: cefoxitin (70 μg/ml), TOB: tobramycin (1024 μg/ml), CZ: cefazolin (1000 μg/ml), CL: cefalonium (1000 μg/ml), DAP: daptomycin (200 μg/ml), LIN: linezolid (20 μg/ml), CX: cefalexin (1000 μg/ml).

C.2. Effect of pre-treatment and combined treatment on biofilm susceptibility:

The compounds were evaluated for their effect on biofilm susceptibility both under pre-treatment and combination treatment regimens. In the pre-treatment regimen, a methicillin resistant S. aureus Mu50 strain (S. aureus ATCC700699) was allowed to form biofilms in the presence of the compounds after which the biofilm was treated with vancomycin (20 μg/ml). In the combination treatment regimen, S. aureus Mu50 was allowed to form a mature biofilm after which it was treated with a combination of a compound and vancomycin. In brief, 100 μl of a standardized inoculum (10$^8$ CFU/ml) was placed in the wells of a round-bottom 96-well microtiter plate. The cells were allowed to adhere to the plate in the absence (combined treatment) or presence (pre-treatment) of the compounds (0.1-250 μM) for 4 h at 37° C. After this adhesion step, non-adhered cells were removed, the wells were rinsed and fresh medium with or without the compounds was added. The plates were incubated for an additional 20 h at 37° C. After this, the medium was removed, biofilms were rinsed with physiological saline and vancomycin (20 μg/ml) was added alone (pre-treatment) or with the compounds (combined treatment, 0.1-250 μM). Plates were placed at 37° C. for 24 h after which medium was removed, wells were rinsed and the surviving cells in each condition were collected. The number of surviving cells under each condition was compared to vancomycin treatment alone and was assessed by conventional plating. Results of these experiments are presented in Table 1. The REF compound (hamamelitannin) was also observed for its effect on biofilm susceptibility towards other antibiotics (incl. vancomycin, cefoxitin, tobramycin, cefazolin, cefalonium, daptomycin, linezolide and cephalexin). Biofilms were formed as described above and were treated with the antibiotics alone or in combination with the REF compound (250 μM). The number of surviving cells under each condition was compared to the untreated control biofilm and was assessed by conventional plating. Results of these experiments are presented in FIG. 3.

Figure 2:
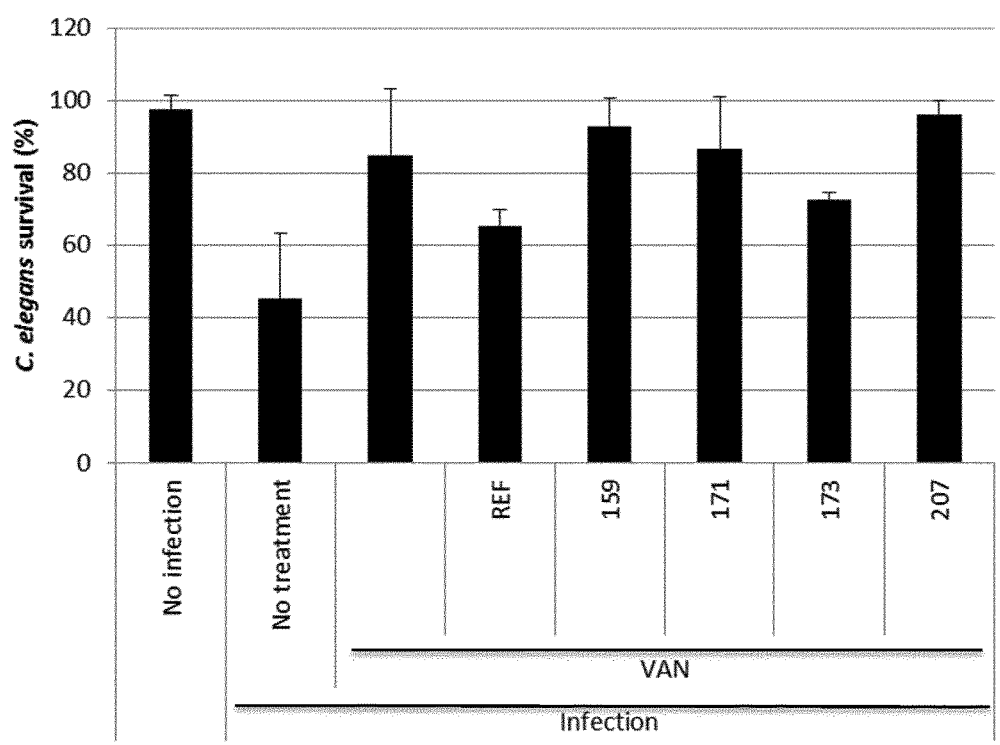
FIG. 2: Survival of infected *C. elegans* nematodes receiving no treatment or a treatment with vancomycin (20 μg/ml) alone or vancomycin (20 μg/ml) used in combination with the REF or the compounds 159, 171, 173 or 207 (50 μM). Survival was scored 48 h p.i.

C.3. The effect on in vivo survival of infected c. elegans nematodes:

The in vivo effect of treatment with the compound alone (FIG. 1) or a combined treatment with a compound and vancomycin (FIG. 2) was evaluated using a C. elegans model system (Brackman et al., 2011). In brief, a suspension of synchronized worms (L4 stage) was divided into 24-well plates containing no bacteria or S. aureus Mu50 cells (2.5× 10$^7$ CFU). The nematodes received no treatment, a treatment with vancomycin alone or vancomycin in combination with a compound. The fraction of dead worms was determined 48 h post-infection by counting the number of dead worms and the total number of worms in each condition using a dissecting microscope.

Figure 4:
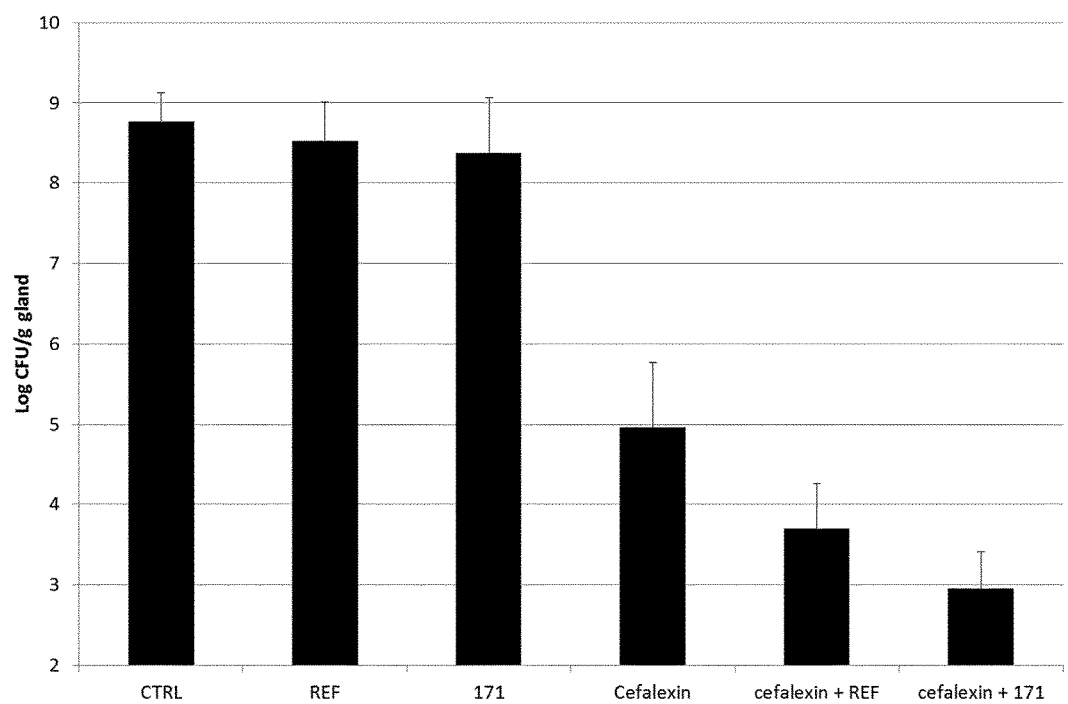
FIG. 4: Log CFU/g gland of *S. aureus* in mouse mammary glands for mice receiving no treatment (CTRL) or a treatment with a selected dose of the REF compound, compound 171 or cefalexin alone or a treatment with a combination of cefalexin and REF or compound 171.

C.4. The in vivo effect of treatment with the compound alone or a combined treatment with a compound and cefalexin (FIG. 4) was evaluated using a murine intramammary S. aureus infection model, i.e. a model of S. aureus mastitis infection (Demon et al., 2012). In brief, CD-1 lactating mice (Harlan Laboratories Inc., Netherlands) were utilized 12-14 days after birth of the offspring. The pups were weaned 1-2 h before bacterial inoculation of the mammary glands. A mixture of oxygen and isoflurane (2-3%) was used for inhalational anesthesia of the lactating mice. A syringe with 32-gauge blunt needle (Thiebaud Biomedical Devices, France) was applied to inoculate both L4 (on the left) and R4 (on the right) glands of the fourth abdominal mammary gland pair with approximately 150 CFU of S. aureus. Each orifice was exposed by a small cut at the near end of the teat and 100 μl of the inoculum was injected slowly through the teat canal. The formulations containing REF, compound 171, cefalexin or a combination of cefalexin and REF or compound 171 were instilled into the mammary gland of anesthetized mice using the desired dose (μg/gland) at 4 h after bacterial inoculation. Immediately thereafter the postoperative analgesic Buprecare (Codifar NV, Belgium) was administered intraperitoneally, i.e. at 4 h after bacterial inoculation. All groups were composed of 5 mice (10 mammary glands). After sacrifice of the mice by cervical dislocation at 14 h post-treatment, mammary glands (two per mouse) were harvested, weighed and homogenized on ice in sterile PBS using a tissue ruptor (QIAGEN Benelux BV, Netherlands). The mammary glands, which are structurally separate, were considered as individual samples. Bacterial CFU counts were obtained by standard plating.

Results of the above assays are detailed in the following table and figures.

TABLE 1

Effect of pre-treatment and combined treatment on biofilm susceptibility.

| N° | Structure | Pretreat (100 μM)[a] | Combin. (100 μM)[a] | Pretreat. (EC50) (μM)[b] | Combin. (EC50) (μM)[b] |
|---|---|---|---|---|---|
| REF | 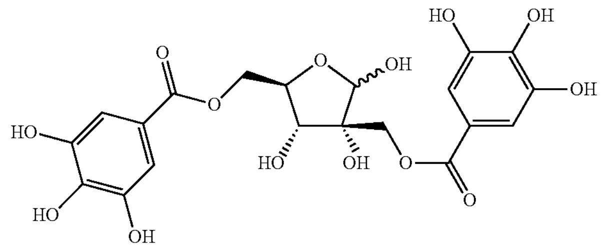 | 43.35 | 43.15 | 145.5 | 166.6 |
| 8 | 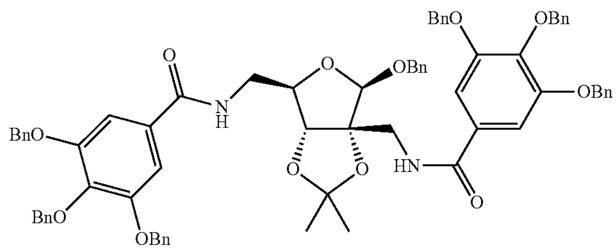 [SMILES: CC1(C)O[C@@H]2[C@@H](CNC(=O)c3cc(OCc4ccccc4)c(OCc4ccccc4)c(OCc4ccccc4)c3)O[C@@H](OCc3ccccc3)[C@]2(CNC(=O)c2cc(OCc3ccccc3)c(OCc3ccccc3)c(OCc3ccccc3)c2)O1] | | | | |
| 9 | 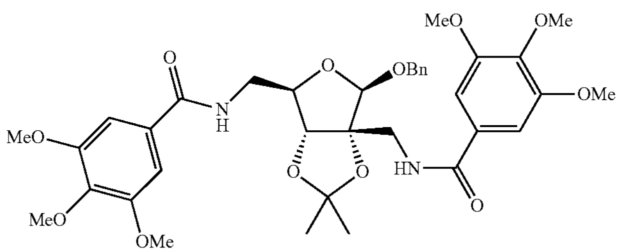 [SMILES: COc1cc(C(=O)NC[C@H]2O[C@@H](OCc3ccccc3)[C@]3(CNC(=O)c4cc(OC)c(OC)c(OC)c4)OC(C)(C)O[C@H]23)cc(OC)c1OC] | | | | |
| 10 | 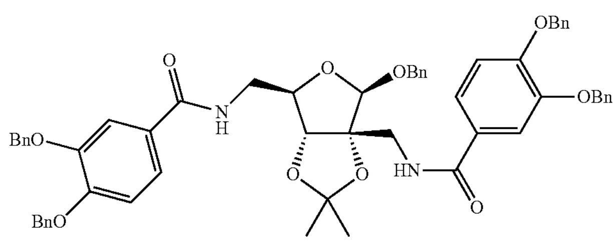 [SMILES: CC1(C)O[C@@H]2[C@@H](CNC(=O)c3ccc(OCc4ccccc4)c(OCc4ccccc4)c3)O[C@@H](OCc3ccccc3)[C@]2(CNC(=O)c2ccc(OCc3ccccc3)c(OCc3ccccc3)c2)O1] | | | | |
| 11 | 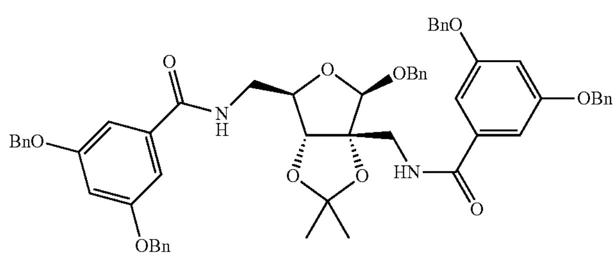 [SMILES: CC1(C)O[C@@H]2[C@@H](CNC(=O)c3cc(OCc4ccccc4)cc(OCc4ccccc4)c3)O[C@@H](OCc3ccccc3)[C@]2(CNC(=O)c2cc(OCc3ccccc3)cc(OCc3ccccc3)c2)O1] | | | | |
| 12 | 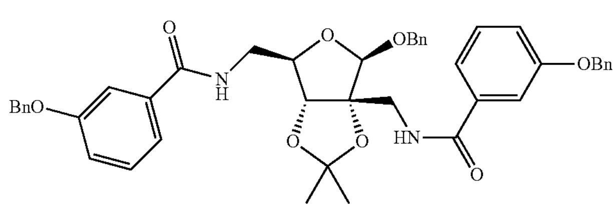 [SMILES: CC1(C)O[C@@H]2[C@@H](CNC(=O)c3cccc(OCc4ccccc4)c3)O[C@@H](OCc3ccccc3)[C@]2(CNC(=O)c2cccc(OCc3ccccc3)c2)O1] | | | | |

TABLE 1-continued
| | | | | | | |
|---|---|---|---|---|---|---|
| 13 | 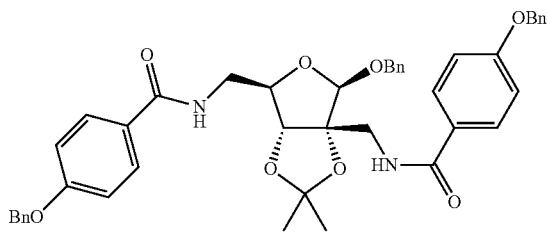 [SMILES: CC1(C)O[C@@H]2[C@@H](CNC(=O)c3ccc(OCc4ccccc4)cc3)O[C@@H](OCc3ccccc3)[C@]2(CNC(=O)c2ccc(OCc3ccccc3)cc2)O1] | | | | | |
| 14 | 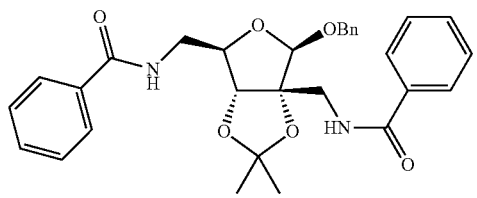 [SMILES: CC1(C)O[C@@H]2[C@@H](CNC(=O)c3ccccc3)O[C@@H](OCc3ccccc3)[C@]2(CNC(=O)c2ccccc2)O1] | | | | | |
| 15 | 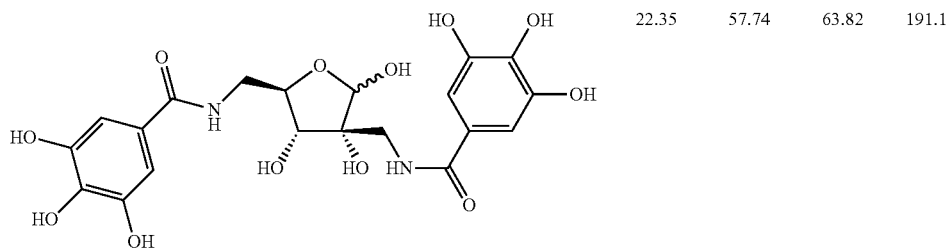 | 22.35 | 57.74 | 63.82 | 191.1 | |
| 16 | 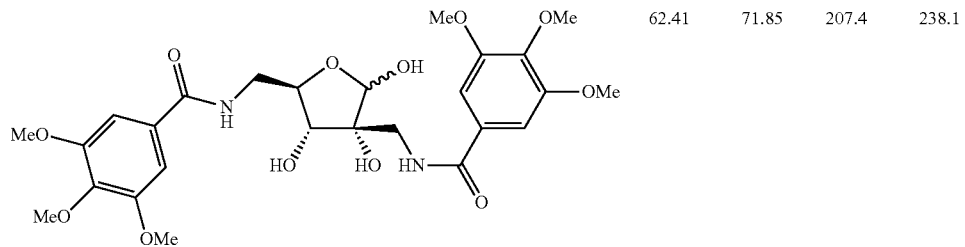 | 62.41 | 71.85 | 207.4 | 238.1 | |
| 17 | 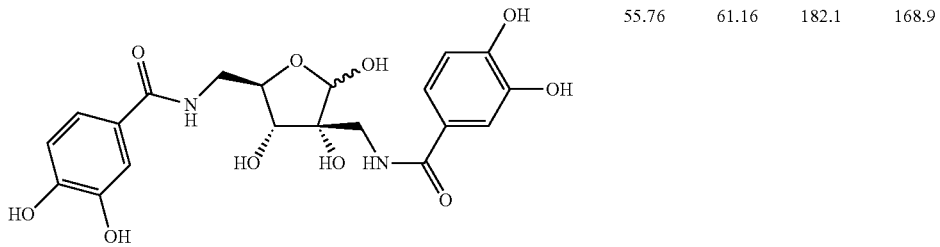 | 55.76 | 61.16 | 182.1 | 168.9 | |
| 18 | 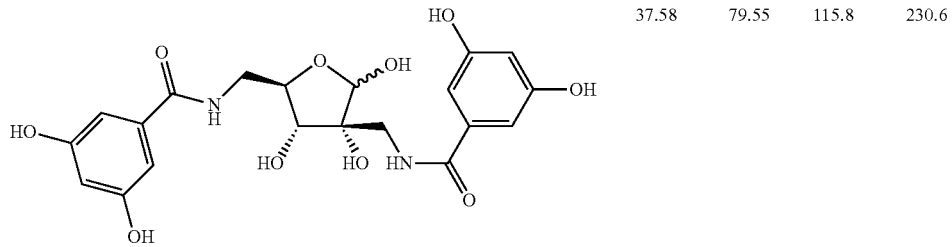 | 37.58 | 79.55 | 115.8 | 230.6 | |

TABLE 1-continued

| | | | | | |
|---|---|---|---|---|---|
| 19 | [structure: furanose with (3-hydroxybenzamido)methyl and 3-hydroxybenzamidomethyl substituents, with OH groups] | 19.78 | 27.23 | 38.53 | 52.31 |
| 20 | [structure: furanose with (4-hydroxybenzamido)methyl and 4-hydroxybenzamidomethyl substituents, with OH groups] | 19.78 | 27.23 | 85.56 | 52.31 |
| 21 | [structure: furanose with benzamidomethyl substituents, with OH groups] | 18.04 | 56.02 | 73.63 | 154.2 |
| 34 | [structure: bicyclic acetonide with (4-methylbenzamido)methyl and benzamidomethyl substituents] | | | | |
| 35 | [structure: bicyclic acetonide with (4-fluorobenzamido)methyl and benzamidomethyl substituents] | | | | |
| 36 | [structure: bicyclic acetonide with (4-chlorobenzamido)methyl and benzamidomethyl substituents] | | | | |
| 37 | [structure: bicyclic acetonide with (4-methoxybenzamido)methyl and benzamidomethyl substituents] | | | | |
| 38 | [structure: bicyclic acetonide with (4-cyanobenzamido)methyl and benzamidomethyl substituents] | | | | |

TABLE 1-continued
| 39 | 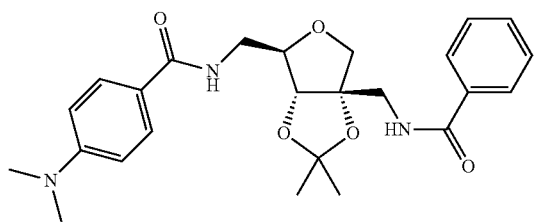 [SMILES: CN(C)c1ccc(C(=O)NC[C@H]2OC[C@]3(CNC(=O)c4ccccc4)OC(C)(C)O[C@H]23)cc1] |
| 40 | 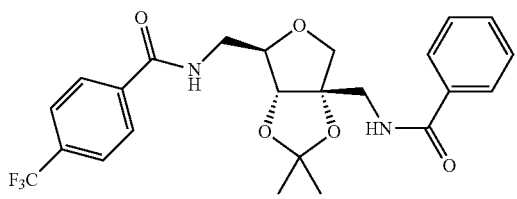 [SMILES: CC1(C)O[C@@H]2[C@@H](CNC(=O)c3ccc(C(F)(F)F)cc3)OC[C@]2(CNC(=O)c2ccccc2)O1] |
| 41 | 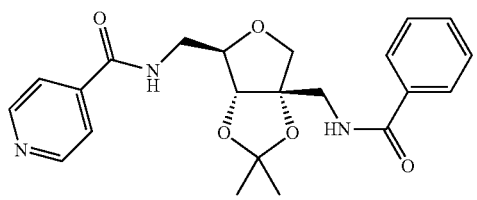 |
| 42 | 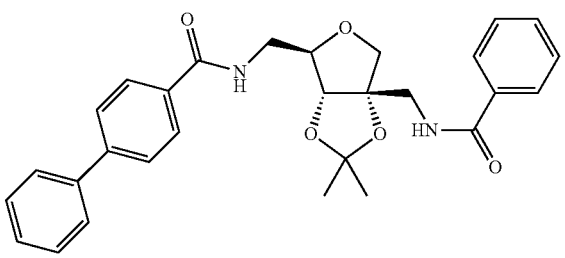 [SMILES: CC1(C)O[C@@H]2[C@@H](CNC(=O)c3ccc(-c4ccccc4)cc3)OC[C@]2(CNC(=O)c2ccccc2)O1] |
| 43 | 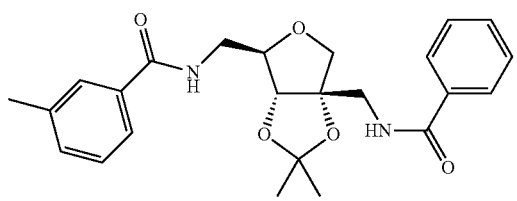 [SMILES: Cc1cccc(C(=O)NC[C@H]2OC[C@]3(CNC(=O)c4ccccc4)OC(C)(C)O[C@H]23)c1] |
| 44 | 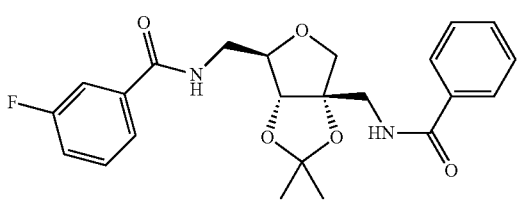 [SMILES: CC1(C)O[C@@H]2[C@@H](CNC(=O)c3cccc(F)c3)OC[C@]2(CNC(=O)c2ccccc2)O1] |
| 45 | 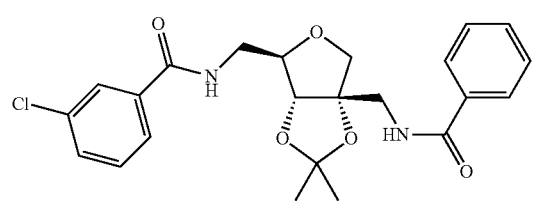 [SMILES: CC1(C)O[C@@H]2[C@@H](CNC(=O)c3cccc(Cl)c3)OC[C@]2(CNC(=O)c2ccccc2)O1] |

TABLE 1-continued
46 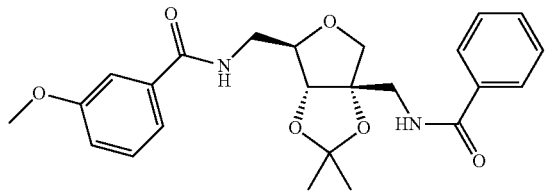
47 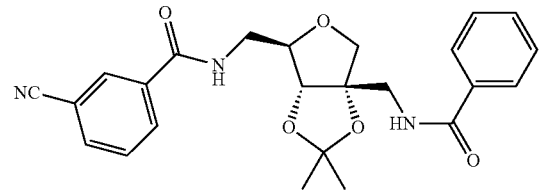 [SMILES: CC1(C)O[C@@H]2[C@@H](CNC(=O)c3cccc(C#N)c3)OC[C@]2(CNC(=O)c2ccccc2)O1]
48 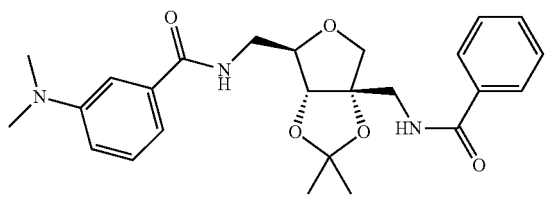 [SMILES: CN(C)c1cccc(C(=O)NC[C@H]2OC[C@]3(CNC(=O)c4ccccc4)OC(C)(C)O[C@H]23)c1]
49 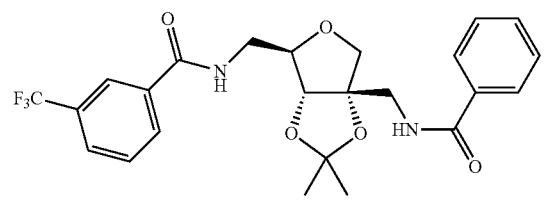
50 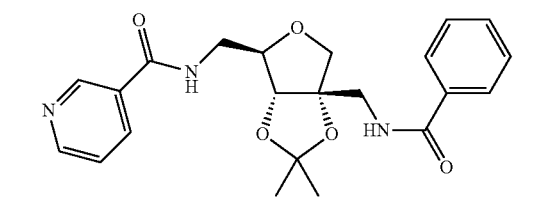 [SMILES: CC1(C)O[C@@H]2[C@@H](CNC(=O)c3cccnc3)OC[C@]2(CNC(=O)c2ccccc2)O1]
51 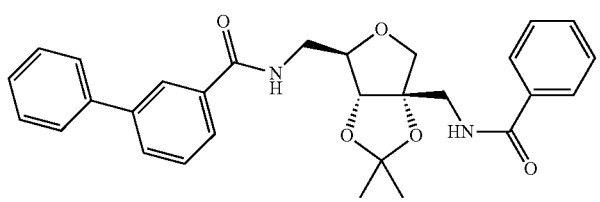 [SMILES: CC1(C)O[C@@H]2[C@@H](CNC(=O)c3cccc(-c4ccccc4)c3)OC[C@]2(CNC(=O)c2ccccc2)O1]
52 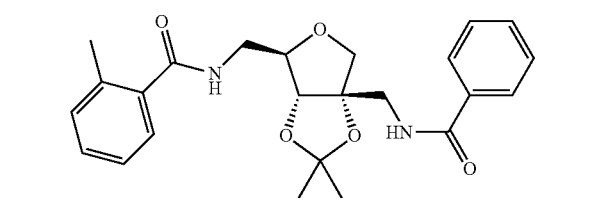
53 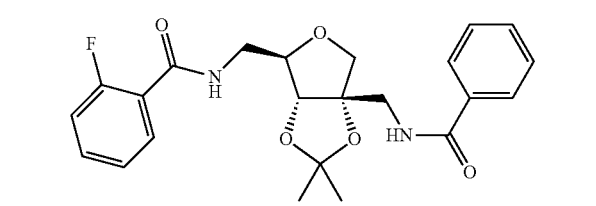 [SMILES: CC1(C)O[C@@H]2[C@@H](CNC(=O)c3ccccc3F)OC[C@]2(CNC(=O)c2ccccc2)O1]

TABLE 1-continued
| 54 | 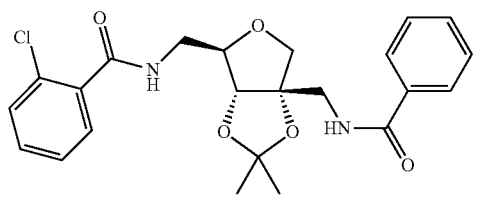 |
| 55 | 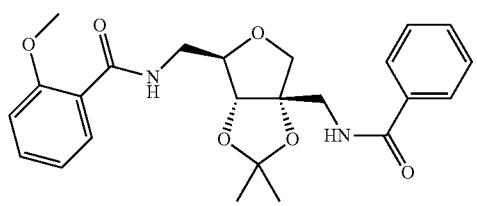 [SMILES: COc1ccccc1C(=O)NC[C@H]1OC[C@]2(CNC(=O)c3ccccc3)OC(C)(C)O[C@H]12] |
| 56 | 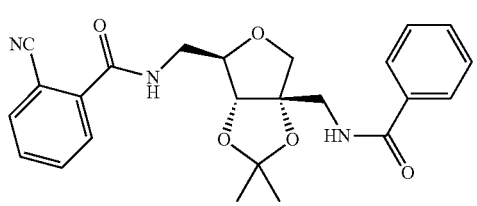 |
| 57 | 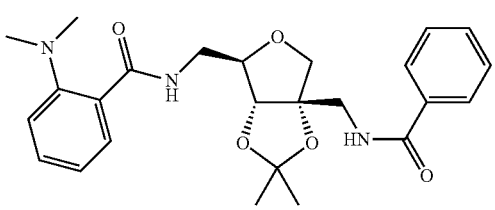 |
| 58 | 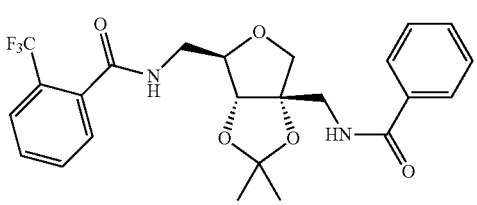 [SMILES: CC1(C)O[C@@H]2[C@@H](CNC(=O)c3ccccc3C#N)OC[C@]2(CNC(=O)c2ccccc2)O1] |
| 59 | 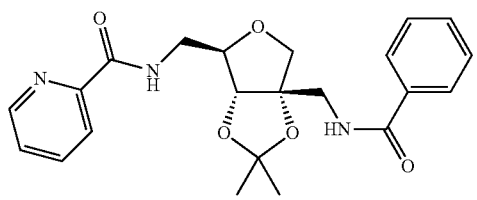 |
| 60 | 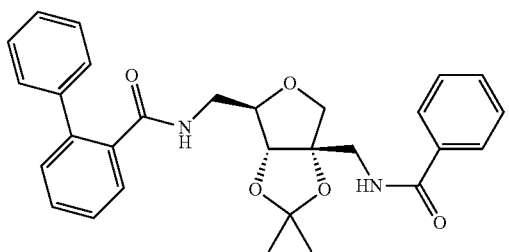 [SMILES: CC1(C)O[C@@H]2[C@@H](CNC(=O)c3ccccc3-c3ccccc3)OC[C@]2(CNC(=O)c2ccccc2)O1] |

TABLE 1-continued
| | |
|---|---|
| 61 | 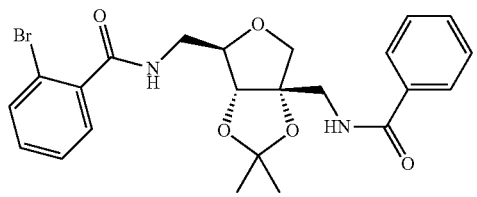 [SMILES: CC1(C)O[C@@H]2[C@@H](CNC(=O)c3ccccc3Br)OC[C@]2(CNC(=O)c2ccccc2)O1] |
| 62 | 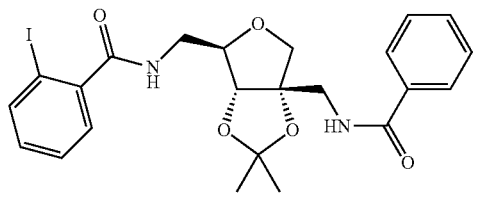 [SMILES: CC1(C)O[C@@H]2[C@@H](CNC(=O)c3ccccc3I)OC[C@]2(CNC(=O)c2ccccc2)O1] |
| 63 | 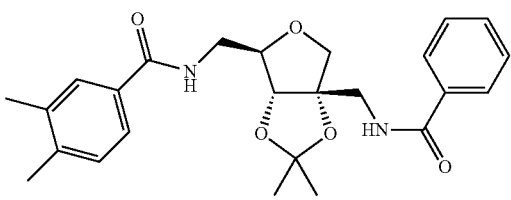 [SMILES: Cc1ccc(C(=O)NC[C@H]2OC[C@]3(CNC(=O)c4ccccc4)OC(C)(C)O[C@H]23)cc1C] |
| 64 | 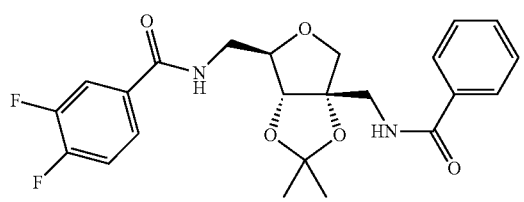 [SMILES: CC1(C)O[C@@H]2[C@@H](CNC(=O)c3ccc(F)c(F)c3)OC[C@]2(CNC(=O)c2ccccc2)O1] |
| 65 | 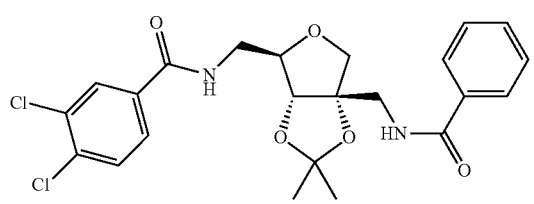 [SMILES: CC1(C)O[C@@H]2[C@@H](CNC(=O)c3ccc(Cl)c(Cl)c3)OC[C@]2(CNC(=O)c2ccccc2)O1] |
| 66 | 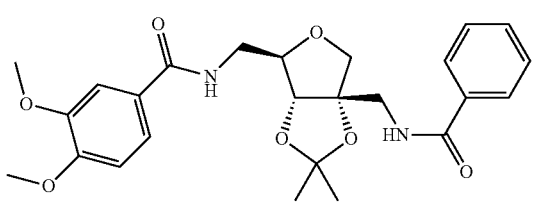 [SMILES: COc1ccc(C(=O)NC[C@H]2OC[C@]3(CNC(=O)c4ccccc4)OC(C)(C)O[C@H]23)cc1OC] |
| 67 | 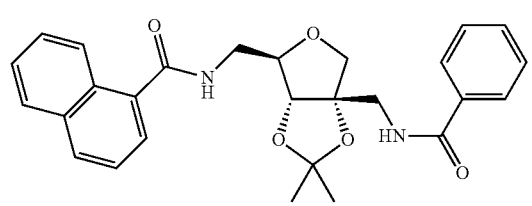 [SMILES: CC1(C)O[C@@H]2[C@@H](CNC(=O)c3cccc4ccccc34)OC[C@]2(CNC(=O)c2ccccc2)O1] |
| 68 | 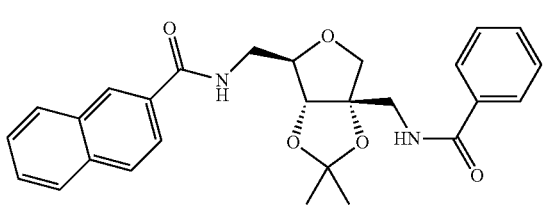 [SMILES: CC1(C)O[C@@H]2[C@@H](CNC(=O)c3ccc4ccccc4c3)OC[C@]2(CNC(=O)c2ccccc2)O1] |

TABLE 1-continued
69 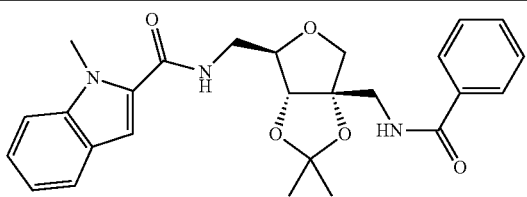
70 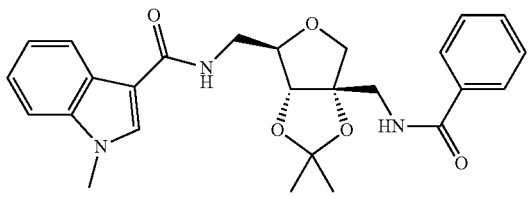 [SMILES: Cn1cc(C(=O)NC[C@H]2OC[C@]3(CNC(=O)c4ccccc4)OC(C)(C)O[C@H]23)c2ccccc21]
71 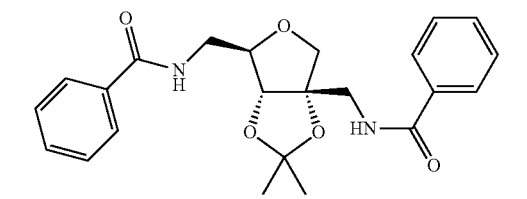 [SMILES: CC1(C)O[C@@H]2[C@@H](CNC(=O)c3ccccc3)OC[C@]2(CNC(=O)c2ccccc2)O1]
72 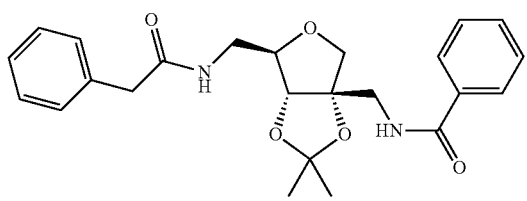 [SMILES: CC1(C)O[C@@H]2[C@@H](CNC(=O)Cc3ccccc3)OC[C@]2(CNC(=O)c2ccccc2)O1]
73 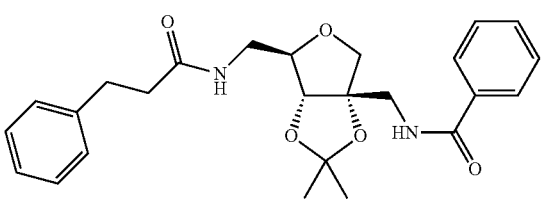 [SMILES: CC1(C)O[C@@H]2[C@@H](CNC(=O)CCc3ccccc3)OC[C@]2(CNC(=O)c2ccccc2)O1]
74 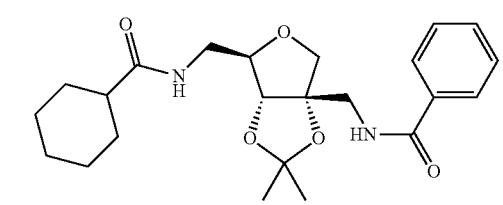 [SMILES: CC1(C)O[C@@H]2[C@@H](CNC(=O)C3CCCCC3)OC[C@]2(CNC(=O)c2ccccc2)O1]
75 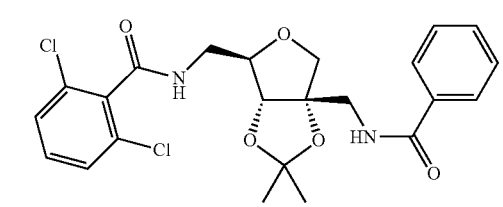 [SMILES: CC1(C)O[C@@H]2[C@@H](CNC(=O)c3c(Cl)cccc3Cl)OC[C@]2(CNC(=O)c2ccccc2)O1]
76 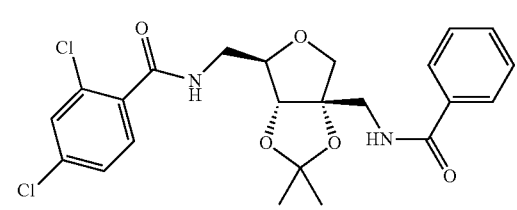

TABLE 1-continued
| 77 | 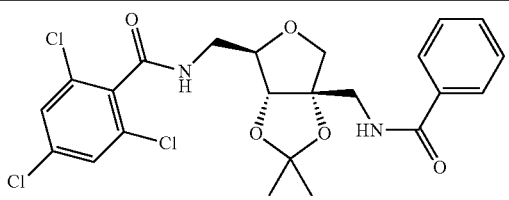 |
| --- | --- |
| 78 | 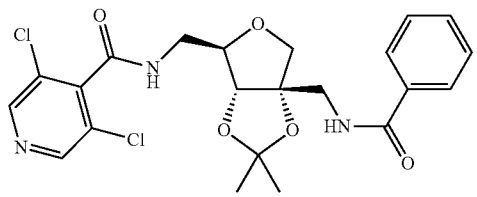 |
| 79 | 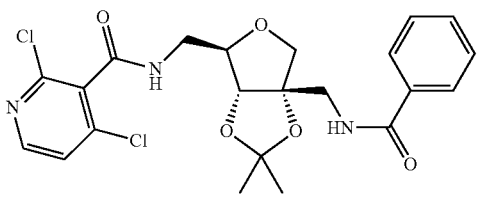 [SMILES: CC1(C)O[C@@H]2[C@@H](CNC(=O)c3c(Cl)ccnc3Cl)OC[C@]2(CNC(=O)c2ccccc2)O1] |
| 80 | 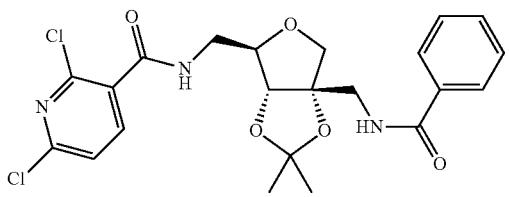 |
| 81 | 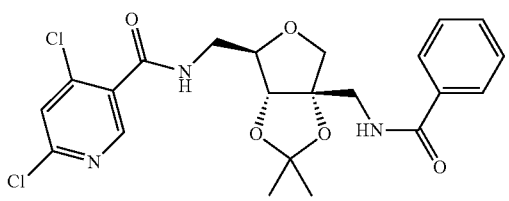 |
| 82 | 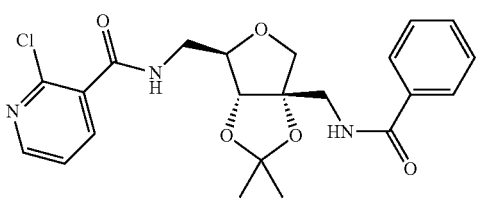 [SMILES: CC1(C)O[C@@H]2[C@@H](CNC(=O)c3cccnc3Cl)OC[C@]2(CNC(=O)c2ccccc2)O1] |
| 83 | 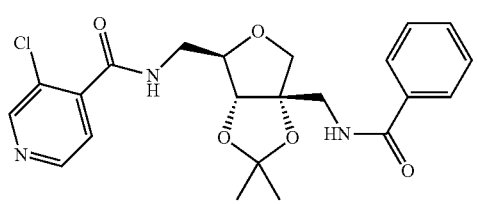 [SMILES: CC1(C)O[C@@H]2[C@@H](CNC(=O)c3ccncc3Cl)OC[C@]2(CNC(=O)c2ccccc2)O1] |
| 84 | 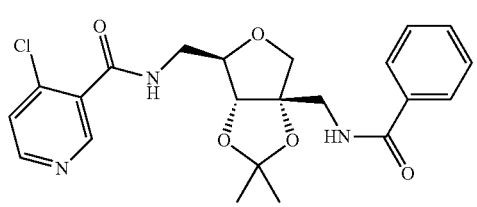 |

TABLE 1-continued
85 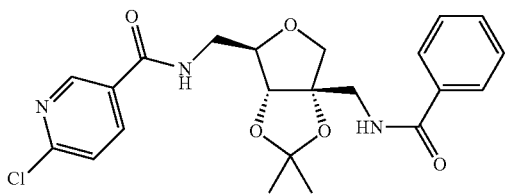 [SMILES: CC1(C)O[C@@H]2[C@@H](CNC(=O)c3ccc(Cl)nc3)OC[C@]2(CNC(=O)c2ccccc2)O1]
86 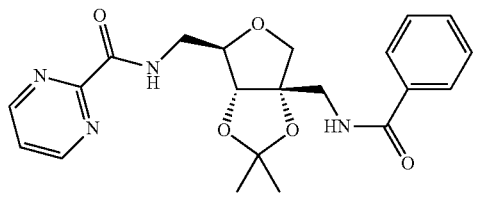
87 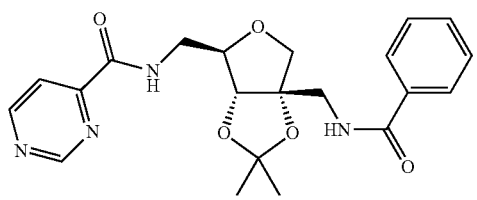 [SMILES: CC1(C)O[C@@H]2[C@@H](CNC(=O)c3ccncn3)OC[C@]2(CNC(=O)c2ccccc2)O1]
88 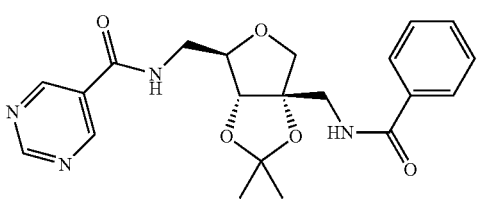 [SMILES: CC1(C)O[C@@H]2[C@@H](CNC(=O)c3cncnc3)OC[C@]2(CNC(=O)c2ccccc2)O1]
89 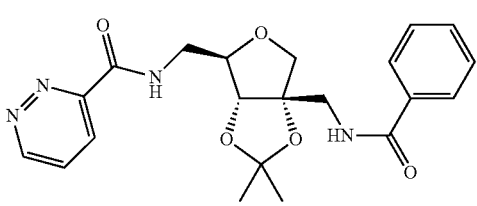
90 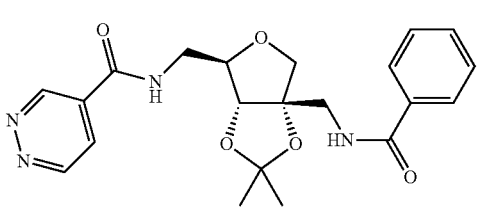 [SMILES: CC1(C)O[C@@H]2[C@@H](CNC(=O)c3ccnnc3)OC[C@]2(CNC(=O)c2ccccc2)O1]
91 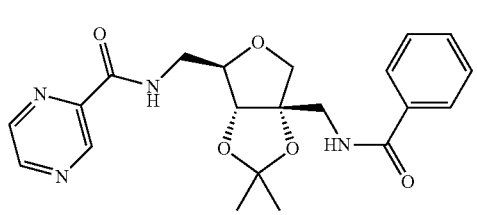
92 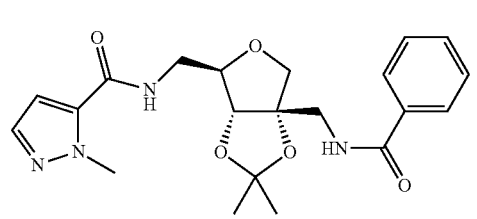 [SMILES: Cn1nccc1C(=O)NC[C@H]1OC[C@]2(CNC(=O)c3ccccc3)OC(C)(C)O[C@H]12]

TABLE 1-continued
| | |
|---|---|
| 93 | 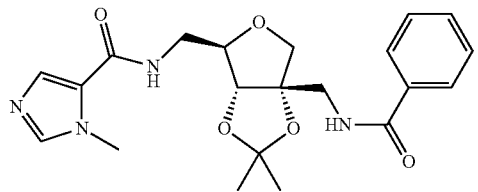 [SMILES: Cn1cncc1C(=O)NC[C@H]1OC[C@]2(CNC(=O)c3ccccc3)OC(C)(C)O[C@H]12] |
| 94 | 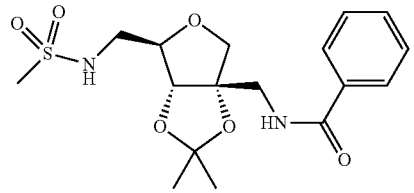 [SMILES: CC1(C)O[C@@H]2[C@@H](CNS(C)(=O)=O)OC[C@]2(CNC(=O)c2ccccc2)O1] |
| 95 | 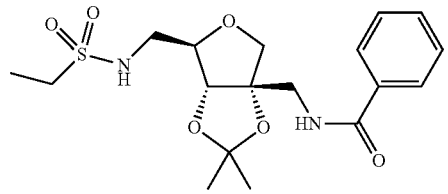 |
| 96 | 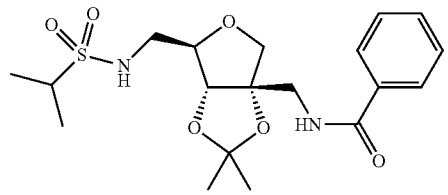 |
| 97 | 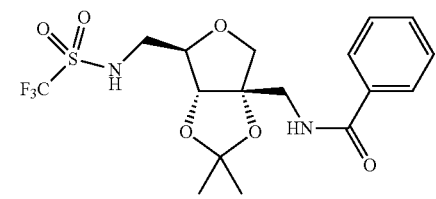 [SMILES: CC1(C)O[C@@H]2[C@@H](CNS(=O)(=O)C(F)(F)F)OC[C@]2(CNC(=O)c2ccccc2)O1] |
| 98 | 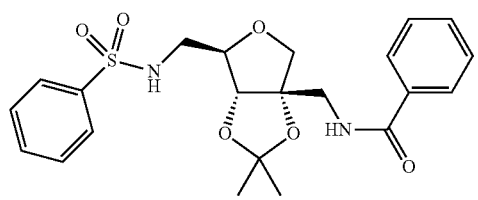 [SMILES: CC1(C)O[C@@H]2[C@@H](CNS(=O)(=O)c3ccccc3)OC[C@]2(CNC(=O)c2ccccc2)O1] |
| 99 | 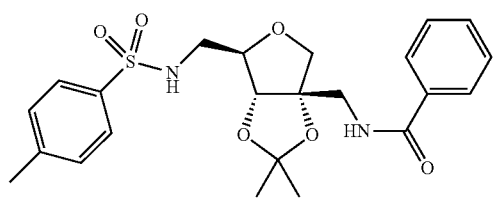 [SMILES: Cc1ccc(S(=O)(=O)NC[C@H]2OC[C@]3(CNC(=O)c4ccccc4)OC(C)(C)O[C@H]23)cc1] |
| 100 | 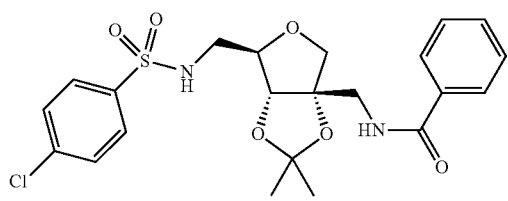 [SMILES: CC1(C)O[C@@H]2[C@@H](CNS(=O)(=O)c3ccc(Cl)cc3)OC[C@]2(CNC(=O)c2ccccc2)O1] |

TABLE 1-continued
| | |
|---|---|
| 101 | 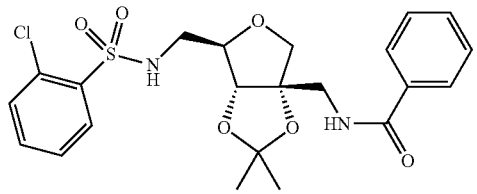 [SMILES: CC1(C)O[C@@H]2[C@@H](CNS(=O)(=O)c3ccccc3Cl)OC[C@]2(CNC(=O)c2ccccc2)O1] |
| 102 | 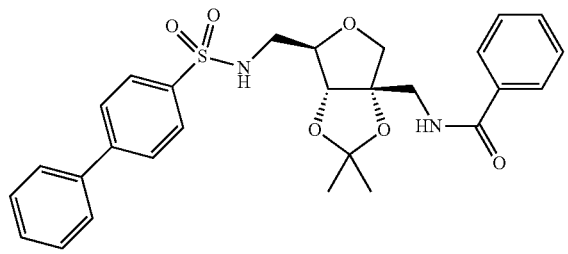 [SMILES: CC1(C)O[C@@H]2[C@@H](CNS(=O)(=O)c3ccc(-c4ccccc4)cc3)OC[C@]2(CNC(=O)c2ccccc2)O1] |
| 103 | 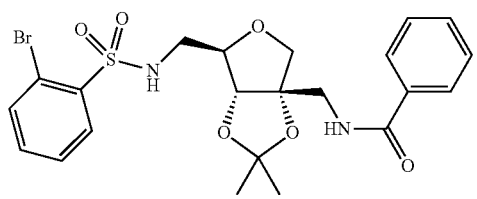 [SMILES: CC1(C)O[C@@H]2[C@@H](CNS(=O)(=O)c3ccccc3Br)OC[C@]2(CNC(=O)c2ccccc2)O1] |
| 104 | 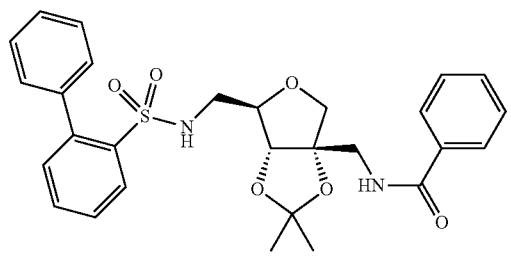 [SMILES: CC1(C)O[C@@H]2[C@@H](CNS(=O)(=O)c3ccccc3-c3ccccc3)OC[C@]2(CNC(=O)c2ccccc2)O1] |
| 105 | 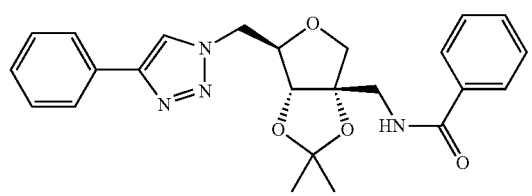 [SMILES: CC1(C)O[C@@H]2[C@@H](Cn3cc(-c4ccccc4)nn3)OC[C@]2(CNC(=O)c2ccccc2)O1] |
| 106 | 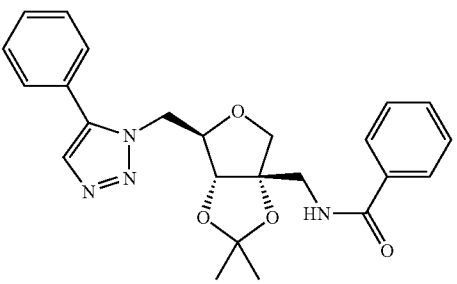 [SMILES: CC1(C)O[C@@H]2[C@@H](Cn3nncc3-c3ccccc3)OC[C@]2(CNC(=O)c2ccccc2)O1] |
| 107 | 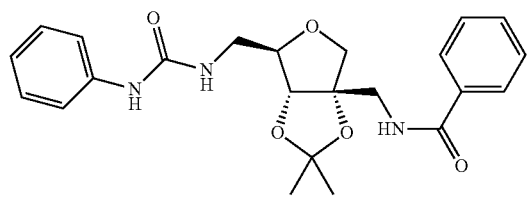 |

TABLE 1-continued
| 108 | 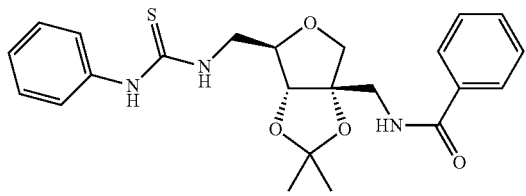 [SMILES: CC1(C)O[C@@H]2[C@@H](CNC(=S)Nc3ccccc3)OC[C@]2(CNC(=O)c2ccccc2)O1] |
| --- | --- |
| 109 | 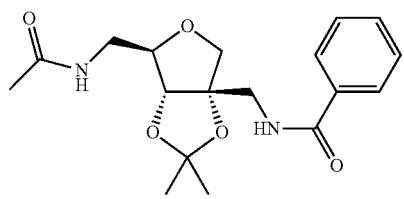 [SMILES: CC(=O)NC[C@H]1OC[C@]2(CNC(=O)c3ccccc3)OC(C)(C)O[C@H]12] |
| 110 | 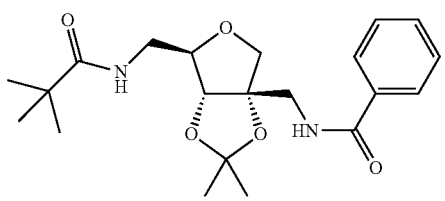 [SMILES: CC1(C)O[C@@H]2[C@@H](CNC(=O)C(C)(C)C)OC[C@]2(CNC(=O)c2ccccc2)O1] |
| 111 | 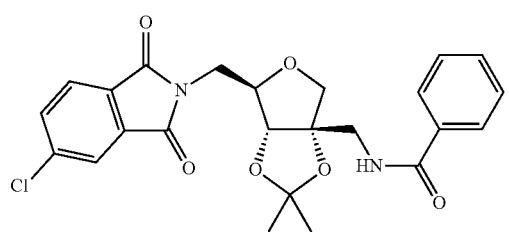 [SMILES: CC1(C)O[C@@H]2[C@@H](CN3C(=O)c4ccc(Cl)cc4C3=O)OC[C@]2(CNC(=O)c2ccccc2)O1] |
| 112 | 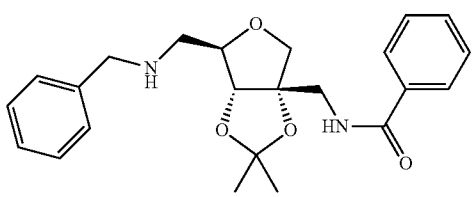 [SMILES: CC1(C)O[C@@H]2[C@@H](CNCc3ccccc3)OC[C@]2(CNC(=O)c2ccccc2)O1] |
| 113 | 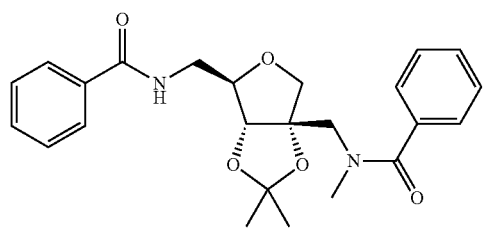 [SMILES: CN(C[C@]12CO[C@H](CNC(=O)c3ccccc3)[C@H]1OC(C)(C)O2)C(=O)c1ccccc1] |
| 114 | 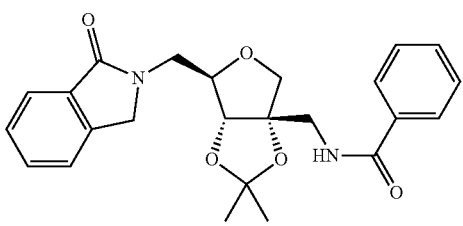 [SMILES: CC1(C)O[C@@H]2[C@@H](CN3Cc4ccccc4C3=O)OC[C@]2(CNC(=O)c2ccccc2)O1] |

TABLE 1-continued
| 115 | 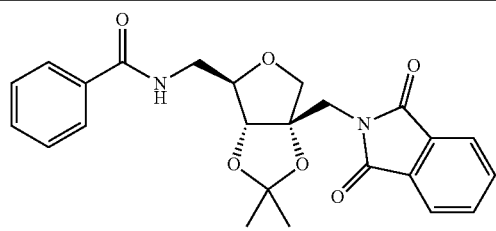 |
| 116 | 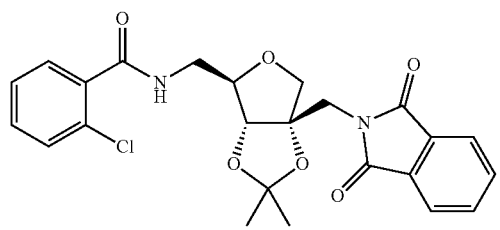 [SMILES: CC1(C)O[C@@H]2[C@@H](CNC(=O)c3ccccc3Cl)OC[C@]2(CN2C(=O)c3ccccc3C2=O)O1] |
| 119 | 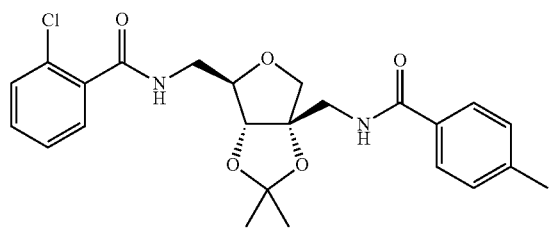 [SMILES: Cc1ccc(C(=O)NC[C@]23CO[C@H](CNC(=O)c4ccccc4Cl)[C@H]2OC(C)(C)O3)cc1] |
| 120 | 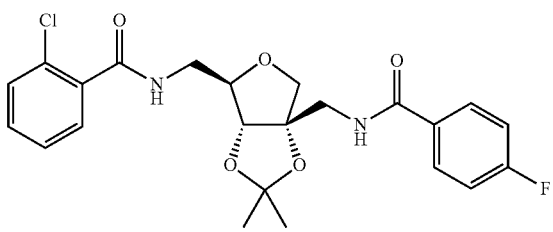 [SMILES: CC1(C)O[C@@H]2[C@@H](CNC(=O)c3ccccc3Cl)OC[C@]2(CNC(=O)c2ccc(F)cc2)O1] |
| 121 | 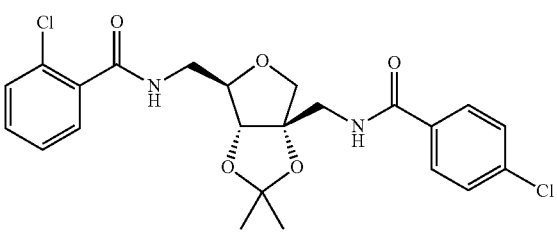 [SMILES: CC1(C)O[C@@H]2[C@@H](CNC(=O)c3ccccc3Cl)OC[C@]2(CNC(=O)c2ccc(Cl)cc2)O1] |
| 122 | 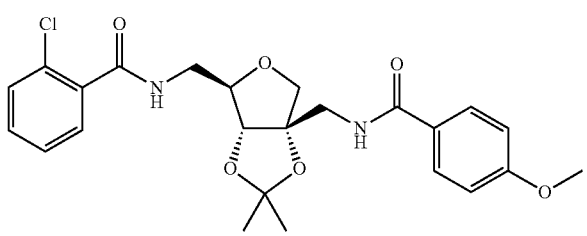 [SMILES: COc1ccc(C(=O)NC[C@]23CO[C@H](CNC(=O)c4ccccc4Cl)[C@H]2OC(C)(C)O3)cc1] |
| 123 | 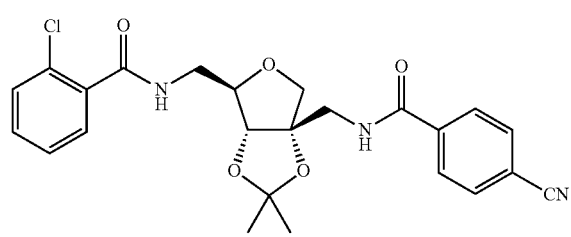 [SMILES: CC1(C)O[C@@H]2[C@@H](CNC(=O)c3ccccc3Cl)OC[C@]2(CNC(=O)c2ccc(C#N)cc2)O1] |

TABLE 1-continued
| 124 | 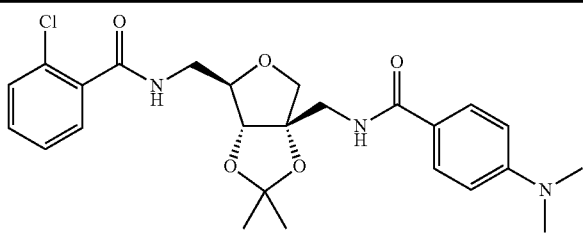 |
| 125 | 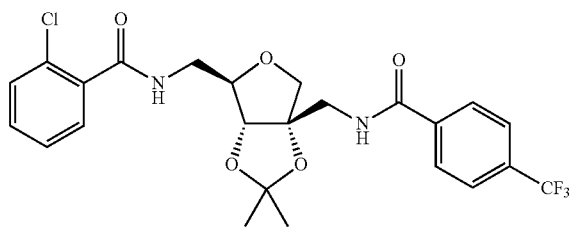 [SMILES: CC1(C)O[C@@H]2[C@@H](CNC(=O)c3ccccc3Cl)OC[C@]2(CNC(=O)c2ccc(C(F)(F)F)cc2)O1] |
| 126 | 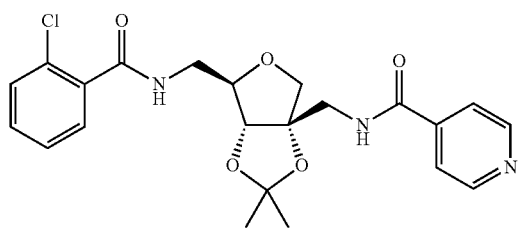 [SMILES: CC1(C)O[C@@H]2[C@@H](CNC(=O)c3ccccc3Cl)OC[C@]2(CNC(=O)c2ccncc2)O1] |
| 127 | 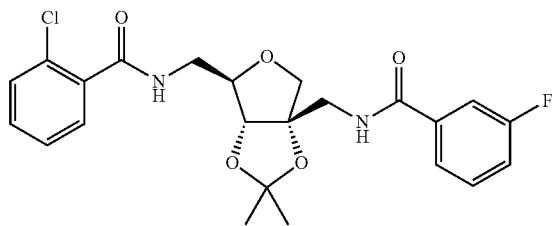 [SMILES: CC1(C)O[C@@H]2[C@@H](CNC(=O)c3ccccc3Cl)OC[C@]2(CNC(=O)c2cccc(F)c2)O1] |
| 128 | 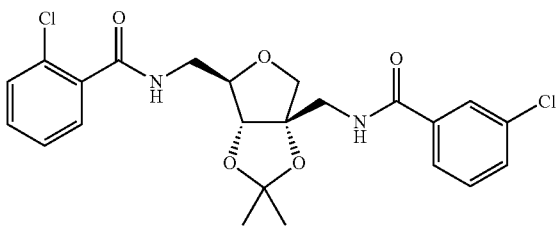 [SMILES: CC1(C)O[C@@H]2[C@@H](CNC(=O)c3ccccc3Cl)OC[C@]2(CNC(=O)c2cccc(Cl)c2)O1] |
| 129 | 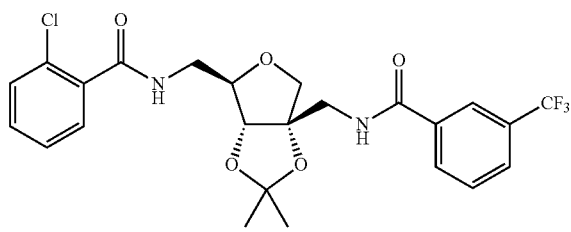 [SMILES: CC1(C)O[C@@H]2[C@@H](CNC(=O)c3ccccc3Cl)OC[C@]2(CNC(=O)c2cccc(C(F)(F)F)c2)O1] |
| 130 | 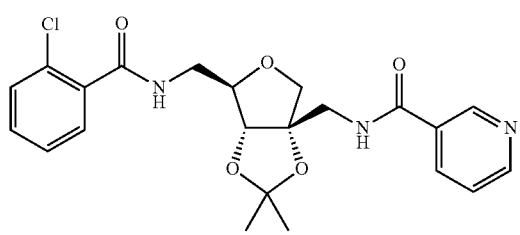 [SMILES: CC1(C)O[C@@H]2[C@@H](CNC(=O)c3ccccc3Cl)OC[C@]2(CNC(=O)c2cccnc2)O1] |

TABLE 1-continued
| 131 | 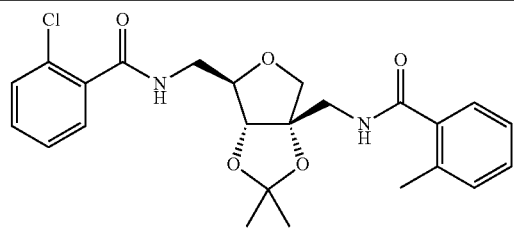 |
| 132 | 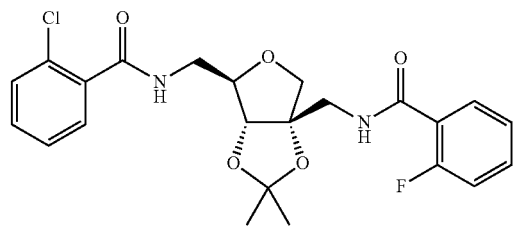 |
| 133 | 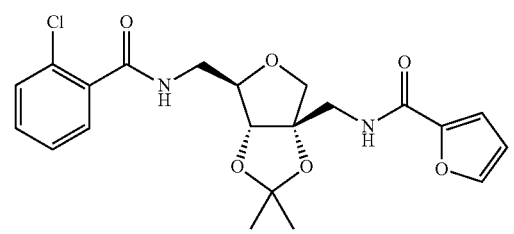 [SMILES: CC1(C)O[C@@H]2[C@@H](CNC(=O)c3ccccc3Cl)OC[C@]2(CNC(=O)c2ccco2)O1] |
| 134 | 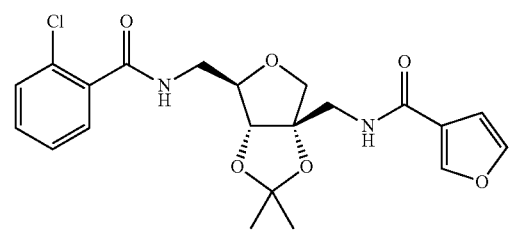 [SMILES: CC1(C)O[C@@H]2[C@@H](CNC(=O)c3ccccc3Cl)OC[C@]2(CNC(=O)c2ccoc2)O1] |
| 135 | 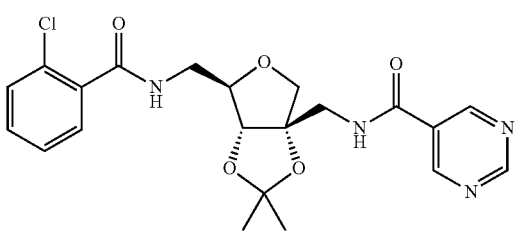 [SMILES: CC1(C)O[C@@H]2[C@@H](CNC(=O)c3ccccc3Cl)OC[C@]2(CNC(=O)c2cncnc2)O1] |
| 136 | 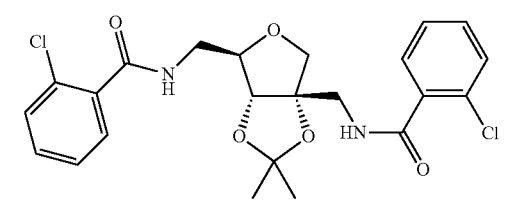 [SMILES: CC1(C)O[C@@H]2[C@@H](CNC(=O)c3ccccc3Cl)OC[C@]2(CNC(=O)c2ccccc2Cl)O1] |
| 137 | 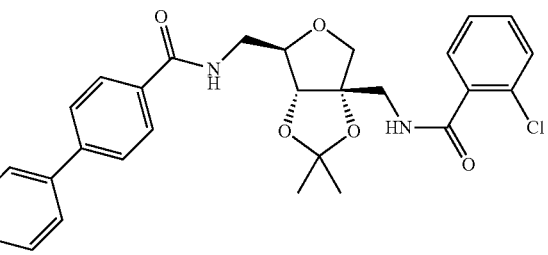 |

| | |
|---|---|
| 138 | 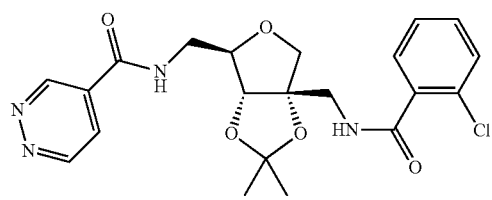 [SMILES: CC1(C)O[C@@H]2[C@@H](CNC(=O)c3ccnnc3)OC[C@]2(CNC(=O)c2ccccc2Cl)O1] |
| 139 | 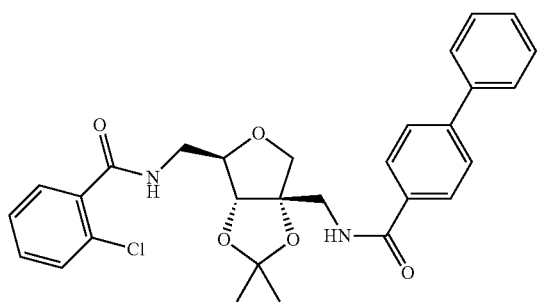 [SMILES: CC1(C)O[C@@H]2[C@@H](CNC(=O)c3ccccc3Cl)OC[C@]2(CNC(=O)c2ccc(-c3ccccc3)cc2)O1] |
| 140 | 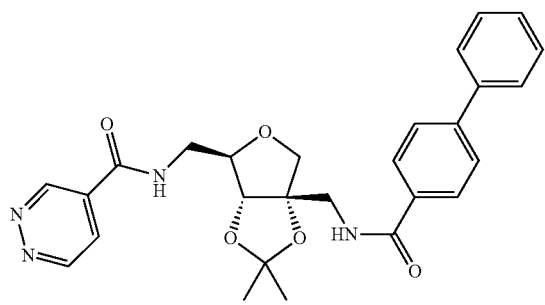 [SMILES: CC1(C)O[C@@H]2[C@@H](CNC(=O)c3ccnnc3)OC[C@]2(CNC(=O)c2ccc(-c3ccccc3)cc2)O1] |
| 141 | 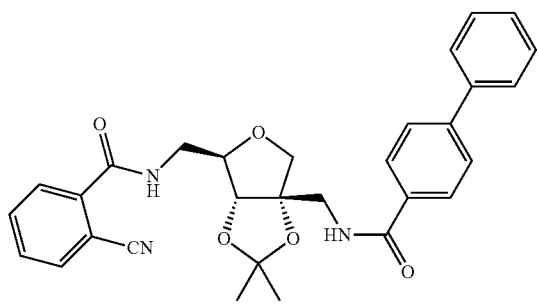 [SMILES: CC1(C)O[C@@H]2[C@@H](CNC(=O)c3ccccc3C#N)OC[C@]2(CNC(=O)c2ccc(-c3ccccc3)cc2)O1] |
| 142 | 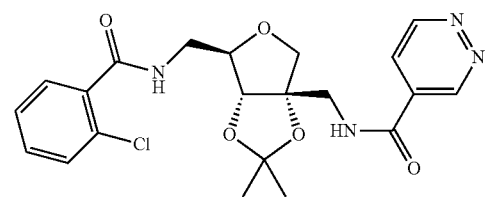 [SMILES: CC1(C)O[C@@H]2[C@@H](CNC(=O)c3ccccc3Cl)OC[C@]2(CNC(=O)c2ccnnc2)O1] |
| 143 | 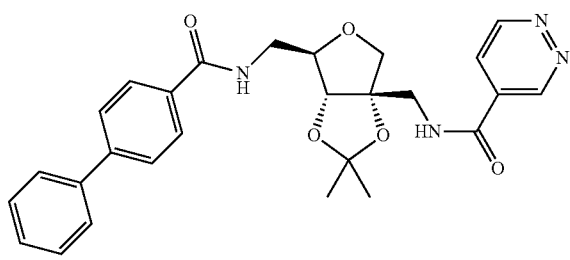 [SMILES: CC1(C)O[C@@H]2[C@@H](CNC(=O)c3ccc(-c4ccccc4)cc3)OC[C@]2(CNC(=O)c2ccnnc2)O1] |

TABLE 1-continued
| | | | |
|---|---|---|---|
| 144 | 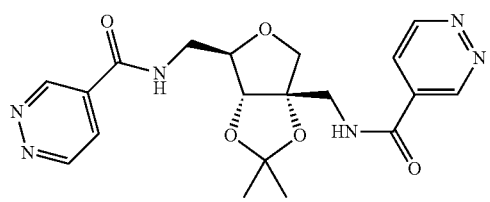 [SMILES: CC1(C)O[C@@H]2[C@@H](CNC(=O)c3ccnnc3)OC[C@]2(CNC(=O)c2ccnnc2)O1] | | |
| 145 | 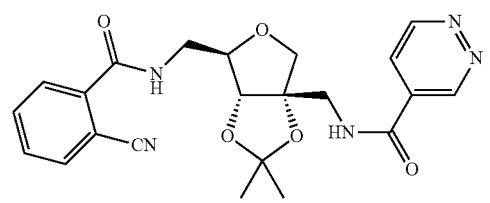 [SMILES: CC1(C)O[C@@H]2[C@@H](CNC(=O)c3ccccc3C#N)OC[C@]2(CNC(=O)c2ccnnc2)O1] | | |
| 146 | 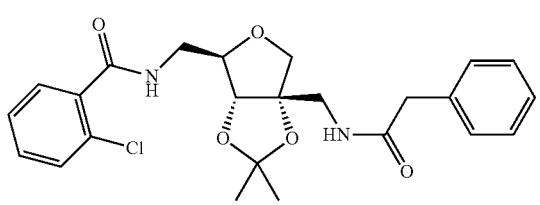 [SMILES: CC1(C)O[C@@H]2[C@@H](CNC(=O)c3ccccc3Cl)OC[C@]2(CNC(=O)Cc2ccccc2)O1] | | |
| 147 | 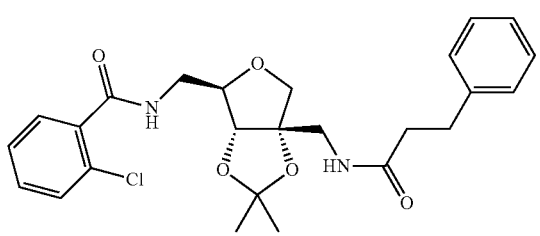 [SMILES: CC1(C)O[C@@H]2[C@@H](CNC(=O)c3ccccc3Cl)OC[C@]2(CNC(=O)CCc2ccccc2)O1] | | |
| 150 | 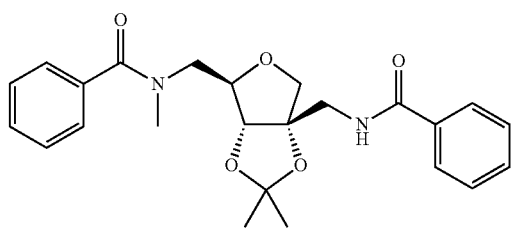 [SMILES: CN(C[C@H]1OC[C@]2(CNC(=O)c3ccccc3)OC(C)(C)O[C@H]12)C(=O)c1ccccc1] | | |
| 151 | 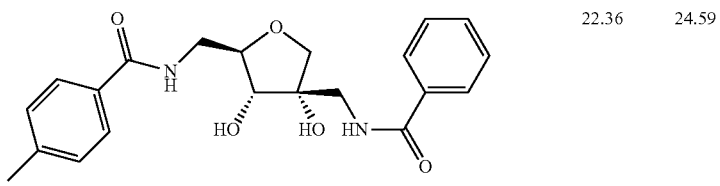 | 22.36 | 24.59 |
| 152 | 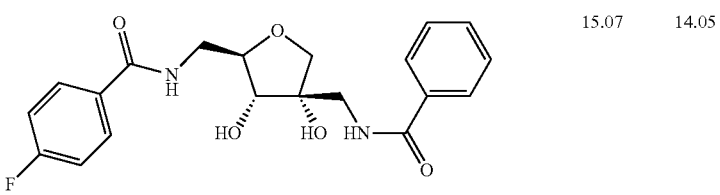 | 15.07 | 14.05 |

TABLE 1-continued

| # | Structure | | | |
|---|---|---|---|---|
| 153 | 4-Cl-C6H4-C(O)NH-CH2-[tetrahydrofuran(3,4-diOH)]-CH2-NHC(O)-C6H5 | 9.185 | 8.577 | 18.01 | 21.39 |
| 154 | 4-MeO-C6H4-C(O)NH-CH2-[tetrahydrofuran(3,4-diOH)]-CH2-NHC(O)-C6H5 | 19.34 | 22.56 | | |
| 155 | 4-NC-C6H4-C(O)NH-CH2-[tetrahydrofuran(3,4-diOH)]-CH2-NHC(O)-C6H5 | 15.57 | 16.06 | | |
| 156 | 4-(Me2N)-C6H4-C(O)NH-CH2-[tetrahydrofuran(3,4-diOH)]-CH2-NHC(O)-C6H5 | 16.58 | 11.27 | | |
| 157 | 4-CF3-C6H4-C(O)NH-CH2-[tetrahydrofuran(3,4-diOH)]-CH2-NHC(O)-C6H5 | 15.95 | 11.25 | | |
| 158 | pyridin-4-yl-C(O)NH-CH2-[tetrahydrofuran(3,4-diOH)]-CH2-NHC(O)-C6H5 | 7.268 | 13.89 | 9.943 | 19.16 |
| 159 | biphenyl-4-yl-C(O)NH-CH2-[tetrahydrofuran(3,4-diOH)]-CH2-NHC(O)-C6H5 | 10.97 | 6.966 | 6.379 | 11.32 |
| 160 | 3-Me-C6H4-C(O)NH-CH2-[tetrahydrofuran(3,4-diOH)]-CH2-NHC(O)-C6H5 | 23.09 | 23.39 | | |

TABLE 1-continued

| | | | | | |
|---|---|---|---|---|---|
| 161 | (3-fluorobenzamide structure) | 9.353 | 16.57 | | |
| 162 | (3-chlorobenzamide structure) | 24.07 | 29.06 | | |
| 163 | (3-methoxybenzamide structure) | 28.44 | 27.21 | | |
| 164 | (3-cyanobenzamide structure) | 22.11 | 14.49 | | |
| 165 | (3-dimethylaminobenzamide structure) | 16.00 | 26.43 | | |
| 166 | (3-trifluoromethylbenzamide structure) | 10.16 | 12.34 | 9.135 | 12.27 |
| 167 | (nicotinamide structure) | 9.813 | 15.22 | | |
| 168 | (biphenyl-3-carboxamide structure) | 9.830 | 32.61 | | |
| 169 | (2-methylbenzamide structure) | 11.68 | 13.87 | 13.67 | 52.62 |

TABLE 1-continued
| | | | | | |
|---|---|---|---|---|---|
| 170 | 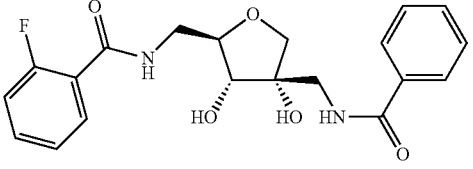 | 11.84 | 16.30 | | |
| 171 | 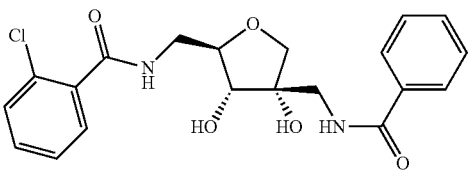 | 11.56 | 7.776 | 0.3890 | 7.976 |
| 172 | 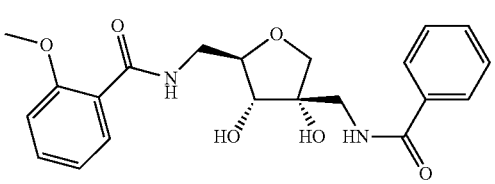 [SMILES: COc1ccccc1C(=O)NC[C@H]1OC[C@@](O)(CNC(=O)c2ccccc2)[C@@H]1O] | 15.37 | 31.40 | | |
| 173 | 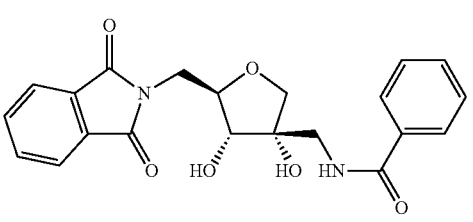 [SMILES: O=C(NC[C@]1(O)CO[C@H](CN2C(=O)c3ccccc3C2=O)[C@H]1O)c1ccccc1] | 11.18 | 8.805 | 5.013 | 8.298 |
| 174 | 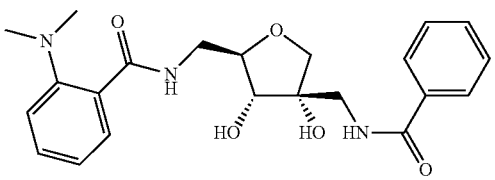 [SMILES: CN(C)c1ccccc1C(=O)NC[C@H]1OC[C@@](O)(CNC(=O)c2ccccc2)[C@@H]1O] | 28.01 | 11.11 | | |
| 175 | 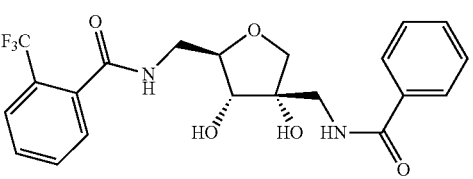 [SMILES: O=C(NC[C@]1(O)CO[C@H](CNC(=O)c2ccccc2C(F)(F)F)[C@H]1O)c1ccccc1] | 22.48 | 34.85 | | |
| 176 | 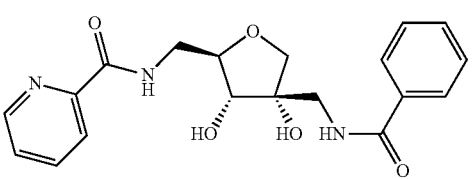 [SMILES: O=C(NC[C@]1(O)CO[C@H](CNC(=O)c2ncccn2)[C@H]1O)c1ccccc1] | 21.56 | 36.02 | | |
| 177 | 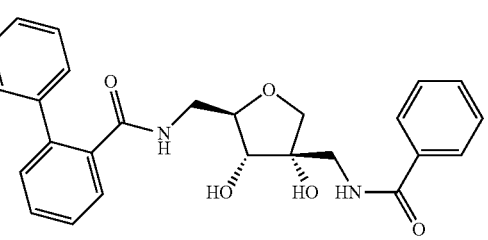 | 15.07 | 13.23 | | |

TABLE 1-continued

| # | Structure | A | B | C | D |
|---|---|---|---|---|---|
| 178 | 2-bromobenzamide derivative | 4.10 | 17.51 | 9.845 | 19.74 |
| 179 | 2-iodobenzamide derivative | 3.84 | 16.46 | 1.855 | 20.38 |
| 180 | 3,4-dimethylbenzamide derivative | 79.13 | 65.66 | | |
| 181 | 3,4-difluorobenzamide derivative | 67.74 | 59.09 | | |
| 182 | 3,4-dichlorobenzamide derivative | 42.13 | 33.81 | | |
| 183 | 3,4-dimethoxybenzamide derivative | 60.04 | 61.60 | | |
| 184 | 1-naphthamide derivative | 33.91 | 40.23 | | |
| 185 | 2-naphthamide derivative | 22.11 | 36.32 | | |

TABLE 1-continued

| # | Structure | | | | |
|---|---|---|---|---|---|
| 186 | (1-methylindole-2-carboxamide derivative) | 41.45 | 42.75 | | |
| 187 | (1-methylindole-3-carboxamide derivative) | 32.91 | 29.24 | | |
| 188 | (benzamide derivative) | 34.36 | 34.64 | | |
| 189 | (phenylacetamide derivative) | 59.77 | 58.95 | | |
| 190 | (3-phenylpropanamide derivative) | 64.43 | 29.24 | | |
| 191 | (cyclohexanecarboxamide derivative) | 32.28 | 19.28 | | |
| 192 | (2,6-dichlorobenzamide derivative) | 31.41 | 43.74 | 59.24 | 136.2 |
| 193 | (2,4-dichlorobenzamide derivative) | 10.80 | 11.25 | 11.37 | 11.74 |

TABLE 1-continued

| # | Structure | | | | |
|---|---|---|---|---|---|
| 194 | 2,4,6-trichlorobenzamide derivative | 20.50 | 13.31 | | |
| 195 | 3,5-dichloropyridine-4-carboxamide derivative | 18.31 | 18.55 | 7.203 | 9.261 |
| 196 | 2,4-dichloropyridine-3-carboxamide derivative | 21.86 | 8.072 | 12.97 | 7.876 |
| 197 | 2,6-dichloropyridine-3-carboxamide derivative | 18.75 | 16.84 | 7.919 | 8.268 |
| 198 | 4,6-dichloropyridine-3-carboxamide derivative | 19.18 | 11.25 | 10.78 | 7.517 |
| 199 | 2-chloropyridine-3-carboxamide derivative | 68.76 | 65.56 | >250 | >250 |
| 200 | 3-chloropyridine-4-carboxamide derivative | 58.59 | 48.93 | >250 | 232.3 |
| 201 | 4-chloropyridine-3-carboxamide derivative | 51.81 | 74.81 | 199.6 | >250 |

TABLE 1-continued

| | | | | | | |
|---|---|---|---|---|---|---|
| 202 | (structure) | 14.00 | 18.24 | | |
| 203 | (structure) | 41.20 | 31.95 | | |
| 204 | (structure) | 13.04 | 15.85 | | |
| 205 | (structure) | 6.699 | 16.51 | | |
| 206 | (structure) | 6.460 | 15.17 | | |
| 207 | (structure) | 6.950 | 13.70 | 7.279 | 8.535 |
| 208 | (structure) | 10.52 | 18.77 | | |
| 209 | (structure) | 22.47 | 21.74 | 29.33 | 23.48 |

TABLE 1-continued

| # | Structure | | | | |
|---|---|---|---|---|---|
| 210 | (1-methylimidazole-5-carboxamide derivative) | 22.10 | 26.95 | 52.34 | 58.24 |
| 211 | (methanesulfonamide derivative) | 31.02 | 38.03 | | |
| 212 | (ethanesulfonamide derivative) | 50.68 | 52.64 | | |
| 213 | (isopropylsulfonamide derivative) | 28.32 | 32.67 | | |
| 214 | (trifluoromethanesulfonamide derivative) | 29.28 | 42.85 | | |
| 215 | (benzenesulfonamide derivative) | 22.23 | 31.29 | | |
| 216 | (p-toluenesulfonamide derivative) | 16.96 | 25.95 | | |
| 217 | (4-chlorobenzenesulfonamide derivative) | 14.04 | 14.85 | 23.46 | 27.78 |

TABLE 1-continued

| | | | |
|---|---|---|---|
| 218 | (structure) | 35.03 | 26.88 |
| 219 | (structure) | 16.13 | 17.02 |
| 220 | (structure) | 25.63 | 29.85 |
| 221 | (structure) | 54.01 | 33.81 |
| 222 | (structure) | 47.10 | 73.90 |
| 223 | (structure) | 23.99 | 18.72 |
| 224 | (structure) | 20.22 | 27.33 |

TABLE 1-continued

| # | Structure | | | |
|---|---|---|---|---|
| 225 | [structure] | 23.96 | 27.38 | | |
| 226 | [structure] | 50.74 | 28.64 | | |
| 227 | [structure] | 77.57 | 61.81 | | |
| 228 | [structure] | 18.68 | 22.13 | 41.2 | 45.2 |
| 229 | [structure] | 7.17 | 11.15 | 5.820 | 8.920 |
| 230 | [structure] | 24.90 | 30.15 | 57.70 | 60.20 |
| 231 | [structure] | 8.18 | 28.85 | 2.632 | 38.97 |
| 249 | [structure] | 6.67 | 13.59 | 5.357 | 28.42 |

TABLE 1-continued
| | | | | | |
|---|---|---|---|---|---|
| 250 | 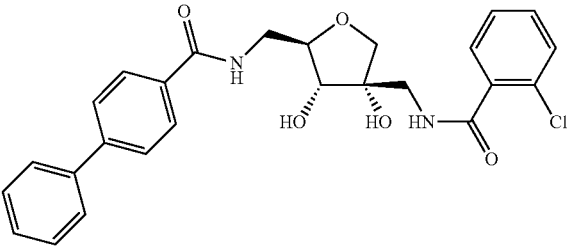 [SMILES: O=C(NC[C@H]1OC[C@@](O)(CNC(=O)c2ccccc2Cl)[C@@H]1O)c1ccc(-c2ccccc2)cc1] | 18.82 | 29.48 | 23.04 | 61.29 |
| 251 | 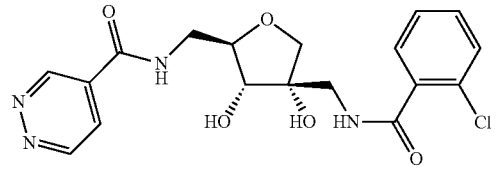 [SMILES: O=C(NC[C@H]1OC[C@@](O)(CNC(=O)c2ccccc2Cl)[C@@H]1O)c1ccnnc1] | 3.85 | 37.03 | 3.376 | 98.93 |
| 252 | 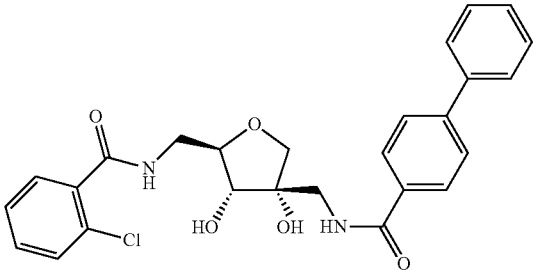 [SMILES: O=C(NC[C@]1(O)CO[C@H](CNC(=O)c2ccccc2Cl)[C@H]1O)c1ccc(-c2ccccc2)cc1] | 2.25 | 29.40 | 11.84 | 69.17 |
| 253 | 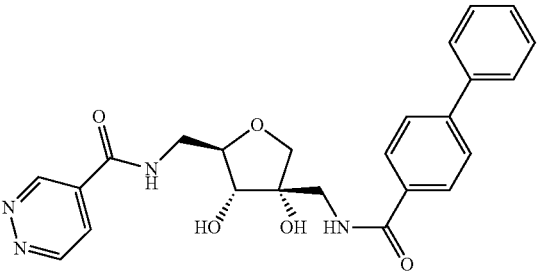 [SMILES: O=C(NC[C@H]1OC[C@@](O)(CNC(=O)c2ccc(-c3ccccc3)cc2)[C@@H]1O)c1ccnnc1] | 4.25 | 22.50 | 8.537 | 45.40 |
| 254 | 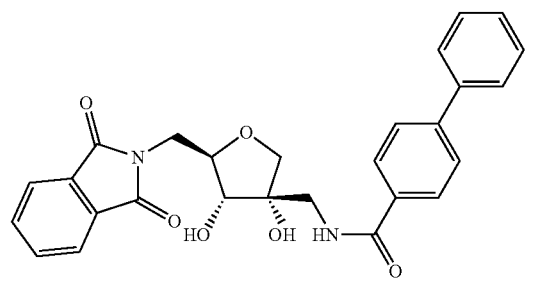 [SMILES: O=C(NC[C@]1(O)CO[C@H](CN2C(=O)c3ccccc3C2=O)[C@H]1O)c1ccc(-c2ccccc2)cc1] | 3.52 | 30.44 | 4.793 | 57.12 |
| 255 | 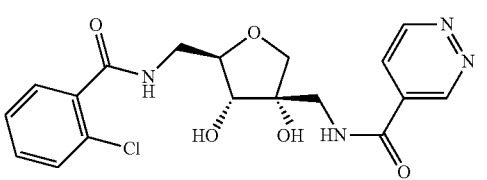 [SMILES: O=C(NC[C@]1(O)CO[C@H](CNC(=O)c2ccccc2Cl)[C@H]1O)c1ccnnc1] | 8.03 | 25.78 | 14.95 | 55.71 |

TABLE 1-continued

| # | Structure | | | | |
|---|---|---|---|---|---|
| 256 | (biphenyl-C(O)NH-CH2-[tetrahydrofuran(OH)(OH)]-CH2-NHC(O)-pyridazinyl) | 14.25 | 29.97 | 15.46 | 53.39 |
| 257 | (pyridazinyl-C(O)NH-CH2-[tetrahydrofuran(OH)(OH)]-CH2-NHC(O)-pyridazinyl) | 1.71 | 17.13 | 7.135 | 17.98 |
| 258 | (phthalimido-CH2-[tetrahydrofuran(OH)(OH)]-CH2-NHC(O)-pyridazinyl) | 0.73 | 23.56 | 5.853 | 11.41 |
| 259 | (2-Cl-C6H4-C(O)NH-CH2-[tetrahydrofuran(OH)(OH)]-CH2-NHC(O)CH2-Ph) | 55.12 | 71.25 | | |
| 260 | (2-Cl-C6H4-C(O)NH-CH2-[tetrahydrofuran(OH)(OH)]-CH2-NHC(O)CH2CH2-Ph) | 57.01 | 71.12 | | |
| 261 | (Ph-C(O)N(Me)-CH2-[tetrahydrofuran(OH)(OH)]-CH2-NHC(O)-Ph) | 6.09 | 10.02 | 8.499 | 24.29 |
| 263 | (3,4,5-tri-BnO-C6H2-C(O)NH-CH2-[tetrahydrofuran with acetonide]-CH2-NHC(O)-C6H2-3,4,5-tri-OBn) | | | | |

TABLE 1-continued

| N° | Structure | Pretreat. (25 μM)[a] | Combin. (25 μM)[a] | Pretreat (EC50) (μM)[b] | Combin. (EC50) (μM)[b] |
|---|---|---|---|---|---|
| 264 | 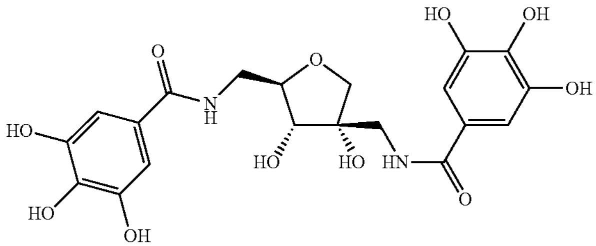 [SMILES: O=C(NC[C@H]1OC[C@@](O)(CNC(=O)c2cc(O)c(O)c(O)c2)[C@@H]1O)c1cc(O)c(O)c(O)c1] | 22.35 | 57.74 | 63.82 | 191.1 |
| 270 | 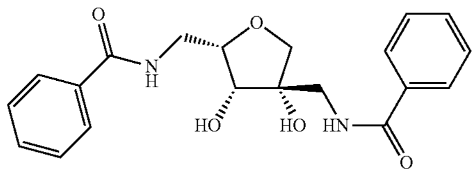 [SMILES: O=C(NC[C@@H]1OC[C@@](O)(CNC(=O)c2ccccc2)[C@@H]1O)c1ccccc1] | 51.80 | 55.70 | 224 | >250 |
| REF | 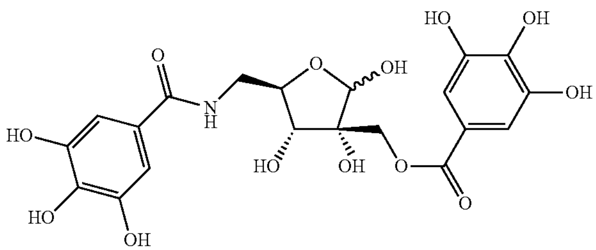 | 61.63 | 65.94 | 145.5 | 166.6 |
| 232 | 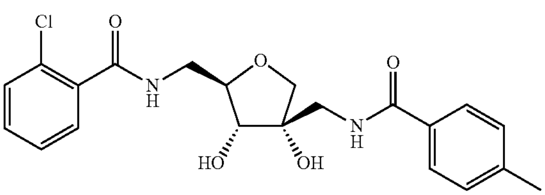 [SMILES: Cc1ccc(C(=O)NC[C@]2(O)CO[C@H](CNC(=O)c3ccccc3Cl)[C@H]2O)cc1] | 52.41 | 42.16 | 79.69 | 41.88 |
| 233 | 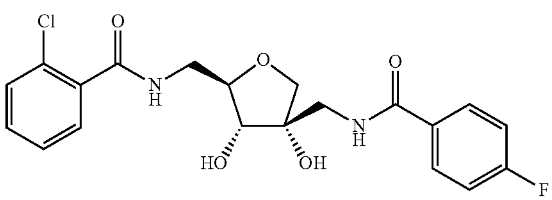 [SMILES: O=C(NC[C@]1(O)CO[C@H](CNC(=O)c2ccccc2Cl)[C@H]1O)c1ccc(F)cc1] | 88.61 | 91.63 | | |
| 234 | 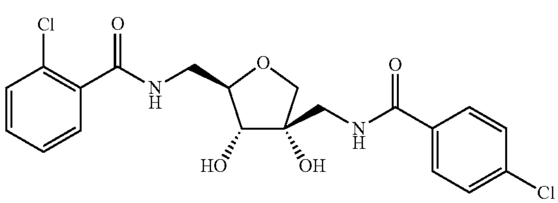 [SMILES: O=C(NC[C@]1(O)CO[C@H](CNC(=O)c2ccccc2Cl)[C@H]1O)c1ccc(Cl)cc1] | 61.12 | 56.96 | | |
| 235 | 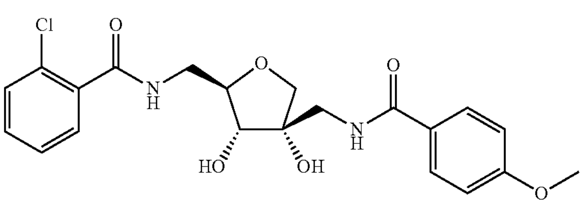 [SMILES: COc1ccc(C(=O)NC[C@]2(O)CO[C@H](CNC(=O)c3ccccc3Cl)[C@H]2O)cc1] | 66.10 | 57.35 | | |

TABLE 1-continued
| 236 | 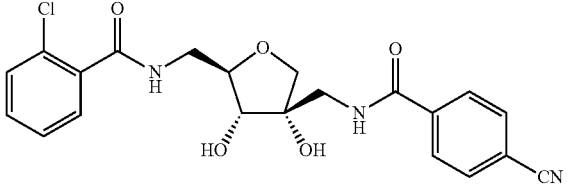 [SMILES: N#Cc1ccc(C(=O)NC[C@]2(O)CO[C@H](CNC(=O)c3ccccc3Cl)[C@H]2O)cc1] | 73.00 | 70.73 | | |
| 237 | 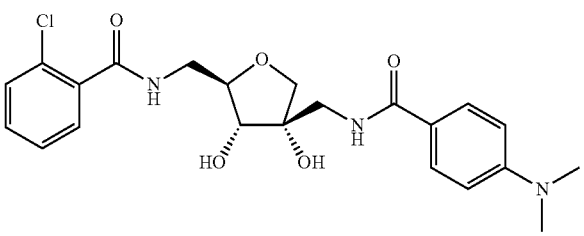 [SMILES: CN(C)c1ccc(C(=O)NC[C@]2(O)CO[C@H](CNC(=O)c3ccccc3Cl)[C@H]2O)cc1] | 58.79 | 47.56 | 47.63 | 69.73 |
| 238 | 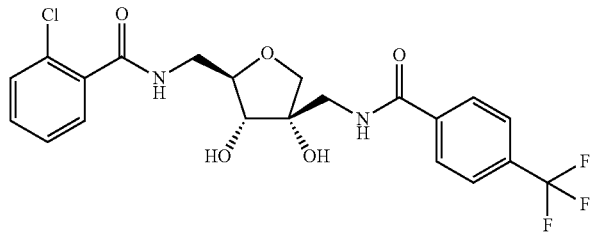 [SMILES: O=C(NC[C@]1(O)CO[C@H](CNC(=O)c2ccccc2Cl)[C@H]1O)c1ccc(C(F)(F)F)cc1] | 45.03 | 68.51 | 84.56 | 75.23 |
| 239 | 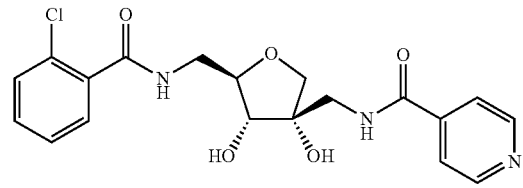 [SMILES: O=C(NC[C@]1(O)CO[C@H](CNC(=O)c2ccccc2Cl)[C@H]1O)c1ccncc1] | 49.98 | 58.76 | | |
| 240 | 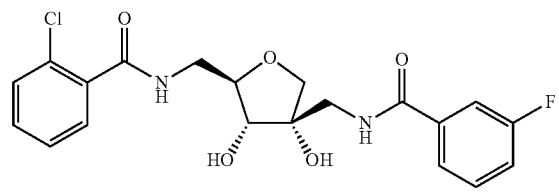 [SMILES: O=C(NC[C@]1(O)CO[C@H](CNC(=O)c2ccccc2Cl)[C@H]1O)c1cccc(F)c1] | 118.37 | 91.32 | | |
| 241 | 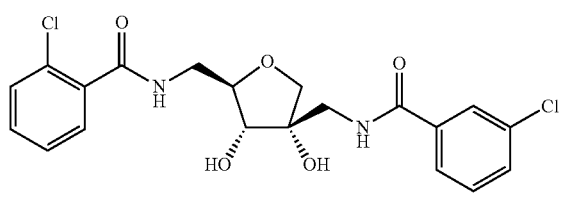 [SMILES: O=C(NC[C@]1(O)CO[C@H](CNC(=O)c2ccccc2Cl)[C@H]1O)c1cccc(Cl)c1] | 98.17 | 81.35 | | |
| 242 | 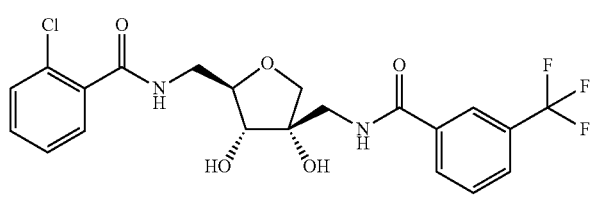 [SMILES: O=C(NC[C@]1(O)CO[C@H](CNC(=O)c2ccccc2Cl)[C@H]1O)c1cccc(C(F)(F)F)c1] | 117.15 | 87.14 | | |

TABLE 1-continued

| # | Structure | | | | |
|---|---|---|---|---|---|
| 243 | (2-Cl-benzamide)-CH2-tetrahydrofuran(OH,OH)-CH2-NH-C(O)-pyridin-3-yl | 85.00 | 51.83 | | |
| 244 | (2-Cl-benzamide)-CH2-tetrahydrofuran(OH,OH)-CH2-NH-C(O)-(2-methylphenyl) | 41.07 | 54.77 | 56.44 | 123.6 |
| 245 | (2-Cl-benzamide)-CH2-tetrahydrofuran(OH,OH)-CH2-NH-C(O)-(2-fluorophenyl) | 61.75 | 44.14 | 48.56 | 62.18 |
| 246 | (2-Cl-benzamide)-CH2-tetrahydrofuran(OH,OH)-CH2-NH-C(O)-furan-2-yl | 87.98 | 62.82 | | |
| 247 | (2-Cl-benzamide)-CH2-tetrahydrofuran(OH,OH)-CH2-NH-C(O)-furan-3-yl | 42.14 | 49.94 | 68.47 | 76.65 |
| 248 | (2-Cl-benzamide)-CH2-tetrahydrofuran(OH,OH)-CH2-NH-C(O)-pyrimidin-5-yl | 64.01 | 65.41 | | |

[a] percentage Colony Forming Units (CFU's) per biofilm when biofilms are treated with VAN alone (20 μg/ml) or in combination with HAM or a HAM-analogue compared to the untreated (negative) control.
[b] $EC_{50}$ values are expressed as the concentration of the analogue needed to get 50% killing of the bacteria compared to treatment with antibiotic alone (general activity of the antibiotic) and complete killing (max activity).
REF = hamamelitannin

REFERENCES

Simone, M. I., A. A. Edwards, G. E. Tranter and G. W. J. Fleet (2008). "Carbon-branched δ-tetrahydrofuran sugar amino acids (SAAs) as dipeptide isostere scaffolds." Tetrahedron: Asymmetry 19(24): 2887-2894.

Bouisset, T., G. Gosselin, L. Griffe, J.-C. Meillon and R. Storer (2008). "Synthesis of 2'-C-methyl-branched isonucleosides." Tetrahedron 64(28): 6657-6661.

Boren, B. C., S. Narayan, L. K. Rasmussen, L. Zhang, H. Zhao, Z. Lin, G. Jia and V. V. Fokin (2008). "Ruthenium-Catalyzed Azide-Alkyne Cycloaddition: Scope and Mechanism." Journal of the American Chemical Society 130(28): 8923-8930.

Brackman, G., Cos, P., Maes, L., Nelis, H. J. & Coenye, T. (2011). Quorum sensing inhibitors increase the susceptibility of bacterial biofilms to antibiotics in vitro and in vivo. Antimicrob Ag Chemother 55:2655-2661

Garcia-Moreno, M. I., J. M. Benito, C. Ortiz Mellet and J. M. Garcia Fernandez * (2000). "Nitrogen versus sulfur acylation in sugar thioureas: regioselectivity and conformational consequences." Tetrahedron: Asymmetry 11(6): 1331-1341.

Taki, M., M. Desaki, A. Ojida, S. Iyoshi, T. Hirayama, I. Hamachi and Y. Yamamoto (2008). "Fluorescence imaging of intracellular cadmium using a dual-excitation ratiometric chemosensor." J Am Chem Soc 130(38): 12564-12565.

Batra, H.; Moriarty, R. M.; Penmasta, R.; Sharma, V.; Stanciuc, G.; Staszewski, J. P.; Tuladhar, S. M.; Walsh, D. A.; Datla, S.; Krishnaswamy, S. A Concise, Efficient and Production-Scale Synthesis of a Protected I-Lyxonolactone Derivative: An Important Aldonolactone Core. Organic Process Research & Development 2006, 10, 484-486.

Demon D, Ludwig C, Breyne K, Guédé D, Dörner J C, Froyman R, Meyer E. The intramammary efficacy of first generation cephalosporins against Staphylococcus aureus mastitis in mice. Vet Microbiol. 2012 Nov. 9; 160(1-2): 141-50.

Bouisset, T., G. Gosselin, L. Griffe, J.-C. Meillon and R. Storer (2008). "Synthesis of 2'-C-methyl-branched isonucleosides." Tetrahedron 64(28): 6657-6661.

The invention claimed is:

1. A compound of Formula I,

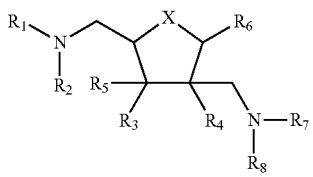

Wherein

X is selected from N—$R_9$, O and S—$R_9$;

$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;

$R_2$ is selected from —H and —$C_{1-6}$alkyl, or $R_1$ taken together with $R_2$ forms $Het_3$;

$R_3$ is absent or selected from —H, —OH, and -halo;

$R_4$ is selected from —H, —OH, and -halo;

or $R_3$ taken together with $R_4$ forms a dioxolane moiety, which is optionally substituted with from 1 to 3 substituents selected from —OH, —$C_{1-6}$alkyl, and -halo;

$R_5$ is selected from —H, —OH, =O, and -halo;

$R_6$ is selected from —H, —OH, -halo, —$C_{1-6}$alkyl, —O—$C_{1-6}$alkyl, —S—$C_{1-6}$alkyl, and —CN;

$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;

$R_8$ is selected from —H and —$C_{1-6}$alkyl;

or $R_7$ taken together with $R_8$ forms $Het_4$;

$R_9$ is selected from —H, —$C_{1-6}$alkyl, —(C=O)—$C_{1-6}$alkyl, —(C=O)—$Ar_3$ and —$Ar_3$ when X is N;

absent when X is O; or absent or selected from =O, and —$O_2$ when X is S;

$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH—$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;

$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{19}$, —$C_{3-6}$cycloalkyl, -$Het_2$ and —$Ar_2$;

$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;

$Ar_1$, $Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{20}R_{21}$;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{22}R_{23}$.

2. A compound according to claim 1,

Wherein

X is selected from N—$R_9$, O and S—$R_9$;

$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;

$R_2$ is selected from —H and —$C_{1-6}$alkyl, or $R_1$ taken together with $R_2$ forms $Het_3$;

$R_3$ taken together with $R_4$ forms a dioxolane moiety, which is optionally substituted with from 1 to 3 substituents selected from —OH, —$C_{1-6}$alkyl, and -halo;

$R_5$ is selected from —H, —OH, =O, and -halo;

$R_6$ is selected from —H, —OH, -halo, —$C_{1-6}$alkyl, —O—$C_{1-6}$alkyl, —S—$C_{1-6}$alkyl, and —CN;

$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;

$R_8$ is selected from —H and —$C_{1-6}$alkyl;

or $R_7$ taken together with $R_8$ forms $Het_4$;

$R_9$ is selected from —H, —$C_{1-6}$alkyl, —(C=O)—$C_{1-6}$alkyl, —(C=O)—$Ar_3$ and —$Ar_3$ when X is N;

absent when X is O; or absent or selected from =O, and —$O_2$ when X is S;

$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;

$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{19}$, —$C_{3-6}$cycloalkyl, -$Het_2$ and —$Ar_2$;

$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;

$Ar_1$, $Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{20}R_{21}$;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{22}R_{23}$.

3. A compound according to claim 1,

Wherein

X is selected from N—$R_9$, O and S—$R_9$;

$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;

$R_2$ is selected from —H and —$C_{1-6}$alkyl, or $R_1$ taken together with $R_2$ forms $Het_3$;

$R_3$ is —OH;

$R_4$ is —OH;

$R_5$ is selected from —H, —OH, =O, and -halo;

$R_6$ is selected from —H, —OH, -halo, —$C_{1-6}$alkyl, —O—$C_{1-6}$alkyl, —S—$C_{1-6}$alkyl, and —CN;

$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;

$R_8$ is selected from —H and —$C_{1-6}$alkyl;

or $R_7$ taken together with $R_8$ forms $Het_4$;

$R_9$ is selected from —H, —$C_{1-6}$alkyl, —(C=O)—$C_{1-6}$alkyl, —(C=O)—$Ar_3$ and —$Ar_3$ when X is N;

absent when X is O; or absent or selected from =O, and —$O_2$ when X is S;

$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;

$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{19}$, —$C_{3-6}$cycloalkyl, -$Het_2$ and —$Ar_2$;

$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;

$Ar_1$, $Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{20}R_{21}$;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{22}R_{23}$.

4. A compound according to claim 1,

Wherein

X is selected from N—$R_9$, O and S—$R_9$;

$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;

$R_2$ is selected from —H and —$C_{1-6}$alkyl, or $R_1$ taken together with $R_2$ forms $Het_3$;

$R_3$ is absent or selected from —H, —OH, and -halo;

$R_4$ is selected from —H, —OH, and -halo;

or $R_3$ taken together with $R_4$ forms a dioxolane moiety, which is optionally substituted with from 1 to 3 substituents selected from —OH, —$C_{1-6}$alkyl, and -halo;

$R_5$ is selected from —H, —OH, =O, and -halo;

$R_6$ is —H;

$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;

$R_8$ is selected from —H and —$C_{1-6}$alkyl or $R_7$ taken together with $R_8$ forms $Het_4$;

$R_9$ is selected from —H, —$C_{1-6}$alkyl, —(C=O)—$C_{1-6}$alkyl, —(C=O)—$Ar_3$ and —$Ar_3$ when X is N;

absent when X is O; or absent or selected from =O, and —$O_2$ when X is S;

$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;

$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{19}$, —$C_{3-6}$cycloalkyl, -$Het_2$ and —$Ar_2$;

$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;

$Ar_1$, $Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{20}R_{21}$;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{22}R_{23}$.

5. A compound according to claim 1,
Wherein
X is O;
$R_1$ is selected from —$C_{1-6}$alkyl, —$Ar_4$, —(C=O)—$R_{13}$, —(C=S)—$R_{14}$, and —$SO_2$—$R_{15}$; wherein said —$C_{1-6}$alkyl may be further substituted with —$R_{24}$;
$R_2$ is selected from —H and —$C_{1-6}$alkyl, or $R_1$ taken together with $R_2$ forms $Het_3$;
$R_3$ is absent or selected from —H, —OH, and -halo;
or $R_3$ taken together with $R_4$ forms a dioxolane moiety, which is optionally substituted with from 1 to 3 substituents selected from —OH, —$C_{1-6}$alkyl, and -halo;
$R_4$ is selected from —H, —OH, and -halo;
$R_5$ is selected from —H, —OH, =O, and -halo;
$R_6$ is selected from —H, —OH, -halo, —$C_{1-6}$alkyl, —O—$C_{1-6}$alkyl, —S—$C_{1-6}$alkyl, and —CN;
$R_7$ is selected from —$C_{1-6}$alkyl, —$Ar_5$, —(C=O)—$R_{10}$, —(C=S)—$R_{11}$, and —$SO_2$—$R_{12}$; wherein said —$C_{1-6}$alkyl may be further substituted with —$R_{25}$;
$R_8$ is selected from —H and —$C_{1-6}$alkyl or $R_7$ taken together with $R_8$ forms $Het_4$;
$R_9$ is absent;
$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, —NH—$C_{1-6}$alkyl, —NH-$Het_1$ and —NH—$Ar_1$; wherein each of said —$C_{1-6}$alkyl is optionally and independently substituted with from 1 to 3 substituents selected from =O, —OH, -halo, —O—$C_{1-6}$alkyl, —S—$C_{1-6}$alkyl, —CN, —$NR_{16}R_{17}$, —$C_{3-6}$cycloalkyl, -$Het_1$ and —$Ar_1$;
$R_{10}$, $R_{11}$ and $R_{12}$ are each independently selected from —$C_{1-6}$alkyl, —$C_{3-6}$cycloalkyl, —$Ar_2$, $Het_2$, —NH-$Het_2$ and —NH—$Ar_2$; wherein each of said —$C_{1-6}$alkyl is optionally substituted with from 1 to 3 substituents selected from =O, —OH, -halo, —O—$C_{1-6}$alkyl, —S—$C_{1-6}$alkyl, —CN, —$NR_{18}R_{19}$, —$C_{3-6}$cycloalkyl, -$Het_2$ and —$Ar_2$;
$R_{16}$, $R_{17}$, $R_{18}$, $R_{19}$, $R_{20}$, $R_{21}$, $R_{22}$ and $R_{23}$ are each independently selected from —H, and —$C_{1-6}$alkyl;
$Ar_1$, $Ar_2$, $Ar_3$, $Ar_4$ and $Ar_5$ are each independently a 5-10 membered aromatic mono- or bicycle; wherein each of said $Ar_1$, $Ar_2$, $Ar_3$, $Ar_4$ and $Ar_5$ is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{20}R_{21}$;

$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, —O—$C_{1-6}$alkyl, —CN, —$CF_3$, or —$NR_{22}R_{23}$.

6. A compound according to claim 1,
Wherein
X is O;
$R_1$ is selected from —$C_{1-6}$alkyl, —(C=O)—$R_{13}$, —(C=S)—$R_{14}$, and —$SO_2$—$R_{15}$; wherein said —$C_{1-6}$alkyl may be further substituted with —$R_{24}$;
$R_2$ is —H; or $R_1$ taken together with $R_2$ forms $Het_3$;
$R_3$ is
selected from —H, and —OH;
or $R_3$ taken together with $R_4$ forms a dioxolane moiety, which is optionally substituted with from 1 to 3 —$C_{1-6}$alkyl substituents;
$R_4$ is —OH;
$R_5$ is —H;
$R_6$ is selected from —H, and —OH;
$R_7$ is selected from —$C_{1-6}$alkyl, and (C=O)—$R_{10}$; wherein said —$C_{1-6}$alkyl may be further substituted with —$R_{25}$;
$R_8$ is —H; or $R_7$ taken together with $R_8$ forms $Het_4$;
$R_9$ is absent;
$R_{13}$, $R_{14}$, $R_{15}$, $R_{24}$, and $R_{25}$ are each independently selected from —$C_{1-6}$alkyl, —$C_{3-6}$cycloalkyl, —$Ar_1$, $Het_1$, and —NH—$Ar_1$; wherein each of said —$C_{1-6}$alkyl is optionally and independently substituted with from 1 to 3 substituents selected from -halo and —$Ar_1$;
$R_{10}$, is independently selected from —$C_{1-6}$alkyl, —$Ar_2$, and $Het_2$; wherein each of said —$C_{1-6}$alkyl is optionally substituted with from 1 to 3 substituents selected halo and $Ar_2$;
$R_{20}$, and $R_{21}$, are each independently selected from —H, and —$C_{1-6}$alkyl;
$Ar_1$, and $Ar_2$, are each independently a 5-10 membered aromatic mono- or bicycle; wherein each of said $Ar_1$, and $Ar_2$, is optionally and independently substituted with from 1 to 3 substituents selected from =O, —OH, -halo, —$C_{1-6}$alkyl, —O—$C_{1-6}$alkyl, —CN, —$CF_3$, —$NR_{20}R_{21}$, and -phenyl;
$Het_1$, $Het_2$, $Het_3$ and $Het_4$ are each independently a 5-10 membered mono- or bicyclic heteroaryl comprising from 1 to 3 heteroatoms selected from N, O and S; wherein each of said $Het_1$, $Het_2$, $Het_3$ and $Het_4$ is optionally and independently substituted with from 1 to 3 substituents selected from =O, —OH, -halo, —$C_{1-6}$alkyl, —O—$C_{1-6}$alkyl, —CN, —$CF_3$, —$NR_{22}R_{23}$, and -phenyl; wherein said phenyl is optionally substituted with from 1 to 3 substituents selected from =O, —OH, -halo, —$C_{1-6}$alkyl, and phenyl.

7. A compound according to claim 1,
Wherein
X is O;
$R_1$ is selected from —$C_{1-6}$alkyl, (C=O)—$R_{13}$, and —$SO_2$—$R_{15}$; wherein said —$C_{1-6}$alkyl may be further substituted with —$R_{24}$;
$R_2$ is H; or $R_1$ taken together with $R_2$ forms $Het_3$;

R$_3$ and R$_4$ are —OH; or R$_3$ taken together with R$_4$ forms a dioxolane moiety, which is optionally substituted with from 1 to 3 —C$_{1-6}$alkyl substituents;

R$_5$ is —H;

R$_6$ is selected from —H, and —OH;

R$_7$ is selected from —C$_{1-6}$alkyl, and —(C=O)—R$_{10}$; wherein said —C$_{1-6}$alkyl may be further substituted with —R$_{25}$;

R$_8$ is —H; or R$_7$ taken together with R$_8$ forms Het$_4$;

R$_9$ is absent;

R$_{13}$, R$_{15}$, R$_{24}$, and R$_{25}$ are each independently selected from —C$_{1-6}$alkyl, —C$_{3-6}$cycloalkyl, —Ar$_1$, Het$_1$, and —NH—Ar$_1$; wherein each of said —C$_{1-6}$alkyl is optionally and independently substituted with from 1 to 3 substituents selected from -halo and —Ar$_1$;

R$_{10}$, is independently selected from —Ar$_2$, and Het$_2$;

R$_{20}$, and R$_{21}$, are each independently selected from —H, and —C$_{1-6}$alkyl;

Ar$_1$, and Ar$_2$, are each independently a 5-10 membered aromatic mono- or bicycle; wherein each of said Ar$_1$, and Ar$_2$, is optionally and independently substituted with from 1 to 3 substituents selected from =O, —OH, -halo, —C$_{1-6}$alkyl, —O—C$_{1-6}$alkyl, —CN, —CF$_3$, —NR$_{20}$R$_{21}$, and -phenyl;

Het$_1$, Het$_2$, and Het$_3$ are each independently a 5-10 membered mono- or bicyclic heteroaryl comprising from 1 to 3 heteroatoms selected from N, O and S; wherein each of said Het$_1$, Het$_2$, and Het$_3$ is optionally and independently substituted with from 1 to 3 substituents selected from =O, —OH, -halo, and -phenyl.

8. A compound according to claim 1, wherein the compound has the stereoisomeric configuration as represented in formula II:

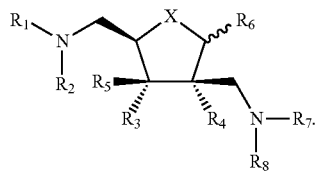

9. A compound according to claim 1 or a stereoisomer, tautomer, racemic, salt, hydrate, or solvate thereof, and optionally a metabolite, pre- or prodrug thereof.

10. A combination of a compound as defined in claim 1 with an antimicrobial agent.

11. A pharmaceutical composition comprising a compound as defined in claim 1 and a pharmaceutically acceptable excipient, diluent and/or carrier.

12. A pharmaceutical composition according to claim 11, wherein said pharmaceutical composition is administered orally, systemically or topically.

13. A medical device comprising one or more compounds according to claim 1.

14. A medical device according to claim 13, wherein said device is selected from the group consisting of grafts, membranes, tubes, connectors, surgical instruments, intra-aortic balloons, stents, blood bags, catheters, sutures, prostheses, heart valves, tissue adhesives, cardiac pacemaker leads, artificial organs, lenses for the eye, blood handling equipment, apheresis equipment, bio sensors, dental devices, skin patches, wound dressings, implantable devices, tampons, bandages, drug delivery systems, bodily implants, and protein-eluting scaffolds for tissue regeneration.

15. A medical device according to claim 13, wherein the one or more compounds is formulated in or applied on the device.

16. A method for the reduction and/or treatment of a bacterial infection and/or biofilm formation in a subject in need thereof, said method comprising administering a therapeutic effective amount of a compound as defined in claim 1 to said subject.

17. The method according to claim 16, wherein the infection is a *Staphylococcus aureus* infection.

18. The method according to claim 16, said method resulting in the reduction and/or treatment of wound infections, skin ulcers, diabetic foot ulcers, burn wound infections, catheter-associated infections, stent-associated infections, infections resulting from animal bites, mastitis, pneumonia or sepsis.

* * * * *